US011578427B2

(12) United States Patent
Binz et al.

(10) Patent No.: US 11,578,427 B2
(45) Date of Patent: *Feb. 14, 2023

(54) DESIGNED ANKYRIN REPEAT DOMAINS WITH ALTERED SURFACE RESIDUES

(71) Applicant: MOLECULAR PARTNERS AG, Zurich-Schlieren (CH)

(72) Inventors: Hans Kaspar Binz, Zurich-Schlieren (CH); Johannes Schilling, Ehrendingen (CH); Patrik Forrer, Steinen (CH); Victor Levitsky, Birmensdorf (CH); Natalia Venetz, Zurich (CH); Marcel Walser, Winterthur (CH)

(73) Assignee: MOLECULAR PARTNERS AG, Zurich-Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/400,471

(22) Filed: Aug. 12, 2021

(65) Prior Publication Data

US 2022/0064234 A1 Mar. 3, 2022

Related U.S. Application Data

(63) Continuation of application No. PCT/EP2020/085855, filed on Dec. 11, 2020.

(30) Foreign Application Priority Data

Dec. 11, 2019 (EP) ..................................... 19215433
Dec. 11, 2019 (EP) ..................................... 19215434
Dec. 11, 2019 (EP) ..................................... 19215435
Dec. 11, 2019 (EP) ..................................... 19215436
Mar. 4, 2020 (EP) ..................................... 20161059
Jun. 19, 2020 (EP) ..................................... 20181234

(51) Int. Cl.
C07K 14/47 (2006.01)
C40B 40/10 (2006.01)
A61K 38/00 (2006.01)

(52) U.S. Cl.
CPC .............. *C40B 40/10* (2013.01); *C07K 14/47* (2013.01); *A61K 38/00* (2013.01); *C07K 2318/20* (2013.01)

(58) Field of Classification Search
None
See application file for complete search history.

(56) References Cited

U.S. PATENT DOCUMENTS

| | | | |
|---|---|---|---|
| 7,417,130 B2 | 8/2008 | Stumpp et al. | |
| 8,710,187 B2 | 4/2014 | Binz et al. | |
| 8,722,618 B2 | 5/2014 | Jacobs et al. | |
| 8,846,577 B2 | 9/2014 | Steiner et al. | |
| 8,901,076 B2 | 12/2014 | Binz et al. | |
| 9,163,070 B2 | 10/2015 | Baumann | |
| 9,221,892 B2 | 12/2015 | Binz | |
| 9,284,361 B2 | 3/2016 | Steiner et al. | |
| 9,365,629 B2 | 6/2016 | Parmeggiani et al. | |
| 9,458,211 B1 | 10/2016 | Bakker et al. | |
| 10,370,414 B2 | 8/2019 | Fiedler et al. | |
| 10,717,772 B2 | 7/2020 | Metz et al. | |
| 2008/0206201 A1 | 8/2008 | Beier et al. | |
| 2012/0277143 A1 | 11/2012 | Jacobs et al. | |
| 2015/0284463 A1 | 10/2015 | Tamaskovic et al. | |
| 2016/0251404 A1 | 9/2016 | Tresch et al. | |
| 2016/0362453 A1 | 12/2016 | Bakker et al. | |
| 2020/0385488 A1 | 12/2020 | Reichen et al. | |
| 2021/0347835 A1* | 11/2021 | Amstutz | C07K 16/10 |
| 2021/0395318 A1 | 12/2021 | Rigamonti et al. | |
| 2022/0106707 A1 | 4/2022 | Levitsky et al. | |

FOREIGN PATENT DOCUMENTS

| | | |
|---|---|---|
| EP | 2 738 180 A1 | 6/2014 |
| WO | WO 2003/070752 A2 | 8/2003 |
| WO | WO 2009/015842 A2 | 2/2009 |
| WO | WO 2014/060365 A1 | 4/2014 |
| WO | WO 2014/083208 A1 | 6/2014 |
| WO | WO 2015/136072 A1 | 9/2015 |
| WO | WO 2016/023898 A1 | 2/2016 |
| WO | WO 2016/154246 A1 | 9/2016 |
| WO | WO 2019/099689 A1 | 5/2019 |
| WO | WO 2020/245171 A1 | 12/2020 |
| WO | WO 2020/245173 A1 | 12/2020 |
| WO | WO 2020/245175 A1 | 12/2020 |
| WO | WO 2021/116470 A2 | 6/2021 |
| WO | WO 2021/229076 A1 | 11/2021 |

OTHER PUBLICATIONS www.uniprot.org/uniprot/A0A1G0, Feb. 15, 2017.
International Search Report for International Application No. PCT/EP2020/085855, dated Mar. 29, 2021.
Written Opinion of the International Search Authority for International Application No. PCT/EP2020/085855.
Amstutz et al., "Intracellular Kinase Inhibitors Selected from Combinatorial Libraries of Designed Ankyrin Repeat Proteins," JBC (2005) vol. 280 No. 26, pp. 24715-24722.
Amstutz et al., "Rapid selection of specific MAP kinase-binders from designed ankyrin repeat protein libraries," Protein Engineering, Design & Selection (2006) 19(5), pp. 219-229.
Bandeiras et al., "Structure of wild-type Plk-1 kinase domain in complex with a selective DARPin", Acta Cryst. (2008) D64, pp. 339-353.

(Continued)

*Primary Examiner* — Anand U Desai
(74) *Attorney, Agent, or Firm* — Finnegan, Henderson, Farabow, Garrett & Dunner, LLP

(57) ABSTRACT

The present invention relates to designed ankyrin repeat domains with altered surface residues, as well as to proteins comprising such a designed ankyrin repeat domain, nucleic acids encoding such domains or proteins, methods of preparing such proteins, pharmaceutical compositions comprising such proteins or nucleic acids, and the use of such proteins, nucleic acids or pharmaceutical compositions in the treatment of diseases.

21 Claims, 4 Drawing Sheets

Specification includes a Sequence Listing.

(56) References Cited

OTHER PUBLICATIONS

Binz, "Designing Repeat Proteins: Well-expressed, Soluble and Stable Proteins from Combinatorial Libraries of Consensus Ankyrin Repeat Proteins" J Mol Biol (2003) 332, pp. 489-503.
Binz et al., "High-affinity binders selected from designed ankyrin repeat protein libraries", Nature Biotechnology (2004) 22(5), pp. 575-582.
Binz et al., "Designed Repeat Proteins—Molecules with Antibody-like Binding Properties," BIOforum Europe 4, 2005, pp. 34-36, Git Verlag GmbH & Co. KG (3 pages).
Binz et al., "Engineered proteins as specific binding reagents," Current Opinion in Biotechnology (2005) 16, p. 459-469.
Binz et al., "Engineering novel binding proteins from nonimmunoglobulin domains," Nature Biotechnology (2005) 23(10), p. 1257-1268.
Binz et al., "Crystal Structure of a Consensus-Designed Ankyrin Repeat Protein: Implications for Stability," Proteins: Structure, Function, and Bioinformatics 65 (2006) pp. 280-284.
Binz et al., "Design and characterization of MP0250, a tri-specific anti-HGF/anti-VEGF DARPin® drug candidate," mAbs (2017) vol. 9 No. 8, pp. 1262-1269.
Boersma et al., "DARPins and other repeat protein scaffolds: advances in engineering and applications," CurrOpin Biotechnol (2011) 22(6), p. 849-57.
Denisova et al., "Construction and Use of Darpin Library for the Discovery of Tumor Specific Antigen Binder Proteins", May 22, 2015, 8th Annual Canadian Cancer Immunotherapy Consortium Meeting (1 page).
Eggel et al., "DARPins as Bispecific Receptor Antagonists Analyzed for Immunoglobulin E Receptor Blockage", J Mol Biol (2009) 393, pp. 598-607.
Fiedler et al., "MP0250, a VEGF and HGF neutralizing DARPin® molecule shows high anti-tumor efficacy in mouse xenografts and patient-derived tumor models," Oncotarget 2017, vol. 8, No. 58, pp. 98371-98383.
Fiedler et al., "Supplementary Materials of 'MP0250, a VEGF and HGF neutralizing DARPin® molecule shows high anti-tumor efficacy in mouse xenografts and patient-derived tumor models'," Oncotarget 2017, vol. 8, No. 58 (2 pages).
Forrer et al., "A novel strategy to design binding molecules harnessing the modular nature of repeat proteins," FEBS Letters (2003) 539, pp. 2-6.
Forrer et al., "Consensus Design of Repeat Proteins," ChemBioChem (2004) 5, pp. 183-189.
Hanes et al., "In vitro selection and evolution of functional proteins by using ribosome display," Proc Natl Acad Sci USA (1997) 94(10), pp. 4937-4942.
He et al., "Ribosome display: cell-free protein display technology," Brief Fund Genomic Proteomic (2002) 1(2), p. 204-212.
Interlandi et al., "Characterization and further stabilization of designed ankyrin repeat proteins by combining molecular dynamics simulations and experiments," J Mol Biol (2008) 375(3), p. 837-854.
Kawe et al., "Isolation of Intracellular Proteinase Inhibitors Derived from Designed Ankyrin Repeat Proteins by Genetic Screening," J Biol Chem (2006) 281, pp. 40252-40263.
Kohl et al., "Designed to be stable: Crystal structure of a consensus ankyrin repeat protein", PNAS (2003) 100(4), pp. 1700-1705.
Kramer et al., "Structural Determinants for Improved Stability of Designed Ankyrin Repeat Proteins with a Redesigned C-Capping Module", J Mol Biol (2010) 404, p. 381-391.
Merz et al., "Stabilizing Ionic Interactions in a Full-consensus Ankyrin Repeat Protein", J. Mol. Biol. (2008) 376, pp. 232-240.
Molecular Partners AG, "Molecular Partners: Building Tomorrow's Breakthroughs," Nov. 11, 2019, A presentation of Molecular Partners AG (42 pages).
Molecular Partners AG, "Translating the DARPin difference into patient benefit," Jun. 29, 2019, archived webpage from Molecular Partners AG website, retrieved from web.archive.org/web/20190629154324/www.molecularpartners.com/our-approach/ on Jun. 23, 2021 (2 pages).
Molecular Partners AG, Molecular Partners Announces Scientific Leadership Transition After Successful Transformation of Research Organization to Focus on Novel DARPin Therapeutics in Oncology, Press Release from Molecular Partners AG website, Jun. 11, 2019, retrieved from www.molecularpartners.com/molecular-partners-announces-scientific-leadership-transition-after-successful-transformation-of-research-organization-to-focus-on-novel-darpin-therapeutics-in-oncolo (5 pages).
Nilsen, "Affinity maturation of a T cell receptor by use of phage display," 2014. Thesis for Master's degree. www.duo.uio.no/handle/10852/40693?show=full (77 pages).
Orf Names:A2143_11365, "A0A1GODY05", Feb. 15, 2017, retrieved from the Internet on Sep. 18, 2020: URL:www.uniprot.org/uniprot/A0A1GODY05.txt?version=10 (1 page).
Plückthun et al., "Designed ankyrin repeat proteins (DARPins): binding proteins for research, diagnostics, and therapy," Annu Rev Pharmacol Toxicol. 2015;55, pp. 489-511.
Schilling et al.,"Thermostable designed ankyrin repeat proteins (DARPins) as building blocks for innovative drugs", bioRxiv preprint doi:https://doi.org/10.1101/2021.04.27.441521; posted Apr. 27, 2021 (12 pages).
Sennhauser et al., "Chaperone-Assisted Crystallography with DARPins", Structure (2008) 16, p. 1443-1453.
Skora et al., "Generation of MANAbodies specific to HLA-restricted epitopes encoded by somatically mutated genes," Proc Natl Acad Sci U S A, 2015;112(32) pp. 9967-9972.
Steiner et al., "Efficient Selection of DARPins with Sub-nanomolar Affinities using SRP Phage Display", J Mol Biol 2008, 382(5), p. 1211-1227.
Steiner et al., "Supplementary Material of 'Efficient Selection of DARPins with Sub-nanomolar Affinities using SRP Phage Display'," J Mol Biol 2008, 382(5) (17 pages).
Steiner et al., "Half-life extension using serum albumin-binding DARPin® domains", PEDS (2017), pp. 1-9.
Stumpp et al., "Designing Repeat Proteins: Modular Leucine-rich Repeat Protein Libraries Based on the Mammalian Ribonuclease Inhibitor Family", J Mol Biol (2003) 332, pp. 471-487.
Stumpp et al., "DARPins: A true alternative to antibodies," Curr Opin Drug Discov Devel. (2007) 10(2), p. 153-159.
Stumpp et al., "DARPins: A new generation of protein therapeutics", Drug Discovery Today (2008) 13(15-16), p. 695-701.
Stumpp et al., "Beyond Antibodies: The DARPin(R) Drug Platform", BioDrugs, 2020: 423-433.
Tassev, "Generation and Use of HLA-A2-Restricted, Peptidespecific Monoclonal Antibodies and Chimeric Antigen Receptors," Thesis for PhD degree, 2011. www.sloankettering.edu/sites/default/files/node/165658/document/final-dimiter-tassev.pdf (176 pages).
Theurillat et al., "Designed ankyrin repeat proteins: a novel tool fortesting epidermal growth factor receptor 2 expression in breast cancer", Modern Pathology (2010), p. 1-9.
Veesler et al., "Crystal Structure and Function of a DARPin Neutralizing Inhibitor of Lactococcal Phage TP901-1", J Biol Chem (2009) 284(44), p. 30718-30726.
Walser et al., "Highly potent anti-SARS-CoV-2 multivalent DARPin therapeutic candidates", BioRxiv preprint, Aug. 26, 2020 (39 pages).
Walser et al., "Highly potent anti-SARS-CoV-2 multivalent DARPin therapeutic candidates", BioRxiv preprint, Nov. 20, 2020 (46 pages).
Wetzel et al., "Folding and Unfolding Mechanism of Highly Stable Full Consensus Ankyrin Repeat Proteins," J. Mol. Bio (2008), pp. 241-257.
Wetzel et al., "Residue-Resolved Stability of Full Consensus Ankyrin Repeat Proteins Probed by NMR", J. Mol. Biol. (2010) 402, pp. 241-258.
Zahnd et al., "Selection and Characterization of Her2 Binding-designed Ankyrin Repeat Proteins," J Biol Chem (2006) 281(46), pp. 35167-35175.
Zahnd et al., "A designed ankyrin repeat protein evolved to picomolar affinity to Her2," J Mol Biol (2007) 369(4), p. 1015-1028.

(56) References Cited

OTHER PUBLICATIONS

Zahnd et al., "Ribosome display: selecting and evolving proteins in vitro that specifically bind to a target," Nature Methods (2007) 4(3), pp. 269-279.
Zahnd et al., "Efficient tumor targeting with high-affinity designed ankyrin repeat proteins: effects of affinity and molecular size", Cancer Res (2010) 70(4), pp. 1595-1605.
Zahnd et al., "Supplementary Information for 'Efficient tumor targeting with high-affinity designed ankyrin repeat proteins: effects of affinity and molecular size'," Cancer Res (2010) 70(4) (23 pages).
Zhao et al., "Affinity maturation of T-cell receptor-like antibodies for Wilms tumor 1 peptide greatly enhances therapeutic potential," Leukemia, 2015;29(11), pp. 2238-2247.
International Search Report for International Application No. PCT/EP2020/085863, dated Sep. 27, 2021 (7 pages).
International Search Report for International Application No. PCT/EP2020/085864, dated Sep. 28, 2021 (8 pages).
Written Opinion of the International Searching Authority for International Application No. PCT/EP2020/085863 (9 pages).
Written Opinion of the International Searching Authority for International Application No. PCT/EP2020/085864 (9 pages).
3rd party observation submitted on Jun. 23, 2021 in PCT/EP2020/085863 (54 pages).
3rd party observation submitted on Jun. 23, 2021 in PCT/EP2020/085864 (54 pages).
3rd party observation submitted on Apr. 11, 2022 in PCT/EP2020/085855 (13 pages).
3rd party observation submitted on Feb. 22, 2022 in PCT/EP2020/085863 (8 pages).
3rd party observation submitted on Feb. 22, 2022 in PCT/EP2020/085864 (8 pages).
NCBI Reference Sequence: XP_022289373.1, tankyrase-1-like [Crassostrea virginica], published Sep. 14, 2017, www.ncbi.nlm.nih.gov/protein/xp_022289373.1 (2 pages).

* cited by examiner

Fig. 2

```
                              1         2         3
                    1         0         0         0
SEQ ID NO: 69:      DLGKKLLEAARAGQDDEVRELLKAGADVNA
SEQ ID NO: 70:      DLGXKLLEAAXXGQDDEVRELLKAGADVNA
SEQ ID NO: 71:      DLGXKLLEAAXXGQDDXVRXLLXAGADVNA
SEQ ID NO: 72:      DLGXXLLEAAXXGQDDXVRXLXXXGADVNA
SEQ ID NO: 73:      XXXXXLLEAAXXGXDXXXXXXXXXGADVNA
SEQ ID NO: 74:      XXXXXXXEXXXXXXDXXXXXXXXXGADVNA
SEQ ID NO: 75:      DLGKKLLQAARAGQLDEVRELLKAGADVNA
SEQ ID NO: 76:      DLGSKLLQAARAGQLDTVRTLLQAGADVNA
SEQ ID NO: 77:      DLGXKLLQAAXXGQLDEVRELLKAGADVNA
SEQ ID NO: 78:      DLGXKLLQAAXXGQLDXVRXLLXAGADVNA
SEQ ID NO: 79:      DLGXXLLQAAXXGQLDXVRXLXXXGADVNA
SEQ ID NO: 80:      XXXXXLLQAAXXGXLXXXXXXXXXGADVNA
SEQ ID NO: 81:      XXXXXXXQXXXXXXLXXXXXXXXXGADVNA
SEQ ID NO: 107:     DLGKKLLQAARAGQLDEVRELLKA
SEQ ID NO: 108:     DLGSKLLQAARAGQLDTVRTLLQA
SEQ ID NO: 109:     DLGXKLLQAAXXGQLDEVRELLKA
SEQ ID NO: 110:     DLGXKLLQAAXXGQLDXVRXLLXA
SEQ ID NO: 111:     DLGXXLLQAAXXGQLDXVRXLXXX
```

Fig. 3

```
                              1         2         2
                    1         0         0         8
SEQ ID NO: 82:      QDKSGKTPADLAADAGHEDIAEVLQKAA
SEQ ID NO: 83:      XDXXGXTPADXAADXGHEDIAEVLQKAA
SEQ ID NO: 84:      XDXXGXTPADXAADXGHEXIAXVLQXAA
SEQ ID NO: 85:      XDXXGXTPXXXAADXGXEXXXXXXXXAA
SEQ ID NO: 86:      XDXXGXTPXXXXADXXXEXXXXXXXXX
SEQ ID NO: 87:      XDXXGXTPXXXXXDXXXEXXXXXXXAA
SEQ ID NO: 88:      QDKSGKTPADLAARAGHQDIAEVLQKAA
SEQ ID NO: 89:      QDTQGTTPADLAARAGHQQIASVLQQAA
SEQ ID NO: 90:      XDXXGXTPADXAARXGHQDIAEVLQKAA
SEQ ID NO: 91:      XDXXGXTPADXAARXGHQXIAXVLQXAA
SEQ ID NO: 92:      XDXXGXTPXXXAARXGXQXXXXXXXXAA
SEQ ID NO: 93:      XDXXGXTPXXXXARXXXQXXXXXXXXX
SEQ ID NO: 94:      XDXXGXTPXXXXXRXXXQXXXXXXXAA
```

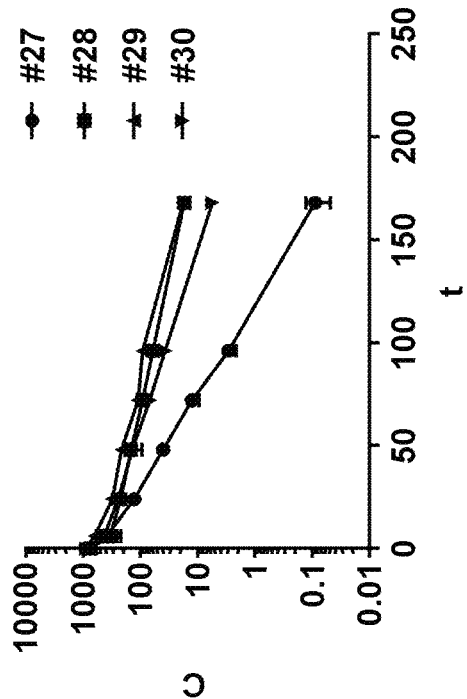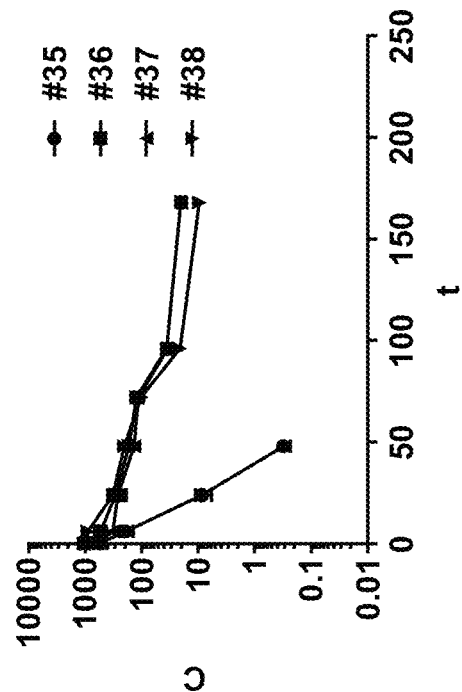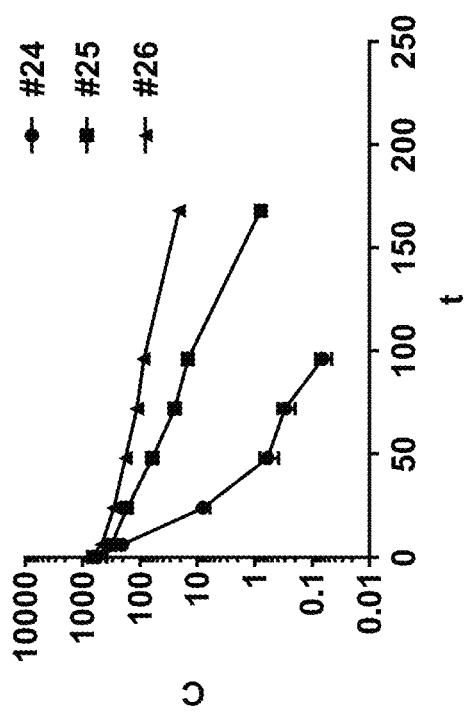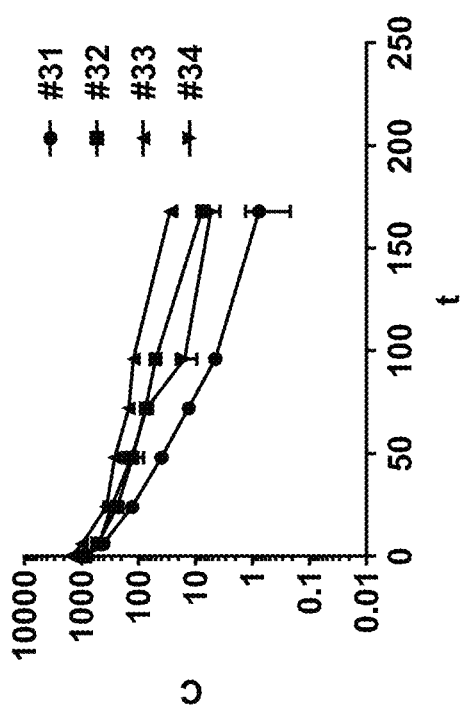

SEQUENCE LISTING

<160> NUMBER OF SEQ ID NOS: 142

<210> SEQ ID NO 1
<211> LENGTH: 12
<212> TYPE: PRT

<213> ORGANISM: Artificial Sequence
<220> FEATURE:
<223> OTHER INFORMATION: His-tag

<400> SEQUENCE: 1

```
Met Arg Gly Ser His His His His His His Gly Ser
1               5                   10
```

<210> SEQ ID NO 2
<211> LENGTH: 22
<212> TYPE: PRT
<213> ORGANISM: Artificial Sequence
<220> FEATURE:
<223> OTHER INFORMATION: GS-rich peptide linker

<400> SEQUENCE: 2

```
Gly Gly Gly Gly Ser Gly Gly Gly Ser Gly Gly Gly Gly Ser Gly
1               5                   10                  15

Gly Gly Gly Ser Gly Ser
            20
```

<210> SEQ ID NO 3
<211> LENGTH: 24
<212> TYPE: PRT
<213> ORGANISM: Artificial Sequence
<220> FEATURE:
<223> OTHER INFORMATION: PT-rich peptide linker

<400> SEQUENCE: 3

```
Gly Ser Pro Thr Pro Thr Pro Thr Thr Pro Thr Pro Thr Pro Thr Thr
1               5                   10                  15

Pro Thr Pro Thr Pro Thr Gly Ser
            20
```

<210> SEQ ID NO 4
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 4

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala
        115                 120
```

<210> SEQ ID NO 5
<211> LENGTH: 124
<212> TYPE: PRT

-continued

```
<213> ORGANISM: Artificial Sequence
<220> FEATURE:
<223> OTHER INFORMATION: Ankyrin repeat domain

<400> SEQUENCE: 5

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala
        115                 120

<210> SEQ ID NO 6
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 6

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Ala Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala
        115                 120

<210> SEQ ID NO 7
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 7

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30
```

-continued

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
 50                  55                  60

Asp Phe Ala Gly Lys Thr Pro Leu His Leu Ala Ala Asn Asp Gly His
 65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala
            115                 120

<210> SEQ ID NO 8
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 8

Asp Leu Gly Lys Lys Leu Leu Glu Ala Ala Arg Ala Gly Gln Asp Asp
 1               5                  10                  15

Glu Val Arg Ile Leu Met Ala Asn Gly Ala Asp Val Asn Ala Lys Asp
            20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
 50                  55                  60

Asp Phe Ala Gly Lys Thr Pro Leu His Leu Ala Ala Asn Asp Gly His
 65                  70                  75                  80

Leu Glu Ile Val Glu Val Leu Leu Lys His Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala
            115                 120

<210> SEQ ID NO 9
<211> LENGTH: 157
<212> TYPE: PRT
<213> ORGANISM: Artificial Sequence
<220> FEATURE:
<223> OTHER INFORMATION: Ankyrin repeat domain

<400> SEQUENCE: 9

Asp Leu Gly Lys Lys Leu Leu Glu Ala Ala Arg Ala Gly Gln Asp Asp
 1               5                  10                  15

Glu Val Arg Glu Leu Leu Lys Ala Gly Ala Asp Val Asn Ala Lys Asp
            20                  25                  30

Gln Ile Gly Trp Thr Pro Leu His Leu Ala Ala Asn Tyr Gly His Leu
            35                  40                  45

Glu Ile Val Glu Val Leu Leu Lys Ala Gly Ala Asp Val Asn Ala Lys
 50                  55                  60

Asp Leu Trp Gly Gln Thr Pro Leu His Leu Ala Ala Trp Lys Gly His
 65                  70                  75                  80

Leu Glu Ile Val Glu Val Leu Leu Lys Ala Gly Ala Asp Val Asn Ala

```
            85                  90                  95
Lys Asp Thr Asp Gly Leu Thr Pro Leu His Leu Ala Ala Ile Arg Gly
            100                 105                 110

His Leu Glu Ile Val Glu Val Leu Lys Ala Gly Ala Asp Val Asn
            115                 120                 125

Ala Gln Asp Lys Ser Gly Lys Thr Pro Ala Asp Leu Ala Ala Asp Ala
            130                 135                 140

Gly His Glu Asp Ile Ala Glu Val Leu Gln Lys Ala Ala
145                 150                 155
```

<210> SEQ ID NO 10
<211> LENGTH: 157
<212> TYPE: PRT
<213> ORGANISM: Artificial Sequence
<220> FEATURE:
<223> OTHER INFORMATION: Ankyrin repeat domain

<400> SEQUENCE: 10

```
Asp Leu Gly Ser Lys Leu Leu Gln Ala Ala Arg Ala Gly Gln Leu Asp
1               5                   10                  15

Thr Val Arg Thr Leu Leu Gln Ala Gly Ala Asp Val Asn Ala Lys Asp
            20                  25                  30

Gln Ile Gly Trp Thr Pro Leu His Leu Ala Ala Asn Tyr Gly His Leu
        35                  40                  45

Glu Ile Val Glu Val Leu Leu Lys Ala Gly Ala Asp Val Asn Ala Lys
    50                  55                  60

Asp Leu Trp Gly Gln Thr Pro Leu His Leu Ala Ala Trp Lys Gly His
65                  70                  75                  80

Leu Glu Ile Val Glu Val Leu Leu Lys Ala Gly Ala Asp Val Asn Ala
                85                  90                  95

Lys Asp Thr Asp Gly Leu Thr Pro Leu His Leu Ala Ala Ile Arg Gly
            100                 105                 110

His Leu Glu Ile Val Glu Val Leu Leu Lys Ala Gly Ala Asp Val Asn
        115                 120                 125

Ala Gln Asp Thr Gln Gly Thr Thr Pro Ala Asp Leu Ala Ala Arg Ala
    130                 135                 140

Gly His Gln Gln Ile Ala Ser Val Leu Gln Gln Ala Ala
145                 150                 155
```

<210> SEQ ID NO 11
<211> LENGTH: 157
<212> TYPE: PRT
<213> ORGANISM: Artificial Sequence
<220> FEATURE:
<223> OTHER INFORMATION: Ankyrin repeat domain

<400> SEQUENCE: 11

```
Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala Lys Asp
            20                  25                  30

Gln Ile Gly Trp Thr Pro Leu His Leu Ala Ala Asn Tyr Gly His Leu
        35                  40                  45

Glu Ile Val Glu Val Leu Leu Lys Ala Gly Ala Asp Val Asn Ala Lys
    50                  55                  60

Asp Leu Trp Gly Gln Thr Pro Leu His Leu Ala Ala Trp Lys Gly His
65                  70                  75                  80
```

```
Leu Glu Ile Val Glu Val Leu Lys Ala Gly Ala Asp Val Asn Ala
                85                  90                  95

Lys Asp Thr Asp Gly Leu Thr Pro Leu His Leu Ala Ala Ile Arg Gly
            100                 105                 110

His Leu Glu Ile Val Glu Val Leu Lys Ala Gly Ala Asp Val Asn
        115                 120                 125

Ala Gln Asp Lys Ser Gly Lys Thr Pro Ala Asp Leu Ala Ala Arg Ala
    130                 135                 140

Gly His Gln Asp Ile Ala Glu Val Leu Gln Lys Ala Ala
145                 150                 155

<210> SEQ ID NO 12
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 12

Asp Leu Gly Leu Lys Leu Leu Thr Ala Ala Trp Glu Gly Gln Asp Asp
1               5                   10                  15

Glu Val Arg Glu Leu Leu Lys Ala Gly Ala Asp Val Asn Ala Lys Asp
            20                  25                  30

Trp Tyr Gly Tyr Thr Pro Leu His Ala Ala Ala Asn Glu Gly His Leu
        35                  40                  45

Glu Ile Val Glu Val Leu Leu Lys Ala Gly Ala Asp Val Asn Ala Lys
    50                  55                  60

Asp Val Val Gly Trp Thr Pro Leu His Ile Ala Ala Tyr Trp Gly His
65                  70                  75                  80

Leu Glu Ile Val Glu Val Leu Lys Ala Gly Ala Asp Val Asn Ala
                85                  90                  95

Gln Asp Gln Thr Gly Gln Thr Pro Ala Asp Leu Ala Ala Trp Gln Gly
            100                 105                 110

His Glu Asp Ile Ala Glu Val Leu Gln Lys Ala Ala
        115                 120

<210> SEQ ID NO 13
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 13

Asp Leu Gly Ser Lys Leu Leu Gln Ala Ala Trp Glu Gly Gln Leu Asp
1               5                   10                  15

Thr Val Arg Thr Leu Leu Gln Ala Gly Ala Asp Val Asn Ala Lys Asp
            20                  25                  30

Trp Tyr Gly Tyr Thr Pro Leu His Ala Ala Ala Asn Glu Gly His Leu
        35                  40                  45

Glu Ile Val Glu Val Leu Leu Lys Ala Gly Ala Asp Val Asn Ala Lys
    50                  55                  60

Asp Val Val Gly Trp Thr Pro Leu His Ile Ala Ala Tyr Trp Gly His
65                  70                  75                  80

Leu Glu Ile Val Glu Val Leu Lys Ala Gly Ala Asp Val Asn Ala
                85                  90                  95

Gln Asp Thr Gln Gly Thr Thr Pro Ala Asp Leu Ala Ala Arg Gln Gly
            100                 105                 110
```

His Gln Gln Ile Ala Ser Val Leu Gln Gln Ala Ala
        115                 120

<210> SEQ ID NO 14
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 14

Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala Lys Asp
            20                  25                  30

Trp Tyr Gly Tyr Thr Pro Leu His Ala Ala Ala Asn Glu Gly His Leu
        35                  40                  45

Glu Ile Val Glu Val Leu Leu Lys Ala Gly Ala Asp Val Asn Ala Lys
    50                  55                  60

Asp Val Val Gly Trp Thr Pro Leu His Ile Ala Ala Tyr Trp Gly His
65                  70                  75                  80

Leu Glu Ile Val Glu Val Leu Leu Lys Ala Gly Ala Asp Val Asn Ala
                85                  90                  95

Gln Asp Lys Ser Gly Lys Thr Pro Ala Asp Leu Ala Ala Arg Ala Gly
            100                 105                 110

His Gln Asp Ile Ala Glu Val Leu Gln Lys Ala Ala
        115                 120

<210> SEQ ID NO 15
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 15

Asp Leu Gly Leu Lys Leu Leu Gln Ala Ala Trp Glu Gly Gln Leu Asp
1               5                   10                  15

Glu Val Arg Glu Leu Leu Lys Ala Gly Ala Asp Val Asn Ala Lys Asp
            20                  25                  30

Trp Tyr Gly Tyr Thr Pro Leu His Ala Ala Ala Asn Glu Gly His Leu
        35                  40                  45

Glu Ile Val Glu Val Leu Leu Lys Ala Gly Ala Asp Val Asn Ala Lys
    50                  55                  60

Asp Val Val Gly Trp Thr Pro Leu His Ile Ala Ala Tyr Trp Gly His
65                  70                  75                  80

Leu Glu Ile Val Glu Val Leu Leu Lys Ala Gly Ala Asp Val Asn Ala
                85                  90                  95

Gln Asp Gln Thr Gly Gln Thr Pro Ala Asp Leu Ala Ala Arg Gln Gly
            100                 105                 110

His Gln Asp Ile Ala Glu Val Leu Gln Lys Ala Ala
        115                 120

<210> SEQ ID NO 16
<211> LENGTH: 124
<212> TYPE: PRT
<213> ORGANISM: Artificial Sequence
<220> FEATURE:
<223> OTHER INFORMATION: Ankyrin repeat domain

```
<400> SEQUENCE: 16

Asp Leu Gly Trp Lys Leu Leu Glu Ala Ala Val Ile Gly Gln Asp Asp
1               5                   10                  15

Glu Val Arg Glu Leu Leu Lys Ala Gly Ala Asp Val Asn Ala Lys Asp
            20                  25                  30

Val Asp Gly Asn Thr Pro Leu His Tyr Ala Ala His Val Gly His Leu
        35                  40                  45

Glu Ile Val Glu Val Leu Leu Lys Ala Gly Ala Asp Val Asn Ala Lys
    50                  55                  60

Asp Glu Gln Gly Tyr Thr Pro Leu His Leu Ala Ala Trp Arg Gly His
65                  70                  75                  80

Leu Glu Ile Val Glu Val Leu Leu Lys Ala Gly Ala Asp Val Asn Ala
                85                  90                  95

Gln Asp Leu Glu Gly Ala Thr Pro Ala Asp Leu Ala Ala His Glu Gly
            100                 105                 110

His Glu Asp Ile Ala Glu Val Leu Gln Lys Ala Ala
            115                 120

<210> SEQ ID NO 17
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 17

Asp Leu Gly Ser Lys Leu Leu Gln Ala Ala Val Ile Gly Gln Leu Asp
1               5                   10                  15

Thr Val Arg Thr Leu Leu Gln Ala Gly Ala Asp Val Asn Ala Lys Asp
            20                  25                  30

Val Asp Gly Asn Thr Pro Leu His Tyr Ala Ala His Val Gly His Leu
        35                  40                  45

Glu Ile Val Glu Val Leu Leu Lys Ala Gly Ala Asp Val Asn Ala Lys
    50                  55                  60

Asp Glu Gln Gly Tyr Thr Pro Leu His Leu Ala Ala Trp Arg Gly His
65                  70                  75                  80

Leu Glu Ile Val Glu Val Leu Leu Lys Ala Gly Ala Asp Val Asn Ala
                85                  90                  95

Gln Asp Thr Gln Gly Thr Thr Pro Ala Asp Leu Ala Ala Arg Glu Gly
            100                 105                 110

His Gln Gln Ile Ala Ser Val Leu Gln Gln Ala Ala
            115                 120

<210> SEQ ID NO 18
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 18

Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala Lys Asp
            20                  25                  30

Val Asp Gly Asn Thr Pro Leu His Tyr Ala Ala His Val Gly His Leu
        35                  40                  45
```

```
Glu Ile Val Glu Val Leu Leu Lys Ala Gly Ala Asp Val Asn Ala Lys
    50                  55                  60

Asp Glu Gln Gly Tyr Thr Pro Leu His Leu Ala Ala Trp Arg Gly His
 65                  70                  75                  80

Leu Glu Ile Val Glu Val Leu Leu Lys Ala Gly Ala Asp Val Asn Ala
                85                  90                  95

Gln Asp Lys Ser Gly Lys Thr Pro Ala Asp Leu Ala Ala Arg Ala Gly
            100                 105                 110

His Gln Asp Ile Ala Glu Val Leu Gln Lys Ala Ala
            115                 120
```

<210> SEQ ID NO 19
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 19

```
Asp Leu Gly Trp Lys Leu Leu Gln Ala Ala Val Ile Gly Gln Leu Asp
 1               5                  10                  15

Glu Val Arg Glu Leu Leu Lys Ala Gly Ala Asp Val Asn Ala Lys Asp
                20                  25                  30

Val Asp Gly Asn Thr Pro Leu His Tyr Ala Ala His Val Gly His Leu
            35                  40                  45

Glu Ile Val Glu Val Leu Leu Lys Ala Gly Ala Asp Val Asn Ala Lys
    50                  55                  60

Asp Glu Gln Gly Tyr Thr Pro Leu His Leu Ala Ala Trp Arg Gly His
 65                  70                  75                  80

Leu Glu Ile Val Glu Val Leu Leu Lys Ala Gly Ala Asp Val Asn Ala
                85                  90                  95

Gln Asp Leu Glu Gly Ala Thr Pro Ala Asp Leu Ala Ala Arg Glu Gly
            100                 105                 110

His Gln Asp Ile Ala Glu Val Leu Gln Lys Ala Ala
            115                 120
```

<210> SEQ ID NO 20
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 20

```
Asp Leu Gly Thr Lys Leu Leu Glu Ala Ala Gln Tyr Gly Gln Asp Asp
 1               5                  10                  15

Glu Val Arg Glu Leu Leu Lys Ala Gly Ala Asp Val Asn Ala Lys Asp
                20                  25                  30

Val Asp Gly Ala Thr Pro Leu His Trp Ala Ala Tyr Lys Gly His Pro
            35                  40                  45

Glu Ile Ile Glu Val Leu Leu Lys Ala Gly Ala Asp Val Asn Ala Lys
    50                  55                  60

Asp Ala Val Gly Trp Thr Pro Leu His Ile Ala Ala Asn His Gly His
 65                  70                  75                  80

Leu Glu Ile Val Glu Val Leu Leu Lys Ala Gly Ala Asp Val Asn Ala
                85                  90                  95

Gln Asp Ser Tyr Gly Ala Thr Pro Ala Asp Leu Ala Ala Ile Trp Gly
```

His Glu Asp Ile Ala Glu Val Leu Gln Lys Ala Ala
        115                 120

<210> SEQ ID NO 21
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 21

Asp Leu Gly Ser Lys Leu Leu Gln Ala Ala Gln Tyr Gly Gln Leu Asp
1               5                   10                  15

Thr Val Arg Thr Leu Leu Gln Ala Gly Ala Asp Val Asn Ala Lys Asp
            20                  25                  30

Val Asp Gly Ala Thr Pro Leu His Trp Ala Ala Tyr Lys Gly His Pro
        35                  40                  45

Glu Ile Ile Glu Val Leu Leu Lys Ala Gly Ala Asp Val Asn Ala Lys
    50                  55                  60

Asp Ala Val Gly Trp Thr Pro Leu His Ile Ala Ala Asn His Gly His
65                  70                  75                  80

Leu Glu Ile Val Glu Val Leu Leu Lys Ala Gly Ala Asp Val Asn Ala
                85                  90                  95

Gln Asp Thr Gln Gly Thr Thr Pro Ala Asp Leu Ala Ala Arg Trp Gly
            100                 105                 110

His Gln Gln Ile Ala Ser Val Leu Gln Gln Ala Ala
        115                 120

<210> SEQ ID NO 22
<211> LENGTH: 124
<212> TYPE: PRT
<213> ORGANISM: Artificial Sequence
<220> FEATURE:
<223> OTHER INFORMATION: Ankyrin repeat domain

<400> SEQUENCE: 22

Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala Lys Asp
            20                  25                  30

Val Asp Gly Ala Thr Pro Leu His Trp Ala Ala Tyr Lys Gly His Pro
        35                  40                  45

Glu Ile Ile Glu Val Leu Leu Lys Ala Gly Ala Asp Val Asn Ala Lys
    50                  55                  60

Asp Ala Val Gly Trp Thr Pro Leu His Ile Ala Ala Asn His Gly His
65                  70                  75                  80

Leu Glu Ile Val Glu Val Leu Leu Lys Ala Gly Ala Asp Val Asn Ala
                85                  90                  95

Gln Asp Lys Ser Gly Lys Thr Pro Ala Asp Leu Ala Ala Arg Ala Gly
            100                 105                 110

His Gln Asp Ile Ala Glu Val Leu Gln Lys Ala Ala
        115                 120

<210> SEQ ID NO 23
<211> LENGTH: 124
<212> TYPE: PRT
<213> ORGANISM: Artificial Sequence
<220> FEATURE:

<223> OTHER INFORMATION: Ankyrin repeat domain

<400> SEQUENCE: 23

Asp Leu Gly Thr Lys Leu Leu Gln Ala Ala Gln Tyr Gly Gln Leu Asp
1               5                   10                  15

Glu Val Arg Glu Leu Leu Lys Ala Gly Ala Asp Val Asn Ala Lys Asp
            20                  25                  30

Val Asp Gly Ala Thr Pro Leu His Trp Ala Ala Tyr Lys Gly His Pro
        35                  40                  45

Glu Ile Ile Glu Val Leu Leu Lys Ala Gly Ala Asp Val Asn Ala Lys
    50                  55                  60

Asp Ala Val Gly Trp Thr Pro Leu His Ile Ala Ala Asn His Gly His
65                  70                  75                  80

Leu Glu Ile Val Glu Val Leu Leu Lys Ala Gly Ala Asp Val Asn Ala
                85                  90                  95

Gln Asp Ser Tyr Gly Ala Thr Pro Ala Asp Leu Ala Ala Arg Trp Gly
            100                 105                 110

His Gln Asp Ile Ala Glu Val Leu Gln Lys Ala Ala
            115                 120

<210> SEQ ID NO 24
<211> LENGTH: 303
<212> TYPE: PRT
<213> ORGANISM: Artificial Sequence
<220> FEATURE:
<223> OTHER INFORMATION: Ankyrin repeat protein

<400> SEQUENCE: 24

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Gly Gly Gly
            115                 120                 125

Ser Gly Gly Gly Gly Ser Gly Gly Gly Ser Gly Gly Gly Gly Ser
    130                 135                 140

Gly Ser Asp Leu Gly Lys Lys Leu Leu Glu Ala Ala Arg Ala Gly Gln
145                 150                 155                 160

Asp Asp Glu Val Arg Glu Leu Leu Lys Ala Gly Ala Asp Val Asn Ala
                165                 170                 175

Lys Asp Gln Ile Gly Trp Thr Pro Leu His Leu Ala Ala Asn Tyr Gly
            180                 185                 190

His Leu Glu Ile Val Glu Val Leu Leu Lys Ala Gly Ala Asp Val Asn
            195                 200                 205

Ala Lys Asp Leu Trp Gly Gln Thr Pro Leu His Leu Ala Ala Trp Lys
            210                 215                 220

Gly His Leu Glu Ile Val Glu Val Leu Leu Lys Ala Gly Ala Asp Val
225                 230                 235                 240

Asn Ala Lys Asp Thr Asp Gly Leu Thr Pro Leu His Leu Ala Ala Ile
                245                 250                 255

Arg Gly His Leu Glu Ile Val Glu Val Leu Leu Lys Ala Gly Ala Asp
            260                 265                 270

Val Asn Ala Gln Asp Lys Ser Gly Lys Thr Pro Ala Asp Leu Ala Ala
        275                 280                 285

Asp Ala Gly His Glu Asp Ile Ala Glu Val Leu Gln Lys Ala Ala
    290                 295                 300

<210> SEQ ID NO 25
<211> LENGTH: 303
<212> TYPE: PRT
<213> ORGANISM: Artificial Sequence
<220> FEATURE:
<223> OTHER INFORMATION: Ankyrin repeat protein

<400> SEQUENCE: 25

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Gly Gly Gly
        115                 120                 125

Ser Gly Gly Gly Gly Ser Gly Gly Gly Ser Gly Gly Gly Gly Ser
    130                 135                 140

Gly Ser Asp Leu Gly Ser Lys Leu Leu Gln Ala Ala Arg Ala Gly Gln
145                 150                 155                 160

Leu Asp Thr Val Arg Thr Leu Leu Gln Ala Gly Ala Asp Val Asn Ala
            165                 170                 175

Lys Asp Gln Ile Gly Trp Thr Pro Leu His Leu Ala Ala Asn Tyr Gly
        180                 185                 190

His Leu Glu Ile Val Glu Val Leu Leu Lys Ala Gly Ala Asp Val Asn
    195                 200                 205

Ala Lys Asp Leu Trp Gly Gln Thr Pro Leu His Leu Ala Ala Trp Lys
210                 215                 220

Gly His Leu Glu Ile Val Glu Val Leu Leu Lys Ala Gly Ala Asp Val
225                 230                 235                 240

Asn Ala Lys Asp Thr Asp Gly Leu Thr Pro Leu His Leu Ala Ala Ile
                245                 250                 255

Arg Gly His Leu Glu Ile Val Glu Val Leu Leu Lys Ala Gly Ala Asp
            260                 265                 270

Val Asn Ala Gln Asp Thr Gln Gly Thr Thr Pro Ala Asp Leu Ala Ala
        275                 280                 285

```
Arg Ala Gly His Gln Gln Ile Ala Ser Val Leu Gln Gln Ala Ala
        290                 295                 300
```

```
<210> SEQ ID NO 26
<211> LENGTH: 303
<212> TYPE: PRT
<213> ORGANISM: Artificial Sequence
<220> FEATURE:
<223> OTHER INFORMATION: Ankyrin repeat protein

<400> SEQUENCE: 26

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Gly Gly Gly
        115                 120                 125

Ser Gly Gly Gly Gly Ser Gly Gly Gly Ser Gly Gly Gly Gly Ser
130                 135                 140

Gly Ser Asp Leu Gly Lys Lys Leu Leu Gln Ala Ala Arg Ala Gly Gln
145                 150                 155                 160

Leu Asp Glu Val Arg Glu Leu Leu Lys Ala Gly Ala Asp Val Asn Ala
                165                 170                 175

Lys Asp Gln Ile Gly Trp Thr Pro Leu His Leu Ala Ala Asn Tyr Gly
            180                 185                 190

His Leu Glu Ile Val Glu Val Leu Leu Lys Ala Gly Ala Asp Val Asn
        195                 200                 205

Ala Lys Asp Leu Trp Gly Gln Thr Pro Leu His Leu Ala Ala Trp Lys
    210                 215                 220

Gly His Leu Glu Ile Val Glu Val Leu Leu Lys Ala Gly Ala Asp Val
225                 230                 235                 240

Asn Ala Lys Asp Thr Asp Gly Leu Thr Pro Leu His Leu Ala Ala Ile
                245                 250                 255

Arg Gly His Leu Glu Ile Val Glu Val Leu Leu Lys Ala Gly Ala Asp
            260                 265                 270

Val Asn Ala Gln Asp Lys Ser Gly Lys Thr Pro Ala Asp Leu Ala Ala
        275                 280                 285

Arg Ala Gly His Gln Asp Ile Ala Glu Val Leu Gln Lys Ala Ala
    290                 295                 300
```

```
<210> SEQ ID NO 27
<211> LENGTH: 270
<212> TYPE: PRT
<213> ORGANISM: Artificial Sequence
<220> FEATURE:
<223> OTHER INFORMATION: Ankyrin repeat protein
```

<400> SEQUENCE: 27

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Gly Gly Gly Gly
        115                 120                 125

Ser Gly Gly Gly Gly Ser Gly Gly Gly Gly Ser Gly Gly Gly Gly Ser
    130                 135                 140

Gly Ser Asp Leu Gly Leu Lys Leu Leu Thr Ala Ala Trp Glu Gly Gln
145                 150                 155                 160

Asp Asp Glu Val Arg Glu Leu Leu Lys Ala Gly Ala Asp Val Asn Ala
                165                 170                 175

Lys Asp Trp Tyr Gly Tyr Thr Pro Leu His Ala Ala Asn Glu Gly
            180                 185                 190

His Leu Glu Ile Val Glu Val Leu Leu Lys Ala Gly Ala Asp Val Asn
        195                 200                 205

Ala Lys Asp Val Val Gly Trp Thr Pro Leu His Ile Ala Ala Tyr Trp
    210                 215                 220

Gly His Leu Glu Ile Val Glu Val Leu Leu Lys Ala Gly Ala Asp Val
225                 230                 235                 240

Asn Ala Gln Asp Gln Thr Gly Gln Thr Pro Ala Asp Leu Ala Ala Trp
                245                 250                 255

Gln Gly His Glu Asp Ile Ala Glu Val Leu Gln Lys Ala Ala
            260                 265                 270
```

<210> SEQ ID NO 28
<211> LENGTH: 270
<212> TYPE: PRT
<213> ORGANISM: Artificial Sequence
<220> FEATURE:
<223> OTHER INFORMATION: Ankyrin repeat protein

<400> SEQUENCE: 28

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
```

```
                    85                  90                  95
Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Gly Gly Gly
        115                 120                 125

Ser Gly Gly Gly Gly Ser Gly Gly Gly Ser Gly Gly Gly Ser
    130                 135                 140

Gly Ser Asp Leu Gly Ser Lys Leu Leu Gln Ala Ala Trp Glu Gly Gln
145                 150                 155                 160

Leu Asp Thr Val Arg Thr Leu Leu Gln Ala Gly Ala Asp Val Asn Ala
                165                 170                 175

Lys Asp Trp Tyr Gly Tyr Thr Pro Leu His Ala Ala Ala Asn Glu Gly
            180                 185                 190

His Leu Glu Ile Val Glu Val Leu Leu Lys Ala Gly Ala Asp Val Asn
        195                 200                 205

Ala Lys Asp Val Val Gly Trp Thr Pro Leu His Ile Ala Ala Tyr Trp
    210                 215                 220

Gly His Leu Glu Ile Val Glu Val Leu Leu Lys Ala Gly Ala Asp Val
225                 230                 235                 240

Asn Ala Gln Asp Thr Gln Gly Thr Thr Pro Ala Asp Leu Ala Ala Arg
                245                 250                 255

Gln Gly His Gln Gln Ile Ala Ser Val Leu Gln Gln Ala Ala
            260                 265                 270

<210> SEQ ID NO 29
<211> LENGTH: 270
<212> TYPE: PRT
<213> ORGANISM: Artificial Sequence
<220> FEATURE:
<223> OTHER INFORMATION: Ankyrin repeat protein

<400> SEQUENCE: 29

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Gly Gly Gly
        115                 120                 125

Ser Gly Gly Gly Gly Ser Gly Gly Gly Ser Gly Gly Gly Ser
    130                 135                 140

Gly Ser Asp Leu Gly Lys Lys Leu Leu Gln Ala Ala Arg Ala Gly Gln
145                 150                 155                 160

Leu Asp Glu Val Arg Glu Leu Leu Lys Ala Gly Ala Asp Val Asn Ala
                165                 170                 175

Lys Asp Trp Tyr Gly Tyr Thr Pro Leu His Ala Ala Ala Asn Glu Gly
```

His Leu Glu Ile Val Glu Val Leu Lys Ala Gly Ala Asp Val Asn
            195                 200                 205

Ala Lys Asp Val Val Gly Trp Thr Pro Leu His Ile Ala Ala Tyr Trp
        210                 215                 220

Gly His Leu Glu Ile Val Glu Val Leu Leu Lys Ala Gly Ala Asp Val
225                 230                 235                 240

Asn Ala Gln Asp Lys Ser Gly Lys Thr Pro Ala Asp Leu Ala Ala Arg
                245                 250                 255

Ala Gly His Gln Asp Ile Ala Glu Val Leu Gln Lys Ala Ala
        260                 265                 270

<210> SEQ ID NO 30
<211> LENGTH: 270
<212> TYPE: PRT
<213> ORGANISM: Artificial Sequence
<220> FEATURE:
<223> OTHER INFORMATION: Ankyrin repeat protein

<400> SEQUENCE: 30

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Gly Gly Gly
        115                 120                 125

Ser Gly Gly Gly Gly Ser Gly Gly Gly Gly Ser Gly Gly Gly Gly Ser
    130                 135                 140

Gly Ser Asp Leu Gly Leu Lys Leu Leu Gln Ala Ala Trp Glu Gly Gln
145                 150                 155                 160

Leu Asp Glu Val Arg Glu Leu Leu Lys Ala Gly Ala Asp Val Asn Ala
                165                 170                 175

Lys Asp Trp Tyr Gly Tyr Thr Pro Leu His Ala Ala Ala Asn Glu Gly
            180                 185                 190

His Leu Glu Ile Val Glu Val Leu Leu Lys Ala Gly Ala Asp Val Asn
        195                 200                 205

Ala Lys Asp Val Val Gly Trp Thr Pro Leu His Ile Ala Ala Tyr Trp
    210                 215                 220

Gly His Leu Glu Ile Val Glu Val Leu Leu Lys Ala Gly Ala Asp Val
225                 230                 235                 240

Asn Ala Gln Asp Gln Thr Gly Gln Thr Pro Ala Asp Leu Ala Ala Arg
                245                 250                 255

Gln Gly His Gln Asp Ile Ala Glu Val Leu Gln Lys Ala Ala
            260                 265                 270

-continued

<210> SEQ ID NO 31
<211> LENGTH: 270
<212> TYPE: PRT
<213> ORGANISM: Artificial Sequence
<220> FEATURE:
<223> OTHER INFORMATION: Ankyrin repeat protein

<400> SEQUENCE: 31

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Gly Gly Gly
        115                 120                 125

Ser Gly Gly Gly Gly Ser Gly Gly Gly Ser Gly Gly Gly Gly Ser
    130                 135                 140

Gly Ser Asp Leu Gly Trp Lys Leu Leu Glu Ala Ala Val Ile Gly Gln
145                 150                 155                 160

Asp Asp Glu Val Arg Glu Leu Leu Lys Ala Gly Ala Asp Val Asn Ala
                165                 170                 175

Lys Asp Val Asp Gly Asn Thr Pro Leu His Tyr Ala Ala His Val Gly
            180                 185                 190

His Leu Glu Ile Val Glu Val Leu Leu Lys Ala Gly Ala Asp Val Asn
        195                 200                 205

Ala Lys Asp Glu Gln Gly Tyr Thr Pro Leu His Leu Ala Ala Trp Arg
    210                 215                 220

Gly His Leu Glu Ile Val Glu Val Leu Leu Lys Ala Gly Ala Asp Val
225                 230                 235                 240

Asn Ala Gln Asp Leu Glu Gly Ala Thr Pro Ala Asp Leu Ala Ala His
                245                 250                 255

Glu Gly His Glu Asp Ile Ala Glu Val Leu Gln Lys Ala Ala
            260                 265                 270
```

<210> SEQ ID NO 32
<211> LENGTH: 270
<212> TYPE: PRT
<213> ORGANISM: Artificial Sequence
<220> FEATURE:
<223> OTHER INFORMATION: Ankyrin repeat protein

<400> SEQUENCE: 32

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45
```

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Gly Gly Gly
                115                 120                 125

Ser Gly Gly Gly Gly Ser Gly Gly Gly Ser Gly Gly Gly Gly Ser
130                 135                 140

Gly Ser Asp Leu Gly Ser Lys Leu Leu Gln Ala Ala Val Ile Gly Gln
145                 150                 155                 160

Leu Asp Thr Val Arg Thr Leu Leu Gln Ala Gly Ala Asp Val Asn Ala
                165                 170                 175

Lys Asp Val Asp Gly Asn Thr Pro Leu His Tyr Ala Ala His Val Gly
                180                 185                 190

His Leu Glu Ile Val Glu Val Leu Leu Lys Ala Gly Ala Asp Val Asn
                195                 200                 205

Ala Lys Asp Glu Gln Gly Tyr Thr Pro Leu His Leu Ala Ala Trp Arg
210                 215                 220

Gly His Leu Glu Ile Val Glu Val Leu Leu Lys Ala Gly Ala Asp Val
225                 230                 235                 240

Asn Ala Gln Asp Thr Gln Gly Thr Thr Pro Ala Asp Leu Ala Ala Arg
                245                 250                 255

Glu Gly His Gln Gln Ile Ala Ser Val Leu Gln Gln Ala Ala
                260                 265                 270

<210> SEQ ID NO 33
<211> LENGTH: 270
<212> TYPE: PRT
<213> ORGANISM: Artificial Sequence
<220> FEATURE:
<223> OTHER INFORMATION: Ankyrin repeat protein

<400> SEQUENCE: 33

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Gly Gly Gly
                115                 120                 125

Ser Gly Gly Gly Gly Ser Gly Gly Gly Ser Gly Gly Gly Gly Ser
130                 135                 140

Gly Ser Asp Leu Gly Lys Lys Leu Leu Gln Ala Ala Arg Ala Gly Gln
145                 150                 155                 160

Leu Asp Glu Val Arg Glu Leu Leu Lys Ala Gly Ala Asp Val Asn Ala
                165                 170                 175

Lys Asp Val Asp Gly Asn Thr Pro Leu His Tyr Ala Ala His Val Gly
                180                 185                 190

His Leu Glu Ile Val Glu Val Leu Lys Ala Gly Ala Asp Val Asn
            195                 200                 205

Ala Lys Asp Glu Gln Gly Tyr Thr Pro Leu His Leu Ala Ala Trp Arg
    210                 215                 220

Gly His Leu Glu Ile Val Glu Val Leu Lys Ala Gly Ala Asp Val
225                 230                 235                 240

Asn Ala Gln Asp Lys Ser Gly Lys Thr Pro Ala Asp Leu Ala Ala Arg
                245                 250                 255

Ala Gly His Gln Asp Ile Ala Glu Val Leu Gln Lys Ala Ala
                260                 265                 270

<210> SEQ ID NO 34
<211> LENGTH: 270
<212> TYPE: PRT
<213> ORGANISM: Artificial Sequence
<220> FEATURE:
<223> OTHER INFORMATION: Ankyrin repeat protein

<400> SEQUENCE: 34

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
                35                  40                  45

Lys Ile Val Glu Val Leu Leu Lys Ala Gly Ala Asp Val Asn Ala Lys
            50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Gly Gly Gly
            115                 120                 125

Ser Gly Gly Gly Ser Gly Gly Gly Ser Gly Gly Gly Ser
130                 135                 140

Gly Ser Asp Leu Gly Trp Lys Leu Leu Gln Ala Ala Val Ile Gly Gln
145                 150                 155                 160

Leu Asp Glu Val Arg Glu Leu Leu Lys Ala Gly Ala Asp Val Asn Ala
                165                 170                 175

Lys Asp Val Asp Gly Asn Thr Pro Leu His Tyr Ala Ala His Val Gly
                180                 185                 190

His Leu Glu Ile Val Glu Val Leu Leu Lys Ala Gly Ala Asp Val Asn
            195                 200                 205

Ala Lys Asp Glu Gln Gly Tyr Thr Pro Leu His Leu Ala Ala Trp Arg
    210                 215                 220

Gly His Leu Glu Ile Val Glu Val Leu Leu Lys Ala Gly Ala Asp Val
225                 230                 235                 240

```
Asn Ala Gln Asp Leu Glu Gly Ala Thr Pro Ala Asp Leu Ala Ala Arg
                245                 250                 255

Glu Gly His Gln Asp Ile Ala Glu Val Leu Gln Lys Ala Ala
        260                 265                 270

<210> SEQ ID NO 35
<211> LENGTH: 270
<212> TYPE: PRT
<213> ORGANISM: Artificial Sequence
<220> FEATURE:
<223> OTHER INFORMATION: Ankyrin repeat protein

<400> SEQUENCE: 35

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Gly Gly Gly Gly
        115                 120                 125

Ser Gly Gly Gly Ser Gly Gly Gly Ser Gly Gly Gly Ser
    130                 135                 140

Gly Ser Asp Leu Gly Thr Lys Leu Leu Glu Ala Ala Gln Tyr Gly Gln
145                 150                 155                 160

Asp Asp Glu Val Arg Glu Leu Leu Lys Ala Gly Ala Asp Val Asn Ala
            165                 170                 175

Lys Asp Val Asp Gly Ala Thr Pro Leu His Trp Ala Ala Tyr Lys Gly
        180                 185                 190

His Pro Glu Ile Ile Glu Val Leu Leu Lys Ala Gly Ala Asp Val Asn
    195                 200                 205

Ala Lys Asp Ala Val Gly Trp Thr Pro Leu His Ile Ala Ala Asn His
    210                 215                 220

Gly His Leu Glu Ile Val Glu Val Leu Leu Lys Ala Gly Ala Asp Val
225                 230                 235                 240

Asn Ala Gln Asp Ser Tyr Gly Ala Thr Pro Ala Asp Leu Ala Ala Ile
            245                 250                 255

Trp Gly His Glu Asp Ile Ala Glu Val Leu Gln Lys Ala Ala
        260                 265                 270

<210> SEQ ID NO 36
<211> LENGTH: 270
<212> TYPE: PRT
<213> ORGANISM: Artificial Sequence
<220> FEATURE:
<223> OTHER INFORMATION: Ankyrin repeat protein

<400> SEQUENCE: 36

Asp Leu Gly Lys Lys Leu Leu Glu Ala Ala Arg Ala Gly Gln Asp Asp
1               5                   10                  15
```

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
 50                  55                  60

Asp Phe Ala Gly Lys Thr Pro Leu His Leu Ala Ala Asn Glu Gly His
 65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Gly Gly Gly
            115                 120                 125

Ser Gly Gly Gly Gly Ser Gly Gly Gly Ser Gly Gly Gly Gly Ser
130                 135                 140

Gly Ser Asp Leu Gly Ser Lys Leu Leu Gln Ala Ala Gln Tyr Gly Gln
145                 150                 155                 160

Leu Asp Thr Val Arg Thr Leu Leu Gln Ala Gly Ala Asp Val Asn Ala
                165                 170                 175

Lys Asp Val Asp Gly Ala Thr Pro Leu His Trp Ala Ala Tyr Lys Gly
            180                 185                 190

His Pro Glu Ile Ile Glu Val Leu Leu Lys Ala Gly Ala Asp Val Asn
            195                 200                 205

Ala Lys Asp Ala Val Gly Trp Thr Pro Leu His Ile Ala Ala Asn His
 210                 215                 220

Gly His Leu Glu Ile Val Glu Val Leu Leu Lys Ala Gly Ala Asp Val
225                 230                 235                 240

Asn Ala Gln Asp Thr Gln Gly Thr Thr Pro Ala Asp Leu Ala Ala Arg
                245                 250                 255

Trp Gly His Gln Gln Ile Ala Ser Val Leu Gln Gln Ala Ala
            260                 265                 270

<210> SEQ ID NO 37
<211> LENGTH: 270
<212> TYPE: PRT
<213> ORGANISM: Artificial Sequence
<220> FEATURE:
<223> OTHER INFORMATION: Ankyrin repeat protein

<400> SEQUENCE: 37

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
 50                  55                  60

Asp Phe Ala Gly Lys Thr Pro Leu His Leu Ala Ala Asn Glu Gly His
 65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

```
His Glu Asp Ile Ala Glu Val Leu Gln Lys Ala Ala Gly Gly Gly
        115                 120                 125

Ser Gly Gly Gly Gly Ser Gly Gly Gly Ser Gly Gly Gly Ser
    130                 135                 140

Gly Ser Asp Leu Gly Lys Lys Leu Leu Gln Ala Arg Ala Gly Gln
145                 150                 155                 160

Leu Asp Glu Val Arg Glu Leu Leu Lys Ala Gly Ala Asp Val Asn Ala
                165                 170                 175

Lys Asp Val Asp Gly Ala Thr Pro Leu His Trp Ala Ala Tyr Lys Gly
            180                 185                 190

His Pro Glu Ile Ile Glu Val Leu Leu Lys Ala Gly Ala Asp Val Asn
            195                 200                 205

Ala Lys Asp Ala Val Gly Trp Thr Pro Leu His Ile Ala Ala Asn His
        210                 215                 220

Gly His Leu Glu Ile Val Glu Val Leu Leu Lys Ala Gly Ala Asp Val
225                 230                 235                 240

Asn Ala Gln Asp Lys Ser Gly Lys Thr Pro Ala Asp Leu Ala Ala Arg
                245                 250                 255

Ala Gly His Gln Asp Ile Ala Glu Val Leu Gln Lys Ala Ala
            260                 265                 270
```

<210> SEQ ID NO 38
<211> LENGTH: 270
<212> TYPE: PRT
<213> ORGANISM: Artificial Sequence
<220> FEATURE:
<223> OTHER INFORMATION: Ankyrin repeat protein

<400> SEQUENCE: 38

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asn Glu Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Gly Gly Gly
        115                 120                 125

Ser Gly Gly Gly Gly Ser Gly Gly Gly Ser Gly Gly Gly Ser
    130                 135                 140

Gly Ser Asp Leu Gly Thr Lys Leu Leu Gln Ala Ala Gln Tyr Gly Gln
145                 150                 155                 160

Leu Asp Glu Val Arg Glu Leu Leu Lys Ala Gly Ala Asp Val Asn Ala
                165                 170                 175

Lys Asp Val Asp Gly Ala Thr Pro Leu His Trp Ala Ala Tyr Lys Gly
            180                 185                 190

His Pro Glu Ile Ile Glu Val Leu Leu Lys Ala Gly Ala Asp Val Asn
            195                 200                 205
```

Ala Lys Asp Ala Val Gly Trp Thr Pro Leu His Ile Ala Ala Asn His
    210                 215                 220

Gly His Leu Glu Ile Val Glu Val Leu Leu Lys Ala Gly Ala Asp Val
225                 230                 235                 240

Asn Ala Gln Asp Ser Tyr Gly Ala Thr Pro Ala Asp Leu Ala Ala Arg
                245                 250                 255

Trp Gly His Gln Asp Ile Ala Glu Val Leu Gln Lys Ala Ala
                260                 265                 270

<210> SEQ ID NO 39
<211> LENGTH: 305
<212> TYPE: PRT
<213> ORGANISM: Artificial Sequence
<220> FEATURE:
<223> OTHER INFORMATION: Ankyrin repeat protein

<400> SEQUENCE: 39

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Lys Ala Gly Ala Asp Val Asn Ala
                85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Thr Pro Thr Pro Thr
    130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Gln Ile Gly Trp Thr Pro Leu His Leu Ala Ala Asn
            180                 185                 190

Tyr Gly His Leu Glu Ile Val Glu Val Leu Leu Lys Ala Gly Ala Asp
        195                 200                 205

Val Asn Ala Lys Asp Leu Trp Gly Gln Thr Pro Leu His Leu Ala Ala
    210                 215                 220

Trp Lys Gly His Leu Glu Ile Val Glu Val Leu Leu Lys Ala Gly Ala
225                 230                 235                 240

Asp Val Asn Ala Lys Asp Thr Asp Gly Leu Thr Pro Leu His Leu Ala
                245                 250                 255

Ala Ile Arg Gly His Leu Glu Ile Val Glu Val Leu Leu Lys Ala Gly
            260                 265                 270

Ala Asp Val Asn Ala Gln Asp Lys Ser Gly Lys Thr Pro Ala Asp Leu
        275                 280                 285

Ala Ala Asp Ala Gly His Glu Asp Ile Ala Glu Val Leu Gln Lys Ala
    290                 295                 300

Ala
305

<210> SEQ ID NO 40
<211> LENGTH: 305
<212> TYPE: PRT
<213> ORGANISM: Artificial Sequence
<220> FEATURE:
<223> OTHER INFORMATION: Ankyrin repeat protein

<400> SEQUENCE: 40

Asp Leu Gly Lys Lys Leu Leu Glu Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr
130                 135                 140

Pro Thr Gly Ser Asp Leu Gly Ser Lys Leu Leu Gln Ala Ala Arg Ala
145                 150                 155                 160

Gly Gln Leu Asp Thr Val Arg Thr Leu Leu Gln Ala Gly Ala Asp Val
                165                 170                 175

Asn Ala Lys Asp Gln Ile Gly Trp Thr Pro Leu His Leu Ala Ala Asn
            180                 185                 190

Tyr Gly His Leu Glu Ile Val Glu Val Leu Leu Lys Ala Gly Ala Asp
        195                 200                 205

Val Asn Ala Lys Asp Leu Trp Gly Gln Thr Pro Leu His Leu Ala Ala
    210                 215                 220

Trp Lys Gly His Leu Glu Ile Val Glu Val Leu Leu Lys Ala Gly Ala
225                 230                 235                 240

Asp Val Asn Ala Lys Asp Thr Asp Gly Leu Thr Pro Leu His Leu Ala
                245                 250                 255

Ala Ile Arg Gly His Leu Glu Ile Glu Val Leu Leu Lys Ala Gly
            260                 265                 270

Ala Asp Val Asn Ala Gln Asp Thr Gln Gly Thr Thr Pro Ala Asp Leu
        275                 280                 285

Ala Ala Arg Ala Gly His Gln Gln Ile Ala Ser Val Leu Gln Gln Ala
    290                 295                 300

Ala
305

<210> SEQ ID NO 41
<211> LENGTH: 305
<212> TYPE: PRT
<213> ORGANISM: Artificial Sequence
<220> FEATURE:
<223> OTHER INFORMATION: Ankyrin repeat protein

<400> SEQUENCE: 41

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr
    130                 135                 140

Pro Thr Gly Ser Asp Leu Gly Lys Lys Leu Leu Gln Ala Ala Arg Ala
145                 150                 155                 160

Gly Gln Leu Asp Glu Val Arg Glu Leu Leu Lys Ala Gly Ala Asp Val
                165                 170                 175

Asn Ala Lys Asp Gln Ile Gly Trp Thr Pro Leu His Leu Ala Ala Asn
            180                 185                 190

Tyr Gly His Leu Glu Ile Val Glu Val Leu Leu Lys Ala Gly Ala Asp
        195                 200                 205

Val Asn Ala Lys Asp Leu Trp Gly Gln Thr Pro Leu His Leu Ala Ala
    210                 215                 220

Trp Lys Gly His Leu Glu Ile Val Glu Val Leu Leu Lys Ala Gly Ala
225                 230                 235                 240

Asp Val Asn Ala Lys Asp Thr Asp Gly Leu Thr Pro Leu His Leu Ala
                245                 250                 255

Ala Ile Arg Gly His Leu Glu Ile Val Glu Val Leu Leu Lys Ala Gly
            260                 265                 270

Ala Asp Val Asn Ala Gln Asp Lys Ser Gly Lys Thr Pro Ala Asp Leu
        275                 280                 285

Ala Ala Arg Ala Gly His Gln Asp Ile Ala Glu Val Leu Gln Lys Ala
    290                 295                 300

Ala
305

<210> SEQ ID NO 42
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 42

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp

```
            20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Pro Thr Pro Thr
        130                 135                 140

Pro Thr Gly Ser Asp Leu Gly Leu Lys Leu Leu Thr Ala Ala Trp Glu
145                 150                 155                 160

Gly Gln Asp Asp Glu Val Arg Glu Leu Leu Lys Ala Gly Ala Asp Val
                165                 170                 175

Asn Ala Lys Asp Trp Tyr Gly Tyr Thr Pro Leu His Ala Ala Ala Asn
                180                 185                 190

Glu Gly His Leu Glu Ile Val Glu Val Leu Leu Lys Ala Gly Ala Asp
            195                 200                 205

Val Asn Ala Lys Asp Val Val Gly Trp Thr Pro Leu His Ile Ala Ala
        210                 215                 220

Tyr Trp Gly His Leu Glu Ile Val Glu Val Leu Leu Lys Ala Gly Ala
225                 230                 235                 240

Asp Val Asn Ala Gln Asp Gln Thr Gly Gln Thr Pro Ala Asp Leu Ala
                245                 250                 255

Ala Trp Gln Gly His Glu Asp Ile Ala Glu Val Leu Gln Lys Ala Ala
                260                 265                 270

<210> SEQ ID NO 43
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 43

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
```

```
            115                 120                 125
Pro Thr Pro Thr Thr Pro Thr Pro Thr Thr Pro Thr Pro Thr
        130                 135                 140
Pro Thr Gly Ser Asp Leu Gly Ser Lys Leu Leu Gln Ala Ala Trp Glu
145                 150                 155                 160
Gly Gln Leu Asp Thr Val Arg Thr Leu Leu Gln Ala Gly Ala Asp Val
                165                 170                 175
Asn Ala Lys Asp Trp Tyr Gly Tyr Thr Pro Leu His Ala Ala Ala Asn
                180                 185                 190
Glu Gly His Leu Glu Ile Val Glu Val Leu Leu Lys Ala Gly Ala Asp
                195                 200                 205
Val Asn Ala Lys Asp Val Val Gly Trp Thr Pro Leu His Ile Ala Ala
                210                 215                 220
Tyr Trp Gly His Leu Glu Ile Val Glu Val Leu Leu Lys Ala Gly Ala
225                 230                 235                 240
Asp Val Asn Ala Gln Asp Thr Gln Gly Thr Thr Pro Ala Asp Leu Ala
                245                 250                 255
Ala Arg Gln Gly His Gln Gln Ile Ala Ser Val Leu Gln Gln Ala Ala
                260                 265                 270

<210> SEQ ID NO 44
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 44

Asp Leu Gly Lys Lys Leu Leu Glu Ala Ala Arg Ala Gly Gln Asp Asp
1               5                   10                  15
Glu Val Arg Glu Leu Leu Lys Ala Gly Ala Asp Val Asn Ala Lys Asp
                20                  25                  30
Tyr Phe Ser His Thr Pro Leu His Leu Ala Ala Arg Asn Gly His Leu
                35                  40                  45
Lys Ile Val Glu Val Leu Leu Lys Ala Gly Ala Asp Val Asn Ala Lys
50                  55                  60
Asp Phe Ala Gly Lys Thr Pro Leu His Leu Ala Ala Asp Gly His
65                  70                  75                  80
Leu Glu Ile Val Glu Val Leu Leu Lys Ala Gly Ala Asp Val Asn Ala
                85                  90                  95
Gln Asp Ile Phe Gly Lys Thr Pro Ala Asp Ile Ala Ala Asp Ala Gly
                100                 105                 110
His Glu Asp Ile Ala Glu Val Leu Gln Lys Ala Ala Gly Ser Pro Thr
                115                 120                 125
Pro Thr Pro Thr Thr Pro Thr Pro Thr Thr Pro Thr Pro Thr
        130                 135                 140
Pro Thr Gly Ser Asp Leu Gly Lys Lys Leu Leu Gln Ala Ala Arg Ala
145                 150                 155                 160
Gly Gln Leu Asp Glu Val Arg Glu Leu Leu Lys Ala Gly Ala Asp Val
                165                 170                 175
Asn Ala Lys Asp Trp Tyr Gly Tyr Thr Pro Leu His Ala Ala Ala Asn
                180                 185                 190
Glu Gly His Leu Glu Ile Val Glu Val Leu Leu Lys Ala Gly Ala Asp
                195                 200                 205
Val Asn Ala Lys Asp Val Val Gly Trp Thr Pro Leu His Ile Ala Ala
```

Tyr Trp Gly His Leu Glu Ile Val Glu Val Leu Leu Lys Ala Gly Ala
225                 230                 235                 240

Asp Val Asn Ala Gln Asp Lys Ser Gly Lys Thr Pro Ala Asp Leu Ala
            245                 250                 255

Ala Arg Ala Gly His Gln Asp Ile Ala Glu Val Leu Gln Lys Ala Ala
            260                 265                 270

<210> SEQ ID NO 45
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 45

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr
        130                 135                 140

Pro Thr Gly Ser Asp Leu Gly Leu Lys Leu Leu Gln Ala Ala Trp Glu
145                 150                 155                 160

Gly Gln Leu Asp Glu Val Arg Glu Leu Leu Lys Ala Gly Ala Asp Val
            165                 170                 175

Asn Ala Lys Asp Trp Tyr Gly Tyr Thr Pro Leu His Ala Ala Ala Asn
            180                 185                 190

Glu Gly His Leu Glu Ile Val Glu Val Leu Leu Lys Ala Gly Ala Asp
        195                 200                 205

Val Asn Ala Lys Asp Val Val Gly Trp Thr Pro Leu His Ile Ala Ala
        210                 215                 220

Tyr Trp Gly His Leu Glu Ile Val Glu Val Leu Leu Lys Ala Gly Ala
225                 230                 235                 240

Asp Val Asn Ala Gln Asp Gln Thr Gly Gln Thr Pro Ala Asp Leu Ala
            245                 250                 255

Ala Arg Gln Gly His Gln Asp Ile Ala Glu Val Leu Gln Lys Ala Ala
            260                 265                 270

<210> SEQ ID NO 46
<211> LENGTH: 272
<212> TYPE: PRT
<213> ORGANISM: Artificial Sequence
<220> FEATURE:
<223> OTHER INFORMATION: Ankyrin repeat protein -continued

<400> SEQUENCE: 46

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Gly Ser Pro Thr
        115                 120                 125

Pro Thr Pro Thr Thr Pro Thr Pro Thr Pro Thr Thr Pro Thr Pro Thr
130                 135                 140

Pro Thr Gly Ser Asp Leu Gly Trp Lys Leu Leu Glu Ala Ala Val Ile
145                 150                 155                 160

Gly Gln Asp Asp Glu Val Arg Glu Leu Leu Lys Ala Gly Ala Asp Val
                165                 170                 175

Asn Ala Lys Asp Val Asp Gly Asn Thr Pro Leu His Tyr Ala Ala His
            180                 185                 190

Val Gly His Leu Glu Ile Val Glu Val Leu Leu Lys Ala Gly Ala Asp
        195                 200                 205

Val Asn Ala Lys Asp Glu Gln Gly Tyr Thr Pro Leu His Leu Ala Ala
    210                 215                 220

Trp Arg Gly His Leu Glu Ile Val Glu Val Leu Leu Lys Ala Gly Ala
225                 230                 235                 240

Asp Val Asn Ala Gln Asp Leu Glu Gly Ala Thr Pro Ala Asp Leu Ala
                245                 250                 255

Ala His Glu Gly His Glu Asp Ile Ala Glu Val Leu Gln Lys Ala Ala
            260                 265                 270

<210> SEQ ID NO 47
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 47

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Ala Asp Gly His
65                  70                  75                  80

```
Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr Thr
    130                 135                 140

Pro Thr Gly Ser Asp Leu Gly Ser Lys Leu Leu Gln Ala Ala Val Ile
145                 150                 155                 160

Gly Gln Leu Asp Thr Val Arg Thr Leu Leu Gln Ala Gly Ala Asp Val
                165                 170                 175

Asn Ala Lys Asp Val Asp Gly Asn Thr Pro Leu His Tyr Ala Ala His
            180                 185                 190

Val Gly His Leu Glu Ile Val Glu Val Leu Leu Lys Ala Gly Ala Asp
        195                 200                 205

Val Asn Ala Lys Asp Glu Gln Gly Tyr Thr Pro Leu His Leu Ala Ala
    210                 215                 220

Trp Arg Gly His Leu Glu Ile Val Glu Val Leu Leu Lys Ala Gly Ala
225                 230                 235                 240

Asp Val Asn Ala Gln Asp Thr Gln Gly Thr Thr Pro Ala Asp Leu Ala
                245                 250                 255

Ala Arg Glu Gly His Gln Ile Ala Ser Val Leu Gln Gln Ala Ala
            260                 265                 270

<210> SEQ ID NO 48
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 48

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr Thr
    130                 135                 140

Pro Thr Gly Ser Asp Leu Gly Lys Lys Leu Leu Gln Ala Ala Arg Ala
145                 150                 155                 160

Gly Gln Leu Asp Glu Val Arg Glu Leu Leu Lys Ala Gly Ala Asp Val
                165                 170                 175
```

Asn Ala Lys Asp Val Asp Gly Asn Thr Pro Leu His Tyr Ala Ala His
                180                 185                 190

Val Gly His Leu Glu Ile Val Glu Val Leu Leu Lys Ala Gly Ala Asp
            195                 200                 205

Val Asn Ala Lys Asp Glu Gln Gly Tyr Thr Pro Leu His Leu Ala Ala
        210                 215                 220

Trp Arg Gly His Leu Glu Ile Val Glu Val Leu Leu Lys Ala Gly Ala
225                 230                 235                 240

Asp Val Asn Ala Gln Asp Lys Ser Gly Lys Thr Pro Ala Asp Leu Ala
                245                 250                 255

Ala Arg Ala Gly His Gln Asp Ile Ala Glu Val Leu Gln Lys Ala Ala
            260                 265                 270

<210> SEQ ID NO 49
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 49

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Thr Pro Thr Pro Thr
130                 135                 140

Pro Thr Gly Ser Asp Leu Gly Trp Lys Leu Leu Gln Ala Ala Val Ile
145                 150                 155                 160

Gly Gln Leu Asp Glu Val Arg Glu Leu Leu Lys Ala Gly Ala Asp Val
                165                 170                 175

Asn Ala Lys Asp Val Asp Gly Asn Thr Pro Leu His Tyr Ala Ala His
            180                 185                 190

Val Gly His Leu Glu Ile Val Glu Val Leu Leu Lys Ala Gly Ala Asp
        195                 200                 205

Val Asn Ala Lys Asp Glu Gln Gly Tyr Thr Pro Leu His Leu Ala Ala
    210                 215                 220

Trp Arg Gly His Leu Glu Ile Val Glu Val Leu Leu Lys Ala Gly Ala
225                 230                 235                 240

Asp Val Asn Ala Gln Asp Leu Glu Gly Ala Thr Pro Ala Asp Leu Ala
                245                 250                 255

Ala Arg Glu Gly His Gln Asp Ile Ala Glu Val Leu Gln Lys Ala Ala
            260                 265                 270

<210> SEQ ID NO 50
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 50

```
Asp Leu Gly Lys Lys Leu Leu Glu Ala Ala Arg Ala Gly Gln Asp Asp
1               5                  10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr
    130                 135                 140

Pro Thr Gly Ser Asp Leu Gly Thr Lys Leu Leu Glu Ala Ala Gln Tyr
145                 150                 155                 160

Gly Gln Asp Asp Glu Val Arg Glu Leu Leu Lys Ala Gly Ala Asp Val
                165                 170                 175

Asn Ala Lys Asp Val Asp Gly Ala Thr Pro Leu His Trp Ala Ala Tyr
            180                 185                 190

Lys Gly His Pro Glu Ile Ile Glu Val Leu Leu Lys Ala Gly Ala Asp
        195                 200                 205

Val Asn Ala Lys Asp Ala Val Gly Trp Thr Pro Leu His Ile Ala Ala
    210                 215                 220

Asn His Gly His Leu Glu Ile Val Glu Val Leu Leu Lys Ala Gly Ala
225                 230                 235                 240

Asp Val Asn Ala Gln Asp Ser Tyr Gly Ala Thr Pro Ala Asp Leu Ala
                245                 250                 255

Ala Ile Trp Gly His Glu Asp Ile Ala Glu Val Leu Gln Lys Ala Ala
            260                 265                 270
```

<210> SEQ ID NO 51
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 51

```
Asp Leu Gly Lys Lys Leu Leu Glu Ala Ala Arg Ala Gly Gln Asp Asp
1               5                  10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45
```

Lys Ile Val Glu Val Leu Leu Lys Ala Gly Ala Asp Val Asn Ala Lys
            50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                    85                  90                  95

Gln Asp Ile Phe Gly Lys Thr Pro Ala Asp Ile Ala Ala Asp Ala Gly
                    100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Pro Thr Pro Thr
            130                 135                 140

Pro Thr Gly Ser Asp Leu Gly Ser Lys Leu Leu Gln Ala Ala Gln Tyr
145                 150                 155                 160

Gly Gln Leu Asp Thr Val Arg Thr Leu Leu Gln Ala Gly Ala Asp Val
                    165                 170                 175

Asn Ala Lys Asp Val Asp Gly Ala Thr Pro Leu His Trp Ala Ala Tyr
            180                 185                 190

Lys Gly His Pro Glu Ile Ile Glu Val Leu Leu Lys Ala Gly Ala Asp
            195                 200                 205

Val Asn Ala Lys Asp Ala Val Gly Trp Thr Pro Leu His Ile Ala Ala
210                 215                 220

Asn His Gly His Leu Glu Ile Val Glu Val Leu Leu Lys Ala Gly Ala
225                 230                 235                 240

Asp Val Asn Ala Gln Asp Thr Gln Gly Thr Thr Pro Ala Asp Leu Ala
                    245                 250                 255

Ala Arg Trp Gly His Gln Gln Ile Ala Ser Val Leu Gln Gln Ala Ala
                    260                 265                 270

<210> SEQ ID NO 52
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 52

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
            50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                    85                  90                  95

Gln Asp Ile Phe Gly Lys Thr Pro Ala Asp Ile Ala Ala Asp Ala Gly
                    100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Pro Thr Pro Thr
            130                 135                 140

```
Pro Thr Gly Ser Asp Leu Gly Lys Lys Leu Leu Gln Ala Ala Arg Ala
145                 150                 155                 160

Gly Gln Leu Asp Glu Val Arg Glu Leu Leu Lys Ala Gly Ala Asp Val
                165                 170                 175

Asn Ala Lys Asp Val Asp Gly Ala Thr Pro Leu His Trp Ala Ala Tyr
            180                 185                 190

Lys Gly His Pro Glu Ile Ile Glu Val Leu Lys Ala Gly Ala Asp
        195                 200                 205

Val Asn Ala Lys Asp Ala Val Gly Trp Thr Pro Leu His Ile Ala Ala
    210                 215                 220

Asn His Gly His Leu Glu Ile Val Glu Val Leu Leu Lys Ala Gly Ala
225                 230                 235                 240

Asp Val Asn Ala Gln Asp Lys Ser Gly Lys Thr Pro Ala Asp Leu Ala
                245                 250                 255

Ala Arg Ala Gly His Gln Asp Ile Ala Glu Val Leu Gln Lys Ala Ala
            260                 265                 270
```

<210> SEQ ID NO 53
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 53

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asp Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Pro Thr Pro Thr
        130                 135                 140

Pro Thr Gly Ser Asp Leu Gly Thr Lys Leu Leu Gln Ala Ala Gln Tyr
145                 150                 155                 160

Gly Gln Leu Asp Glu Val Arg Glu Leu Leu Lys Ala Gly Ala Asp Val
                165                 170                 175

Asn Ala Lys Asp Val Asp Gly Ala Thr Pro Leu His Trp Ala Ala Tyr
            180                 185                 190

Lys Gly His Pro Glu Ile Ile Glu Val Leu Leu Lys Ala Gly Ala Asp
        195                 200                 205

Val Asn Ala Lys Asp Ala Val Gly Trp Thr Pro Leu His Ile Ala Ala
    210                 215                 220

Asn His Gly His Leu Glu Ile Val Glu Val Leu Leu Lys Ala Gly Ala
225                 230                 235                 240
```

```
Asp Val Asn Ala Gln Asp Ser Tyr Gly Ala Thr Pro Ala Asp Leu Ala
                245                 250                 255

Ala Arg Trp Gly His Gln Asp Ile Ala Glu Val Leu Gln Lys Ala Ala
                260                 265                 270
```

<210> SEQ ID NO 54
<211> LENGTH: 305
<212> TYPE: PRT
<213> ORGANISM: Artificial Sequence
<220> FEATURE:
<223> OTHER INFORMATION: Ankyrin repeat protein

<400> SEQUENCE: 54

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
                35                  40                  45

Lys Ile Val Glu Val Leu Leu Lys Ala Gly Ala Asp Val Asn Ala Lys
            50                  55                  60

Asp Phe Ala Gly Lys Thr Pro Leu His Leu Ala Ala Asp Ala Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Thr Pro Thr Pro Thr
            130                 135                 140

Pro Thr Gly Ser Asp Leu Gly Lys Lys Leu Leu Glu Ala Ala Arg Ala
145                 150                 155                 160

Gly Gln Asp Asp Glu Val Arg Glu Leu Leu Lys Ala Gly Ala Asp Val
                165                 170                 175

Asn Ala Lys Asp Gln Ile Gly Trp Thr Pro Leu His Leu Ala Ala Asn
                180                 185                 190

Tyr Gly His Leu Glu Ile Val Glu Val Leu Leu Lys Ala Gly Ala Asp
            195                 200                 205

Val Asn Ala Lys Asp Leu Trp Gly Gln Thr Pro Leu His Leu Ala Ala
                210                 215                 220

Trp Lys Gly His Leu Glu Ile Val Glu Val Leu Leu Lys Ala Gly Ala
225                 230                 235                 240

Asp Val Asn Ala Lys Asp Thr Asp Gly Leu Thr Pro Leu His Leu Ala
                245                 250                 255

Ala Ile Arg Gly His Leu Glu Ile Val Glu Val Leu Leu Lys Ala Gly
                260                 265                 270

Ala Asp Val Asn Ala Gln Asp Lys Ser Gly Lys Thr Pro Ala Asp Leu
                275                 280                 285

Ala Ala Asp Ala Gly His Glu Asp Ile Ala Glu Val Leu Gln Lys Ala
            290                 295                 300

Ala
305
```

<210> SEQ ID NO 55

<211> LENGTH: 305
<212> TYPE: PRT
<213> ORGANISM: Artificial Sequence
<220> FEATURE:
<223> OTHER INFORMATION: Ankyrin repeat protein

<400> SEQUENCE: 55

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Ala Gly His
65                  70                  75                  80

Leu Glu Ile Val Glu Val Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Thr Pro Thr Pro Thr
    130                 135                 140

Pro Thr Gly Ser Asp Leu Gly Ser Lys Leu Leu Gln Ala Ala Arg Ala
145                 150                 155                 160

Gly Gln Leu Asp Thr Val Arg Thr Leu Leu Gln Ala Gly Ala Asp Val
                165                 170                 175

Asn Ala Lys Asp Gln Ile Gly Trp Thr Pro Leu His Leu Ala Ala Asn
            180                 185                 190

Tyr Gly His Leu Glu Ile Val Glu Val Leu Leu Lys Ala Gly Ala Asp
        195                 200                 205

Val Asn Ala Lys Asp Leu Trp Gly Gln Thr Pro Leu His Leu Ala Ala
    210                 215                 220

Trp Lys Gly His Leu Glu Ile Val Glu Val Leu Leu Lys Ala Gly Ala
225                 230                 235                 240

Asp Val Asn Ala Lys Asp Thr Asp Gly Leu Thr Pro Leu His Leu Ala
                245                 250                 255

Ala Ile Arg Gly His Leu Glu Ile Val Glu Val Leu Leu Lys Ala Gly
            260                 265                 270

Ala Asp Val Asn Ala Gln Asp Thr Gln Gly Thr Thr Pro Ala Asp Leu
        275                 280                 285

Ala Ala Arg Ala Gly His Gln Gln Ile Ala Ser Val Leu Gln Gln Ala
    290                 295                 300

Ala
305
```

<210> SEQ ID NO 56
<211> LENGTH: 305
<212> TYPE: PRT
<213> ORGANISM: Artificial Sequence
<220> FEATURE:
<223> OTHER INFORMATION: Ankyrin repeat protein

<400> SEQUENCE: 56

Asp Leu Gly Lys Lys Leu Leu Glu Ala Ala Arg Ala Gly Gln Asp Asp

```
                1               5                   10                  15
            Glu Val Arg Glu Leu Leu Lys Ala Gly Ala Asp Val Asn Ala Lys Asp
                           20                  25                  30
            Tyr Phe Ser His Thr Pro Leu His Leu Ala Ala Arg Asn Gly His Leu
                           35                  40                  45
            Lys Ile Val Glu Val Leu Leu Lys Ala Gly Ala Asp Val Asn Ala Lys
             50                  55                  60
            Asp Phe Ala Gly Lys Thr Pro Leu His Leu Ala Ala Asp Ala Gly His
             65                  70                  75                  80
            Leu Glu Ile Val Glu Val Leu Leu Lys Ala Gly Ala Asp Val Asn Ala
                               85                  90                  95
            Gln Asp Ile Phe Gly Lys Thr Pro Ala Asp Ile Ala Ala Asp Ala Gly
                           100                 105                 110
            His Glu Asp Ile Ala Glu Val Leu Gln Lys Ala Ala Gly Ser Pro Thr
                           115                 120                 125
            Pro Thr Pro Thr Thr Pro Thr Pro Thr Pro Thr Thr Pro Thr Pro Thr
                           130                 135                 140
            Pro Thr Gly Ser Asp Leu Gly Lys Lys Leu Leu Gln Ala Ala Arg Ala
            145                 150                 155                 160
            Gly Gln Leu Asp Glu Val Arg Glu Leu Leu Lys Ala Gly Ala Asp Val
                           165                 170                 175
            Asn Ala Lys Asp Gln Ile Gly Trp Thr Pro Leu His Leu Ala Ala Asn
                           180                 185                 190
            Tyr Gly His Leu Glu Ile Val Glu Val Leu Leu Lys Ala Gly Ala Asp
                           195                 200                 205
            Val Asn Ala Lys Asp Leu Trp Gly Gln Thr Pro Leu His Leu Ala Ala
             210                 215                 220
            Trp Lys Gly His Leu Glu Ile Val Glu Val Leu Leu Lys Ala Gly Ala
            225                 230                 235                 240
            Asp Val Asn Ala Lys Asp Thr Asp Gly Leu Thr Pro Leu His Leu Ala
                           245                 250                 255
            Ala Ile Arg Gly His Leu Glu Ile Val Glu Val Leu Leu Lys Ala Gly
                           260                 265                 270
            Ala Asp Val Asn Ala Gln Asp Lys Ser Gly Lys Thr Pro Ala Asp Leu
                           275                 280                 285
            Ala Ala Arg Ala Gly His Gln Asp Ile Ala Glu Val Leu Gln Lys Ala
                           290                 295                 300
            Ala
            305

<210> SEQ ID NO 57
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 57

Asp Leu Gly Lys Lys Leu Leu Glu Ala Ala Arg Ala Gly Gln Asp Asp
            1               5                   10                  15
            Glu Val Arg Glu Leu Leu Lys Ala Gly Ala Asp Val Asn Ala Lys Asp
                           20                  25                  30
            Tyr Phe Ser His Thr Pro Leu His Leu Ala Ala Arg Asn Gly His Leu
                           35                  40                  45
            Lys Ile Val Glu Val Leu Leu Lys Ala Gly Ala Asp Val Asn Ala Lys
```

```
                50                  55                  60
Asp Phe Ala Gly Lys Thr Pro Leu His Leu Ala Ala Asp Ala Gly His
 65                  70                  75                  80

Leu Glu Ile Val Glu Val Leu Leu Lys Ala Gly Ala Asp Val Asn Ala
                 85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
                115                 120                 125

Pro Thr Pro Thr Thr Pro Thr Pro Thr Pro Thr Thr Pro Thr Pro Thr
130                 135                 140

Pro Thr Gly Ser Asp Leu Gly Leu Lys Leu Leu Thr Ala Ala Trp Glu
145                 150                 155                 160

Gly Gln Asp Asp Glu Val Arg Glu Leu Leu Lys Ala Gly Ala Asp Val
                165                 170                 175

Asn Ala Lys Asp Trp Tyr Gly Tyr Thr Pro Leu His Ala Ala Ala Asn
                180                 185                 190

Glu Gly His Leu Glu Ile Val Glu Val Leu Leu Lys Ala Gly Ala Asp
                195                 200                 205

Val Asn Ala Lys Asp Val Val Gly Trp Thr Pro Leu His Ile Ala Ala
                210                 215                 220

Tyr Trp Gly His Leu Glu Ile Val Glu Val Leu Leu Lys Ala Gly Ala
225                 230                 235                 240

Asp Val Asn Ala Gln Asp Gln Thr Gly Gln Thr Pro Ala Asp Leu Ala
                245                 250                 255

Ala Trp Gln Gly His Glu Asp Ile Ala Glu Val Leu Gln Lys Ala Ala
                260                 265                 270

<210> SEQ ID NO 58
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 58

Asp Leu Gly Lys Lys Leu Leu Glu Ala Ala Arg Ala Gly Gln Asp Asp
 1               5                  10                  15

Glu Val Arg Glu Leu Leu Lys Ala Gly Ala Asp Val Asn Ala Lys Asp
                 20                  25                  30

Tyr Phe Ser His Thr Pro Leu His Leu Ala Ala Arg Asn Gly His Leu
                 35                  40                  45

Lys Ile Val Glu Val Leu Leu Lys Ala Gly Ala Asp Val Asn Ala Lys
                 50                  55                  60

Asp Phe Ala Gly Lys Thr Pro Leu His Leu Ala Ala Asp Ala Gly His
 65                  70                  75                  80

Leu Glu Ile Val Glu Val Leu Leu Lys Ala Gly Ala Asp Val Asn Ala
                 85                  90                  95

Gln Asp Ile Phe Gly Lys Thr Pro Ala Asp Ile Ala Ala Asp Ala Gly
                100                 105                 110

His Glu Asp Ile Ala Glu Val Leu Gln Lys Ala Ala Gly Ser Pro Thr
                115                 120                 125

Pro Thr Pro Thr Thr Pro Thr Pro Thr Pro Thr Thr Pro Thr Pro Thr
130                 135                 140

Pro Thr Gly Ser Asp Leu Gly Ser Lys Leu Leu Gln Ala Ala Trp Glu
```

```
                145                 150                 155                 160
Gly Gln Leu Asp Thr Val Arg Thr Leu Leu Gln Ala Gly Ala Asp Val
                    165                 170                 175
Asn Ala Lys Asp Trp Tyr Gly Tyr Thr Pro Leu His Ala Ala Ala Asn
                180                 185                 190
Glu Gly His Leu Glu Ile Val Glu Val Leu Leu Lys Ala Gly Ala Asp
            195                 200                 205
Val Asn Ala Lys Asp Val Val Gly Trp Thr Pro Leu His Ile Ala Ala
        210                 215                 220
Tyr Trp Gly His Leu Glu Ile Val Glu Val Leu Leu Lys Ala Gly Ala
225                 230                 235                 240
Asp Val Asn Ala Gln Asp Thr Gln Gly Thr Thr Pro Ala Asp Leu Ala
                245                 250                 255
Ala Arg Gln Gly His Gln Gln Ile Ala Ser Val Leu Gln Gln Ala Ala
                    260                 265                 270

<210> SEQ ID NO 59
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 59

Asp Leu Gly Lys Lys Leu Leu Glu Ala Ala Arg Ala Gly Gln Asp Asp
1               5                   10                  15
Glu Val Arg Glu Leu Leu Lys Ala Gly Ala Asp Val Asn Ala Lys Asp
                20                  25                  30
Tyr Phe Ser His Thr Pro Leu His Leu Ala Ala Arg Asn Gly His Leu
            35                  40                  45
Lys Ile Val Glu Val Leu Leu Lys Ala Gly Ala Asp Val Asn Ala Lys
        50                  55                  60
Asp Phe Ala Gly Lys Thr Pro Leu His Leu Ala Ala Asp Ala Gly His
65                  70                  75                  80
Leu Glu Ile Val Glu Val Leu Leu Lys Ala Gly Ala Asp Val Asn Ala
                85                  90                  95
Gln Asp Ile Phe Gly Lys Thr Pro Ala Asp Ile Ala Ala Asp Ala Gly
            100                 105                 110
His Glu Asp Ile Ala Glu Val Leu Gln Lys Ala Ala Gly Ser Pro Thr
        115                 120                 125
Pro Thr Pro Thr Thr Pro Thr Pro Thr Pro Thr Thr Pro Thr Pro Thr
130                 135                 140
Pro Thr Gly Ser Asp Leu Gly Lys Lys Leu Leu Gln Ala Ala Arg Ala
145                 150                 155                 160
Gly Gln Leu Asp Glu Val Arg Glu Leu Leu Lys Ala Gly Ala Asp Val
                165                 170                 175
Asn Ala Lys Asp Trp Tyr Gly Tyr Thr Pro Leu His Ala Ala Ala Asn
                180                 185                 190
Glu Gly His Leu Glu Ile Val Glu Val Leu Leu Lys Ala Gly Ala Asp
            195                 200                 205
Val Asn Ala Lys Asp Val Val Gly Trp Thr Pro Leu His Ile Ala Ala
        210                 215                 220
Tyr Trp Gly His Leu Glu Ile Val Glu Val Leu Leu Lys Ala Gly Ala
225                 230                 235                 240
Asp Val Asn Ala Gln Asp Lys Ser Gly Lys Thr Pro Ala Asp Leu Ala
```

```
            245                 250                 255
Ala Arg Ala Gly His Gln Asp Ile Ala Glu Val Leu Gln Lys Ala Ala
            260                 265                 270

<210> SEQ ID NO 60
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 60

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asp Ala Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Thr Pro Thr Pro Thr
    130                 135                 140

Pro Thr Gly Ser Asp Leu Gly Leu Lys Leu Leu Gln Ala Ala Trp Glu
145                 150                 155                 160

Gly Gln Leu Asp Glu Val Arg Glu Leu Leu Lys Ala Gly Ala Asp Val
                165                 170                 175

Asn Ala Lys Asp Trp Tyr Gly Tyr Thr Pro Leu His Ala Ala Ala Asn
            180                 185                 190

Glu Gly His Leu Glu Ile Val Glu Val Leu Leu Lys Ala Gly Ala Asp
        195                 200                 205

Val Asn Ala Lys Asp Val Val Gly Trp Thr Pro Leu His Ile Ala Ala
    210                 215                 220

Tyr Trp Gly His Leu Glu Ile Val Glu Val Leu Leu Lys Ala Gly Ala
225                 230                 235                 240

Asp Val Asn Ala Gln Asp Gln Thr Gly Gln Thr Pro Ala Asp Leu Ala
                245                 250                 255

Ala Arg Gln Gly His Gln Asp Ile Ala Glu Val Leu Gln Lys Ala Ala
            260                 265                 270

<210> SEQ ID NO 61
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 61

Asp Leu Gly Lys Lys Leu Leu Glu Ala Ala Arg Ala Gly Gln Asp Asp
1               5                   10                  15
```

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
            50                  55                  60

Asp Phe Ala Gly Lys Thr Pro Leu His Leu Ala Ala Asp Ala Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
            115                 120                 125

Pro Thr Pro Thr Thr Pro Thr Pro Thr Pro Thr Pro Thr Pro Thr
            130                 135                 140

Pro Thr Gly Ser Asp Leu Gly Trp Lys Leu Leu Glu Ala Ala Val Ile
145                 150                 155                 160

Gly Gln Asp Asp Glu Val Arg Glu Leu Leu Lys Ala Gly Ala Asp Val
            165                 170                 175

Asn Ala Lys Asp Val Asp Gly Asn Thr Pro Leu His Tyr Ala Ala His
            180                 185                 190

Val Gly His Leu Glu Ile Val Glu Val Leu Leu Lys Ala Gly Ala Asp
            195                 200                 205

Val Asn Ala Lys Asp Glu Gln Gly Tyr Thr Pro Leu His Leu Ala Ala
            210                 215                 220

Trp Arg Gly His Leu Glu Ile Val Glu Val Leu Leu Lys Ala Gly Ala
225                 230                 235                 240

Asp Val Asn Ala Gln Asp Leu Glu Gly Ala Thr Pro Ala Asp Leu Ala
            245                 250                 255

Ala His Glu Gly His Glu Asp Ile Ala Glu Val Leu Gln Lys Ala Ala
            260                 265                 270

<210> SEQ ID NO 62
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 62

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
            50                  55                  60

Asp Phe Ala Gly Lys Thr Pro Leu His Leu Ala Ala Asp Ala Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
           115                 120                 125

Pro Thr Pro Thr Thr Pro Thr Pro Thr Pro Thr Thr Pro Thr Pro Thr
    130                 135                 140

Pro Thr Gly Ser Asp Leu Gly Ser Lys Leu Leu Gln Ala Ala Val Ile
145                 150                 155                 160

Gly Gln Leu Asp Thr Val Arg Thr Leu Leu Gln Ala Gly Ala Asp Val
                165                 170                 175

Asn Ala Lys Asp Val Asp Gly Asn Thr Pro Leu His Tyr Ala Ala His
            180                 185                 190

Val Gly His Leu Glu Ile Val Glu Val Leu Leu Lys Ala Gly Ala Asp
        195                 200                 205

Val Asn Ala Lys Asp Glu Gln Gly Tyr Thr Pro Leu His Leu Ala Ala
    210                 215                 220

Trp Arg Gly His Leu Glu Ile Val Glu Val Leu Leu Lys Ala Gly Ala
225                 230                 235                 240

Asp Val Asn Ala Gln Asp Thr Gln Gly Thr Thr Pro Ala Asp Leu Ala
                245                 250                 255

Ala Arg Glu Gly His Gln Gln Ile Ala Ser Val Leu Gln Gln Ala Ala
            260                 265                 270

<210> SEQ ID NO 63
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 63

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Ala Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Thr Pro Thr Pro Thr
    130                 135                 140

Pro Thr Gly Ser Asp Leu Gly Lys Lys Leu Leu Gln Ala Ala Arg Ala
145                 150                 155                 160

Gly Gln Leu Asp Glu Val Arg Glu Leu Leu Lys Ala Gly Ala Asp Val
                165                 170                 175

Asn Ala Lys Asp Val Asp Gly Asn Thr Pro Leu His Tyr Ala Ala His
            180                 185                 190

Val Gly His Leu Glu Ile Val Glu Val Leu Leu Lys Ala Gly Ala Asp
        195                 200                 205

-continued

Val Asn Ala Lys Asp Glu Gln Gly Tyr Thr Pro Leu His Leu Ala Ala
    210                 215                 220

Trp Arg Gly His Leu Glu Ile Val Glu Val Leu Leu Lys Ala Gly Ala
225                 230                 235                 240

Asp Val Asn Ala Gln Asp Lys Ser Gly Lys Thr Pro Ala Asp Leu Ala
                245                 250                 255

Ala Arg Ala Gly His Gln Asp Ile Ala Glu Val Leu Gln Lys Ala Ala
            260                 265                 270

<210> SEQ ID NO 64
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 64

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Ala Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr Pro Thr
    130                 135                 140

Pro Thr Gly Ser Asp Leu Gly Trp Lys Leu Leu Gln Ala Ala Val Ile
145                 150                 155                 160

Gly Gln Leu Asp Glu Val Arg Glu Leu Leu Lys Ala Gly Ala Asp Val
                165                 170                 175

Asn Ala Lys Asp Val Asp Gly Asn Thr Pro Leu His Tyr Ala Ala His
            180                 185                 190

Val Gly His Leu Glu Ile Val Glu Val Leu Leu Lys Ala Gly Ala Asp
        195                 200                 205

Val Asn Ala Lys Asp Glu Gln Gly Tyr Thr Pro Leu His Leu Ala Ala
    210                 215                 220

Trp Arg Gly His Leu Glu Ile Val Glu Val Leu Leu Lys Ala Gly Ala
225                 230                 235                 240

Asp Val Asn Ala Gln Asp Leu Glu Gly Ala Thr Pro Ala Asp Leu Ala
                245                 250                 255

Ala Arg Glu Gly His Gln Asp Ile Ala Glu Val Leu Gln Lys Ala Ala
            260                 265                 270

<210> SEQ ID NO 65
<211> LENGTH: 272
<212> TYPE: PRT
<213> ORGANISM: Artificial Sequence
<220> FEATURE:

-continued

<223> OTHER INFORMATION: Ankyrin repeat protein

<400> SEQUENCE: 65

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Asp Ala Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Pro Thr Pro Thr
    130                 135                 140

Pro Thr Gly Ser Asp Leu Gly Thr Lys Leu Leu Glu Ala Ala Gln Tyr
145                 150                 155                 160

Gly Gln Asp Asp Glu Val Arg Glu Leu Leu Lys Ala Gly Ala Asp Val
                165                 170                 175

Asn Ala Lys Asp Val Asp Gly Ala Thr Pro Leu His Trp Ala Ala Tyr
            180                 185                 190

Lys Gly His Pro Glu Ile Ile Glu Val Leu Leu Lys Ala Gly Ala Asp
        195                 200                 205

Val Asn Ala Lys Asp Ala Val Gly Trp Thr Pro Leu His Ile Ala Ala
    210                 215                 220

Asn His Gly His Leu Glu Ile Val Glu Val Leu Leu Lys Ala Gly Ala
225                 230                 235                 240

Asp Val Asn Ala Gln Asp Ser Tyr Gly Ala Thr Pro Ala Asp Leu Ala
                245                 250                 255

Ala Ile Trp Gly His Glu Asp Ile Ala Glu Val Leu Gln Lys Ala Ala
            260                 265                 270
```

<210> SEQ ID NO 66
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 66

```
Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
            20                  25                  30

Tyr Phe Ser His Thr Pro Leu His Leu Ala Ala Arg Asn Gly His Leu
        35                  40                  45

Lys Ile Val Glu Val Leu Leu Lys Ala Gly Ala Asp Val Asn Ala Lys
    50                  55                  60

Asp Phe Ala Gly Lys Thr Pro Leu His Leu Ala Ala Asp Ala Gly His
65                  70                  75                  80
```

```
Leu Glu Ile Val Glu Val Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Thr Pro Thr Pro Thr
    130                 135                 140

Pro Thr Gly Ser Asp Leu Gly Ser Lys Leu Leu Gln Ala Ala Gln Tyr
145                 150                 155                 160

Gly Gln Leu Asp Thr Val Arg Thr Leu Leu Gln Ala Gly Ala Asp Val
                165                 170                 175

Asn Ala Lys Asp Val Asp Gly Ala Thr Pro Leu His Trp Ala Ala Tyr
            180                 185                 190

Lys Gly His Pro Glu Ile Ile Glu Val Leu Leu Lys Ala Gly Ala Asp
        195                 200                 205

Val Asn Ala Lys Asp Ala Val Gly Trp Thr Pro Leu His Ile Ala Ala
    210                 215                 220

Asn His Gly His Leu Glu Ile Val Glu Val Leu Leu Lys Ala Gly Ala
225                 230                 235                 240

Asp Val Asn Ala Gln Asp Thr Gln Gly Thr Thr Pro Ala Asp Leu Ala
                245                 250                 255

Ala Arg Trp Gly His Gln Gln Ile Ala Ser Val Leu Gln Gln Ala Ala
            260                 265                 270

<210> SEQ ID NO 67
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 67

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
                20                  25                  30

Tyr Phe Ser His Thr Pro Leu His Leu Ala Ala Arg Asn Gly His Leu
            35                  40                  45

Lys Ile Val Glu Val Leu Leu Lys Ala Gly Ala Asp Val Asn Ala Lys
        50                  55                  60

Asp Phe Ala Gly Lys Thr Pro Leu His Leu Ala Ala Asp Ala Gly His
65                  70                  75                  80

Leu Glu Ile Val Glu Val Leu Leu Lys Ala Gly Ala Asp Val Asn Ala
                85                  90                  95

Gln Asp Ile Phe Gly Lys Thr Pro Ala Asp Ile Ala Ala Asp Ala Gly
            100                 105                 110

His Glu Asp Ile Ala Glu Val Leu Gln Lys Ala Ala Gly Ser Pro Thr
        115                 120                 125

Pro Thr Pro Thr Thr Pro Thr Pro Thr Pro Thr Thr Pro Thr Pro Thr
    130                 135                 140

Pro Thr Gly Ser Asp Leu Gly Lys Lys Leu Leu Gln Ala Ala Arg Ala
145                 150                 155                 160

Gly Gln Leu Asp Glu Val Arg Glu Leu Leu Lys Ala Gly Ala Asp Val
                165                 170                 175
```

-continued

Asn Ala Lys Asp Val Asp Gly Ala Thr Pro Leu His Trp Ala Ala Tyr
             180                 185                 190

Lys Gly His Pro Glu Ile Ile Glu Val Leu Leu Lys Ala Gly Ala Asp
         195                 200                 205

Val Asn Ala Lys Asp Ala Val Gly Trp Thr Pro Leu His Ile Ala Ala
     210                 215                 220

Asn His Gly His Leu Glu Ile Val Glu Val Leu Leu Lys Ala Gly Ala
225                 230                 235                 240

Asp Val Asn Ala Gln Asp Lys Ser Gly Lys Thr Pro Ala Asp Leu Ala
                 245                 250                 255

Ala Arg Ala Gly His Gln Asp Ile Ala Glu Val Leu Gln Lys Ala Ala
             260                 265                 270

<210> SEQ ID NO 68
<211> LENGTH: 272
<212> TYPE: PRT
<213> ORGANISM: Artificial Sequence
<220> FEATURE:
<223> OTHER INFORMATION: Ankyrin repeat protein

<400> SEQUENCE: 68

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala Lys Asp
             20                  25                  30

Tyr Phe Ser His Thr Pro Leu His Leu Ala Ala Arg Asn Gly His Leu
         35                  40                  45

Lys Ile Val Glu Val Leu Leu Lys Ala Gly Ala Asp Val Asn Ala Lys
     50                  55                  60

Asp Phe Ala Gly Lys Thr Pro Leu His Leu Ala Asp Ala Gly His
65                  70                  75                  80

Leu Glu Ile Val Glu Val Leu Leu Lys Ala Gly Ala Asp Val Asn Ala
                 85                  90                  95

Gln Asp Ile Phe Gly Lys Thr Pro Ala Asp Ile Ala Ala Asp Ala Gly
             100                 105                 110

His Glu Asp Ile Ala Glu Val Leu Gln Lys Ala Ala Gly Ser Pro Thr
         115                 120                 125

Pro Thr Pro Thr Thr Pro Thr Pro Thr Pro Thr Pro Thr Pro Thr Pro
     130                 135                 140

Pro Thr Gly Ser Asp Leu Gly Thr Lys Leu Leu Gln Ala Ala Gln Tyr
145                 150                 155                 160

Gly Gln Leu Asp Glu Val Arg Glu Leu Leu Lys Ala Gly Ala Asp Val
                 165                 170                 175

Asn Ala Lys Asp Val Asp Gly Ala Thr Pro Leu His Trp Ala Ala Tyr
             180                 185                 190

Lys Gly His Pro Glu Ile Ile Glu Val Leu Leu Lys Ala Gly Ala Asp
         195                 200                 205

Val Asn Ala Lys Asp Ala Val Gly Trp Thr Pro Leu His Ile Ala Ala
     210                 215                 220

Asn His Gly His Leu Glu Ile Val Glu Val Leu Leu Lys Ala Gly Ala
225                 230                 235                 240

Asp Val Asn Ala Gln Asp Ser Tyr Gly Ala Thr Pro Ala Asp Leu Ala
                 245                 250                 255

Ala Arg Trp Gly His Gln Asp Ile Ala Glu Val Leu Gln Lys Ala Ala
             260                 265                 270

<210> SEQ ID NO 69
<211> LENGTH: 30
<212> TYPE: PRT
<213> ORGANISM: Artificial Sequence
<220> FEATURE:
<223> OTHER INFORMATION: N-terminal capping module

<400> SEQUENCE: 69

Asp Leu Gly Lys Lys Leu Leu Glu Ala Ala Arg Ala Gly Gln Asp Asp
1               5                   10                  15

Glu Val Arg Glu Leu Leu Lys Ala Gly Ala Asp Val Asn Ala
            20                  25                  30

<210> SEQ ID NO 70
<211> LENGTH: 30
<212> TYPE: PRT
<213> ORGANISM: Artificial Sequence
<220> FEATURE:
<223> OTHER INFORMATION: N-terminal capping module
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid

<400> SEQUENCE: 70

Asp Leu Gly Xaa Lys Leu Leu Glu Ala Ala Xaa Xaa Gly Gln Asp Asp
1               5                   10                  15

Glu Val Arg Glu Leu Leu Lys Ala Gly Ala Asp Val Asn Ala
            20                  25                  30

<210> SEQ ID NO 71
<211> LENGTH: 30
<212> TYPE: PRT
<213> ORGANISM: Artificial Sequence
<220> FEATURE:
<223> OTHER INFORMATION: N-terminal capping module
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid

<400> SEQUENCE: 71

```
Asp Leu Gly Xaa Lys Leu Leu Glu Ala Ala Xaa Xaa Gly Gln Asp Asp
1               5                   10                  15

Xaa Val Arg Xaa Leu Leu Xaa Ala Gly Ala Asp Val Asn Ala
            20                  25                  30
```

<210> SEQ ID NO 72
<211> LENGTH: 30
<212> TYPE: PRT
<213> ORGANISM: Artificial Sequence
<220> FEATURE:
<223> OTHER INFORMATION: N-terminal capping module
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 5
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid

<400> SEQUENCE: 72

```
Asp Leu Gly Xaa Xaa Leu Leu Glu Ala Ala Xaa Xaa Gly Gln Asp Asp
1               5                   10                  15

Xaa Val Arg Xaa Leu Xaa Xaa Xaa Gly Ala Asp Val Asn Ala
            20                  25                  30
```

<210> SEQ ID NO 73
<211> LENGTH: 30
<212> TYPE: PRT
<213> ORGANISM: Artificial Sequence
<220> FEATURE:
<223> OTHER INFORMATION: N-terminal capping module
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 2
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT

```
<222> LOCATION: 4
<223> OTHER INFORMATION: Xaa can be any naturally occuring amino acid
<220> FEATURE:
<221> NAME/KEY: VARIANT
<222> LOCATION: 5
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 14
<223> OTHER INFORMATION: Xaa can be any naturally occuring amino acid
<220> FEATURE:
<221> NAME/KEY: VARIANT
<222> LOCATION: 16
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 18
<223> OTHER INFORMATION: Xaa can be any naturally occuring amino acid
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 21
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid

<400> SEQUENCE: 73

Xaa Xaa Xaa Xaa Xaa Leu Leu Glu Ala Ala Xaa Xaa Gly Xaa Asp Xaa
1               5                   10                  15

Xaa Xaa Xaa Xaa Xaa Xaa Xaa Xaa Gly Ala Asp Val Asn Ala
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: N-terminal capping module
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 2
<223> OTHER INFORMATION: Xaa can be any naturally occuring amino acid
<220> FEATURE:
```

```
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 5
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 7
<223> OTHER INFORMATION: Xaa can be any naturally occuring amino acid
<220> FEATURE:
<221> NAME/KEY: VARIANT
<222> LOCATION: 9
<223> OTHER INFORMATION: Xaa can be any naturally occuring amino acid
<220> FEATURE:
<221> NAME/KEY: VARIANT
<222> LOCATION: 10
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 13
<223> OTHER INFORMATION: Xaa can be any naturally occuring amino acid
<220> FEATURE:
<221> NAME/KEY: VARIANT
<222> LOCATION: 14
<223> OTHER INFORMATION: Xaa can be any naturally occuring amino acid
<220> FEATURE:
<221> NAME/KEY: VARIANT
<222> LOCATION: 16
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 18
<223> OTHER INFORMATION: Xaa can be any naturally occuring amino acid
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 21
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
```

<400> SEQUENCE: 74

Xaa Xaa Xaa Xaa Xaa Xaa Xaa Glu Xaa Xaa Xaa Xaa Xaa Asp Xaa
1               5                   10                  15

Xaa Xaa Xaa Xaa Xaa Xaa Xaa Xaa Gly Ala Asp Val Asn Ala
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: N-terminal capping module

<400> SEQUENCE: 75

Asp Leu Gly Lys Lys Leu Leu Gln Ala Ala Arg Ala Gly Gln Leu Asp
1               5                   10                  15

Glu Val Arg Glu Leu Leu Lys Ala Gly Ala Asp Val Asn Ala
            20                  25                  30

<210> SEQ ID NO 76
<211> LENGTH: 30
<212> TYPE: PRT
<213> ORGANISM: Artificial Sequence
<220> FEATURE:
<223> OTHER INFORMATION: N-terminal capping module

<400> SEQUENCE: 76

Asp Leu Gly Ser Lys Leu Leu Gln Ala Ala Arg Ala Gly Gln Leu Asp
1               5                   10                  15

Thr Val Arg Thr Leu Leu Gln Ala Gly Ala Asp Val Asn Ala
            20                  25                  30

<210> SEQ ID NO 77
<211> LENGTH: 30
<212> TYPE: PRT
<213> ORGANISM: Artificial Sequence
<220> FEATURE:
<223> OTHER INFORMATION: N-terminal capping module
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid

<400> SEQUENCE: 77

Asp Leu Gly Xaa Lys Leu Leu Gln Ala Ala Xaa Xaa Gly Gln Leu Asp
1               5                   10                  15

Glu Val Arg Glu Leu Leu Lys Ala Gly Ala Asp Val Asn Ala
            20                  25                  30

<210> SEQ ID NO 78
<211> LENGTH: 30
<212> TYPE: PRT
<213> ORGANISM: Artificial Sequence
<220> FEATURE:
<223> OTHER INFORMATION: N-terminal capping module
<220> FEATURE:
<221> NAME/KEY: VARIANT
<222> LOCATION: 4

```
<223> OTHER INFORMATION: Xaa can be any occuring amino acid
<220> FEATURE:
<221> NAME/KEY: VARIANT
<222> LOCATION: 11
<223> OTHER INFORMATION: Xaa can be any occuring amino acid
<220> FEATURE:
<221> NAME/KEY: VARIANT
<222> LOCATION: 12
<223> OTHER INFORMATION: Xaa can be any occuring amino acid
<220> FEATURE:
<221> NAME/KEY: VARIANT
<222> LOCATION: 17
<223> OTHER INFORMATION: Xaa can be any occuring amino acid
<220> FEATURE:
<221> NAME/KEY: VARIANT
<222> LOCATION: 20
<223> OTHER INFORMATION: Xaa can be any occuring amino acid
<220> FEATURE:
<221> NAME/KEY: VARIANT
<222> LOCATION: 23
<223> OTHER INFORMATION: Xaa can be any occuring amino acid

<400> SEQUENCE: 78

Asp Leu Gly Xaa Lys Leu Leu Gln Ala Ala Xaa Xaa Gly Gln Leu Asp
1               5                   10                  15

Xaa Val Arg Xaa Leu Leu Xaa Ala Gly Ala Asp Val Asn Ala
            20                  25                  30

<210> SEQ ID NO 79
<211> LENGTH: 30
<212> TYPE: PRT
<213> ORGANISM: Artificial Sequence
<220> FEATURE:
<223> OTHER INFORMATION: N-terminal capping module
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 5
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid

<400> SEQUENCE: 79

Asp Leu Gly Xaa Xaa Leu Leu Gln Ala Ala Xaa Xaa Gly Gln Leu Asp
1               5                   10                  15
```

Xaa Val Arg Xaa Leu Xaa Xaa Xaa Gly Ala Asp Val Asn Ala
        20                  25                  30

<210> SEQ ID NO 80
<211> LENGTH: 30
<212> TYPE: PRT
<213> ORGANISM: Artificial Sequence
<220> FEATURE:
<223> OTHER INFORMATION: N-terminal capping module
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 2
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 5
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 14
<223> OTHER INFORMATION: Xaa can be any naturally occuring amino acid
<220> FEATURE:
<221> NAME/KEY: VARIANT
<222> LOCATION: 16
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 18
<223> OTHER INFORMATION: Xaa can be any naturally occuring amino acid
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 21
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid

<400> SEQUENCE: 80

Xaa Xaa Xaa Xaa Xaa Leu Leu Gln Ala Ala Xaa Xaa Gly Xaa Leu Xaa
1               5                   10                  15

Xaa Xaa Xaa Xaa Xaa Xaa Xaa Xaa Gly Ala Asp Val Asn Ala
            20                  25                  30

<210> SEQ ID NO 81
<211> LENGTH: 30
<212> TYPE: PRT
<213> ORGANISM: Artificial Sequence
<220> FEATURE:
<223> OTHER INFORMATION: N-terminal capping module
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 2
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 5
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 7
<223> OTHER INFORMATION: Xaa can be any naturally occuring amino acid
<220> FEATURE:
<221> NAME/KEY: VARIANT
<222> LOCATION: 9
<223> OTHER INFORMATION: Xaa can be any naturally occuring amino acid
<220> FEATURE:
<221> NAME/KEY: VARIANT
<222> LOCATION: 10
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 13
<223> OTHER INFORMATION: Xaa can be any naturally occuring amino acid
<220> FEATURE:
<221> NAME/KEY: VARIANT
<222> LOCATION: 14
<223> OTHER INFORMATION: Xaa can be any naturally occuring amino acid
<220> FEATURE:
<221> NAME/KEY: VARIANT
<222> LOCATION: 16
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 18
<223> OTHER INFORMATION: Xaa can be any naturally occuring amino acid

```
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 21
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid

<400> SEQUENCE: 81

Xaa Xaa Xaa Xaa Xaa Xaa Xaa Gln Xaa Xaa Xaa Xaa Xaa Xaa Leu Xaa
1               5                   10                  15

Xaa Xaa Xaa Xaa Xaa Xaa Xaa Xaa Gly Ala Asp Val Asn Ala
            20                  25                  30

<210> SEQ ID NO 82
<211> LENGTH: 28
<212> TYPE: PRT
<213> ORGANISM: Artificial Sequence
<220> FEATURE:
<223> OTHER INFORMATION: C-terminal capping module

<400> SEQUENCE: 82

Gln Asp Lys Ser Gly Lys Thr Pro Ala Asp Leu Ala Ala Asp Ala Gly
1               5                   10                  15

His Glu Asp Ile Ala Glu Val Leu Gln Lys Ala Ala
            20                  25

<210> SEQ ID NO 83
<211> LENGTH: 28
<212> TYPE: PRT
<213> ORGANISM: Artificial Sequence
<220> FEATURE:
<223> OTHER INFORMATION: C-terminal capping module
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 15
```

<223> OTHER INFORMATION: Xaa can be any naturally occuring amino acid

<400> SEQUENCE: 83

Xaa Asp Xaa Xaa Gly Xaa Thr Pro Ala Asp Xaa Ala Ala Asp Xaa Gly
1               5                   10                  15

His Glu Asp Ile Ala Glu Val Leu Gln Lys Ala Ala
            20                  25

<210> SEQ ID NO 84
<211> LENGTH: 28
<212> TYPE: PRT
<213> ORGANISM: Artificial Sequence
<220> FEATURE:
<223> OTHER INFORMATION: C-terminal capping module
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 26
<223> OTHER INFORMATION: Xaa can be any naturally occuring amino acid

<400> SEQUENCE: 84

Xaa Asp Xaa Xaa Gly Xaa Thr Pro Ala Asp Xaa Ala Ala Asp Xaa Gly
1               5                   10                  15

His Glu Xaa Ile Ala Xaa Val Leu Gln Xaa Ala Ala
            20                  25

<210> SEQ ID NO 85
<211> LENGTH: 28
<212> TYPE: PRT
<213> ORGANISM: Artificial Sequence
<220> FEATURE:
<223> OTHER INFORMATION: C-terminal capping module
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT

```
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 9
<223> OTHER INFORMATION: Xaa can be any naturally occuring amino acid
<220> FEATURE:
<221> NAME/KEY: VARIANT
<222> LOCATION: 10
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 21
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 25
<223> OTHER INFORMATION: Xaa can be any naturally occuring amino acid
<220> FEATURE:
<221> NAME/KEY: VARIANT
<222> LOCATION: 26
<223> OTHER INFORMATION: Xaa can be any naturally occuring amino acid

<400> SEQUENCE: 85

Xaa Asp Xaa Xaa Gly Xaa Thr Pro Xaa Xaa Xaa Ala Ala Asp Xaa Gly
1               5                   10                  15

Xaa Glu Xaa Xaa Xaa Xaa Xaa Xaa Xaa Ala Ala
            20                  25

<210> SEQ ID NO 86
<211> LENGTH: 28
<212> TYPE: PRT
<213> ORGANISM: Artificial Sequence
<220> FEATURE:
<223> OTHER INFORMATION: C-terminal capping module
<220> FEATURE:
<221> NAME/KEY: VARIANT
<222> LOCATION: 1
<223> OTHER INFORMATION: Xaa can be any naturally occuring amino acid
<220> FEATURE:
```

```
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 9
<223> OTHER INFORMATION: Xaa can be any naturally occuring amino acid
<220> FEATURE:
<221> NAME/KEY: VARIANT
<222> LOCATION: 10
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
<222> LOCATION: 16
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 21
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 25
<223> OTHER INFORMATION: Xaa can be any naturally occuring amino acid
<220> FEATURE:
<221> NAME/KEY: VARIANT
<222> LOCATION: 26
<223> OTHER INFORMATION: Xaa can be any naturally occuring amino acid
<220> FEATURE:
<221> NAME/KEY: VARIANT
<222> LOCATION: 27
<223> OTHER INFORMATION: Xaa can be any naturally occuring amino acid
<220> FEATURE:
<221> NAME/KEY: VARIANT
<222> LOCATION: 28
<223> OTHER INFORMATION: Xaa can be any naturally occuring amino acid
```

<400> SEQUENCE: 86

Xaa Asp Xaa Xaa Gly Xaa Thr Pro Xaa Xaa Xaa Xaa Ala Asp Xaa Xaa
1               5                   10                  15

Xaa Glu Xaa Xaa Xaa Xaa Xaa Xaa Xaa Xaa Xaa Xaa
            20                  25

<210> SEQ ID NO 87
<211> LENGTH: 28
<212> TYPE: PRT
<213> ORGANISM: Artificial Sequence
<220> FEATURE:
<223> OTHER INFORMATION: C-terminal capping module
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 9
<223> OTHER INFORMATION: Xaa can be any naturally occuring amino acid
<220> FEATURE:
<221> NAME/KEY: VARIANT
<222> LOCATION: 10
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 13
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
<222> LOCATION: 16
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 21
<223> OTHER INFORMATION: Xaa can be any naturally occuring amino acid
<220> FEATURE:
<221> NAME/KEY: VARIANT
<222> LOCATION: 22

<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 25
<223> OTHER INFORMATION: Xaa can be any naturally occuring amino acid
<220> FEATURE:
<221> NAME/KEY: VARIANT
<222> LOCATION: 26
<223> OTHER INFORMATION: Xaa can be any naturally occuring amino acid

<400> SEQUENCE: 87

Xaa Asp Xaa Xaa Gly Xaa Thr Pro Xaa Xaa Xaa Xaa Xaa Asp Xaa Xaa
1               5                   10                  15

Xaa Glu Xaa Xaa Xaa Xaa Xaa Xaa Xaa Xaa Ala Ala
            20                  25

<210> SEQ ID NO 88
<211> LENGTH: 28
<212> TYPE: PRT
<213> ORGANISM: Artificial Sequence
<220> FEATURE:
<223> OTHER INFORMATION: C-terminal capping module

<400> SEQUENCE: 88

Gln Asp Lys Ser Gly Lys Thr Pro Ala Asp Leu Ala Ala Arg Ala Gly
1               5                   10                  15

His Gln Asp Ile Ala Glu Val Leu Gln Lys Ala Ala
            20                  25

<210> SEQ ID NO 89
<211> LENGTH: 28
<212> TYPE: PRT
<213> ORGANISM: Artificial Sequence
<220> FEATURE:
<223> OTHER INFORMATION: C-terminal capping module

<400> SEQUENCE: 89

Gln Asp Thr Gln Gly Thr Thr Pro Ala Asp Leu Ala Ala Arg Ala Gly
1               5                   10                  15

His Gln Gln Ile Ala Ser Val Leu Gln Gln Ala Ala
            20                  25

<210> SEQ ID NO 90
<211> LENGTH: 28
<212> TYPE: PRT
<213> ORGANISM: Artificial Sequence
<220> FEATURE:
<223> OTHER INFORMATION: C-terminal capping module
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT

```
<222> LOCATION: 6
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid

<400> SEQUENCE: 90

Xaa Asp Xaa Xaa Gly Xaa Thr Pro Ala Asp Xaa Ala Ala Arg Xaa Gly
1               5                   10                  15

His Gln Asp Ile Ala Glu Val Leu Gln Lys Ala Ala
            20                  25

<210> SEQ ID NO 91
<211> LENGTH: 28
<212> TYPE: PRT
<213> ORGANISM: Artificial Sequence
<220> FEATURE:
<223> OTHER INFORMATION: C-terminal capping module
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 26
<223> OTHER INFORMATION: Xaa can be any naturally occuring amino acid

<400> SEQUENCE: 91

Xaa Asp Xaa Xaa Gly Xaa Thr Pro Ala Asp Xaa Ala Ala Arg Xaa Gly
1               5                   10                  15

His Gln Xaa Ile Ala Xaa Val Leu Gln Xaa Ala Ala
            20                  25

<210> SEQ ID NO 92
<211> LENGTH: 28
<212> TYPE: PRT
<213> ORGANISM: Artificial Sequence
<220> FEATURE:
<223> OTHER INFORMATION: C-terminal capping module
<220> FEATURE:
```

```
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 9
<223> OTHER INFORMATION: Xaa can be any naturally occuring amino acid
<220> FEATURE:
<221> NAME/KEY: VARIANT
<222> LOCATION: 10
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 21
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 25
<223> OTHER INFORMATION: Xaa can be any naturally occuring amino acid
<220> FEATURE:
<221> NAME/KEY: VARIANT
<222> LOCATION: 26
<223> OTHER INFORMATION: Xaa can be any naturally occuring amino acid

<400> SEQUENCE: 92

Xaa Asp Xaa Xaa Gly Xaa Thr Pro Xaa Xaa Xaa Ala Ala Arg Xaa Gly
1               5                   10                  15

Xaa Gln Xaa Xaa Xaa Xaa Xaa Xaa Xaa Xaa Ala Ala
            20                  25

<210> SEQ ID NO 93
<211> LENGTH: 28
```

```
<212> TYPE: PRT
<213> ORGANISM: Artificial Sequence
<220> FEATURE:
<223> OTHER INFORMATION: C-terminal capping module
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 9
<223> OTHER INFORMATION: Xaa can be any naturally occuring amino acid
<220> FEATURE:
<221> NAME/KEY: VARIANT
<222> LOCATION: 10
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
<222> LOCATION: 16
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 21
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 25
<223> OTHER INFORMATION: Xaa can be any naturally occuring amino acid
<220> FEATURE:
<221> NAME/KEY: VARIANT
<222> LOCATION: 26
```

```
<223> OTHER INFORMATION: Xaa can be any naturally occuring amino acid
<220> FEATURE:
<221> NAME/KEY: VARIANT
<222> LOCATION: 27
<223> OTHER INFORMATION: Xaa can be any naturally occuring amino acid
<220> FEATURE:
<221> NAME/KEY: VARIANT
<222> LOCATION: 28
<223> OTHER INFORMATION: Xaa can be any naturally occuring amino acid

<400> SEQUENCE: 93

Xaa Asp Xaa Xaa Gly Xaa Thr Pro Xaa Xaa Xaa Xaa Ala Arg Xaa Xaa
1               5                   10                  15

Xaa Gln Xaa Xaa Xaa Xaa Xaa Xaa Xaa Xaa Xaa Xaa
            20                  25

<210> SEQ ID NO 94
<211> LENGTH: 28
<212> TYPE: PRT
<213> ORGANISM: Artificial Sequence
<220> FEATURE:
<223> OTHER INFORMATION: C-terminal capping module
<220> FEATURE:
<221> NAME/KEY: VARIANT
<222> LOCATION: 1
<223> OTHER INFORMATION: Xaa can be any naturally occuring amino acid
<220> FEATURE:
<221> NAME/KEY: VARIANT
<222> LOCATION: 3
<223> OTHER INFORMATION: Xaa can be any naturally occuring amino acid
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 6
<223> OTHER INFORMATION: Xaa can be any naturally occuring amino acid
<220> FEATURE:
<221> NAME/KEY: VARIANT
<222> LOCATION: 9
<223> OTHER INFORMATION: Xaa can be any naturally occuring amino acid
<220> FEATURE:
<221> NAME/KEY: VARIANT
<222> LOCATION: 10
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 13
<223> OTHER INFORMATION: Xaa can be any naturally occuring amino acid
<220> FEATURE:
<221> NAME/KEY: VARIANT
<222> LOCATION: 15
<223> OTHER INFORMATION: Xaa can be any naturally occuring amino acid
<220> FEATURE:
<221> NAME/KEY: VARIANT
<222> LOCATION: 16
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 19
<223> OTHER INFORMATION: Xaa can be any naturally occuring amino acid
<220> FEATURE:
<221> NAME/KEY: VARIANT
```

```
<222> LOCATION: 20
<223> OTHER INFORMATION: Xaa can be any naturally occuring amino acid
<220> FEATURE:
<221> NAME/KEY: VARIANT
<222> LOCATION: 21
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 25
<223> OTHER INFORMATION: Xaa can be any naturally occuring amino acid
<220> FEATURE:
<221> NAME/KEY: VARIANT
<222> LOCATION: 26
<223> OTHER INFORMATION: Xaa can be any naturally occuring amino acid

<400> SEQUENCE: 94

Xaa Asp Xaa Xaa Gly Xaa Thr Pro Xaa Xaa Xaa Xaa Arg Xaa Xaa
1               5                   10                  15

Xaa Gln Xaa Xaa Xaa Xaa Xaa Xaa Xaa Ala Ala
            20                  25

<210> SEQ ID NO 95
<211> LENGTH: 91
<212> TYPE: PRT
<213> ORGANISM: Artificial Sequence
<220> FEATURE:
<223> OTHER INFORMATION: Ankyrin repeat domain
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 31
<223> OTHER INFORMATION: Xaa can be any naturally occuring amino acid
<220> FEATURE:
<221> NAME/KEY: VARIANT
<222> LOCATION: 33
<223> OTHER INFORMATION: Xaa can be any naturally occuring amino acid
<220> FEATURE:
```

```
<221> NAME/KEY: VARIANT
<222> LOCATION: 34
<223> OTHER INFORMATION: Xaa can be any naturally occuring amino acid
<220> FEATURE:
<221> NAME/KEY: VARIANT
<222> LOCATION: 36
<223> OTHER INFORMATION: Xaa can be any naturally occuring amino acid
<220> FEATURE:
<221> NAME/KEY: VARIANT
<222> LOCATION: 41
<223> OTHER INFORMATION: Xaa can be any naturally occuring amino acid
<220> FEATURE:
<221> NAME/KEY: VARIANT
<222> LOCATION: 44
<223> OTHER INFORMATION: Xaa can be any naturally occuring amino acid
<220> FEATURE:
<221> NAME/KEY: VARIANT
<222> LOCATION: 45
<223> OTHER INFORMATION: Xaa can be any naturally occuring amino acid
<220> FEATURE:
<221> NAME/KEY: VARIANT
<222> LOCATION: 57
<223> OTHER INFORMATION: Xaa can be any naturally occuring amino acid
<220> FEATURE:
<221> NAME/KEY: VARIANT
<222> LOCATION: 64
<223> OTHER INFORMATION: Xaa can be any naturally occuring amino acid
<220> FEATURE:
<221> NAME/KEY: VARIANT
<222> LOCATION: 66
<223> OTHER INFORMATION: Xaa can be any naturally occuring amino acid
<220> FEATURE:
<221> NAME/KEY: VARIANT
<222> LOCATION: 67
<223> OTHER INFORMATION: Xaa can be any naturally occuring amino acid
<220> FEATURE:
<221> NAME/KEY: VARIANT
<222> LOCATION: 69
<223> OTHER INFORMATION: Xaa can be any naturally occuring amino acid
<220> FEATURE:
<221> NAME/KEY: VARIANT
<222> LOCATION: 74
<223> OTHER INFORMATION: Xaa can be any naturally occuring amino acid
<220> FEATURE:
<221> NAME/KEY: VARIANT
<222> LOCATION: 78
<223> OTHER INFORMATION: Xaa can be any naturally occuring amino acid
<220> FEATURE:
<221> NAME/KEY: VARIANT
<222> LOCATION: 90
<223> OTHER INFORMATION: Xaa can be any naturally occuring amino acid
<220> FEATURE:
<221> NAME/KEY: VARIANT
<222> LOCATION: 91
<223> OTHER INFORMATION: Xaa can be any naturally occuring amino acid

<400> SEQUENCE: 95

Asp Leu Gly Xaa Lys Leu Leu Gln Ala Ala Xaa Xaa Gly Gln Leu Asp
1               5                   10                  15

Glu Val Arg Xaa Leu Xaa Xaa Xaa Gly Ala Asp Val Asn Ala Xaa Asp
            20                  25                  30

Xaa Xaa Gly Xaa Thr Pro Leu His Xaa Ala Ala Xaa Xaa Gly His Leu
        35                  40                  45

Glu Ile Val Glu Val Leu Leu Lys Xaa Gly Ala Asp Val Asn Ala Xaa
    50                  55                  60

Asp Xaa Xaa Gly Xaa Thr Pro Ala Asp Xaa Ala Ala Arg Xaa Gly His
65                  70                  75                  80

Gln Asp Ile Ala Glu Val Leu Gln Lys Xaa Xaa
                85                  90

<210> SEQ ID NO 96
<211> LENGTH: 124
```

-continued

```
<212> TYPE: PRT
<213> ORGANISM: Artificial Sequence
<220> FEATURE:
<223> OTHER INFORMATION: Ankyrin repeat domain
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 31
<223> OTHER INFORMATION: Xaa can be any naturally occuring amino acid
<220> FEATURE:
<221> NAME/KEY: VARIANT
<222> LOCATION: 33
<223> OTHER INFORMATION: Xaa can be any naturally occuring amino acid
<220> FEATURE:
<221> NAME/KEY: VARIANT
<222> LOCATION: 34
<223> OTHER INFORMATION: Xaa can be any naturally occuring amino acid
<220> FEATURE:
<221> NAME/KEY: VARIANT
<222> LOCATION: 36
<223> OTHER INFORMATION: Xaa can be any naturally occuring amino acid
<220> FEATURE:
<221> NAME/KEY: VARIANT
<222> LOCATION: 41
<223> OTHER INFORMATION: Xaa can be any naturally occuring amino acid
<220> FEATURE:
<221> NAME/KEY: VARIANT
<222> LOCATION: 44
<223> OTHER INFORMATION: Xaa can be any naturally occuring amino acid
<220> FEATURE:
<221> NAME/KEY: VARIANT
<222> LOCATION: 45
<223> OTHER INFORMATION: Xaa can be any naturally occuring amino acid
<220> FEATURE:
<221> NAME/KEY: VARIANT
<222> LOCATION: 57
<223> OTHER INFORMATION: Xaa can be any naturally occuring amino acid
<220> FEATURE:
<221> NAME/KEY: VARIANT
<222> LOCATION: 64
<223> OTHER INFORMATION: Xaa can be any naturally occuring amino acid
<220> FEATURE:
<221> NAME/KEY: VARIANT
<222> LOCATION: 66
<223> OTHER INFORMATION: Xaa can be any naturally occuring amino acid
<220> FEATURE:
<221> NAME/KEY: VARIANT
<222> LOCATION: 67
<223> OTHER INFORMATION: Xaa can be any naturally occuring amino acid
<220> FEATURE:
<221> NAME/KEY: VARIANT
<222> LOCATION: 69
```

<223> OTHER INFORMATION: Xaa can be any naturally occuring amino acid
<220> FEATURE:
<221> NAME/KEY: VARIANT
<222> LOCATION: 74
<223> OTHER INFORMATION: Xaa can be any naturally occuring amino acid
<220> FEATURE:
<221> NAME/KEY: VARIANT
<222> LOCATION: 77
<223> OTHER INFORMATION: Xaa can be any naturally occuring amino acid
<220> FEATURE:
<221> NAME/KEY: VARIANT
<222> LOCATION: 78
<223> OTHER INFORMATION: Xaa can be any naturally occuring amino acid
<220> FEATURE:
<221> NAME/KEY: VARIANT
<222> LOCATION: 90
<223> OTHER INFORMATION: Xaa can be any naturally occuring amino acid
<220> FEATURE:
<221> NAME/KEY: VARIANT
<222> LOCATION: 97
<223> OTHER INFORMATION: Xaa can be any naturally occuring amino acid
<220> FEATURE:
<221> NAME/KEY: VARIANT
<222> LOCATION: 99
<223> OTHER INFORMATION: Xaa can be any naturally occuring amino acid
<220> FEATURE:
<221> NAME/KEY: VARIANT
<222> LOCATION: 100
<223> OTHER INFORMATION: Xaa can be any naturally occuring amino acid
<220> FEATURE:
<221> NAME/KEY: VARIANT
<222> LOCATION: 102
<223> OTHER INFORMATION: Xaa can be any naturally occuring amino acid
<220> FEATURE:
<221> NAME/KEY: VARIANT
<222> LOCATION: 107
<223> OTHER INFORMATION: Xaa can be any naturally occuring amino acid
<220> FEATURE:
<221> NAME/KEY: VARIANT
<222> LOCATION: 111
<223> OTHER INFORMATION: Xaa can be any naturally occuring amino acid
<220> FEATURE:
<221> NAME/KEY: VARIANT
<222> LOCATION: 123
<223> OTHER INFORMATION: Xaa can be any naturally occuring amino acid
<220> FEATURE:
<221> NAME/KEY: VARIANT
<222> LOCATION: 124
<223> OTHER INFORMATION: Xaa can be any naturally occuring amino acid

<400> SEQUENCE: 96

```
Asp Leu Gly Xaa Lys Leu Leu Gln Ala Ala Xaa Xaa Gly Gln Leu Asp
1               5                   10                  15

Glu Val Arg Xaa Leu Xaa Xaa Xaa Gly Ala Asp Val Asn Ala Xaa Asp
            20                  25                  30

Xaa Xaa Gly Xaa Thr Pro Leu His Xaa Ala Ala Xaa Xaa Gly His Leu
        35                  40                  45

Glu Ile Val Glu Val Leu Leu Lys Xaa Gly Ala Asp Val Asn Ala Xaa
    50                  55                  60

Asp Xaa Xaa Gly Xaa Thr Pro Leu His Xaa Ala Ala Xaa Xaa Gly His
65                  70                  75                  80

Leu Glu Ile Val Glu Val Leu Leu Lys Xaa Gly Ala Asp Val Asn Ala
                85                  90                  95

Xaa Asp Xaa Xaa Gly Xaa Thr Pro Ala Asp Xaa Ala Ala Arg Xaa Gly
            100                 105                 110

His Gln Asp Ile Ala Glu Val Leu Gln Lys Xaa Xaa
        115                 120
```

<210> SEQ ID NO 97
<211> LENGTH: 157

```
<212> TYPE: PRT
<213> ORGANISM: Artificial Sequence
<220> FEATURE:
<223> OTHER INFORMATION: Ankyrin repeat domain
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 31
<223> OTHER INFORMATION: Xaa can be any naturally occuring amino acid
<220> FEATURE:
<221> NAME/KEY: VARIANT
<222> LOCATION: 33
<223> OTHER INFORMATION: Xaa can be any naturally occuring amino acid
<220> FEATURE:
<221> NAME/KEY: VARIANT
<222> LOCATION: 34
<223> OTHER INFORMATION: Xaa can be any naturally occuring amino acid
<220> FEATURE:
<221> NAME/KEY: VARIANT
<222> LOCATION: 36
<223> OTHER INFORMATION: Xaa can be any naturally occuring amino acid
<220> FEATURE:
<221> NAME/KEY: VARIANT
<222> LOCATION: 41
<223> OTHER INFORMATION: Xaa can be any naturally occuring amino acid
<220> FEATURE:
<221> NAME/KEY: VARIANT
<222> LOCATION: 44
<223> OTHER INFORMATION: Xaa can be any naturally occuring amino acid
<220> FEATURE:
<221> NAME/KEY: VARIANT
<222> LOCATION: 45
<223> OTHER INFORMATION: Xaa can be any naturally occuring amino acid
<220> FEATURE:
<221> NAME/KEY: VARIANT
<222> LOCATION: 57
<223> OTHER INFORMATION: Xaa can be any naturally occuring amino acid
<220> FEATURE:
<221> NAME/KEY: VARIANT
<222> LOCATION: 64
<223> OTHER INFORMATION: Xaa can be any naturally occuring amino acid
<220> FEATURE:
<221> NAME/KEY: VARIANT
<222> LOCATION: 66
<223> OTHER INFORMATION: Xaa can be any naturally occuring amino acid
<220> FEATURE:
<221> NAME/KEY: VARIANT
<222> LOCATION: 67
<223> OTHER INFORMATION: Xaa can be any naturally occuring amino acid
<220> FEATURE:
<221> NAME/KEY: VARIANT
<222> LOCATION: 69
```

```
<223> OTHER INFORMATION: Xaa can be any naturally occuring amino acid
<220> FEATURE:
<221> NAME/KEY: VARIANT
<222> LOCATION: 74
<223> OTHER INFORMATION: Xaa can be any naturally occuring amino acid
<220> FEATURE:
<221> NAME/KEY: VARIANT
<222> LOCATION: 77
<223> OTHER INFORMATION: Xaa can be any naturally occuring amino acid
<220> FEATURE:
<221> NAME/KEY: VARIANT
<222> LOCATION: 78
<223> OTHER INFORMATION: Xaa can be any naturally occuring amino acid
<220> FEATURE:
<221> NAME/KEY: VARIANT
<222> LOCATION: 90
<223> OTHER INFORMATION: Xaa can be any naturally occuring amino acid
<220> FEATURE:
<221> NAME/KEY: VARIANT
<222> LOCATION: 97
<223> OTHER INFORMATION: Xaa can be any naturally occuring amino acid
<220> FEATURE:
<221> NAME/KEY: VARIANT
<222> LOCATION: 99
<223> OTHER INFORMATION: Xaa can be any naturally occuring amino acid
<220> FEATURE:
<221> NAME/KEY: VARIANT
<222> LOCATION: 100
<223> OTHER INFORMATION: Xaa can be any naturally occuring amino acid
<220> FEATURE:
<221> NAME/KEY: VARIANT
<222> LOCATION: 102
<223> OTHER INFORMATION: Xaa can be any naturally occuring amino acid
<220> FEATURE:
<221> NAME/KEY: VARIANT
<222> LOCATION: 107
<223> OTHER INFORMATION: Xaa can be any naturally occuring amino acid
<220> FEATURE:
<221> NAME/KEY: VARIANT
<222> LOCATION: 110
<223> OTHER INFORMATION: Xaa can be any naturally occuring amino acid
<220> FEATURE:
<221> NAME/KEY: VARIANT
<222> LOCATION: 111
<223> OTHER INFORMATION: Xaa can be any naturally occuring amino acid
<220> FEATURE:
<221> NAME/KEY: VARIANT
<222> LOCATION: 123
<223> OTHER INFORMATION: Xaa can be any naturally occuring amino acid
<220> FEATURE:
<221> NAME/KEY: VARIANT
<222> LOCATION: 130
<223> OTHER INFORMATION: Xaa can be any naturally occuring amino acid
<220> FEATURE:
<221> NAME/KEY: VARIANT
<222> LOCATION: 132
<223> OTHER INFORMATION: Xaa can be any naturally occuring amino acid
<220> FEATURE:
<221> NAME/KEY: VARIANT
<222> LOCATION: 133
<223> OTHER INFORMATION: Xaa can be any naturally occuring amino acid
<220> FEATURE:
<221> NAME/KEY: VARIANT
<222> LOCATION: 135
<223> OTHER INFORMATION: Xaa can be any naturally occuring amino acid
<220> FEATURE:
<221> NAME/KEY: VARIANT
<222> LOCATION: 140
<223> OTHER INFORMATION: Xaa can be any naturally occuring amino acid
<220> FEATURE:
<221> NAME/KEY: VARIANT
<222> LOCATION: 144
<223> OTHER INFORMATION: Xaa can be any naturally occuring amino acid
<220> FEATURE:
<221> NAME/KEY: VARIANT
<222> LOCATION: 156
<223> OTHER INFORMATION: Xaa can be any naturally occuring amino acid
<220> FEATURE:
<221> NAME/KEY: VARIANT
```

```
<222> LOCATION: 157
<223> OTHER INFORMATION: Xaa can be any naturally occuring amino acid

<400> SEQUENCE: 97

Asp Leu Gly Xaa Lys Leu Leu Gln Ala Ala Xaa Xaa Gly Gln Leu Asp
1               5                   10                  15

Glu Val Arg Xaa Leu Xaa Xaa Xaa Gly Ala Asp Val Asn Ala Xaa Asp
            20                  25                  30

Xaa Xaa Gly Xaa Thr Pro Leu His Xaa Ala Ala Xaa Xaa Gly His Leu
        35                  40                  45

Glu Ile Val Glu Val Leu Leu Lys Xaa Gly Ala Asp Val Asn Ala Xaa
50                  55                  60

Asp Xaa Xaa Gly Xaa Thr Pro Leu His Xaa Ala Ala Xaa Xaa Gly His
65                  70                  75                  80

Leu Glu Ile Val Glu Val Leu Leu Lys Xaa Gly Ala Asp Val Asn Ala
                85                  90                  95

Xaa Asp Xaa Xaa Gly Xaa Thr Pro Leu His Xaa Ala Ala Xaa Xaa Gly
            100                 105                 110

His Leu Glu Ile Val Glu Val Leu Leu Lys Xaa Gly Ala Asp Val Asn
        115                 120                 125

Ala Xaa Asp Xaa Xaa Gly Xaa Thr Pro Ala Asp Xaa Ala Ala Arg Xaa
    130                 135                 140

Gly His Gln Asp Ile Ala Glu Val Leu Gln Lys Xaa Xaa
145                 150                 155

<210> SEQ ID NO 98
<211> LENGTH: 190
<212> TYPE: PRT
<213> ORGANISM: Artificial Sequence
<220> FEATURE:
<223> OTHER INFORMATION: Ankyrin repeat domain
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 31
<223> OTHER INFORMATION: Xaa can be any naturally occuring amino acid
<220> FEATURE:
<221> NAME/KEY: VARIANT
<222> LOCATION: 33
<223> OTHER INFORMATION: Xaa can be any naturally occuring amino acid
<220> FEATURE:
```

```
<221> NAME/KEY: VARIANT
<222> LOCATION: 34
<223> OTHER INFORMATION: Xaa can be any naturally occuring amino acid
<220> FEATURE:
<221> NAME/KEY: VARIANT
<222> LOCATION: 36
<223> OTHER INFORMATION: Xaa can be any naturally occuring amino acid
<220> FEATURE:
<221> NAME/KEY: VARIANT
<222> LOCATION: 41
<223> OTHER INFORMATION: Xaa can be any naturally occuring amino acid
<220> FEATURE:
<221> NAME/KEY: VARIANT
<222> LOCATION: 44
<223> OTHER INFORMATION: Xaa can be any naturally occuring amino acid
<220> FEATURE:
<221> NAME/KEY: VARIANT
<222> LOCATION: 45
<223> OTHER INFORMATION: Xaa can be any naturally occuring amino acid
<220> FEATURE:
<221> NAME/KEY: VARIANT
<222> LOCATION: 57
<223> OTHER INFORMATION: Xaa can be any naturally occuring amino acid
<220> FEATURE:
<221> NAME/KEY: VARIANT
<222> LOCATION: 64
<223> OTHER INFORMATION: Xaa can be any naturally occuring amino acid
<220> FEATURE:
<221> NAME/KEY: VARIANT
<222> LOCATION: 66
<223> OTHER INFORMATION: Xaa can be any naturally occuring amino acid
<220> FEATURE:
<221> NAME/KEY: VARIANT
<222> LOCATION: 67
<223> OTHER INFORMATION: Xaa can be any naturally occuring amino acid
<220> FEATURE:
<221> NAME/KEY: VARIANT
<222> LOCATION: 69
<223> OTHER INFORMATION: Xaa can be any naturally occuring amino acid
<220> FEATURE:
<221> NAME/KEY: VARIANT
<222> LOCATION: 74
<223> OTHER INFORMATION: Xaa can be any naturally occuring amino acid
<220> FEATURE:
<221> NAME/KEY: VARIANT
<222> LOCATION: 77
<223> OTHER INFORMATION: Xaa can be any naturally occuring amino acid
<220> FEATURE:
<221> NAME/KEY: VARIANT
<222> LOCATION: 78
<223> OTHER INFORMATION: Xaa can be any naturally occuring amino acid
<220> FEATURE:
<221> NAME/KEY: VARIANT
<222> LOCATION: 90
<223> OTHER INFORMATION: Xaa can be any naturally occuring amino acid
<220> FEATURE:
<221> NAME/KEY: VARIANT
<222> LOCATION: 97
<223> OTHER INFORMATION: Xaa can be any naturally occuring amino acid
<220> FEATURE:
<221> NAME/KEY: VARIANT
<222> LOCATION: 99
<223> OTHER INFORMATION: Xaa can be any naturally occuring amino acid
<220> FEATURE:
<221> NAME/KEY: VARIANT
<222> LOCATION: 100
<223> OTHER INFORMATION: Xaa can be any naturally occuring amino acid
<220> FEATURE:
<221> NAME/KEY: VARIANT
<222> LOCATION: 102
<223> OTHER INFORMATION: Xaa can be any naturally occuring amino acid
<220> FEATURE:
<221> NAME/KEY: VARIANT
<222> LOCATION: 107
<223> OTHER INFORMATION: Xaa can be any naturally occuring amino acid
<220> FEATURE:
<221> NAME/KEY: VARIANT
<222> LOCATION: 110
<223> OTHER INFORMATION: Xaa can be any naturally occuring amino acid
```

```
<220> FEATURE:
<221> NAME/KEY: VARIANT
<222> LOCATION: 111
<223> OTHER INFORMATION: Xaa can be any naturally occuring amino acid
<220> FEATURE:
<221> NAME/KEY: VARIANT
<222> LOCATION: 123
<223> OTHER INFORMATION: Xaa can be any naturally occuring amino acid
<220> FEATURE:
<221> NAME/KEY: VARIANT
<222> LOCATION: 130
<223> OTHER INFORMATION: Xaa can be any naturally occuring amino acid
<220> FEATURE:
<221> NAME/KEY: VARIANT
<222> LOCATION: 132
<223> OTHER INFORMATION: Xaa can be any naturally occuring amino acid
<220> FEATURE:
<221> NAME/KEY: VARIANT
<222> LOCATION: 133
<223> OTHER INFORMATION: Xaa can be any naturally occuring amino acid
<220> FEATURE:
<221> NAME/KEY: VARIANT
<222> LOCATION: 135
<223> OTHER INFORMATION: Xaa can be any naturally occuring amino acid
<220> FEATURE:
<221> NAME/KEY: VARIANT
<222> LOCATION: 140
<223> OTHER INFORMATION: Xaa can be any naturally occuring amino acid
<220> FEATURE:
<221> NAME/KEY: VARIANT
<222> LOCATION: 143
<223> OTHER INFORMATION: Xaa can be any naturally occuring amino acid
<220> FEATURE:
<221> NAME/KEY: VARIANT
<222> LOCATION: 144
<223> OTHER INFORMATION: Xaa can be any naturally occuring amino acid
<220> FEATURE:
<221> NAME/KEY: VARIANT
<222> LOCATION: 156
<223> OTHER INFORMATION: Xaa can be any naturally occuring amino acid
<220> FEATURE:
<221> NAME/KEY: VARIANT
<222> LOCATION: 163
<223> OTHER INFORMATION: Xaa can be any naturally occuring amino acid
<220> FEATURE:
<221> NAME/KEY: VARIANT
<222> LOCATION: 165
<223> OTHER INFORMATION: Xaa can be any naturally occuring amino acid
<220> FEATURE:
<221> NAME/KEY: VARIANT
<222> LOCATION: 166
<223> OTHER INFORMATION: Xaa can be any naturally occuring amino acid
<220> FEATURE:
<221> NAME/KEY: VARIANT
<222> LOCATION: 168
<223> OTHER INFORMATION: Xaa can be any naturally occuring amino acid
<220> FEATURE:
<221> NAME/KEY: VARIANT
<222> LOCATION: 173
<223> OTHER INFORMATION: Xaa can be any naturally occuring amino acid
<220> FEATURE:
<221> NAME/KEY: VARIANT
<222> LOCATION: 177
<223> OTHER INFORMATION: Xaa can be any naturally occuring amino acid
<220> FEATURE:
<221> NAME/KEY: VARIANT
<222> LOCATION: 189
<223> OTHER INFORMATION: Xaa can be any naturally occuring amino acid
<220> FEATURE:
<221> NAME/KEY: VARIANT
<222> LOCATION: 190
<223> OTHER INFORMATION: Xaa can be any naturally occuring amino acid

<400> SEQUENCE: 98

Asp Leu Gly Xaa Lys Leu Leu Gln Ala Ala Xaa Xaa Gly Gln Leu Asp
1               5                   10                  15

Glu Val Arg Xaa Leu Xaa Xaa Xaa Gly Ala Asp Val Asn Ala Xaa Asp
```

```
                20                  25                  30
Xaa Xaa Gly Xaa Thr Pro Leu His Xaa Ala Ala Xaa Xaa G

```
<220> FEATURE:
<221> NAME/KEY: VARIANT
<222> LOCATION: 45
<223> OTHER INFORMATION: Xaa can be any naturally occuring amino acid
<220> FEATURE:
<221> NAME/KEY: VARIANT
<222> LOCATION: 57
<223> OTHER INFORMATION: Xaa can be any naturally occuring amino acid
<220> FEATURE:
<221> NAME/KEY: VARIANT
<222> LOCATION: 64
<223> OTHER INFORMATION: Xaa can be any naturally occuring amino acid
<220> FEATURE:
<221> NAME/KEY: VARIANT
<222> LOCATION: 74
<223> OTHER INFORMATION: Xaa can be any naturally occuring amino acid
<220> FEATURE:
<221> NAME/KEY: VARIANT
<222> LOCATION: 78
<223> OTHER INFORMATION: Xaa can be any naturally occuring amino acid
<220> FEATURE:
<221> NAME/KEY: VARIANT
<222> LOCATION: 90
<223> OTHER INFORMATION: Xaa can be any naturally occuring amino acid
<220> FEATURE:
<221> NAME/KEY: VARIANT
<222> LOCATION: 91
<223> OTHER INFORMATION: Xaa can be any naturally occuring amino acid

<400> SEQUENCE: 99

Asp Leu Gly Ser Lys Leu Leu Gln Ala Ala Xaa Xaa Gly Gln Leu Asp
1               5                   10                  15

Thr Val Arg Thr Leu Xaa Gln Xaa Gly Ala Asp Val Asn Ala Xaa Asp
            20                  25                  30

Xaa Xaa Gly Xaa Thr Pro Leu His Xaa Ala Ala Xaa Xaa Gly His Leu
        35                  40                  45

Glu Ile Val Glu Val Leu Leu Lys Xaa Gly Ala Asp Val Asn Ala Xaa
50                  55                  60

Asp Thr Gln Gly Thr Thr Pro Ala Asp Xaa Ala Ala Arg Xaa Gly His
65                  70                  75                  80

Gln Gln Ile Ala Ser Val Leu Gln Gln Xaa Xaa
                85                  90

<210> SEQ ID NO 100
<211> LENGTH: 124
<212> TYPE: PRT
<213> ORGANISM: Artificial Sequence
<220> FEATURE:
<223> OTHER INFORMATION: Ankyrin repeat domain
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 31
<223> OTHER INFORMATION: Xaa can be any naturally occuring amino acid
<220> FEATURE:
<221> NAME/KEY: VARIANT
<222> LOCATION: 33
```

```
<223> OTHER INFORMATION: Xaa can be any naturally occuring amino acid
<220> FEATURE:
<221> NAME/KEY: VARIANT
<222> LOCATION: 34
<223> OTHER INFORMATION: Xaa can be any naturally occuring amino acid
<220> FEATURE:
<221> NAME/KEY: VARIANT
<222> LOCATION: 36
<223> OTHER INFORMATION: Xaa can be any naturally occuring amino acid
<220> FEATURE:
<221> NAME/KEY: VARIANT
<222> LOCATION: 41
<223> OTHER INFORMATION: Xaa can be any naturally occuring amino acid
<220> FEATURE:
<221> NAME/KEY: VARIANT
<222> LOCATION: 44
<223> OTHER INFORMATION: Xaa can be any naturally occuring amino acid
<220> FEATURE:
<221> NAME/KEY: VARIANT
<222> LOCATION: 45
<223> OTHER INFORMATION: Xaa can be any naturally occuring amino acid
<220> FEATURE:
<221> NAME/KEY: VARIANT
<222> LOCATION: 57
<223> OTHER INFORMATION: Xaa can be any naturally occuring amino acid
<220> FEATURE:
<221> NAME/KEY: VARIANT
<222> LOCATION: 64
<223> OTHER INFORMATION: Xaa can be any naturally occuring amino acid
<220> FEATURE:
<221> NAME/KEY: VARIANT
<222> LOCATION: 66
<223> OTHER INFORMATION: Xaa can be any naturally occuring amino acid
<220> FEATURE:
<221> NAME/KEY: VARIANT
<222> LOCATION: 67
<223> OTHER INFORMATION: Xaa can be any naturally occuring amino acid
<220> FEATURE:
<221> NAME/KEY: VARIANT
<222> LOCATION: 69
<223> OTHER INFORMATION: Xaa can be any naturally occuring amino acid
<220> FEATURE:
<221> NAME/KEY: VARIANT
<222> LOCATION: 74
<223> OTHER INFORMATION: Xaa can be any naturally occuring amino acid
<220> FEATURE:
<221> NAME/KEY: VARIANT
<222> LOCATION: 77
<223> OTHER INFORMATION: Xaa can be any naturally occuring amino acid
<220> FEATURE:
<221> NAME/KEY: VARIANT
<222> LOCATION: 78
<223> OTHER INFORMATION: Xaa can be any naturally occuring amino acid
<220> FEATURE:
<221> NAME/KEY: VARIANT
<222> LOCATION: 90
<223> OTHER INFORMATION: Xaa can be any naturally occuring amino acid
<220> FEATURE:
<221> NAME/KEY: VARIANT
<222> LOCATION: 97
<223> OTHER INFORMATION: Xaa can be any naturally occuring amino acid
<220> FEATURE:
<221> NAME/KEY: VARIANT
<222> LOCATION: 107
<223> OTHER INFORMATION: Xaa can be any naturally occuring amino acid
<220> FEATURE:
<221> NAME/KEY: VARIANT
<222> LOCATION: 111
<223> OTHER INFORMATION: Xaa can be any naturally occuring amino acid
<220> FEATURE:
<221> NAME/KEY: VARIANT
<222> LOCATION: 123
<223> OTHER INFORMATION: Xaa can be any naturally occuring amino acid
<220> FEATURE:
<221> NAME/KEY: VARIANT
<222> LOCATION: 124
<223> OTHER INFORMATION: Xaa can be any naturally occuring amino acid

<400> SEQUENCE: 100
```

-continued

Asp Leu Gly Ser Lys Leu Leu Gln Ala Ala Xaa Xaa Gly Gln Leu Asp
1               5                   10                  15

Thr Val Arg Thr Leu Xaa Gln Xaa Gly Ala Asp Val Asn Ala Xaa Asp
            20                  25                  30

Xaa Xaa Gly Xaa Thr Pro Leu His Xaa Ala Ala Xaa Xaa Gly His Leu
        35                  40                  45

Glu Ile Val Glu Val Leu Leu Lys Xaa Gly Ala Asp Val Asn Ala Xaa
    50                  55                  60

Asp Xaa Xaa Gly Xaa Thr Pro Leu His Xaa Ala Ala Xaa Xaa Gly His
65              70                  75                  80

Leu Glu Ile Val Glu Val Leu Leu Lys Xaa Gly Ala Asp Val Asn Ala
            85                  90                  95

Xaa Asp Thr Gln Gly Thr Thr Pro Ala Asp Xaa Ala Ala Arg Xaa Gly
                100                 105                 110

His Gln Gln Ile Ala Ser Val Leu Gln Gln Xaa Xaa
        115                 120

<210> SEQ ID NO 101
<211> LENGTH: 157
<212> TYPE: PRT
<213> ORGANISM: Artificial Sequence
<220> FEATURE:
<223> OTHER INFORMATION: Ankyrin repeat domain
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 31
<223> OTHER INFORMATION: Xaa can be any naturally occuring amino acid
<220> FEATURE:
<221> NAME/KEY: VARIANT
<222> LOCATION: 33
<223> OTHER INFORMATION: Xaa can be any naturally occuring amino acid
<220> FEATURE:
<221> NAME/KEY: VARIANT
<222> LOCATION: 34
<223> OTHER INFORMATION: Xaa can be any naturally occuring amino acid
<220> FEATURE:
<221> NAME/KEY: VARIANT
<222> LOCATION: 36
<223> OTHER INFORMATION: Xaa can be any naturally occuring amino acid
<220> FEATURE:
<221> NAME/KEY: VARIANT
<222> LOCATION: 41
<223> OTHER INFORMATION: Xaa can be any naturally occuring amino acid
<220> FEATURE:
<221> NAME/KEY: VARIANT
<222> LOCATION: 44
<223> OTHER INFORMATION: Xaa can be any naturally occuring amino acid
<220> FEATURE:
<221> NAME/KEY: VARIANT
<222> LOCATION: 45
<223> OTHER INFORMATION: Xaa can be any naturally occuring amino acid
<220> FEATURE:
<221> NAME/KEY: VARIANT
<222> LOCATION: 57

-continued

```
<223> OTHER INFORMATION: Xaa can be any naturally occuring amino acid
<220> FEATURE:
<221> NAME/KEY: VARIANT
<222> LOCATION: 64
<223> OTHER INFORMATION: Xaa can be any naturally occuring amino acid
<220> FEATURE:
<221> NAME/KEY: VARIANT
<222> LOCATION: 66
<223> OTHER INFORMATION: Xaa can be any naturally occuring amino acid
<220> FEATURE:
<221> NAME/KEY: VARIANT
<222> LOCATION: 67
<223> OTHER INFORMATION: Xaa can be any naturally occuring amino acid
<220> FEATURE:
<221> NAME/KEY: VARIANT
<222> LOCATION: 69
<223> OTHER INFORMATION: Xaa can be any naturally occuring amino acid
<220> FEATURE:
<221> NAME/KEY: VARIANT
<222> LOCATION: 74
<223> OTHER INFORMATION: Xaa can be any naturally occuring amino acid
<220> FEATURE:
<221> NAME/KEY: VARIANT
<222> LOCATION: 77
<223> OTHER INFORMATION: Xaa can be any naturally occuring amino acid
<220> FEATURE:
<221> NAME/KEY: VARIANT
<222> LOCATION: 78
<223> OTHER INFORMATION: Xaa can be any naturally occuring amino acid
<220> FEATURE:
<221> NAME/KEY: VARIANT
<222> LOCATION: 90
<223> OTHER INFORMATION: Xaa can be any naturally occuring amino acid
<220> FEATURE:
<221> NAME/KEY: VARIANT
<222> LOCATION: 97
<223> OTHER INFORMATION: Xaa can be any naturally occuring amino acid
<220> FEATURE:
<221> NAME/KEY: VARIANT
<222> LOCATION: 99
<223> OTHER INFORMATION: Xaa can be any naturally occuring amino acid
<220> FEATURE:
<221> NAME/KEY: VARIANT
<222> LOCATION: 100
<223> OTHER INFORMATION: Xaa can be any naturally occuring amino acid
<220> FEATURE:
<221> NAME/KEY: VARIANT
<222> LOCATION: 102
<223> OTHER INFORMATION: Xaa can be any naturally occuring amino acid
<220> FEATURE:
<221> NAME/KEY: VARIANT
<222> LOCATION: 107
<223> OTHER INFORMATION: Xaa can be any naturally occuring amino acid
<220> FEATURE:
<221> NAME/KEY: VARIANT
<222> LOCATION: 110
<223> OTHER INFORMATION: Xaa can be any naturally occuring amino acid
<220> FEATURE:
<221> NAME/KEY: VARIANT
<222> LOCATION: 111
<223> OTHER INFORMATION: Xaa can be any naturally occuring amino acid
<220> FEATURE:
<221> NAME/KEY: VARIANT
<222> LOCATION: 123
<223> OTHER INFORMATION: Xaa can be any naturally occuring amino acid
<220> FEATURE:
<221> NAME/KEY: VARIANT
<222> LOCATION: 130
<223> OTHER INFORMATION: Xaa can be any naturally occuring amino acid
<220> FEATURE:
<221> NAME/KEY: VARIANT
<222> LOCATION: 140
<223> OTHER INFORMATION: Xaa can be any naturally occuring amino acid
<220> FEATURE:
<221> NAME/KEY: VARIANT
<222> LOCATION: 144
<223> OTHER INFORMATION: Xaa can be any naturally occuring amino acid
<220> FEATURE:
<221> NAME/KEY: VARIANT
```

```
<222> LOCATION: 156
<223> OTHER INFORMATION: Xaa can be any naturally occuring amino acid
<220> FEATURE:
<221> NAME/KEY: VARIANT
<222> LOCATION: 157
<223> OTHER INFORMATION: Xaa can be any naturally occuring amino acid

<400> SEQUENCE: 101

Asp Leu Gly Ser Lys Leu Leu Gln Ala Ala Xaa Xaa Gly Gln Leu Asp
1               5                   10                  15

Thr Val Arg Thr Leu Xaa Gln Xaa Gly Ala Asp Val Asn Ala Xaa Asp
            20                  25                  30

Xaa Xaa Gly Xaa Thr Pro Leu His Xaa Ala Ala Xaa Xaa Gly His Leu
        35                  40                  45

Glu Ile Val Glu Val Leu Leu Lys Xaa Gly Ala Asp Val Asn Ala Xaa
50                  55                  60

Asp Xaa Xaa Gly Xaa Thr Pro Leu His Xaa Ala Ala Xaa Xaa Gly His
65                  70                  75                  80

Leu Glu Ile Val Glu Val Leu Leu Lys Xaa Gly Ala Asp Val Asn Ala
                85                  90                  95

Xaa Asp Xaa Xaa Gly Xaa Thr Pro Leu His Xaa Ala Ala Xaa Xaa Gly
            100                 105                 110

His Leu Glu Ile Val Glu Val Leu Leu Lys Xaa Gly Ala Asp Val Asn
        115                 120                 125

Ala Xaa Asp Thr Gln Gly Thr Thr Pro Ala Asp Xaa Ala Ala Arg Xaa
    130                 135                 140

Gly His Gln Gln Ile Ala Ser Val Leu Gln Gln Xaa Xaa
145                 150                 155

<210> SEQ ID NO 102
<211> LENGTH: 190
<212> TYPE: PRT
<213> ORGANISM: Artificial Sequence
<220> FEATURE:
<223> OTHER INFORMATION: Ankyrin repeat domain
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 31
<223> OTHER INFORMATION: Xaa can be any naturally occuring amino acid
<220> FEATURE:
<221> NAME/KEY: VARIANT
<222> LOCATION: 33
<223> OTHER INFORMATION: Xaa can be any naturally occuring amino acid
<220> FEATURE:
<221> NAME/KEY: VARIANT
<222> LOCATION: 34
<223> OTHER INFORMATION: Xaa can be any naturally occuring amino acid
<220> FEATURE:
<221> NAME/KEY: VARIANT
<222> LOCATION: 36
<223> OTHER INFORMATION: Xaa can be any naturally occuring amino acid
<220> FEATURE:
```

-continued

```
<221> NAME/KEY: VARIANT
<222> LOCATION: 41
<223> OTHER INFORMATION: Xaa can be any naturally occuring amino acid
<220> FEATURE:
<221> NAME/KEY: VARIANT
<222> LOCATION: 44
<223> OTHER INFORMATION: Xaa can be any naturally occuring amino acid
<220> FEATURE:
<221> NAME/KEY: VARIANT
<222> LOCATION: 45
<223> OTHER INFORMATION: Xaa can be any naturally occuring amino acid
<220> FEATURE:
<221> NAME/KEY: VARIANT
<222> LOCATION: 57
<223> OTHER INFORMATION: Xaa can be any naturally occuring amino acid
<220> FEATURE:
<221> NAME/KEY: VARIANT
<222> LOCATION: 64
<223> OTHER INFORMATION: Xaa can be any naturally occuring amino acid
<220> FEATURE:
<221> NAME/KEY: VARIANT
<222> LOCATION: 66
<223> OTHER INFORMATION: Xaa can be any naturally occuring amino acid
<220> FEATURE:
<221> NAME/KEY: VARIANT
<222> LOCATION: 67
<223> OTHER INFORMATION: Xaa can be any naturally occuring amino acid
<220> FEATURE:
<221> NAME/KEY: VARIANT
<222> LOCATION: 69
<223> OTHER INFORMATION: Xaa can be any naturally occuring amino acid
<220> FEATURE:
<221> NAME/KEY: VARIANT
<222> LOCATION: 74
<223> OTHER INFORMATION: Xaa can be any naturally occuring amino acid
<220> FEATURE:
<221> NAME/KEY: VARIANT
<222> LOCATION: 77
<223> OTHER INFORMATION: Xaa can be any naturally occuring amino acid
<220> FEATURE:
<221> NAME/KEY: VARIANT
<222> LOCATION: 78
<223> OTHER INFORMATION: Xaa can be any naturally occuring amino acid
<220> FEATURE:
<221> NAME/KEY: VARIANT
<222> LOCATION: 90
<223> OTHER INFORMATION: Xaa can be any naturally occuring amino acid
<220> FEATURE:
<221> NAME/KEY: VARIANT
<222> LOCATION: 97
<223> OTHER INFORMATION: Xaa can be any naturally occuring amino acid
<220> FEATURE:
<221> NAME/KEY: VARIANT
<222> LOCATION: 99
<223> OTHER INFORMATION: Xaa can be any naturally occuring amino acid
<220> FEATURE:
<221> NAME/KEY: VARIANT
<222> LOCATION: 100
<223> OTHER INFORMATION: Xaa can be any naturally occuring amino acid
<220> FEATURE:
<221> NAME/KEY: VARIANT
<222> LOCATION: 102
<223> OTHER INFORMATION: Xaa can be any naturally occuring amino acid
<220> FEATURE:
<221> NAME/KEY: VARIANT
<222> LOCATION: 107
<223> OTHER INFORMATION: Xaa can be any naturally occuring amino acid
<220> FEATURE:
<221> NAME/KEY: VARIANT
<222> LOCATION: 110
<223> OTHER INFORMATION: Xaa can be any naturally occuring amino acid
<220> FEATURE:
<221> NAME/KEY: VARIANT
<222> LOCATION: 111
<223> OTHER INFORMATION: Xaa can be any naturally occuring amino acid
<220> FEATURE:
<221> NAME/KEY: VARIANT
<222> LOCATION: 123
<223> OTHER INFORMATION: Xaa can be any naturally occuring amino acid
```

```
<220> FEATURE:
<221> NAME/KEY: VARIANT
<222> LOCATION: 130
<223> OTHER INFORMATION: Xaa can be any naturally occuring amino acid
<220> FEATURE:
<221> NAME/KEY: VARIANT
<222> LOCATION: 132
<223> OTHER INFORMATION: Xaa can be any naturally occuring amino acid
<220> FEATURE:
<221> NAME/KEY: VARIANT
<222> LOCATION: 133
<223> OTHER INFORMATION: Xaa can be any naturally occuring amino acid
<220> FEATURE:
<221> NAME/KEY: VARIANT
<222> LOCATION: 135
<223> OTHER INFORMATION: Xaa can be any naturally occuring amino acid
<220> FEATURE:
<221> NAME/KEY: VARIANT
<222> LOCATION: 140
<223> OTHER INFORMATION: Xaa can be any naturally occuring amino acid
<220> FEATURE:
<221> NAME/KEY: VARIANT
<222> LOCATION: 143
<223> OTHER INFORMATION: Xaa can be any naturally occuring amino acid
<220> FEATURE:
<221> NAME/KEY: VARIANT
<222> LOCATION: 144
<223> OTHER INFORMATION: Xaa can be any naturally occuring amino acid
<220> FEATURE:
<221> NAME/KEY: VARIANT
<222> LOCATION: 156
<223> OTHER INFORMATION: Xaa can be any naturally occuring amino acid
<220> FEATURE:
<221> NAME/KEY: VARIANT
<222> LOCATION: 163
<223> OTHER INFORMATION: Xaa can be any naturally occuring amino acid
<220> FEATURE:
<221> NAME/KEY: VARIANT
<222> LOCATION: 173
<223> OTHER INFORMATION: Xaa can be any naturally occuring amino acid
<220> FEATURE:
<221> NAME/KEY: VARIANT
<222> LOCATION: 177
<223> OTHER INFORMATION: Xaa can be any naturally occuring amino acid
<220> FEATURE:
<221> NAME/KEY: VARIANT
<222> LOCATION: 189
<223> OTHER INFORMATION: Xaa can be any naturally occuring amino acid
<220> FEATURE:
<221> NAME/KEY: VARIANT
<222> LOCATION: 190
<223> OTHER INFORMATION: Xaa can be any naturally occuring amino acid

<400> SEQUENCE: 102

Asp Leu Gly Ser Lys Leu Leu Gln Ala Ala Xaa Xaa Gly Gln Leu Asp
1               5                   10                  15

Thr Val Arg Thr Leu Xaa Gln Xaa Gly Ala Asp Val Asn Ala Xaa Asp
            20                  25                  30

Xaa Xaa Gly Xaa Thr Pro Leu His Xaa Ala Ala Xaa Xaa Gly His Leu
        35                  40                  45

Glu Ile Val Glu Val Leu Leu Lys Xaa Gly Ala Asp Val Asn Ala Xaa
50                  55                  60

Asp Xaa Xaa Gly Xaa Thr Pro Leu His Xaa Ala Ala Xaa Xaa Gly His
65                  70                  75                  80

Leu Glu Ile Val Glu Val Leu Leu Lys Xaa Gly Ala Asp Val Asn Ala
                85                  90                  95

Xaa Asp Xaa Xaa Gly Xaa Thr Pro Leu His Xaa Ala Ala Xaa Xaa Gly
            100                 105                 110

His Leu Glu Ile Val Glu Val Leu Leu Lys Xaa Gly Ala Asp Val Asn
        115                 120                 125
```

```
Ala Xaa Asp Xaa Xaa Gly Xaa Thr Pro Leu His Xaa Ala Ala Xaa Xaa
    130                 135                 140

Gly His Leu Glu Ile Val Glu Val Leu Leu Lys Xaa Gly Ala Asp Val
145                 150                 155                 160

Asn Ala Xaa Asp Thr Gln Gly Thr Thr Pro Ala Asp Xaa Ala Ala Arg
                165                 170                 175

Xaa Gly His Gln Gln Ile Ala Ser Val Leu Gln Gln Xaa Xaa
            180                 185                 190

<210> SEQ ID NO 103
<211> LENGTH: 91
<212> TYPE: PRT
<213> ORGANISM: Artificial Sequence
<220> FEATURE:
<223> OTHER INFORMATION: Ankyrin repeat domain
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 31
<223> OTHER INFORMATION: Xaa can be any naturally occuring amino acid
<220> FEATURE:
<221> NAME/KEY: VARIANT
<222> LOCATION: 33
<223> OTHER INFORMATION: Xaa can be any naturally occuring amino acid
<220> FEATURE:
<221> NAME/KEY: VARIANT
<222> LOCATION: 34
<223> OTHER INFORMATION: Xaa can be any naturally occuring amino acid
<220> FEATURE:
<221> NAME/KEY: VARIANT
<222> LOCATION: 36
<223> OTHER INFORMATION: Xaa can be any naturally occuring amino acid
<220> FEATURE:
<221> NAME/KEY: VARIANT
<222> LOCATION: 41
<223> OTHER INFORMATION: Xaa can be any naturally occuring amino acid
<220> FEATURE:
<221> NAME/KEY: VARIANT
<222> LOCATION: 44
<223> OTHER INFORMATION: Xaa can be any naturally occuring amino acid
<220> FEATURE:
<221> NAME/KEY: VARIANT
<222> LOCATION: 45
<223> OTHER INFORMATION: Xaa can be any naturally occuring amino acid
<220> FEATURE:
<221> NAME/KEY: VARIANT
<222> LOCATION: 57
<223> OTHER INFORMATION: Xaa can be any naturally occuring amino acid
```

-continued

```
<220> FEATURE:
<221> NAME/KEY: VARIANT
<222> LOCATION: 64
<223> OTHER INFORMATION: Xaa can be any naturally occuring amino acid
<220> FEATURE:
<221> NAME/KEY: VARIANT
<222> LOCATION: 66
<223> OTHER INFORMATION: Xaa can be any naturally occuring amino acid
<220> FEATURE:
<221> NAME/KEY: VARIANT
<222> LOCATION: 67
<223> OTHER INFORMATION: Xaa can be any naturally occuring amino acid
<220> FEATURE:
<221> NAME/KEY: VARIANT
<222> LOCATION: 69
<223> OTHER INFORMATION: Xaa can be any naturally occuring amino acid
<220> FEATURE:
<221> NAME/KEY: VARIANT
<222> LOCATION: 74
<223> OTHER INFORMATION: Xaa can be any naturally occuring amino acid
<220> FEATURE:
<221> NAME/KEY: VARIANT
<222> LOCATION: 77
<223> OTHER INFORMATION: Xaa can be any naturally occuring amino acid
<220> FEATURE:
<221> NAME/KEY: VARIANT
<222> LOCATION: 78
<223> OTHER INFORMATION: Xaa can be any naturally occuring amino acid
<220> FEATURE:
<221> NAME/KEY: VARIANT
<222> LOCATION: 90
<223> OTHER INFORMATION: Xaa can be any naturally occuring amino acid
<220> FEATURE:
<221> NAME/KEY: VARIANT
<222> LOCATION: 91
<223> OTHER INFORMATION: Xaa can be any naturally occuring amino acid

<400> SEQUENCE: 103

Asp Leu Gly Xaa Lys Leu Leu Glu Ala Ala Xaa Xaa Gly Gln Asp Asp
1               5                   10                  15

Glu Val Arg Xaa Leu Xaa Xaa Xaa Gly Ala Asp Val Asn Ala Xaa Asp
                20                  25                  30

Xaa Xaa Gly Xaa Thr Pro Leu His Xaa Ala Ala Xaa Xaa Gly His Leu
            35                  40                  45

Glu Ile Val Glu Val Leu Leu Lys Xaa Gly Ala Asp Val Asn Ala Xaa
    50                  55                  60

Asp Xaa Xaa Gly Xaa Thr Pro Ala Asp Xaa Ala Ala Xaa Xaa Gly His
65                  70                  75                  80

Glu Asp Ile Ala Glu Val Leu Gln Lys Xaa Xaa
                85                  90

<210> SEQ ID NO 104
<211> LENGTH: 124
<212> TYPE: PRT
<213> ORGANISM: Artificial Sequence
<220> FEATURE:
<223> OTHER INFORMATION: Ankyrin repeat domain
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 20
```

-continued

```
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 31
<223> OTHER INFORMATION: Xaa can be any naturally occuring amino acid
<220> FEATURE:
<221> NAME/KEY: VARIANT
<222> LOCATION: 33
<223> OTHER INFORMATION: Xaa can be any naturally occuring amino acid
<220> FEATURE:
<221> NAME/KEY: VARIANT
<222> LOCATION: 34
<223> OTHER INFORMATION: Xaa can be any naturally occuring amino acid
<220> FEATURE:
<221> NAME/KEY: VARIANT
<222> LOCATION: 36
<223> OTHER INFORMATION: Xaa can be any naturally occuring amino acid
<220> FEATURE:
<221> NAME/KEY: VARIANT
<222> LOCATION: 41
<223> OTHER INFORMATION: Xaa can be any naturally occuring amino acid
<220> FEATURE:
<221> NAME/KEY: VARIANT
<222> LOCATION: 44
<223> OTHER INFORMATION: Xaa can be any naturally occuring amino acid
<220> FEATURE:
<221> NAME/KEY: VARIANT
<222> LOCATION: 45
<223> OTHER INFORMATION: Xaa can be any naturally occuring amino acid
<220> FEATURE:
<221> NAME/KEY: VARIANT
<222> LOCATION: 57
<223> OTHER INFORMATION: Xaa can be any naturally occuring amino acid
<220> FEATURE:
<221> NAME/KEY: VARIANT
<222> LOCATION: 64
<223> OTHER INFORMATION: Xaa can be any naturally occuring amino acid
<220> FEATURE:
<221> NAME/KEY: VARIANT
<222> LOCATION: 66
<223> OTHER INFORMATION: Xaa can be any naturally occuring amino acid
<220> FEATURE:
<221> NAME/KEY: VARIANT
<222> LOCATION: 67
<223> OTHER INFORMATION: Xaa can be any naturally occuring amino acid
<220> FEATURE:
<221> NAME/KEY: VARIANT
<222> LOCATION: 69
<223> OTHER INFORMATION: Xaa can be any naturally occuring amino acid
<220> FEATURE:
<221> NAME/KEY: VARIANT
<222> LOCATION: 74
<223> OTHER INFORMATION: Xaa can be any naturally occuring amino acid
<220> FEATURE:
<221> NAME/KEY: VARIANT
<222> LOCATION: 77
<223> OTHER INFORMATION: Xaa can be any naturally occuring amino acid
<220> FEATURE:
<221> NAME/KEY: VARIANT
<222> LOCATION: 78
<223> OTHER INFORMATION: Xaa can be any naturally occuring amino acid
<220> FEATURE:
<221> NAME/KEY: VARIANT
<222> LOCATION: 90
<223> OTHER INFORMATION: Xaa can be any naturally occuring amino acid
<220> FEATURE:
<221> NAME/KEY: VARIANT
```

```
<222> LOCATION: 97
<223> OTHER INFORMATION: Xaa can be any naturally occuring amino acid
<220> FEATURE:
<221> NAME/KEY: VARIANT
<222> LOCATION: 99
<223> OTHER INFORMATION: Xaa can be any naturally occuring amino acid
<220> FEATURE:
<221> NAME/KEY: VARIANT
<222> LOCATION: 100
<223> OTHER INFORMATION: Xaa can be any naturally occuring amino acid
<220> FEATURE:
<221> NAME/KEY: VARIANT
<222> LOCATION: 102
<223> OTHER INFORMATION: Xaa can be any naturally occuring amino acid
<220> FEATURE:
<221> NAME/KEY: VARIANT
<222> LOCATION: 107
<223> OTHER INFORMATION: Xaa can be any naturally occuring amino acid
<220> FEATURE:
<221> NAME/KEY: VARIANT
<222> LOCATION: 110
<223> OTHER INFORMATION: Xaa can be any naturally occuring amino acid
<220> FEATURE:
<221> NAME/KEY: VARIANT
<222> LOCATION: 111
<223> OTHER INFORMATION: Xaa can be any naturally occuring amino acid
<220> FEATURE:
<221> NAME/KEY: VARIANT
<222> LOCATION: 123
<223> OTHER INFORMATION: Xaa can be any naturally occuring amino acid
<220> FEATURE:
<221> NAME/KEY: VARIANT
<222> LOCATION: 124
<223> OTHER INFORMATION: Xaa can be any naturally occuring amino acid

<400> SEQUENCE: 104

Asp Leu Gly Xaa Lys Leu Leu Glu Ala Ala Xaa Xaa Gly Gln Asp Asp
1               5                   10                  15

Glu Val Arg Xaa Leu Xaa Xaa Xaa Gly Ala Asp Val Asn Ala Xaa Asp
                20                  25                  30

Xaa Xaa Gly Xaa Thr Pro Leu His Xaa Ala Ala Xaa Xaa Gly His Leu
            35                  40                  45

Glu Ile Val Glu Val Leu Leu Lys Xaa Gly Ala Asp Val Asn Ala Xaa
50                  55                  60

Asp Xaa Xaa Gly Xaa Thr Pro Leu His Xaa Ala Ala Xaa Xaa Gly His
65                  70                  75                  80

Leu Glu Ile Val Glu Val Leu Leu Lys Xaa Gly Ala Asp Val Asn Ala
                85                  90                  95

Xaa Asp Xaa Xaa Gly Xaa Thr Pro Ala Asp Xaa Ala Ala Xaa Xaa Gly
            100                 105                 110

His Glu Asp Ile Ala Glu Val Leu Gln Lys Xaa Xaa
            115                 120

<210> SEQ ID NO 105
<211> LENGTH: 157
<212> TYPE: PRT
<213> ORGANISM: Artificial Sequence
<220> FEATURE:
<223> OTHER INFORMATION: Ankyrin repeat domain
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
```

```
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 31
<223> OTHER INFORMATION: Xaa can be any naturally occuring amino acid
<220> FEATURE:
<221> NAME/KEY: VARIANT
<222> LOCATION: 33
<223> OTHER INFORMATION: Xaa can be any naturally occuring amino acid
<220> FEATURE:
<221> NAME/KEY: VARIANT
<222> LOCATION: 34
<223> OTHER INFORMATION: Xaa can be any naturally occuring amino acid
<220> FEATURE:
<221> NAME/KEY: VARIANT
<222> LOCATION: 36
<223> OTHER INFORMATION: Xaa can be any naturally occuring amino acid
<220> FEATURE:
<221> NAME/KEY: VARIANT
<222> LOCATION: 41
<223> OTHER INFORMATION: Xaa can be any naturally occuring amino acid
<220> FEATURE:
<221> NAME/KEY: VARIANT
<222> LOCATION: 44
<223> OTHER INFORMATION: Xaa can be any naturally occuring amino acid
<220> FEATURE:
<221> NAME/KEY: VARIANT
<222> LOCATION: 45
<223> OTHER INFORMATION: Xaa can be any naturally occuring amino acid
<220> FEATURE:
<221> NAME/KEY: VARIANT
<222> LOCATION: 57
<223> OTHER INFORMATION: Xaa can be any naturally occuring amino acid
<220> FEATURE:
<221> NAME/KEY: VARIANT
<222> LOCATION: 64
<223> OTHER INFORMATION: Xaa can be any naturally occuring amino acid
<220> FEATURE:
<221> NAME/KEY: VARIANT
<222> LOCATION: 66
<223> OTHER INFORMATION: Xaa can be any naturally occuring amino acid
<220> FEATURE:
<221> NAME/KEY: VARIANT
<222> LOCATION: 67
<223> OTHER INFORMATION: Xaa can be any naturally occuring amino acid
<220> FEATURE:
<221> NAME/KEY: VARIANT
<222> LOCATION: 69
<223> OTHER INFORMATION: Xaa can be any naturally occuring amino acid
<220> FEATURE:
<221> NAME/KEY: VARIANT
<222> LOCATION: 74
<223> OTHER INFORMATION: Xaa can be any naturally occuring amino acid
<220> FEATURE:
<221> NAME/KEY: VARIANT
<222> LOCATION: 77
<223> OTHER INFORMATION: Xaa can be any naturally occuring amino acid
<220> FEATURE:
<221> NAME/KEY: VARIANT
<222> LOCATION: 78
<223> OTHER INFORMATION: Xaa can be any naturally occuring amino acid
<220> FEATURE:
<221> NAME/KEY: VARIANT
```

```
<222> LOCATION: 90
<223> OTHER INFORMATION: Xaa can be any naturally occuring amino acid
<220> FEATURE:
<221> NAME/KEY: VARIANT
<222> LOCATION: 97
<223> OTHER INFORMATION: Xaa can be any naturally occuring amino acid
<220> FEATURE:
<221> NAME/KEY: VARIANT
<222> LOCATION: 99
<223> OTHER INFORMATION: Xaa can be any naturally occuring amino acid
<220> FEATURE:
<221> NAME/KEY: VARIANT
<222> LOCATION: 100
<223> OTHER INFORMATION: Xaa can be any naturally occuring amino acid
<220> FEATURE:
<221> NAME/KEY: VARIANT
<222> LOCATION: 102
<223> OTHER INFORMATION: Xaa can be any naturally occuring amino acid
<220> FEATURE:
<221> NAME/KEY: VARIANT
<222> LOCATION: 107
<223> OTHER INFORMATION: Xaa can be any naturally occuring amino acid
<220> FEATURE:
<221> NAME/KEY: VARIANT
<222> LOCATION: 110
<223> OTHER INFORMATION: Xaa can be any naturally occuring amino acid
<220> FEATURE:
<221> NAME/KEY: VARIANT
<222> LOCATION: 111
<223> OTHER INFORMATION: Xaa can be any naturally occuring amino acid
<220> FEATURE:
<221> NAME/KEY: VARIANT
<222> LOCATION: 123
<223> OTHER INFORMATION: Xaa can be any naturally occuring amino acid
<220> FEATURE:
<221> NAME/KEY: VARIANT
<222> LOCATION: 130
<223> OTHER INFORMATION: Xaa can be any naturally occuring amino acid
<220> FEATURE:
<221> NAME/KEY: VARIANT
<222> LOCATION: 132
<223> OTHER INFORMATION: Xaa can be any naturally occuring amino acid
<220> FEATURE:
<221> NAME/KEY: VARIANT
<222> LOCATION: 133
<223> OTHER INFORMATION: Xaa can be any naturally occuring amino acid
<220> FEATURE:
<221> NAME/KEY: VARIANT
<222> LOCATION: 135
<223> OTHER INFORMATION: Xaa can be any naturally occuring amino acid
<220> FEATURE:
<221> NAME/KEY: VARIANT
<222> LOCATION: 140
<223> OTHER INFORMATION: Xaa can be any naturally occuring amino acid
<220> FEATURE:
<221> NAME/KEY: VARIANT
<222> LOCATION: 143
<223> OTHER INFORMATION: Xaa can be any naturally occuring amino acid
<220> FEATURE:
<221> NAME/KEY: VARIANT
<222> LOCATION: 144
<223> OTHER INFORMATION: Xaa can be any naturally occuring amino acid
<220> FEATURE:
<221> NAME/KEY: VARIANT
<222> LOCATION: 156
<223> OTHER INFORMATION: Xaa can be any naturally occuring amino acid
<220> FEATURE:
<221> NAME/KEY: VARIANT
<222> LOCATION: 157
<223> OTHER INFORMATION: Xaa can be any naturally occuring amino acid

<400> SEQUENCE: 105

Asp Leu Gly Xaa Lys Leu Leu Glu Ala Ala Xaa Xaa Gly Gln Asp Asp
1               5                   10                  15

Glu Val Arg Xaa Leu Xaa Xaa Xaa Gly Ala Asp Val Asn Ala Xaa Asp
            20                  25                  30
```

```
Xaa Xaa Gly Xaa Thr Pro Leu His Xaa Ala Ala Xaa Xaa Gly His Leu
        35                  40                  45

Glu Ile Val Glu Val Leu Leu Lys Xaa Gly Ala Asp Val Asn Ala Xaa
    50                  55                  60

Asp Xaa Xaa Gly Xaa Thr Pro Leu His Xaa Ala Ala Xaa Xaa Gly His
65                  70                  75                  80

Leu Glu Ile Val Glu Val Leu Leu Lys Xaa Gly Ala Asp Val Asn Ala
                85                  90                  95

Xaa Asp Xaa Xaa Gly Xaa Thr Pro Leu His Xaa Ala Ala Xaa Xaa Gly
            100                 105                 110

His Leu Glu Ile Val Glu Val Leu Leu Lys Xaa Gly Ala Asp Val Asn
        115                 120                 125

Ala Xaa Asp Xaa Xaa Gly Xaa Thr Pro Ala Asp Xaa Ala Ala Xaa Xaa
    130                 135                 140

Gly His Glu Asp Ile Ala Glu Val Leu Gln Lys Xaa Xaa
145                 150                 155
```

<210> SEQ ID NO 106
<211> LENGTH: 190
<212> TYPE: PRT
<213> ORGANISM: Artificial Sequence
<220> FEATURE:
<223> OTHER INFORMATION: Ankyrin repeat domain
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid
<220> FEATURE:
<221> NAME/KEY: VARIANT
<222> LOCATION: 31
<223> OTHER INFORMATION: Xaa can be any naturally occuring amino acid
<220> FEATURE:
<221> NAME/KEY: VARIANT
<222> LOCATION: 33
<223> OTHER INFORMATION: Xaa can be any naturally occuring amino acid
<220> FEATURE:
<221> NAME/KEY: VARIANT
<222> LOCATION: 34
<223> OTHER INFORMATION: Xaa can be any naturally occuring amino acid
<220> FEATURE:
<221> NAME/KEY: VARIANT
<222> LOCATION: 36
<223> OTHER INFORMATION: Xaa can be any naturally occuring amino acid
<220> FEATURE:
<221> NAME/KEY: VARIANT
<222> LOCATION: 41
<223> OTHER INFORMATION: Xaa can be any naturally occuring amino acid

```
<220> FEATURE:
<221> NAME/KEY: VARIANT
<222> LOCATION: 44
<223> OTHER INFORMATION: Xaa can be any naturally occuring amino acid
<220> FEATURE:
<221> NAME/KEY: VARIANT
<222> LOCATION: 45
<223> OTHER INFORMATION: Xaa can be any naturally occuring amino acid
<220> FEATURE:
<221> NAME/KEY: VARIANT
<222> LOCATION: 57
<223> OTHER INFORMATION: Xaa can be any naturally occuring amino acid
<220> FEATURE:
<221> NAME/KEY: VARIANT
<222> LOCATION: 64
<223> OTHER INFORMATION: Xaa can be any naturally occuring amino acid
<220> FEATURE:
<221> NAME/KEY: VARIANT
<222> LOCATION: 66
<223> OTHER INFORMATION: Xaa can be any naturally occuring amino acid
<220> FEATURE:
<221> NAME/KEY: VARIANT
<222> LOCATION: 67
<223> OTHER INFORMATION: Xaa can be any naturally occuring amino acid
<220> FEATURE:
<221> NAME/KEY: VARIANT
<222> LOCATION: 69
<223> OTHER INFORMATION: Xaa can be any naturally occuring amino acid
<220> FEATURE:
<221> NAME/KEY: VARIANT
<222> LOCATION: 74
<223> OTHER INFORMATION: Xaa can be any naturally occuring amino acid
<220> FEATURE:
<221> NAME/KEY: VARIANT
<222> LOCATION: 77
<223> OTHER INFORMATION: Xaa can be any naturally occuring amino acid
<220> FEATURE:
<221> NAME/KEY: VARIANT
<222> LOCATION: 78
<223> OTHER INFORMATION: Xaa can be any naturally occuring amino acid
<220> FEATURE:
<221> NAME/KEY: VARIANT
<222> LOCATION: 90
<223> OTHER INFORMATION: Xaa can be any naturally occuring amino acid
<220> FEATURE:
<221> NAME/KEY: VARIANT
<222> LOCATION: 97
<223> OTHER INFORMATION: Xaa can be any naturally occuring amino acid
<220> FEATURE:
<221> NAME/KEY: VARIANT
<222> LOCATION: 99
<223> OTHER INFORMATION: Xaa can be any naturally occuring amino acid
<220> FEATURE:
<221> NAME/KEY: VARIANT
<222> LOCATION: 100
<223> OTHER INFORMATION: Xaa can be any naturally occuring amino acid
<220> FEATURE:
<221> NAME/KEY: VARIANT
<222> LOCATION: 102
<223> OTHER INFORMATION: Xaa can be any naturally occuring amino acid
<220> FEATURE:
<221> NAME/KEY: VARIANT
<222> LOCATION: 107
<223> OTHER INFORMATION: Xaa can be any naturally occuring amino acid
<220> FEATURE:
<221> NAME/KEY: VARIANT
<222> LOCATION: 110
<223> OTHER INFORMATION: Xaa can be any naturally occuring amino acid
<220> FEATURE:
<221> NAME/KEY: VARIANT
<222> LOCATION: 111
<223> OTHER INFORMATION: Xaa can be any naturally occuring amino acid
<220> FEATURE:
<221> NAME/KEY: VARIANT
<222> LOCATION: 123
<223> OTHER INFORMATION: Xaa can be any naturally occuring amino acid
<220> FEATURE:
<221> NAME/KEY: VARIANT
<222> LOCATION: 130
```

```
<223> OTHER INFORMATION: Xaa can be any naturally occuring amino acid
<220> FEATURE:
<221> NAME/KEY: VARIANT
<222> LOCATION: 132
<223> OTHER INFORMATION: Xaa can be any naturally occuring amino acid
<220> FEATURE:
<221> NAME/KEY: VARIANT
<222> LOCATION: 133
<223> OTHER INFORMATION: Xaa can be any naturally occuring amino acid
<220> FEATURE:
<221> NAME/KEY: VARIANT
<222> LOCATION: 135
<223> OTHER INFORMATION: Xaa can be any naturally occuring amino acid
<220> FEATURE:
<221> NAME/KEY: VARIANT
<222> LOCATION: 140
<223> OTHER INFORMATION: Xaa can be any naturally occuring amino acid
<220> FEATURE:
<221> NAME/KEY: VARIANT
<222> LOCATION: 143
<223> OTHER INFORMATION: Xaa can be any naturally occuring amino acid
<220> FEATURE:
<221> NAME/KEY: VARIANT
<222> LOCATION: 144
<223> OTHER INFORMATION: Xaa can be any naturally occuring amino acid
<220> FEATURE:
<221> NAME/KEY: VARIANT
<222> LOCATION: 156
<223> OTHER INFORMATION: Xaa can be any naturally occuring amino acid
<220> FEATURE:
<221> NAME/KEY: VARIANT
<222> LOCATION: 163
<223> OTHER INFORMATION: Xaa can be any naturally occuring amino acid
<220> FEATURE:
<221> NAME/KEY: VARIANT
<222> LOCATION: 165
<223> OTHER INFORMATION: Xaa can be any naturally occuring amino acid
<220> FEATURE:
<221> NAME/KEY: VARIANT
<222> LOCATION: 166
<223> OTHER INFORMATION: Xaa can be any naturally occuring amino acid
<220> FEATURE:
<221> NAME/KEY: VARIANT
<222> LOCATION: 168
<223> OTHER INFORMATION: Xaa can be any naturally occuring amino acid
<220> FEATURE:
<221> NAME/KEY: VARIANT
<222> LOCATION: 173
<223> OTHER INFORMATION: Xaa can be any naturally occuring amino acid
<220> FEATURE:
<221> NAME/KEY: VARIANT
<222> LOCATION: 176
<223> OTHER INFORMATION: Xaa can be any naturally occuring amino acid
<220> FEATURE:
<221> NAME/KEY: VARIANT
<222> LOCATION: 177
<223> OTHER INFORMATION: Xaa can be any naturally occuring amino acid
<220> FEATURE:
<221> NAME/KEY: VARIANT
<222> LOCATION: 189
<223> OTHER INFORMATION: Xaa can be any naturally occuring amino acid
<220> FEATURE:
<221> NAME/KEY: VARIANT
<222> LOCATION: 190
<223> OTHER INFORMATION: Xaa can be any naturally occuring amino acid

<400> SEQUENCE: 106

Asp Leu Gly Xaa Lys Leu Leu Glu Ala Ala Xaa Xaa Gly Gln Asp Asp
 1               5                  10                  15

Glu Val Arg Xaa Leu Xaa Xaa Xaa Gly Ala Asp Val Asn Ala Xaa Asp
             20                  25                  30

Xaa Xaa Gly Xaa Thr Pro Leu His Xaa Ala Ala Xaa Xaa Gly His Leu
         35                  40                  45

Glu Ile Val Glu Val Leu Leu Lys Xaa Gly Ala Asp Val Asn Ala Xaa
     50                  55                  60
```

```
Asp Xaa Xaa Gly Xaa Thr Pro Leu His Xaa Ala Ala Xaa Xaa Gly His
 65                  70                  75                  80

Leu Glu Ile Val Glu Val Leu Leu Lys Xaa Gly Ala Asp Val Asn Ala
                 85                  90                  95

Xaa Asp Xaa Xaa Gly Xaa Thr Pro Leu His Xaa Ala Ala Xaa Xaa Gly
            100                 105                 110

His Leu Glu Ile Val Glu Val Leu Leu Lys Xaa Gly Ala Asp Val Asn
        115                 120                 125

Ala Xaa Asp Xaa Xaa Gly Xaa Thr Pro Leu His Xaa Ala Ala Xaa Xaa
130                 135                 140

Gly His Leu Glu Ile Val Glu Val Leu Leu Lys Xaa Gly Ala Asp Val
145                 150                 155                 160

Asn Ala Xaa Asp Xaa Xaa Gly Xaa Thr Pro Ala Asp Xaa Ala Ala Xaa
                165                 170                 175

Xaa Gly His Glu Asp Ile Ala Glu Val Leu Gln Lys Xaa Xaa
            180                 185                 190

<210> SEQ ID NO 107
<211> LENGTH: 24
<212> TYPE: PRT
<213> ORGANISM: Artificial Sequence
<220> FEATURE:
<223> OTHER INFORMATION: N-terminal capping module sequence motif

<400> SEQUENCE: 107

Asp Leu Gly Lys Lys Leu Leu Gln Ala Ala Arg Ala Gly Gln Leu Asp
 1               5                  10                  15

Glu Val Arg Glu Leu Leu Lys Ala
            20

<210> SEQ ID NO 108
<211> LENGTH: 24
<212> TYPE: PRT
<213> ORGANISM: Artificial Sequence
<220> FEATURE:
<223> OTHER INFORMATION: N-terminal capping module sequence motif

<400> SEQUENCE: 108

Asp Leu Gly Ser Lys Leu Leu Gln Ala Ala Arg Ala Gly Gln Leu Asp
 1               5                  10                  15

Thr Val Arg Thr Leu Leu Gln Ala
            20

<210> SEQ ID NO 109
<211> LENGTH: 24
<212> TYPE: PRT
<213> ORGANISM: Artificial Sequence
<220> FEATURE:
<223> OTHER INFORMATION: N-terminal capping module sequence motif
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid

<400> SEQUENCE: 109
```

Asp Leu Gly Xaa Lys Leu Leu Gln Ala Ala Xaa Xaa Gly Gln Leu Asp
1               5                   10                  15

Glu Val Arg Glu Leu Leu Lys Ala
            20

<210> SEQ ID NO 110
<211> LENGTH: 24
<212> TYPE: PRT
<213> ORGANISM: Artificial Sequence
<220> FEATURE:
<223> OTHER INFORMATION: N-terminal capping module sequence motif
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid

<400> SEQUENCE: 110

Asp Leu Gly Xaa Lys Leu Leu Gln Ala Ala Xaa Xaa Gly Gln Leu Asp
1               5                   10                  15

Xaa Val Arg Xaa Leu Leu Xaa Ala
            20

<210> SEQ ID NO 111
<211> LENGTH: 24
<212> TYPE: PRT
<213> ORGANISM: Artificial Sequence
<220> FEATURE:
<223> OTHER INFORMATION: N-terminal capping module sequence motif
<220> FEATURE:
<221> NAME/KEY: VARIANT
<222> LOCATION: 4
<223> OTHER INFORMATION: Xaa can be any naturally occuring amino acid
<220> FEATURE:
<221> NAME/KEY: VARIANT
<222> LOCATION: 5
<223> OTHER INFORMATION: Xaa can be any naturally occuring amino acid
<220> FEATURE:
<221> NAME/KEY: VARIANT
<222> LOCATION: 11
<223> OTHER INFORMATION: Xaa can be any naturally occuring amino acid
<220> FEATURE:
<221> NAME/KEY: VARIANT
<222> LOCATION: 12
<223> OTHER INFORMATION: Xaa can be any naturally occuring amino acid
<220> FEATURE:
<221> NAME/KEY: VARIANT
<222> LOCATION: 17
<223> OTHER INFORMATION: Xaa can be any naturally occuring amino acid
<220> FEATURE:
<221> NAME/KEY: VARIANT
<222> LOCATION: 20
<223> OTHER INFORMATION: Xaa can be any naturally occuring amino acid
<220> FEATURE:
<221> NAME/KEY: VARIANT -continued

```
<222> LOCATION: 22
<223> OTHER INFORMATION: Xaa can be any naturally occuring amino acid
<220> FEATURE:
<221> NAME/KEY: VARIANT
<222> LOCATION: 23
<223> OTHER INFORMATION: Xaa can be any naturally occuring amino acid
<220> FEATURE:
<221> NAME/KEY: VARIANT
<222> LOCATION: 24
<223> OTHER INFORMATION: Xaa can be any naturally occuring amino acid

<400> SEQUENCE: 111

Asp Leu Gly Xaa Xaa Leu Leu Gln Ala Ala Xaa Xaa Gly Gln Leu Asp
1               5                   10                  15

Xaa Val Arg Xaa Leu Xaa Xaa Xaa
            20

<210> SEQ ID NO 112
<211> LENGTH: 32
<212> TYPE: PRT
<213> ORGANISM: Artificial Sequence
<220> FEATURE:
<223> OTHER INFORMATION: N-terminal capping module

<400> SEQUENCE: 112

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

<210> SEQ ID NO 113
<211> LENGTH: 32
<212> TYPE: PRT
<213> ORGANISM: Artificial Sequence
<220> FEATURE:
<223> OTHER INFORMATION: N-terminal capping module

<400> SEQUENCE: 113

Gly Ser Asp Leu Gly Lys Lys Leu Leu Gln Ala Ala Arg Ala Gly Gln
1               5                   10                  15

Leu Asp Glu Val Arg Ile Leu Leu Lys Ala Gly Ala Asp Val Asn Ala
            20                  25                  30

<210> SEQ ID NO 114
<211> LENGTH: 32
<212> TYPE: PRT
<213> ORGANISM: Artificial Sequence
<220> FEATURE:
<223> OTHER INFORMATION: N-terminal capping module

<400> SEQUENCE: 114

Gly Ser Asp Leu Gly Lys Lys Leu Leu Gln Ala Ala Arg Ala Gly Gln
1               5                   10                  15

Leu Asp Glu Val Arg Ile Leu Leu Ala Ala Gly Ala Asp Val Asn Ala
            20                  25                  30

<210> SEQ ID NO 115
<211> LENGTH: 340
<212> TYPE: PRT
<213> ORGANISM: Artificial Sequence
<220> FEATURE:
<223> OTHER INFORMATION: Ankyrin repeat protein specific for NY-ESO-1
      pMHC

<400> SEQUENCE: 115

Gly Ser Asp Leu Gly Lys Lys Leu Leu Gln Ala Ala Arg Ala Gly Gln
```

```
              1               5              10              15
            Leu Asp Glu Val Arg Glu Leu Leu Lys Ala Gly Ala Asp Val Asn Ala
                             20              25              30
            Lys Asp Leu Ile Gly Val Thr Pro Leu His Leu Ala Ala Phe Ser Gly
                             35              40              45
            His Leu Glu Ile Val Glu Val Leu Leu Lys Ala Ser Ala Asp Val Asn
                             50              55              60
            Ala Lys Asp Val Ser Gly Arg Thr Pro Leu His Val Ala Ala Lys His
             65              70              75              80
            Gly His Leu Glu Ile Val Glu Val Leu Leu Lys Ala Gly Ala Asp Val
                             85              90              95
            Asn Ala Lys Asp Leu Ile Gly Phe Thr Pro Leu His Leu Ala Ala Gln
                            100             105             110
            Phe Gly His Leu Glu Ile Val Glu Val Leu Leu Lys Ala Gly Ala Asp
                            115             120             125
            Val Asn Ala Gln Asp Lys Ser Gly Lys Thr Pro Ala Asp Leu Ala Ala
                            130             135             140
            Arg Ala Gly His Gln Asp Ile Ala Glu Val Leu Gln Lys Ala Ala Gly
            145             150             155             160
            Ser Pro Thr Pro Thr Pro Thr Thr Pro Thr Pro Thr Pro Thr Thr Pro
                            165             170             175
            Thr Pro Thr Pro Thr Gly Ser Asp Leu Gly Lys Lys Leu Leu Gln Ala
                            180             185             190
            Ala Arg Ala Gly Gln Leu Asp Glu Val Arg Glu Leu Leu Lys Ala Gly
                            195             200             205
            Ala Asp Val Asn Ala Lys Asp Leu Ile Gly Val Thr Pro Leu His Leu
            210             215             220
            Ala Ala Phe Ser Gly His Leu Glu Ile Val Glu Val Leu Leu Lys Ala
            225             230             235             240
            Ser Ala Asp Val Asn Ala Lys Asp Val Ser Gly Arg Thr Pro Leu His
                            245             250             255
            Val Ala Ala Lys His Gly His Leu Glu Ile Val Glu Val Leu Leu Lys
                            260             265             270
            Ala Gly Ala Asp Val Asn Ala Lys Asp Leu Ile Gly Phe Thr Pro Leu
                            275             280             285
            His Leu Ala Ala Gln Phe Gly His Leu Glu Ile Val Glu Val Leu Leu
                            290             295             300
            Lys Ala Gly Ala Asp Val Asn Ala Gln Asp Lys Ser Gly Lys Thr Pro
            305             310             315             320
            Ala Asp Leu Ala Ala Arg Ala Gly His Gln Asp Ile Ala Glu Val Leu
                            325             330             335
            Gln Lys Ala Ala
                            340

<210> SEQ ID NO 116
<211> LENGTH: 340
<212> TYPE: PRT
<213> ORGANISM: Artificial Sequence
<220> FEATURE:
<223> OTHER INFORMATION: Ankyrin repeat protein specific for NY-ESO-1
      pMHC

<400> SE

Leu Asp Glu Val Arg Glu Leu Leu Lys Ala Gly Ala Asp Val Asn Ala
            20                  25                  30

Lys Asp Gln Ser Gly Ala Thr Pro Leu His Leu Ala Ala Phe Arg Gly
        35                  40                  45

His Leu Glu Ile Val Glu Val Leu Leu Lys Ala Gly Ala Asp Val Asn
 50                  55                  60

Ala Lys Asp Ala Ala Gly Tyr Thr Pro Leu His Ile Ala Ala Val Tyr
65                  70                  75                  80

Gly His Leu Glu Ile Val Glu Val Leu Leu Lys Ala Gly Ala Asp Val
                85                  90                  95

Asn Ala Lys Asp Ser Ala Gly Thr Pro Leu His Leu Ala Ala Tyr
            100                 105                 110

Ala Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala Gly
145                 150                 155                 160

Ser Pro Thr Pro Thr Pro Thr Thr Pro Thr Pro Thr Pro Thr Thr Pro
                165                 170                 175

Thr Pro Thr Pro Thr Gly Ser Asp Leu Gly Lys Lys Leu Leu Gln Ala
            180                 185                 190

Ala Arg Ala Gly Gln Leu Asp Glu Val Arg Glu Leu Leu Lys Ala Gly
        195                 200                 205

Ala Asp Val Asn Ala Lys Asp Leu Ile Gly Val Thr Pro Leu His Leu
210                 215                 220

Ala Ala Phe Ser Gly His Leu Glu Ile Val Glu Val Leu Leu Lys Ala
225                 230                 235                 240

Ser Ala Asp Val Asn Ala Lys Asp Val Ser Gly Arg Thr Pro Leu His
                245                 250                 255

Val Ala Ala Lys His Gly His Leu Glu Ile Val Glu Val Leu Leu Lys
            260                 265                 270

Ala Gly Ala Asp Val Asn Ala Lys Asp Leu Ile Gly Phe Thr Pro Leu
        275                 280                 285

His Leu Ala Ala Gln Phe Gly His Leu Glu Ile Val Glu Val Leu Leu
    290                 295                 300

Lys Ala Gly Ala Asp Val Asn Ala Gln Asp Lys Ser Gly Lys Thr Pro
305                 310                 315                 320

Ala Asp Leu Ala Ala Arg Ala Gly His Gln Asp Ile Ala Glu Val Leu
                325                 330                 335

Gln Lys Ala Ala
            340

<210> SEQ ID NO 117
<211> LENGTH: 340
<212> TYPE: PRT
<213> ORGANISM: Artificial Sequence
<220> FEATURE:
<223> OTHER INFORMATION: Ankyrin repeat protein specific for NY-ESO-1
      pMHC

<400> SEQUENCE: 117

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

```
Lys Asp Leu Ile Gly Val Thr Pro Leu His Leu Ala Ala Phe Ser Gly
            35                  40                  45

His Leu Glu Ile Val Glu Val Leu Leu Lys Ala Ser Ala Asp Val Asn
     50                  55                  60

Ala Lys Asp Val Ser Gly Arg Thr Pro Leu His Val Ala Ala Lys His
 65                  70                  75                  80

Gly His Leu Glu Ile Val Glu Val Leu Leu Lys Ala Gly Ala Asp Val
                 85                  90                  95

Asn Ala Lys Asp Leu Ile Gly Phe Thr Pro Leu His Leu Ala Ala Gln
            100                 105                 110

Phe Gly His Leu Glu Ile Val Glu Val Leu Leu Lys Ala Gly Ala Asp
            115                 120                 125

Val Asn Ala Gln Asp Lys Ser Gly Lys Thr Pro Ala Asp Leu Ala Ala
        130                 135                 140

Arg Ala Gly His Gln Asp Ile Ala Glu Val Leu Gln Lys Ala Ala Gly
145                 150                 155                 160

Ser Pro Thr Pro Thr Pro Thr Pro Thr Pro Thr Pro Thr Pro Thr Pro
                165                 170                 175

Thr Pro Thr Pro Thr Gly Ser Asp Leu Gly Lys Lys Leu Leu Gln Ala
            180                 185                 190

Ala Arg Ala Gly Gln Leu Asp Glu Val Arg Glu Leu Leu Lys Ala Gly
        195                 200                 205

Ala Asp Val Asn Ala Lys Asp Ala Ile Gly Phe Thr Pro Leu His Leu
    210                 215                 220

Ala Ala Phe Ser Gly His Leu Glu Ile Val Glu Val Leu Leu Lys Ala
225                 230                 235                 240

Gly Ala Asp Val Asn Ala Lys Asp Val Ala Gly Tyr Thr Pro Leu His
                245                 250                 255

Val Ala Ala Leu Tyr Gly His Leu Val Ile Val Glu Val Leu Leu Lys
            260                 265                 270

Ala Gly Ala Asp Val Asn Ala Lys Asp Lys Ala Gly Glu Thr Pro Leu
        275                 280                 285

His Leu Ala Ala Phe Ala Gly His Leu Glu Ile Val Glu Val Leu Leu
    290                 295                 300

Lys Ala Gly Ala Asp Val Asn Ala Gln Asp Lys Ser Gly Lys Thr Pro
305                 310                 315                 320

Ala Asp Leu Ala Ala Arg Ala Gly His Gln Asp Ile Ala Glu Val Leu
                325                 330                 335

Gln Lys Ala Ala
        340

<210> SEQ ID NO 118
<211> LENGTH: 159
<212> TYPE: PRT
<213> ORGANISM: Artificial Sequence
<220> FEATURE:
<223> OTHER INFORMATION: Ankyrin repeat domain specific for NY-ESO-1
      pMHC

<400> SEQUENCE: 118

Gly Ser Asp Leu Gly Lys Lys Leu Leu Gln Ala Ala Arg Ala Gly Gln
 1               5                  10                  15

Leu Asp Glu Val Arg Glu Leu Leu Lys Ala Gly Ala Asp Val Asn Ala
             20                  25                  30

Lys Asp Gln Ser Gly Ala Thr Pro Leu His Leu Ala Ala Phe Arg Gly
```

```
                35                  40                  45
His Leu Glu Ile Val Glu Val Leu Leu Lys Ala Gly Ala Asp Val Asn
    50                  55                  60

Ala Lys Asp Ala Ala Gly Tyr Thr Pro Leu His Ile Ala Ala Val Tyr
65                  70                  75                  80

Gly His Leu Glu Ile Val Glu Val Leu Leu Lys Ala Gly Ala Asp Val
                85                  90                  95

Asn Ala Lys Asp Ser Ala Gly Glu Thr Pro Leu His Leu Ala Ala Tyr
            100                 105                 110

Ala Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155

<210> SEQ ID NO 119
<211> LENGTH: 159
<212> TYPE: PRT
<213> ORGANISM: Artificial Sequence
<220> FEATURE:
<223> OTHER INFORMATION: Ankyrin repeat domain specific for NY-ESO-1
      pMHC

<400> SEQUENCE: 119

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Leu Ile Gly Val Thr Pro Leu His Leu Ala Ala Phe Ser Gly
        35                  40                  45

His Leu Glu Ile Val Glu Val Leu Leu Lys Ala Ser Ala Asp Val Asn
    50                  55                  60

Ala Lys Asp Val Ser Gly Arg Thr Pro Leu His Val Ala Ala Lys His
65                  70                  75                  80

Gly His Leu Glu Ile Val Glu Val Leu Leu Lys Ala Gly Ala Asp Val
                85                  90                  95

Asn Ala Lys Asp Leu Ile Gly Phe Thr Pro Leu His Leu Ala Ala Gln
            100                 105                 110

Phe Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155

<210> SEQ ID NO 120
<211> LENGTH: 159
<212> TYPE: PRT
<213> ORGANISM: Artificial Sequence
<220> FEATURE:
<223> OTHER INFORMATION: Ankyrin repeat domain specific for NY-ESO-1
      pMHC

<400> SEQUENCE: 120

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
```

```
                20              25              30
Lys Asp Ala Ile Gly Phe Thr Pro Leu His Leu Ala Ala Phe Ser Gly
            35              40              45

His Leu Glu Ile Val Glu Val Leu Leu Lys Ala Gly Ala Asp Val Asn
        50              55              60

Ala Lys Asp Val Ala Gly Tyr Thr Pro Leu His Val Ala Ala Leu Tyr
65              70              75              80

Gly His Leu Val Ile Val Glu Val Leu Leu Lys Ala Gly Ala Asp Val
                85              90              95

Asn Ala Lys Asp Lys Ala Gly Glu Thr Pro Leu His Leu Ala Ala Phe
            100             105             110

Ala Gly His Leu Glu Ile Val Glu Val Leu Leu Lys Ala Gly Ala Asp
        115             120             125

Val Asn Ala Gln Asp Lys Ser Gly Lys Thr Pro Ala Asp Leu Ala Ala
    130             135             140

Arg Ala Gly His Gln Asp Ile Ala Glu Val Leu Gln Lys Ala Ala
145             150             155

<210> SEQ ID NO 121
<211> LENGTH: 159
<212> TYPE: PRT
<213> ORGANISM: Artificial Sequence
<220> FEATURE:
<223> OTHER INFORMATION: Ankyrin repeat domain specific for NY-ESO-1
      pMHC

<400> SEQUENCE: 121

Gly Ser Asp Leu Gly Lys Lys Leu Leu Gln Ala Ala Arg Ala Gly Gln
1               5               10              15

Leu Asp Glu Val Arg Glu Leu Leu Lys Ala Gly Ala Asp Val Asn Ala
            20              25              30

Lys Asp Arg Ala Gly Ser Thr Pro Leu His Leu Ala Ala Phe Arg Gly
            35              40              45

His Leu Glu Ile Val Glu Val Leu Leu Lys Ala Gly Ala Asp Val Asn
        50              55              60

Ala Lys Asp Ala Ala Gly Tyr Thr Pro Leu His Leu Ala Ala Leu Tyr
65              70              75              80

Gly His Leu Glu Ile Val Glu Val Leu Leu Lys Ala Gly Ala Asp Val
                85              90              95

Asn Ala Lys Asp His Ala Gly Ser Thr Pro Leu His Leu Ala Ala Leu
            100             105             110

Ala Gly His Leu Glu Ile Val Glu Val Leu Leu Lys Ala Gly Ala Asp
        115             120             125

Val Asn Ala Gln Asp Lys Ser Gly Lys Thr Pro Ala Asp Leu Ala Ala
    130             135             140

Arg Ala Gly His Gln Asp Ile Ala Glu Val Leu Gln Lys Ala Ala
145             150             155

<210> SEQ ID NO 122
<211> LENGTH: 158
<212> TYPE: PRT
<213> ORGANISM: Artificial Sequence
<220> FEATURE:
<223> OTHER INFORMATION: Ankyrin repeat domain specific for NY-ESO-1
      pMHC

<400> SEQUENCE: 122

Gly Ser Asp Leu Gly Lys Lys Leu Leu Gln Ala Ala Arg Ala Gly Gln
```

```
                1               5                  10                 15
Leu Asp Glu Val Arg Glu Leu Leu Lys Ala Gly Ala Asp Val Asn Ala
                20                 25                 30

Lys Asp Arg Phe Gly Ile Pro Leu His Ile Ala Ala Ser Gln Gly His
                35                 40                 45

Leu Glu Ile Val Glu Val Leu Leu Lys Ala Gly Ala Asp Val Asn Ala
        50                 55                 60

Lys Asp His Trp Gly Glu Thr Pro Leu His Leu Ala Ala Val Phe Gly
65                  70                 75                  80

His Leu Glu Ile Val Glu Val Leu Leu Lys Ala Gly Ala Asp Val Asn
                    85                 90                 95

Ala Lys Asp His Thr Gly Gln Thr Pro Leu His Leu Ala Ala Tyr Leu
                100                105                110

Gly His Leu Glu Ile Val Glu Val Leu Leu Lys Ala Gly Ala Asp Val
                115                120                125

Asn Ala Gln Asp Lys Ser Gly Lys Thr Pro Ala Asp Leu Ala Ala Arg
                130                135                140

Ala Gly His Gln Asp Ile Ala Glu Val Leu Gln Lys Ala Ala
145                 150                155
```

<210> SEQ ID NO 123
<211> LENGTH: 159
<212> TYPE: PRT
<213> ORGANISM: Artificial Sequence
<220> FEATURE:
<223> OTHER INFORMATION: Ankyrin repeat domain specific for NY-ESO-1
       pMHC

<400> SEQUENCE: 123

```
Gly Ser Asp Leu Gly Lys Lys Leu Leu Gln Ala Ala Arg Ala Gly Gln
1               5                  10                 15

Leu Asp Glu Val Arg Glu Leu Leu Lys Ala Gly Ala Asp Val Asn Ala
                20                 25                 30

Lys Asp Ala Thr Gly Gln Thr Pro Leu His Val Ala Ala Phe Arg Gly
                35                 40                 45

His Leu Glu Ile Val Glu Val Leu Leu Lys Ala Gly Ala Asp Val Asn
        50                 55                 60

Ala Lys Asp Lys Ala Gly Tyr Thr Pro Leu His Ile Ala Ala Tyr Ala
65                  70                 75                  80

Gly His Leu Glu Ile Val Glu Val Leu Leu Lys Ala Gly Ala Asp Val
                    85                 90                 95

Asn Ala Lys Asp His Ala Gly Trp Thr Pro Leu His Leu Ala Ala Ile
                100                105                110

Leu Gly His Leu Glu Ile Val Glu Val Leu Leu Lys Ala Gly Ala Asp
                115                120                125

Val Asn Ala Gln Asp Lys Ser Gly Lys Thr Pro Ala Asp Leu Ala Ala
                130                135                140

Arg Ala Gly His Gln Asp Ile Ala Glu Val Leu Gln Lys Ala Ala
145                 150                155
```

<210> SEQ ID NO 124
<211> LENGTH: 158
<212> TYPE: PRT
<213> ORGANISM: Artificial Sequence
<220> FEATURE:
<223> OTHER INFORMATION: Ankyrin repeat domain specific for NY-ESO-1
       pMHC

```
<400> SEQUENCE: 124

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Tyr Phe Gly Ser Thr Pro Leu His Leu Ala Gln Leu Gly His
        35                  40                  45

Leu Glu Ile Val Glu Val Leu Leu Lys Ala Gly Ala Asp Val Asn Ala
50                  55                  60

Lys Asp Tyr Gln Gly His Thr Pro Leu His Val Asp Ala Phe His Gly
65                  70                  75                  80

His Leu Glu Ile Val Glu Val Leu Leu Lys Ala Gly Ala Asp Val Asn
                85                  90                  95

Ala Lys Asp Gln Trp Gly Val Thr Pro Leu His Leu Ala Ala Glu Trp
            100                 105                 110

Gly His Leu Glu Ile Val Glu Val Leu Leu Lys Ala Gly Ala Asp Val
        115                 120                 125

Asn Ala Gln Asp Lys Ser Gly Lys Thr Pro Ala Asp Leu Ala Ala Arg
130                 135                 140

Ala Gly His Gln Asp Ile Ala Glu Val Leu Gln Lys Ala Ala
145                 150                 155

<210> SEQ ID NO 125
<211> LENGTH: 159
<212> TYPE: PRT
<213> ORGANISM: Artificial Sequence
<220> FEATURE:
<223> OTHER INFORMATION: Ankyrin repeat domain specific for NY-ESO-1
      pMHC

<400> SEQUENCE: 125

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Ala Ile Gly Gln Thr Pro Leu His Leu Ala Ala Phe Arg Gly
        35                  40                  45

His Leu Glu Ile Val Glu Val Leu Leu Lys Ala Gly Ala Asp Val Asn
        50                  55                  60

Ala Lys Asp Val Ala Gly Trp Thr Pro Leu His Ile Ala Ala Tyr
65                  70                  75                  80

Gly His Leu Glu Ile Val Glu Val Leu Leu Lys Ala Gly Ala Asp Val
                85                  90                  95

Asn Ala Lys Asp Ala Tyr Gly Gln Thr Pro Leu His Leu Ala Ala Phe
            100                 105                 110

Gln Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
130                 135                 140

Arg Ala Gly His Gln Asp Ile Ala Glu Val Leu Gln Lys Ala Ala
145                 150                 155

<210> SEQ ID NO 126
<211> LENGTH: 159
<212> TYPE: PRT
<213> ORGANISM: Artificial Sequence
<220> FEATURE:
```

<223> OTHER INFORMATION: Ankyrin repeat domain specific for EBNA-1 pMHC

<400> SEQUENCE: 126

Gly Ser Asp Leu Gly L

```
<220> FEATURE:
<223> OTHER INFORMATION: Ankyrin repeat domain specific for EBNA-1 pMHC

<400> SEQUENCE: 128

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Gln Glu Gly Arg Thr Pro Leu His Ile Ala Ala His Gly
        35                  40                  45

His Leu Glu Ile Val Glu Val Leu Leu Lys Ala Gly Ala Asp Val Asn
    50                  55                  60

Ala Lys Asp Ala Tyr Gly Tyr Thr Pro Leu His Leu Ala Ala Phe Ile
65                  70                  75                  80

Gly His Leu Glu Ile Val Glu Val Leu Leu Lys Ala Gly Ala Glu Val
                85                  90                  95

Asn Ala Lys Asp Lys Tyr Gly Glu Thr Pro Leu His Ile Ala Ala Leu
            100                 105                 110

Thr Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155

<210> SEQ ID NO 129
<211> LENGTH: 159
<212> TYPE: PRT
<213> ORGANISM: Artificial Sequence
<220> FEATURE:
<223> OTHER INFORMATION: Ankyrin repeat domain specific for EBNA-1 pMHC

<400> SEQUENCE: 129

Gly Ser Asp Leu Gly Lys Lys Leu Leu Gln Ala

```
<213> ORGANISM: Artificial Sequence
<220> FEATURE:
<223> OTHER INFORMATION: Ankyrin repeat domain specific for EBNA-1 pMHC

<400> SEQUENCE: 130

Gly Ser Asp Leu Gly Lys Lys Leu Leu Gln Ala Ala Arg Ala Gly Gln
1               5                   10                  15

Leu Asp Glu Val Arg Glu Leu Le

```
<212> TYPE: PRT
<213> ORGANISM: Artificial Sequence
<220> FEATURE:
<223> OTHER INFORMATION: Ankyrin repeat domain specific for EBNA-1 pMHC

<400> SEQUENCE: 132

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Leu Ser Gly Val Thr Pro Leu His Ile Ala Ala Arg Ser Gly
        35                  40                  45

His Leu Glu Ile Val Glu Val Leu Leu Lys Ala Gly Ala Asp Val Asn
    50                  55                  60

Ala Lys Asp Ala Trp Gly Tyr Thr Pro Leu His Val Ala Ala Glu His
65                  70                  75                  80

Gly His Leu Glu Ile Val Glu Val Leu Leu Lys Ala Gly Ala Asp Val
                85                  90                  95

Asn Ala Lys Asp His Leu Gly Ser Thr Pro Leu His Ile Ala Ala Ser
                100                 105                 110

His Gly His Leu Glu Ile Val Glu Val Leu Leu Lys Ala Gly Ala Asp
            115                 120                 125

Val Asn Ala Gln Asp Lys Ser Gly Lys Thr Pro Ala Asp Leu Ala Ala
        130                 135                 140

Arg Ala Gly His Gln Asp Ile Ala Glu Val Leu Gln Lys Ala Ala
145                 150                 155

<210> SEQ ID NO 133
<211> LENGTH: 159
<212> TYPE: PRT
<213> ORGANISM: Artificial Sequence
<220> FEATURE:
<223> OTHER INFORMATION: Ankyrin repeat domain specific for EBNA-1 pMHC

<400> SEQUENCE: 133

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Ala Ala Gly Trp Thr Pro Leu His Leu Ala Ala Glu Gly
        35                  40                  45

His Leu Glu Ile Val Glu Val Leu Leu Lys Ala Gly Ala Asp Val Asn
    50                  55                  60

Ala Lys Asp Val Val Gly Gln Thr Pro Leu His Val Ala Ala Val Ile
65                  70                  75                  80

Gly His Leu Glu Ile Val Glu Val Leu Leu Lys Ala Gly Ala Asp Val
                85                  90                  95

Asn Ala Lys Asp Ser Gly Tyr Thr Pro Leu His Leu Ala Ala Arg
                100                 105                 110

Glu Gly His Leu Glu Ile Val Glu Val Leu Leu Lys Ala Gly Ala Asp
            115                 120                 125

Val Asn Ala Gln Asp Lys Ser Gly Lys Thr Pro Ala Asp Leu Ala Ala
        130                 135                 140

Arg Ala Gly His Gln Asp Ile Ala Glu Val Leu Gln Lys Ala Ala
145                 150                 155

<210> SEQ ID NO 134
```

```
<211> LENGTH: 159
<212> TYPE: PRT
<213> ORGANISM: Artificial Sequence
<220> FEATURE:
<223> OTHER INFORMATION: Ankyrin repeat domain specific for MAGE-A3 pMHC

<400> SEQUENCE: 134
```

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Ser Ser Gly Trp Thr Pro Leu His Leu Ala Ala Tyr Thr Gly
        35                  40                  45

His Leu Glu Ile Val Glu Val Leu Leu Lys Ala Gly Ala Asp Val Asn
    50                  55                  60

Ala Lys Asp Gln Trp Gly Leu Thr Pro Leu His Leu Ala Ala Leu Glu
65                  70                  75                  80

Gly His Leu Glu Ile Val Glu Val Leu Leu Lys Ala Gly Ala Asp Val
                85                  90                  95

Asn Ala Lys Asp His Thr Gly Lys Thr Pro Leu His Leu Ala Ala Gln
            100                 105                 110

Gln Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155

```
<210> SEQ ID NO 135
<211> LENGTH: 159
<212> TYPE: PRT
<213> ORGANISM: Artificial Sequence
<220> FEATURE:
<223> OTHER INFORMATION: Ankyrin repeat domain specific for MAGE-A3 pMHC

<400> SEQUENCE: 135
```

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Glu Thr Gly Phe Thr Pro Leu His Leu Ala Ala Tyr His Gly
        35                  40                  45

His Leu Glu Ile Val Glu Val Leu Leu Lys Ala Gly Val Asp Val Asn
    50                  55                  60

Ala Lys Asp His Tyr Gly Leu Thr Pro Leu His Leu Ala Ala Leu Glu
65                  70                  75                  80

Gly His Leu Glu Ile Val Glu Val Leu Leu Lys Ala Gly Ala Asp Val
                85                  90                  95

Asn Ala Lys Asp Glu Leu Gly Ala Thr Pro Leu His Leu Ala Ala Val
            100                 105                 110

Thr Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155

<210> SEQ ID NO 136
<211> LENGTH: 159
<212> TYPE: PRT
<213> ORGANISM: Artificial Sequence
<220> FEATURE:
<223> OTHER INFORMATION: Ankyrin repeat domain specific for MAGE-A3 pMHC

<400> SEQUENCE: 136

```
Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp His Trp Gly Lys Thr Pro Leu His Leu Ala Ala Tyr Glu Gly
        35                  40                  45

His Leu Glu Ile Val Glu Val Leu Leu Lys Ala Gly Ala Asp Val Asn
    50                  55                  60

Ala Lys Asp Leu Phe Gly Leu Thr Pro Leu His Leu Ala Ala Ile Glu
65                  70                  75                  80

Gly His Leu Glu Ile Val Glu Val Leu Leu Lys Ala Gly Ala Asp Val
                85                  90                  95

Asn Ala Lys Asp Ser Phe Gly Tyr Thr Pro Leu His Val Ala Ala Gln
            100                 105                 110

Val Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155
```

<210> SEQ ID NO 137
<211> LENGTH: 159
<212> TYPE: PRT
<213> ORGANISM: Artificial Sequence
<220> FEATURE:
<223> OTHER INFORMATION: Ankyrin repeat domain specific for MAGE-A3 pMHC

<400> SEQUENCE: 137

```
Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Ser Ser Gly Trp Thr Pro Leu His Leu Ala Ala Tyr Arg Gly
        35                  40                  45

His Leu Glu Ile Val Glu Val Leu Leu Lys Val Gly Ala Asp Val Asn
    50                  55                  60

Ala Lys Asp Ala Tyr Gly Leu Thr Pro Leu His Leu Ala Ala Ile Glu
65                  70                  75                  80

Gly His Leu Glu Ile Val Glu Val Leu Leu Lys Ala Gly Ala Asp Val
                85                  90                  95

Asn Ala Lys Asp Ser Val Gly His Thr Pro Leu His Ile Ala Ala Arg
            100                 105                 110

Ile Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155
```

```
<210> SEQ ID NO 138
<211> LENGTH: 159
<212> TYPE: PRT
<213> ORGANISM: Artificial Sequence
<220> FEATURE:
<223> OTHER INFORMATION: Ankyrin repeat domain specific for MAGE-A3 pMHC

<400> SEQUENCE: 138

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Thr Val Gly Trp Thr Pro Leu His Ile Ala Ala Tyr Thr Gly
        35                  40                  45

His Leu Glu Ile Val Glu Val Leu Leu Lys Ala Gly Ala Asp Val Asn
    50                  55                  60

Ala Lys Asp Glu Trp Gly Val Thr Pro Leu His Leu Ala Ala Leu Glu
65                  70                  75                  80

Gly His Leu Glu Ile Val Glu Val Leu Leu Lys Ala Gly Ala Asp Val
                85                  90                  95

Asn Ala Lys Asp Glu Ala Gly Glu Thr Pro Leu His Ile Ala Ala Trp
            100                 105                 110

His Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155

<210> SEQ ID NO 139
<211> LENGTH: 159
<212> TYPE: PRT
<213> ORGANISM: Artificial Sequence
<220> FEATURE:
<223> OTHER INFORMATION: Ankyrin repeat domain specific for MAGE-A3 pMHC

<400> SEQUENCE: 139

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Glu Trp Gly Ala Thr Pro Leu His Leu Ala Ala Tyr Ala Gly
        35                  40                  45

His Leu Glu Ile Val Glu Val Leu Leu Lys Ala Gly Ala Asp Val Asn
    50                  55                  60

Ala Lys Asp Arg Trp Gly Leu Thr Pro Leu His Val Ala Ala Val Glu
65                  70                  75                  80

Gly His Leu Glu Ile Val Glu Val Leu Leu Lys Ala Gly Ala Asp Val
                85                  90                  95

Asn Ala Lys Asp Ile Glu Gly Glu Thr Pro Leu His Ile Ala Ala Phe
            100                 105                 110

Thr Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Val Ala Glu Val Leu Gln Lys Ala Ala
145                 150                 155
```

-continued

<210> SEQ ID NO 140
<211> LENGTH: 159
<212> TYPE: PRT
<213> ORGANISM: Artificial Sequence
<220> FEATURE:
<223> OTHER INFORMATION: Ankyrin repeat domain specific for MAGE-A3 pMHC

<400> SEQUENCE: 140

Gly Ser Asp Leu Gly Lys Lys Leu Leu Gln Ala Ala Arg Ala Gly Gln
1               5                   10                  15

Leu Asp Glu Val Arg Glu Leu Leu Lys Ala Gly Ala Asp Val Asn Ala
            20                  25                  30

Lys Asp Ser Ser Gly Trp Thr Pro Leu His Leu Ala Ala Tyr His Gly
        35                  40                  45

His Leu Glu Ile Val Glu Val Leu Leu Lys Ala Gly Ala Asp Val Asn
    50                  55                  60

Ala Lys Asp Glu Trp Gly Leu Thr Pro Leu His Leu Ala Ala Ile Glu
65                  70                  75                  80

Gly His Leu Glu Ile Val Glu Val Leu Leu Lys Ala Gly Ala Asp Val
                85                  90                  95

Asn Ala Lys Asp Val Thr Gly Tyr Thr Pro Leu His Ile Ala Ala Ala
            100                 105                 110

Thr Gly His Leu Glu Ile Val Glu Val Leu Leu Lys Val Gly Val Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala
145                 150                 155

<210> SEQ ID NO 141
<211> LENGTH: 159
<212> TYPE: PRT
<213> ORGANISM: Artificial Sequence
<220> FEATURE:
<223> OTHER INFORMATION: Ankyrin repeat domain specific for HBVc18 pMHC

<400> SEQUENCE: 141

Gly Ser Asp Leu Gly Lys Lys Leu Leu Ser Ala Ala Gln Ser Gly Gln
1               5                   10                  15

Asp Asp Glu Val Arg Ile Leu Leu Gly Ala Gly Ala Asp Val Asn Ala
            20                  25                  30

Lys Asp Lys Trp Gly His Thr Pro Leu His Leu Ala Ala Val Lys Gly
        35                  40                  45

His Leu Glu Ile Ala Glu Val Leu Leu Lys Ala Gly Ala Asp Val Asn
    50                  55                  60

Ala Lys Asp Glu Trp Gly Ser Thr Pro Leu His Leu Ala Ala Ser Gln
65                  70                  75                  80

Gly His Leu Glu Ile Val Glu Val Leu Leu Lys Ala Gly Ala Asp Val
                85                  90                  95

Asn Ala Lys Asp Lys Lys Gly Ala Thr Pro Leu His Leu Ala Ala Leu
            100                 105                 110

Val Gly His Leu Glu Ile Val Glu Val Leu Leu Lys Val Ala Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ile Ala Glu Val Leu Gln Lys Ala Ala

```
145             150             155

<210> SEQ ID NO 142
<211> LENGTH: 159
<212> TYPE: PRT
<213> ORGANISM: Artificial Sequence
<220> FEATURE:
<223> OTHER INFORMATION: Ankyrin repeat domain specific for HBVc18 pMHC

<400> SEQUENCE: 142

Gly Ser Asp Leu Gly Lys Lys Leu Leu Gln Ala Ala Arg Ala Gly Gln
1               5                   10                  15

Leu Asp Glu Val His Glu Leu Leu Lys Ala Gly Ala Asp Val Asn Ala
            20                  25                  30

Lys Asp Gln His Gly Lys Thr Pro Met His Leu Ala Ala Gln Ile Gly
        35                  40                  45

His Leu Glu Ile Val Glu Val Leu Leu Lys Ala Gly Ala Asp Val Asn
    50                  55                  60

Ala Lys Asp His Ile Gly Trp Thr Pro Leu His Leu Ala Ala Ser Val
65                  70                  75                  80

Gly His Leu Glu Ile Val Glu Val Leu Leu Lys Ala Gly Ala Asp Val
                85                  90                  95

Asn Ala Lys Asp Gln Glu Gly Trp Thr Pro Leu His Val Ala Ala Gln
            100                 105                 110

Leu Gly His Leu Glu Ile Val Glu Val Leu Leu Lys Ala Gly Ala Asp
        115                 120                 125

Val Asn Ala Gln Asp Lys Ser Gly Lys Thr Pro Ala Asp Leu Ala Ala
    130                 135                 140

Arg Ala Gly His Gln Asp Ser Ala Glu Val Leu Gln Lys Ala Ala
145                 150                 155
```

DESIGNED ANKYRIN REPEAT DOMAINS WITH ALTERED SURFACE RESIDUES

CROSS-REFERENCE TO RELATED APPLICATIONS

The present application is a continuation of International Application No. PCT/EP2020/085855, filed Dec. 11, 2020, which claims the benefit of priority to EP 19215433.4, filed on Dec. 11, 2019; EP 19215434.2, filed on Dec. 11, 2019; EP 19215435.9, filed on Dec. 11, 2019; EP 19215436.7, filed on Dec. 11, 2019; EP 20161059.9, filed on Mar. 4, 2020; and EP 20181234.4, filed on Jun. 19, 2020. All of the aforementioned applications are incorporated herein for all purposes by reference in their entirety.

FIELD OF THE INVENTION

The present invention relates to designed ankyrin repeat domains with altered surface residues, as well as to proteins comprising such a designed ankyrin repeat domain, nucleic acids encoding such domains or proteins, methods of preparing such proteins, pharmaceutical compositions comprising such proteins or nucleic acids, and the use of such proteins, nucleic acids or pharmaceutical compositions in the treatment of diseases.

BACKGROUND OF THE INVENTION

Designed ankyrin repeat domains are useful for the creation of drug candidates (WO2002020565; WO2011135067; WO2016156596; WO2018054971) for the treatment of disease. The designed ankyrin repeat domains comprised in such drug candidates typically bind target molecules with high affinity, thereby acting pharmacodynamically on the target, e.g. antagonizing target activity. To achieve a long systemic half-life of drug candidates based on designed ankyrin repeat domains, the drug candidate typically needs to comprise a moiety conferring long half-life, which can be achieved, e.g., by chemical modification with polyethylene glycol (PEG; WO2011135067) or by including one or more genetically fused designed ankyrin repeat domains with binding specificity for serum albumin (WO2012069654). Using the latter approach, drug candidates having long terminal half-life have been generated and described (WO2016156596; WO2018054971). Such designed ankyrin repeat domains with binding specificity for serum albumin can prolong the terminal half-life of proteins, e.g., to a terminal half-life similar to that of serum albumin (Steiner et al., Protein Eng Des Sel. 30(9):583-591 (2017)). As described in more detail below, Applicant has observed, however, that some designed ankyrin repeat domains exhibit fast clearance and thus short terminal half-life despite the fact that they are genetically fused to a designed ankyrin repeat domain with binding specificity for serum albumin. The importance of good pharmacokinetic properties of biologic drugs is well known in the art (see, e.g., Strohl, BioDrugs 29:215-239 (2015)).

Thus, there still remains a need for new methods or approaches of improving the pharmacokinetic properties (including prolonging the terminal half-life) of proteins, such as designed ankyrin repeat domains and proteins comprising one or more designed ankyrin repeat domain(s).

SUMMARY OF THE INVENTION

Applicant has unexpectedly observed that some designed ankyrin repeat domains exhibit fast clearance and thus short terminal half-life despite the fact that they are genetically fused to a designed ankyrin repeat domain with binding specificity for serum albumin (See e.g. Example 6 and FIG. 5 for Proteins #24, #27, #31, and #35). In efforts to understand this observation, the inventors have surprisingly discovered that altering certain amino acid residues in the N-terminal capping module and/or the C-terminal capping module of the designed ankyrin repeat domain results in improved pharmacokinetic properties, including a prolonged terminal half-life, of the designed ankyrin repeat domain and of proteins comprising the designed ankyrin repeat domain. The altered amino acid residues are mostly surface exposed residues. Thus, the present invention provides amino acid sequences that lead to improved pharmacokinetic properties of a designed ankyrin repeat domain and of proteins comprising the designed ankyrin repeat domain.

The invention provides designed ankyrin repeat domains comprising novel amino acid sequences. In one embodiment said designed ankyrin repeat domains comprise an amino acid sequence selected from the group consisting of SEQ ID NOs: 75 to 81, 88 to 94, and 107 to 111, wherein X represents any amino acid. In one embodiment, said designed ankyrin repeat domain comprises (i) an amino acid sequence selected from the group consisting of SEQ ID NOs: 75 to 81 and 107 to 111, wherein X represents any amino acid, and (ii) an amino acid sequence selected from the group consisting of SEQ ID NOs: 88 to 94, wherein X represents any amino acid. In one embodiment, said designed ankyrin repeat domain comprises (i) the amino acid sequence of SEQ ID NO: 78, wherein X represents any amino acid, and (ii) the amino acid sequence of SEQ ID NOs: 91, wherein X represents any amino acid. In one embodiment, said designed ankyrin repeat domain comprises an amino acid sequence selected from the group consisting of SEQ ID NOs: 95 to 102, wherein X represents any amino acid. The invention further provides a protein comprising (i) at least one designed ankyrin repeat domain of the invention, and (ii) at least one moiety for half-life extension. In one embodiment, said moiety for half-life extension is a designed ankyrin repeat domain with binding specificity for serum albumin. In one embodiment, said ankyrin repeat domain with binding specificity for serum albumin comprises an amino acid sequence with at least 80% amino acid sequence identity with any one of SEQ ID NOs: 4 to 8. In one embodiment, said protein further comprises at least one polypeptide linker. In one embodiment, said polypeptide linker is a glycine-serine (GS)-rich linker or a proline-threonine (PT)-rich linker, wherein preferably said polypeptide linker has the amino acid sequence of SEQ ID NO: 2 or 3, or of variants thereof. In one embodiment, said protein is a recombinant binding protein. The invention also provides a protein comprising (i) at least one, two, or three designed ankyrin repeat domains of the invention, and (ii) at least one or two designed ankyrin repeat domains with binding specificity for serum albumin, wherein preferably each of said designed ankyrin repeat domain(s) with binding specificity for serum albumin independently comprises an amino acid sequence with at least 80% amino acid sequence identity with any one of SEQ ID NOs: 4 to 8. In one embodiment, said protein is a recombinant binding protein. FIG. 1 further illustrates the invention schematically. The invention further provides nucleic acids encoding a designed ankyrin repeat of the invention or a protein of the invention. The invention further provides a pharmaceutical composition comprising a designed ankyrin repeat domain of the invention, a protein of the invention, or a nucleic acid of the invention. The invention further provides a method of treating a medical condition, the method comprising the step of administering, to a patient in need of such treatment, a therapeutically effective amount of a pharmaceutical composition of the invention. The invention further provides a method for preparing a protein, the method comprising the steps of (A) preparing a nucleic acid that encodes in one open reading frame (i) at least one designed ankyrin repeat domain of the invention, and (ii) at least one designed ankyrin repeat domain with binding specificity for serum albumin, and (B) transferring said nucleic acid into an expression host. In one embodiment, the expression host is *E. coli*.

BRIEF DESCRIPTION OF THE FIGURES

FIG. 2. Sequence alignment of amino acid sequences present in N-terminal capping modules. SEQ ID NOs: 69 to 74 correspond to amino acid sequences found in N-terminal capping modules of designed ankyrin repeat domains known in the art (see, e.g., WO2012069655). SEQ ID NOs: 75 to 81 and 107 to 111 correspond to amino acid sequences of the present invention. Residue numbers are indicated above the sequences.

FIG. 3. Sequence alignment of amino acid sequences present in C-terminal capping modules. SEQ ID NOs: 82 to 87 correspond to amino acid sequences found in C-terminal capping modules of designed ankyrin repeat domains known in the art (see, e.g., WO2014001442 or WO2016156596). SEQ ID NOs: 88 to 94 correspond to amino acid sequences of the present invention. Residue numbers are indicated above the sequences.

FIG. 4A: SDS-PAGE of Proteins #9 to #23; FIG. 4B: SDS-PAGE of Proteins #24 to #38. Proteins #9 to 38 (corresponding to SEQ ID NOs: 9 to 38, additionally having a His-tag (SEQ ID NO: 1) at the N-terminus) were expressed and purified as described in Example 2, subjected to a stability study as described in Example 3, and subjected to SDS-PAGE analysis as described in Example 4. All proteins were highly pure. M: molecular weight marker, molecular weight is indicated at the left of each figure; −80° C. control; +: Protein sample incubated at 60° C. for 1 week.

FIGS. 5A to 5D. Pharmacokinetic profiles in mouse of variants of designed ankyrin repeat domains (each genetically linked to an identical designed ankyrin repeat domain with binding specificity for serum albumin via an identical polypeptide linker). FIG. 5A: Pharmacokinetic profile in mouse of Protein #24, and variant Proteins #25 and #26. FIG. 5B: Pharmacokinetic profile in mouse of Protein #27, and variant Proteins #28, #29, and #30. FIG. 5C: Pharmacokinetic profile in mouse of Protein #31, and variant Proteins #32 #33, and #34. FIG. 5D: Pharmacokinetic profile in mouse of Protein #35, and variant Proteins #36, #37, and #38. The experiment was performed as described in Example 6 using Balb/c mice and 1 mg/kg intravenous dosing. Proteins #24 to #38 (comprising SEQ ID NOs: 24 to 38, respectively, with each having a His-tag (SEQ ID NO: 1) at the N terminus; symbol indicated in the figure) were produced and purified as described in Example 2. C: concentration in [nM]; t: time in [hours].

DETAILED DESCRIPTION OF THE INVENTION

Figure 1:
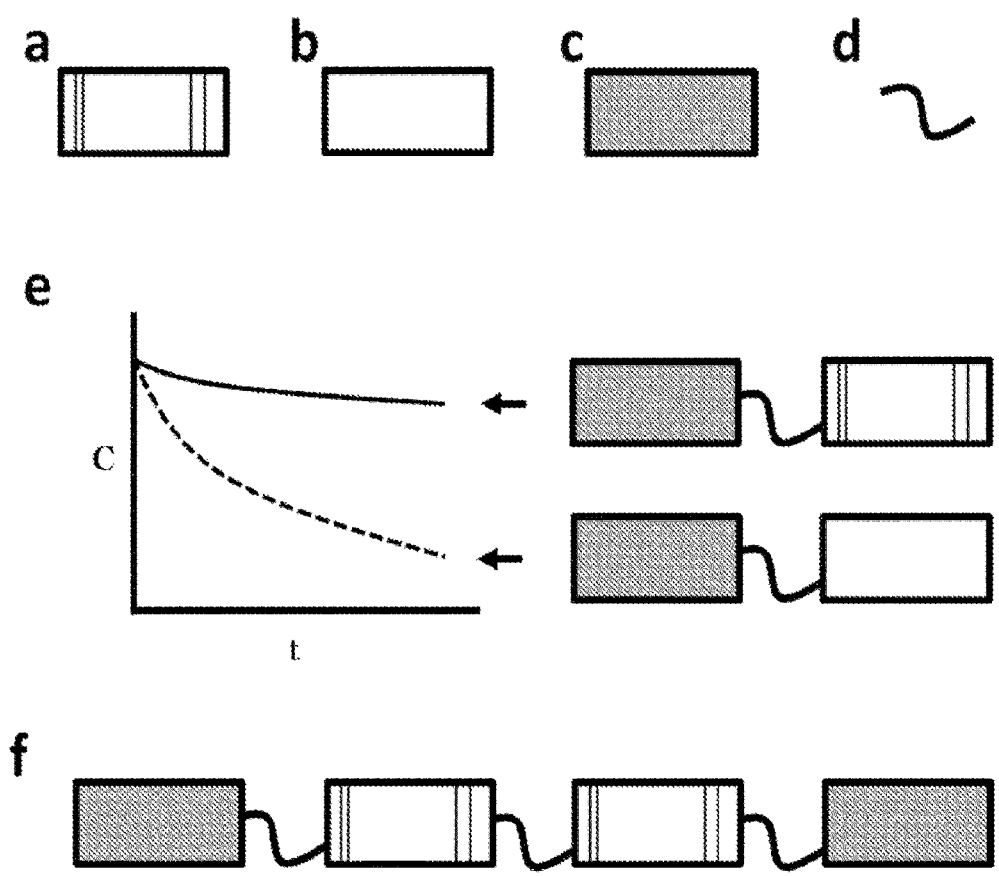
FIG. 1. Schematic illustration of the invention. (a) Schematic representation of a designed ankyrin repeat domain of the invention. The designed ankyrin repeat domain (rectangle) comprises certain amino acids at defined positions, illustrated by the vertical black lines. (b) Schematic representation of a comparator designed ankyrin repeat domain. The comparator designed ankyrin repeat domain comprises different amino acids than (a) in the corresponding positions. For example, (a) may include SEQ ID NO: 75 (of the present invention), whereas (b) may include SEQ ID NO: 69 (i.e. a sequence known in the art). (c) Schematic illustration of a designed ankyrin repeat domain with binding specificity for serum albumin. A designed ankyrin repeat domain consisting of SEQ ID NO: 4 is an example of such a designed ankyrin repeat domain with binding specificity for serum albumin. (d) Schematic illustration of a polypeptide linker. SEQ ID NOs: 2 and 3 are examples of such polypeptide linkers. (e) Schematic illustration of the pharmacokinetic profile of a designed ankyrin repeat domain (covalently bound to a designed ankyrin repeat domain with binding specificity for serum albumin via a polypeptide linker) in comparison to a comparator designed ankyrin repeat domain (covalently bound to an identical designed ankyrin repeat domain with binding specificity for serum albumin via an identical polypeptide linker). The pharmacokinetic traces are schematically shown on the left, the respective construct is shown schematically on the right, with arrows indicating which curve is observed with which protein. C: Concentration, t: time. (f) Schematic representation of an example of a protein of the invention. The protein comprises, from N terminus (left) to C terminus (right), a first designed ankyrin repeat domain with binding specificity for serum albumin, a first polypeptide linker, a first designed ankyrin repeat domain of the invention, a second polypeptide linker, a second designed ankyrin repeat domain of the invention, a third polypeptide linker, and a second designed ankyrin repeat domain with binding specificity for serum albumin. The designed ankyrin repeat domains of the invention may be binding domains with specificity for one target or for different targets. The order and number of the different domains may vary in the proteins of the invention.

In a first aspect, the present invention provides a designed ankyrin repeat domain comprising novel amino acid sequence motifs in the N-terminal capping module and/or the C-terminal capping module.

In one embodiment, the designed ankyrin repeat domain of the invention comprises an amino acid sequence selected from the group consisting of SEQ ID NOs: 75 to 81, 88 to 94, and 107 to 111, wherein X represents any amino acid. Amino acid sequences SEQ ID NOs: 75 to 81 and 107 to 111 are examples of sequences of the invention present in N-terminal capping modules of designed ankyrin repeat domains of the invention. These sequences are further illustrated in FIG. 2. Amino acid sequences SEQ ID NOs: 69 to 74 are examples of sequences present in N-terminal capping modules of designed ankyrin repeat domains known in the art (see also FIG. 2). Amino acid sequences SEQ ID NOs: 88 to 94 are examples of sequences of the invention present in C-terminal capping modules of designed ankyrin repeat domains of the invention. These sequences are further illustrated in FIG. 3. Amino acid sequences SEQ ID NOs: 82 to 87 are examples of sequences present in C-terminal capping modules of designed ankyrin repeat domains known in the art (see also FIG. 3). In one embodiment, any of the amino acid sequences selected from SEQ ID NOs: 75 to 81 and 107 to 111 is present in the N-terminal capping module of a designed ankyrin repeat domain. In one embodiment, any of the amino acid sequences selected from SEQ ID NOs: 88 to 94 is present in the C-terminal capping module of a designed ankyrin repeat domain.

In one embodiment, said designed ankyrin repeat domain comprises an amino acid sequence selected from the group consisting of SEQ ID NOs: 75 to 81, more preferably SEQ ID NOs: 77 to 81, more preferably SEQ ID NOs: 78 to 81, more preferably SEQ ID NOs: 79 to 81, more preferably SEQ ID NOs: 80 to 81, most preferably SEQ ID NO: 81, wherein X represents any amino acid. In one embodiment, said designed ankyrin repeat domain comprises the amino acid sequence of SEQ ID NO: 81, wherein X represents any amino acid. In one embodiment, said designed ankyrin repeat domain comprises the amino acid sequence of SEQ ID NO: 80, wherein X represents any amino acid. In one embodiment, said designed ankyrin repeat domain comprises the amino acid sequence of SEQ ID NO: 79, wherein X represents any amino acid. In one embodiment, said designed ankyrin repeat domain comprises the amino acid sequence of SEQ ID NO: 78, wherein X represents any amino acid. In one embodiment, said designed ankyrin repeat domain comprises the amino acid sequence of SEQ ID NO: 77, wherein X represents any amino acid. In one embodiment, said designed ankyrin repeat domain comprises the amino acid sequence of SEQ ID NO: 75 or 76. In one embodiment, said designed ankyrin repeat domain comprises the amino acid sequence of SEQ ID NO: 75. In one embodiment, said designed ankyrin repeat domain comprises the amino acid sequence of SEQ ID NO: 76.

In another embodiment, said designed ankyrin repeat domain comprises an amino acid sequence selected from the group consisting of SEQ ID NOs: 107 to 111, more preferably 108 to 111, more preferably 109 to 111, more preferably 110 to 111, most preferably 111, wherein X represents any amino acid. In one embodiment, said designed ankyrin repeat domain comprises the amino acid sequence of SEQ ID NO: 111, wherein X represents any amino acid. In one embodiment, said designed ankyrin repeat domain comprises the amino acid sequence of SEQ ID NO: 110, wherein X represents any amino acid. In one embodiment, said designed ankyrin repeat domain comprises the amino acid sequence of SEQ ID NO: 109, wherein X represents any amino acid. In one embodiment, said designed ankyrin repeat domain comprises the amino acid sequence of SEQ ID NO: 107 or 108. In one embodiment, said designed ankyrin repeat domain comprises the amino acid sequence of SEQ ID NO: 107. In one embodiment, said designed ankyrin repeat domain comprises the amino acid sequence of SEQ ID NO: 108.

In a further embodiment, said designed ankyrin repeat domain comprises an amino acid sequence selected from the group consisting of SEQ ID NOs: 88 to 94, more preferably 90 to 94, more preferably 91 to 94, more preferably 92 to 94, more preferably 93 to 94, most preferably 94, wherein X represents any amino acid. In one embodiment, said designed ankyrin repeat domain comprises the amino acid sequence of SEQ ID NO: 94, wherein X represents any amino acid. In one embodiment, said designed ankyrin repeat domain comprises the amino acid sequence of SEQ ID NO: 93, wherein X represents any amino acid. In one embodiment, said designed ankyrin repeat domain comprises the amino acid sequence of SEQ ID NO: 92, wherein X represents any amino acid. In one embodiment, said designed ankyrin repeat domain comprises the amino acid sequence of SEQ ID NO: 91, wherein X represents any amino acid. In one embodiment, said designed ankyrin repeat domain comprises the amino acid sequence of SEQ ID NO: 90, wherein X represents any amino acid. In one embodiment, said designed ankyrin repeat domain comprises the amino acid sequence of SEQ ID NOs: 88 or 89.

In one embodiment, said designed ankyrin repeat domain comprises the amino acid sequence of SEQ ID NO: 88. In one embodiment, said designed ankyrin repeat domain comprises the amino acid sequence of SEQ ID NO: 89.

In a further embodiment, the designed ankyrin repeat domain of the invention comprises (i) an amino acid sequence selected from the group consisting of SEQ ID NOs: 75 to 81 and 107 to 111, wherein X represents any amino acid, and (ii) an amino acid sequence selected from the group consisting of SEQ ID NOs: 88 to 94, wherein X represents any amino acid. In one embodiment, said designed ankyrin repeat domain comprises (i) the amino acid sequence of SEQ ID NO: 81, wherein X represents any amino acid, and (ii) the amino acid sequence of SEQ ID NO: 93, wherein X represents any amino acid.

In one embodiment, said designed ankyrin repeat domain comprises (i) the amino acid sequence of SEQ ID NO: 81, wherein X represents any amino acid, and (ii) the amino acid sequence of SEQ ID NO: 94, wherein X represents any amino acid.

In one embodiment, said designed ankyrin repeat domain comprises (i) the amino acid sequence of SEQ ID NO: 80, wherein X represents any amino acid, and (ii) the amino acid sequence of SEQ ID NO: 93, wherein X represents any amino acid.

In one embodiment, said designed ankyrin repeat domain comprises (i) the amino acid sequence of SEQ ID NO: 80, wherein X represents any amino acid, and (ii) the amino acid sequence of SEQ ID NO: 94, wherein X represents any amino acid.

In one embodiment, said designed ankyrin repeat domain comprises (i) the amino acid sequence of SEQ ID NO: 79, wherein X represents any amino acid, and (ii) the amino acid sequence of SEQ ID NO: 92, wherein X represents any amino acid.

In one embodiment, said designed ankyrin repeat domain comprises (i) the amino acid sequence of SEQ ID NO: 78, wherein X represents any amino acid, and (ii) the amino acid sequence of SEQ ID NO: 91, wherein X represents any amino acid.

In one embodiment, said designed ankyrin repeat domain comprises (i) the amino acid sequence of SEQ ID NO: 77, wherein X represents any amino acid, and (ii) the amino acid sequence of SEQ ID NO: 90, wherein X represents any amino acid.

In one embodiment, said designed ankyrin repeat domain comprises (i) the amino acid sequence of SEQ ID NO: 76, wherein X represents any amino acid, and (ii) the amino acid sequence of SEQ ID NO: 89, wherein X represents any amino acid.

In one embodiment, said designed ankyrin repeat domain comprises (i) the amino acid sequence of SEQ ID NO: 75, wherein X represents any amino acid, and (ii) the amino acid sequence of SEQ ID NO: 88, wherein X represents any amino acid.

In one embodiment, said designed ankyrin repeat domain comprises (i) the amino acid sequence of SEQ ID NO: 111, wherein X represents any amino acid, and (ii) the amino acid sequence of SEQ ID NO: 94, wherein X represents any amino acid.

In one embodiment, said designed ankyrin repeat domain comprises (i) the amino acid sequence of SEQ ID NO: 111, wherein X represents any amino acid, and (ii) the amino acid sequence of SEQ ID NO: 93, wherein X represents any amino acid.

In one embodiment, said designed ankyrin repeat domain comprises (i) the amino acid sequence of SEQ ID NO: 111, wherein X represents any amino acid, and (ii) the amino acid sequence of SEQ ID NO: 92, wherein X represents any amino acid.

In one embodiment, said designed ankyrin repeat domain comprises (i) the amino acid sequence of SEQ ID NO: 110, wherein X represents any amino acid, and (ii) the amino acid sequence of SEQ ID NO: 91, wherein X represents any amino acid.

In one embodiment, said designed ankyrin repeat domain comprises (i) the amino acid sequence of SEQ ID NO: 109, wherein X represents any amino acid, and (ii) the amino acid sequence of SEQ ID NO: 90, wherein X represents any amino acid.

In one embodiment, said designed ankyrin repeat domain comprises (i) the amino acid sequence of SEQ ID NO: 108, wherein X represents any amino acid, and (ii) the amino acid sequence of SEQ ID NO: 89, wherein X represents any amino acid.

In one embodiment, said designed ankyrin repeat domain comprises (i) the amino acid sequence of SEQ ID NO: 108, wherein X represents any amino acid, and (ii) the amino acid sequence of SEQ ID NO: 88, wherein X represents any amino acid.

In one embodiment, said designed ankyrin repeat domain comprises (i) the amino acid sequence of SEQ ID NO: 107, wherein X represents any amino acid, and (ii) the amino acid sequence of SEQ ID NO: 88, wherein X represents any amino acid.

In one embodiment, said designed ankyrin repeat domain comprises (i) the amino acid sequence of SEQ ID NO: 107, wherein X represents any amino acid, and (ii) the amino acid sequence of SEQ ID NO: 89, wherein X represents any amino acid.

In a further embodiment, the designed ankyrin repeat domain of the invention comprises an N-terminal capping module having an amino acid sequence wherein the amino acid at position 8 is Q and/or the amino acid at position 15 is L. In one embodiment, said designed ankyrin repeat domain comprises a N-terminal capping module having an amino acid sequence wherein the amino acid at position 4 is S, the amino acid at position 8 is Q, the amino acid at position 15 is L, the amino acid at position 17 is T, the amino acid at position 20 is T, and/or the amino acid at position 23 is Q. In a preferred embodiment, said N-terminal capping module comprises an amino acid sequence of 30 amino acids. In a further preferred embodiment, said N-terminal capping module consists of an amino acid sequence of 30 amino acids. Preferably, said position numbers of positions of the N-terminal capping module are determined by alignment to SEQ ID NO: 69 using the position numbers of SEQ ID NO: 69. Preferably, said alignment comprises no amino acid gaps. Sequence alignment generation is a procedure well known in the art.

In one embodiment, the designed ankyrin repeat domain of the invention comprises a C-terminal capping module having an amino acid sequence wherein the amino acid at position 14 is R and/or the amino acid at position 18 is Q. In one embodiment, said designed ankyrin repeat domain comprises a C-terminal capping module having an amino acid sequence wherein the amino acid at position 3 is T, the amino acid at position 4 is Q, the amino acid at position 6 is T, the amino acid at position 14 is R, the amino acid at position 18 is Q, the amino acid at position 19 is Q, the amino acid at position 22 is S, and/or the amino acid at position 26 is Q. In a preferred embodiment, said C-terminal capping module comprises an amino acid sequence of 28 amino acids. In a further preferred embodiment, said C-terminal capping module consists of an amino acid sequence of 28 amino acids. Preferably, said position numbers of positions of the C-terminal capping module are determined by alignment to SEQ ID NO: 82 using the position numbers of SEQ ID NO: 82. Preferably, said alignment comprises no amino acid gaps.

In one embodiment, the designed ankyrin repeat domain of the invention comprises (i) an N-terminal capping module having an amino acid sequence wherein the amino acid at position 8 is Q and/or the amino acid at position 15 is L, and/or (ii) a C-terminal capping module having an amino acid sequence wherein the amino acid at position 14 is R and/or the amino acid at position 18 is Q. In one embodiment, the designed ankyrin repeat domain of the invention comprises (i) an N-terminal capping module having an amino acid sequence wherein the amino acid at position 8 is Q and/or the amino acid at position 15 is L, and (ii) a C-terminal capping module having an amino acid sequence wherein the amino acid at position 14 is R and/or the amino acid at position 18 is Q. In one embodiment, said designed ankyrin repeat domain of the invention comprises (i) an N-terminal capping module having an amino acid sequence wherein the amino acid at position 8 is Q, and (ii) a C-terminal capping module having an amino acid sequence wherein the amino acid at position 14 is R and/or the amino acid at position 18 is Q. In one embodiment, said designed ankyrin repeat domain of the invention comprises (i) an N-terminal capping module having an amino acid sequence wherein the amino acid at position 15 is L, and (ii) a C-terminal capping module having an amino acid sequence wherein the amino acid at position 14 is R and/or the amino acid at position 18 is Q. In one embodiment, said designed ankyrin repeat domain of the invention comprises (i) an N-terminal capping module having an amino acid sequence wherein the amino acid at position 8 is Q and/or the amino acid at position 15 is L, and (ii) a C-terminal capping module having an amino acid sequence wherein the amino acid at position 14 is R. In one embodiment, said designed ankyrin repeat domain of the invention comprises (i) an N-terminal capping module having an amino acid sequence wherein the amino acid at position 8 is Q and/or the amino acid at position 15 is L, and (ii) a C-terminal capping module having an amino acid sequence wherein the amino acid at position 18 is Q. In one embodiment, said designed ankyrin repeat domain of the invention comprises (i) an N-terminal capping module having an amino acid sequence wherein the amino acid at position 8 is Q and the amino acid at position 15 is L, and (ii) a C-terminal capping module having an amino acid sequence wherein the amino acid at position 14 is R and the amino acid at position 18 is Q. In a preferred embodiment, said N-terminal capping module comprises an amino acid sequence of 30 amino acids and said C-terminal capping module comprises an amino acid sequence of 28 amino acids. In a further preferred embodiment, said N-terminal capping module consists of an amino acid sequence of 30 amino acids and said C-terminal capping module consists of an amino acid sequence of 28 amino acids.

Preferably, said position numbers of positions of the N-terminal capping module are determined by alignment to SEQ ID NO: 69 using the position numbers of SEQ ID NO: 69, and said position numbers of positions of the C-terminal capping module are determined by alignment to SEQ ID NO: 82 using the position numbers of SEQ ID NO: 82. Preferably, said alignments comprise no amino acid gaps.

In a further embodiment, the designed ankyrin repeat domain of the invention comprises an N-terminal capping module having an amino acid sequence DLGKKLLQAARAGQLDEVRELLKAGADVNA (SEQ ID NO: 75), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 75 in positions other than position 8 and position 15 are optionally exchanged by other amino acids.

In a further embodiment, the designed ankyrin repeat domain of the invention comprises an N-terminal capping module having an amino acid sequence DLGSKLLQAARAGQLDTVRTLLQAGADVNA (SEQ ID NO: 76), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 76 in positions other than positions 4, 8, 15, 17, 20 and 23 are optionally exchanged by other amino acids.

In one embodiment, the designed ankyrin repeat domain of the invention comprises a C-terminal capping module having an amino acid sequence QDKSGKTPADLAARAGHQDIAEVLQKAA (SEQ ID NO: 88), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 88 in positions other than position 14 and position 18 are optionally exchanged by other amino acids.

In one embodiment, the designed ankyrin repeat domain of the invention comprises a C-terminal capping module having an amino acid sequence QDTQGTTPADLAARAGHQQIASVLQQAA (SEQ ID NO: 89), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 89 in positions other than positions 3, 4, 6, 14, 18, 19, 22 and 26 are optionally exchanged by other amino acids.

In one embodiment, the designed ankyrin repeat domain of the invention comprises (i) an N-terminal capping module having an amino acid sequence DLGKKLLQAARAGQLDEVRELLKAGADVNA (SEQ ID NO: 75), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 75 in positions other than position 8 and position 15 are optionally exchanged by other amino acids, and (ii) a C-terminal capping module having an amino acid sequence QDKSGKTPADLAARAGHQDIAEVLQKAA (SEQ ID NO: 88), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 88 in positions other than position 14 and position 18 are optionally exchanged by other amino acids.

In one embodiment, said designed ankyrin repeat domain comprises (i) an N-terminal capping module having an amino acid sequence DLGKKLLQAARAGQLDEVRELLKAGADVNA (SEQ ID NO: 75), wherein up to 10 amino acids of SEQ ID NO: 75 in positions other than position 8 and position 15 are optionally exchanged by other amino acids, and (ii) a C-terminal capping module having an amino acid sequence QDKSGKTPADLAARAGHQDIAEVLQKAA (SEQ ID NO: 88), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 88 in positions other than position 14 and position 18 are optionally exchanged by other amino acids.

In one embodiment, said designed ankyrin repeat domain comprises (i) an N-terminal capping module having an amino acid sequence DLGKKLLQAARAGQLDEVRELLKAGADVNA (SEQ ID NO: 75), wherein up to 9 amino acids of SEQ ID NO: 75 in positions other than position 8 and position 15 are optionally exchanged by other amino acids, and (ii) a C-terminal capping module having an amino acid sequence QDKSGKTPADLAARAGHQDIAEVLQKAA (SEQ ID NO: 88), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 88 in positions other than position 14 and position 18 are optionally exchanged by other amino acids.

In one embodiment, said designed ankyrin repeat domain comprises (i) an N-terminal capping module having an amino acid sequence DLGKKLLQAARAGQLDEVRELLKAGADVNA (SEQ ID NO: 75), wherein up to 8 amino acids of SEQ ID NO: 75 in positions other than position 8 and position 15 are optionally exchanged by other amino acids, and (ii) a C-terminal capping module having an amino acid sequence QDKSGKTPADLAARAGHQDIAEVLQKAA (SEQ ID NO: 88), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 88 in positions other than position 14 and position 18 are optionally exchanged by other amino acids.

In one embodiment, said designed ankyrin repeat domain comprises (i) an N-terminal capping module having an amino acid sequence DLGKKLLQAARAGQLDEVRELLKAGADVNA (SEQ ID NO: 75), wherein up to 7 amino acids of SEQ ID NO: 75 in positions other than position 8 and position 15 are optionally exchanged by other amino acids, and (ii) a C-terminal capping module having an amino acid sequence QDKSGKTPADLAARAGHQDIAEVLQKAA (SEQ ID NO: 88), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 88 in positions other than position 14 and position 18 are optionally exchanged by other amino acids.

In one embodiment, said designed ankyrin repeat domain comprises (i) an N-terminal capping module having an amino acid sequence DLGKKLLQAARAGQLDEVRELLKAGADVNA (SEQ ID NO: 75), wherein up to 6 amino acids of SEQ ID NO: 75 in positions other than position 8 and position 15 are optionally exchanged by other amino acids, and (ii) a C-terminal capping module having an amino acid sequence QDKSGKTPADLAARAGHQDIAEVLQKAA (SEQ ID NO: 88), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 88 in positions other than position 14 and position 18 are optionally exchanged by other amino acids.

In one embodiment, said designed ankyrin repeat domain comprises (i) an N-terminal capping module having an amino acid sequence DLGKKLLQAARAGQLDEVRELLKAGADVNA (SEQ ID NO: 75), wherein up to 5 amino acids of SEQ ID NO: 75 in positions other than position 8 and position 15 are optionally exchanged by other amino acids, and (ii) a C-terminal capping module having an amino acid sequence QDKSGKTPADLAARAGHQDIAEVLQKAA (SEQ ID NO: 88), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 88 in positions other than position 14 and position 18 are optionally exchanged by other amino acids. In one embodiment, said designed ankyrin repeat domain comprises (i) an N-terminal capping module having an amino acid sequence DLGKKLLQAARAGQLDEVRELLKAGADVNA (SEQ ID NO: 75), wherein up to 4 amino acids of SEQ ID NO: 75 in positions other than position 8 and position 15 are optionally exchanged by other amino acids, and (ii) a C-terminal capping module having an amino acid sequence QDKSGKTPADLAARAGHQDIAEVLQKAA (SEQ ID NO: 88), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 88 in positions other than position 14 and position 18 are optionally exchanged by other amino acids. In one embodiment, said designed ankyrin repeat domain comprises (i) an N-terminal capping module having an amino acid sequence DLGKKLLQAARAGQLDEVRELLKAGADVNA (SEQ ID NO: 75), wherein up to 3 amino acids of SEQ ID NO: 75 in positions other than position 8 and position 15 are optionally exchanged by other amino acids, and (ii) a C-terminal capping module having an amino acid sequence QDKSGKTPADLAARAGHQDIAEVLQKAA (SEQ ID NO: 88), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 88 in positions other than position 14 and position 18 are optionally exchanged by other amino acids. In one embodiment, said designed ankyrin repeat domain comprises (i) an N-terminal capping module having an amino acid sequence DLGKKLLQAARAGQLDEVRELLKAGADVNA (SEQ ID NO: 75), wherein up to 2 amino acids of SEQ ID NO: 75 in positions other than position 8 and position 15 are optionally exchanged by other amino acids, and (ii) a C-terminal capping module having an amino acid sequence QDKSGKTPADLAARAGHQDIAEVLQKAA (SEQ ID NO: 88), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 88 in positions other than position 14 and position 18 are optionally exchanged by other amino acids. In one embodiment, said designed ankyrin repeat domain comprises (i) an N-terminal capping module having an amino acid sequence DLGKKLLQAARAGQLDEVRELLKAGADVNA (SEQ ID NO: 75), wherein up to one amino acid of SEQ ID NO: 75 in a position other than position 8 and position 15 is optionally exchanged by another amino acid, and (ii) a C-terminal capping module having an amino acid sequence QDKSGKTPADLAARAGHQDIAEVLQKAA (SEQ ID NO: 88), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 88 in positions other than position 14 and position 18 are optionally exchanged by other amino acids.

In a further embodiment, the designed ankyrin repeat domain of the invention comprises (i) an N-terminal capping module having an amino acid sequence DLGSKLLQAARAGQLDTVRTLLQAGADVNA (SEQ ID NO: 76), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 75 in positions other than positions 4, 8, 15, 17, 20 and 23 are optionally exchanged by other amino acids, and (ii) a C-terminal capping module having an amino acid sequence QDTQGTTPADLAARAGHQQIASVLQQAA (SEQ ID NO: 89), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 89 in positions other than positions 3, 4, 6, 14, 18, 19, 22 and 26 are optionally exchanged by other amino acids.

In one embodiment, said designed ankyrin repeat domain comprises (i) an N-terminal capping module having an amino acid sequence DLGSKLLQAARAGQLDTVRTLLQAGADVNA (SEQ ID NO: 76), wherein up to 10 amino acids of SEQ ID NO: 76 in positions other than positions 4, 8, 15, 17, 20 and 23 are optionally exchanged by other amino acids, and (ii) a C-terminal capping module having an amino acid sequence QDTQGTTPADLAARAGHQQIASVLQQAA (SEQ ID NO: 89), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 89 in positions other than positions 3, 4, 6, 14, 18, 19, 22 and 26 are optionally exchanged by other amino acids. In one embodiment, said designed ankyrin repeat domain comprises (i) an N-terminal capping module having an amino acid sequence DLGSKLLQAARAGQLDTVRTLLQAGADVNA (SEQ ID NO: 76), wherein up to 9 amino acids of SEQ ID NO: 76 in positions other than positions 4, 8, 15, 17, 20 and 23 are optionally exchanged by other amino acids, and (ii) a C-terminal capping module having an amino acid sequence QDTQGTTPADLAARAGHQQIASVLQQAA (SEQ ID NO: 89), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 89 in positions other than positions 3, 4, 6, 14, 18, 19, 22 and 26 are optionally exchanged by other amino acids. In one embodiment, said designed ankyrin repeat domain comprises (i) an N-terminal capping module having an amino acid sequence DLGSKLLQAARAGQLDTVRTLLQAGADVNA (SEQ ID NO: 76), wherein up to 8 amino acids of SEQ ID NO: 76 in positions other than positions 4, 8, 15, 17, 20 and 23 are optionally exchanged by other amino acids, and (ii) a C-terminal capping module having an amino acid sequence QDTQGTTPADLAARAGHQQIASVLQQAA (SEQ ID NO: 89), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 89 in positions other than positions 3, 4, 6, 14, 18, 19, 22 and 26 are optionally exchanged by other amino acids. In one embodiment, said designed ankyrin repeat domain comprises (i) an N-terminal capping module having an amino acid sequence DLGSK-LLQAARAGQLDTVRTLLQAGADVNA (SEQ ID NO: 76), wherein up to 7 amino acids of SEQ ID NO: 76 in positions other than positions 4, 8, 15, 17, 20 and 23 are optionally exchanged by other amino acids, and (ii) a C-terminal capping module having an amino acid sequence QDTQGTTPADLAARAGHQQIASVLQQAA (SEQ ID NO: 89), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 89 in positions other than positions 3, 4, 6, 14, 18, 19, 22 and 26 are optionally exchanged by other amino acids. In one embodiment, said designed ankyrin repeat domain comprises (i) an N-terminal capping module having an amino acid sequence DLGSK-LLQAARAGQLDTVRTLLQAGADVNA (SEQ ID NO: 76), wherein up to 6 amino acids of SEQ ID NO: 76 in positions other than positions 4, 8, 15, 17, 20 and 23 are optionally exchanged by other amino acids, and (ii) a C-terminal capping module having an amino acid sequence QDTQGTTPADLAARAGHQQIASVLQQAA (SEQ ID NO: 89), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 89 in positions other than positions 3, 4, 6, 14, 18, 19, 22 and 26 are optionally exchanged by other amino acids. In one embodiment, said designed ankyrin repeat domain comprises (i) an N-terminal capping module having an amino acid sequence DLGSK-LLQAARAGQLDTVRTLLQAGADVNA (SEQ ID NO: 76), wherein up to 5 amino acids of SEQ ID NO: 76 in positions other than positions 4, 8, 15, 17, 20 and 23 are optionally exchanged by other amino acids, and (ii) a C-terminal capping module having an amino acid sequence QDTQGTTPADLAARAGHQQIASVLQQAA (SEQ ID NO: 89), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 89 in positions other than positions 3, 4, 6, 14, 18, 19, 22 and 26 are optionally exchanged by other amino acids. In one embodiment, said designed ankyrin repeat domain comprises (i) an N-terminal capping module having an amino acid sequence DLGSK-LLQAARAGQLDTVRTLLQAGADVNA (SEQ ID NO: 76), wherein up to 4 amino acids of SEQ ID NO: 76 in positions other than positions 4, 8, 15, 17, 20 and 23 are optionally exchanged by other amino acids, and (ii) a C-terminal capping module having an amino acid sequence QDTQGTTPADLAARAGHQQIASVLQQAA (SEQ ID NO: 89), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 89 in positions other than positions 3, 4, 6, 14, 18, 19, 22 and 26 are optionally exchanged by other amino acids. In one embodiment, said designed ankyrin repeat domain comprises (i) an N-terminal capping module having an amino acid sequence DLGSK-LLQAARAGQLDTVRTLLQAGADVNA (SEQ ID NO: 76), wherein up to 3 amino acids of SEQ ID NO: 76 in positions other than positions 4, 8, 15, 17, 20 and 23 are optionally exchanged by other amino acids, and (ii) a C-terminal capping module having an amino acid sequence QDTQGTTPADLAARAGHQQIASVLQQAA (SEQ ID NO: 89), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 89 in positions other than positions 3, 4, 6, 14, 18, 19, 22 and 26 are optionally exchanged by other amino acids. In one embodiment, said designed ankyrin repeat domain comprises (i) an N-terminal capping module having an amino acid sequence DLGSK-LLQAARAGQLDTVRTLLQAGADVNA (SEQ ID NO: 76), wherein up to 2 amino acids of SEQ ID NO: 76 in positions other than positions 4, 8, 15, 17, 20 and 23 are optionally exchanged by other amino acids, and (ii) a C-terminal capping module having an amino acid sequence QDTQGTTPADLAARAGHQQIASVLQQAA (SEQ ID NO: 89), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 89 in positions other than positions 3, 4, 6, 14, 18, 19, 22 and 26 are optionally exchanged by other amino acids. In one embodiment, said designed ankyrin repeat domain comprises (i) an N-terminal capping module having an amino acid sequence DLGSK-LLQAARAGQLDTVRTLLQAGADVNA (SEQ ID NO: 76), wherein up to one amino acid of SEQ ID NO: 76 in a position other than positions 4, 8, 15, 17, 20 and 23 is optionally exchanged by another amino acid, and (ii) a C-terminal capping module having an amino acid sequence QDTQGTTPADLAARAGHQQIASVLQQAA (SEQ ID NO: 89), wherein up to 10 amino acids, up to 9 amino acids, up to 8 amino acids, up to 7 amino acids, up to 6 amino acids, up to 5 amino acids, up to 4 amino acids, up to 3 amino acids, up to 2 amino acids, or up to one amino acid of SEQ ID NO: 89 in positions other than positions 3, 4, 6, 14, 18, 19, 22 and 26 are optionally exchanged by other amino acids.

In a further embodiment, the designed ankyrin repeat domain of the invention comprises (i) an N-terminal capping module having an amino acid sequence selected from SEQ ID NOs: 69 to 74, preferably SEQ ID NOs: 70 to 74, more preferably SEQ ID NOs: 71 to 74, more preferably SEQ ID NOs: 72 to 74, more preferably SEQ ID NOs: 73 to 74, most preferably SEQ ID NO: 74, and (ii) a C-terminal capping module having an amino acid sequence selected from SEQ ID NOs: 82 to 87, preferably SEQ ID NOs: 83 to 87, more preferably SEQ ID NOs: 84 to 87, more preferably SEQ ID NOs: 85 to 87, more preferably SEQ ID NOs: 86 to 87, most preferably SEQ ID NO: 87, wherein 3 or 4, preferably 4, amino acid residues comprising a negatively charged side chain in said N- and C-terminal capping modules of said designed ankyrin repeat domain are exchanged by amino acids selected from the group consisting of L, Q, R, S, and T, more preferably L, Q, and R, in positions other than X. Amino acid residues comprising a negatively charged side chain include D and E.

In one embodiment, said designed ankyrin repeat domain comprises (i) an N-terminal capping module having the amino acid sequence of SEQ ID NO: 74 and (ii) a C-terminal capping module having the amino acid sequence of SEQ ID NO: 87, wherein 3 or 4, preferably 4, amino acid residues comprising a negatively charged side chain in said N- and C-terminal capping modules of said designed ankyrin repeat domain are exchanged by amino acids selected from the group consisting of L, Q, R, S, and T, more preferably L, Q, and R, in positions other than X.

In one embodiment, said designed ankyrin repeat domain comprises (i) an N-terminal capping module having the amino acid sequence of SEQ ID NO: 73 and (ii) a C-terminal capping module having the amino acid sequence of SEQ ID NO: 86, wherein 3 or 4, preferably 4, amino acid residues comprising a negatively charged side chain in said N- and C-terminal capping modules of said designed ankyrin repeat domain are exchanged by amino acids selected from the group consisting of L, Q, R, S, and T, more preferably L, Q, and R, in positions other than X.

In one embodiment, said designed ankyrin repeat domain comprises (i) an N-terminal capping module having the amino acid sequence of SEQ ID NO: 72 and (ii) a C-terminal capping module having the amino acid sequence of SEQ ID NO: 85, wherein 3 or 4, preferably 4, amino acid residues comprising a negatively charged side chain in said N- and C-terminal capping modules of said designed ankyrin repeat domain are exchanged by amino acids selected from the group consisting of L, Q, R, S, and T, more preferably L, Q, and R, in positions other than X.

In one embodiment, said designed ankyrin repeat domain comprises (i) an N-terminal capping module having the amino acid sequence of SEQ ID NO: 71 and (ii) a C-terminal capping module having the amino acid sequence of SEQ ID NO: 84, wherein 3 or 4, preferably 4, amino acid residues comprising a negatively charged side chain in said N- and C-terminal capping modules of said designed ankyrin repeat domain are exchanged by amino acids selected from the group consisting of L, Q, R, S, and T, more preferably L, Q, and R, in positions other than X.

In one embodiment, said designed ankyrin repeat domain comprises (i) an N-terminal capping module having the amino acid sequence of SEQ ID NO: 70 and (ii) a C-terminal capping module having the amino acid sequence of SEQ ID NO: 83, wherein 3 or 4, preferably 4, amino acid residues comprising a negatively charged side chain in said N- and C-terminal capping modules of said designed ankyrin repeat domain are exchanged by amino acids selected from the group consisting of L, Q, R, S, and T, more preferably L, Q, and R, in positions other than X.

In one embodiment, said designed ankyrin repeat domain comprises (i) an N-terminal capping module having the amino acid sequence of SEQ ID NO: 71 and (ii) a C-terminal capping module having the amino acid sequence of SEQ ID NO: 83, wherein 3 or 4, preferably 4, amino acid residues comprising a negatively charged side chain in said N- and C-terminal capping modules of said designed ankyrin repeat domain are exchanged by amino acids selected from the group consisting of L, Q, R, S, and T, more preferably L, Q, and R, in positions other than X.

In one embodiment, said designed ankyrin repeat domain comprises (i) an N-terminal capping module having the amino acid sequence of SEQ ID NO: 72 and (ii) a C-terminal capping module having the amino acid sequence of SEQ ID NO: 84, wherein 3 or 4, preferably 4, amino acid residues comprising a negatively charged side chain in said N- and C-terminal capping modules of said designed ankyrin repeat domain are exchanged by amino acids selected from the group consisting of L, Q, R, S, and T, more preferably L, Q, and R, in positions other than X.

In a further embodiment, the designed ankyrin repeat domain of the invention comprises an N-terminal capping module consisting of the amino acid sequence of SEQ ID NO: 75. In one embodiment, the designed ankyrin repeat domain of the invention comprises an N-terminal capping module consisting of the amino acid sequence of SEQ ID NO: 76. In one embodiment, the designed ankyrin repeat domain of the invention comprises an N-terminal capping module consisting of the amino acid sequence of SEQ ID NO: 107. In one embodiment, the designed ankyrin repeat domain of the invention comprises an N-terminal capping module consisting of the amino acid sequence of SEQ ID NO: 108. In one embodiment, the designed ankyrin repeat domain of the invention comprises a C-terminal capping module consisting of the amino acid sequence of SEQ ID NO: 88. In one embodiment, the designed ankyrin repeat domain of the invention comprises a C-terminal capping module consisting of the amino acid sequence of SEQ ID NO: 89.

In a further embodiment, the designed ankyrin repeat domain of the invention comprises an amino acid sequence selected from the group consisting of SEQ ID NOs: 95 to 102, wherein X represents any amino acid. In one embodiment, said designed ankyrin repeat domain comprises an amino acid sequence selected from the group consisting of SEQ ID NOs: 95 to 98, wherein X represents any amino acid. In one embodiment, said designed ankyrin repeat domain comprises an amino acid sequence selected from the group consisting of SEQ ID NOs: 99 to 102, wherein X represents any amino acid. In one embodiment, said designed ankyrin repeat domain comprises an amino acid sequence selected from the group consisting of SEQ ID NOs: 96 and 97, wherein X represents any amino acid. In one embodiment, said designed ankyrin repeat domain comprises the amino acid sequence of SEQ ID NO: 96, wherein X represents any amino acid. In one embodiment, said designed ankyrin repeat domain comprises the amino acid sequence of SEQ ID NO: 97, wherein X represents any amino acid. In one embodiment, said designed ankyrin repeat domain comprises the amino acid sequence of SEQ ID NO: 95, wherein X represents any amino acid. In one embodiment, said designed ankyrin repeat domain comprises the amino acid sequence of SEQ ID NO: 98, wherein X represents any amino acid. In one embodiment, said designed ankyrin repeat domain comprises the amino acid sequence of SEQ ID NO: 99, wherein X represents any amino acid. In one embodiment, said designed ankyrin repeat domain comprises the amino acid sequence of SEQ ID NO: 100, wherein X represents any amino acid. In one embodiment, said designed ankyrin repeat domain comprises the amino acid sequence of SEQ ID NO: 101, wherein X represents any amino acid. In one embodiment, said designed ankyrin repeat domain comprises the amino acid sequence of SEQ ID NO: 102, wherein X represents any amino acid.

In a further embodiment, the designed ankyrin repeat domain of the invention comprises the amino acid sequence DLGX$_1$KLLQAAX$_2$X$_3$GQLDEVRX$_4$LX$_5$X$_6$X$_7$GADVNAX$_8$DX$_9$X$_{10}$GX$_{11}$TPLHX$_{12}$AAX$_{13}$X$_{14}$GHLE IVEVLLKX$_{15}$GADVNAX$_{16}$DX$_{17}$X$_{18}$GX$_{19}$TPLHX$_{20}$AAX$_{21}$X$_{22}$GHLEIVEVLLKX$_{23}$GADVNAX$_{24}$DX$_{25}$X$_{26}$GX$_{27}$TPADX$_{28}$AARX$_{29}$GHEDIAEVLQKX$_{30}$X$_{31}$ (SEQ ID NO: 96), wherein $X_1$ represents any amino acid, preferably K or S;
$X_2$ represents any amino acid, preferably R;
$X_3$ represents any amino acid, preferably A;
$X_4$ represents any amino acid, preferably E or I;
$X_5$ represents any amino acid, preferably M, L, I, more preferably L;
$X_6$ represents any amino acid, preferably A or K; more preferably K;
$X_7$ represents any amino acid, preferably A or N; more preferably A;
$X_8$ and $X_{16}$ represent any amino acid, preferably K;

$X_9$, $X_{10}$, $X_{11}$, $X_{12}$, $X_{13}$, $X_{14}$, $X_{17}$, $X_{18}$, $X_{19}$, $X_{20}$, $X_{21}$, and $X_{22}$ represent any amino acid, preferably any amino acid selected from the group consisting of A, D, E, F, H, I, K, L, N, P, Q, R, S, T, V, W, Y;

$X_{15}$, and $X_{23}$ represent any amino acid, preferably A, N, H, or Y; more preferably A;

$X_{24}$ represents any amino acid, preferably K or Q, more preferably Q;

$X_{25}$ represents any amino acid, preferably K or T, more preferably K;

$X_{26}$ represents any amino acid, preferably S or Q, more preferably S;

$X_{27}$ represents any amino acid, preferably K or T, more preferably K;

$X_{28}$ represents any amino acid, preferably L or I, more preferably L;

$X_{29}$ represents any amino acid, preferably A or N, more preferably A;

$X_{30}$ represents any amino acid, L or A, more preferably A; and $X_{31}$ represents any amino acid, N or A, more preferably A.

In one embodiment, the designed ankyrin repeat domain of the invention comprises the amino acid sequence DLGX$_1$KLLQAAX$_2$X$_3$GQLDEVRX$_4$LX$_5$X$_6$X$_7$GADVNA X$_8$DX$_9$X$_{10}$GX$_{11}$TPLHX$_{12}$AAX$_{13}$X$_{14}$GHLE IVEVLLKX$_{15}$GADVNAX$_{16}$DX$_{17}$X$_{18}$GX$_{19}$TPLHX$_{20}$ AAX$_{21}$X$_{22}$GHLEIVEVLLKX$_{23}$GADVNAX$_{24}$DX$_{25}$X$_{26}$ GX$_{27}$TPLHX$_{28}$AAX$_{29}$X$_{30}$GHLEIVEVLLKX$_{31}$GADVNA X$_{32}$DX$_{33}$X$_{34}$GX$_{35}$TPADX$_{36}$AARX$_{37}$G HEDIAEVLQKX$_{38}$X$_{39}$ (SEQ ID NO: 97), wherein $X_1$ represents any amino acid, preferably K or S;
$X_2$ represents any amino acid, preferably R;
$X_3$ represents any amino acid, preferably A;
$X_4$ represents any amino acid, preferably E or I;
$X_5$ represents any amino acid, preferably M, L, I, more preferably L;
$X_6$ represents any amino acid, preferably A or K; more preferably K;
$X_7$ represents any amino acid, preferably A or N; more preferably A;
$X_8$, $X_{16}$, and $X_{24}$ represent any amino acid, preferably K;
$X_9$, $X_{10}$, $X_{11}$, $X_{12}$, $X_{13}$, $X_{14}$, $X_{17}$, $X_{18}$, $X_{19}$, $X_{20}$, $X_{21}$, $X_{22}$, $X_{25}$, $X_{26}$, $X_{27}$, $X_{28}$, $X_{29}$, and $X_{30}$ represent any amino acid, preferably any amino acid selected from the group consisting of A, D, E, F, H, I, K, L, N, P, Q, R, S, T, V, W, Y;
$X_{15}$, $X_{23}$, and $X_{31}$ represent any amino acid, preferably A, N, H, or Y; more preferably A;
$X_{32}$ represents any amino acid, preferably K or Q, more preferably Q;
$X_{33}$ represents any amino acid, preferably K or T, more preferably K;
$X_{34}$ represents any amino acid, preferably S or Q, more preferably S;
$X_{35}$ represents any amino acid, preferably K or T, more preferably K;
$X_{36}$ represents any amino acid, preferably L or I, more preferably L;
$X_{37}$ represents any amino acid, preferably A or N, more preferably A;
$X_{38}$ represents any amino acid, L or A, more preferably A; and
$X_{39}$ represents any amino acid, N or A, more preferably A.

In a further embodiment, the designed ankyrin repeat domain of the invention consists of an amino acid sequence wherein the amino acid at position 8 is Q, the amino acid at position 15 is L, the amino acid at position 110 is R, and the amino acid at position 114 is Q. In a preferred embodiment, said designed ankyrin repeat domain consists of an amino acid sequence with a length of 124 amino acids. Preferably, said position numbers are determined by alignment to SEQ ID NO: 96 using the position numbers of SEQ ID NO: 96. Preferably, said alignment comprises no amino acid gaps. Sequence alignment generation is a procedure well known in the art.

In one embodiment, the designed ankyrin repeat domain of the invention consists of an amino acid sequence wherein the amino acid at position 8 is Q, the amino acid at position 15 is L, the amino acid at position 143 is R, and the amino acid at position 147 is Q. In a preferred embodiment, said designed ankyrin repeat domain consists of an amino acid sequence of 157 amino acids. Preferably, said position numbers are determined by alignment to SEQ ID NO: 97 using the position numbers of SEQ ID NO: 97. Preferably, said alignment comprises no amino acid gaps. Sequence alignment generation is a procedure well known in the art.

In one embodiment, the designed ankyrin repeat domain of the invention consists of an amino acid sequence wherein the amino acid at position 8 is Q, the amino acid at position 15 is L, the amino acid at position 77 is R, and the amino acid at position 81 is Q. In a preferred embodiment, said designed ankyrin repeat domain consists of an amino acid sequence of 91 amino acids. Preferably, said position numbers are determined by alignment to SEQ ID NO: 95 using the position numbers of SEQ ID NO: 95. Preferably, said alignment comprises no amino acid gaps. Sequence alignment generation is a procedure well known in the art.

In one embodiment, the designed ankyrin repeat domain of the invention consists of an amino acid sequence wherein the amino acid at position 8 is Q, the amino acid at position 15 is L, the amino acid at position 176 is R, and the amino acid at position 180 is Q. In a preferred embodiment, said designed ankyrin repeat domain consists of an amino acid sequence of 190 amino acids. Preferably, said position numbers are determined by alignment to SEQ ID NO: 98 using the position numbers of SEQ ID NO: 98. Preferably, said alignment comprises no amino acid gaps. Sequence alignment generation is a procedure well known in the art.

In a further embodiment, the designed ankyrin repeat domain of the invention has an amino acid sequence which differs from SEQ ID NO: 104 by at least one, preferably at least two, more preferably at least three amino acids, and by up to 30, up to 25, up to 20, up to 15, up to 14, up to 13, up to 12, up to 11, up to ten, up to 9, up to 8, up to 7, up to 6, up to 5, preferably up to 4 amino acids, outside the positions comprising X, and wherein X represents any amino acid. In one embodiment, said designed ankyrin repeat domain has an amino acid sequence which differs from SEQ ID NO: 104 by the amino acids at positions 15 and 114, more preferably positions 8, 15, and 114, more preferably positions 8, 15, 110, and 114, and wherein X represents any amino acid. In one embodiment, said designed ankyrin repeat domain has an amino acid sequence which differs from SEQ ID NO: 104 by the amino acids at positions 15 and 114, more preferably positions 8, 15, and 114, more preferably positions 8, 15, 110, and 114, and wherein said amino acid at position 8 is Q, said amino acid at position 15 is L, said amino acid at position 110 is R, and said amino acid at position 114 is Q, and wherein X represents any amino acid. In one embodiment, said designed ankyrin repeat domain has an amino acid sequence which differs from SEQ ID NO: 104 by the amino acids at positions 4, 8, 15, 17, 20, 23, 99, 100, 102, 110, 114, 115, 118, and 122, and wherein X represents any amino acid. In one embodiment, said designed ankyrin repeat domain has an amino acid sequence which differs from SEQ ID NO: 104 by the amino acids at positions 4, 8, 15, 17, 20, 23, 99, 100, 102, 110, 114, 115, 118, and 122, and wherein said amino acid at position 4 is S, said amino acid at position 8 is Q, said amino acid at position 15 is L, said amino acid at position 17 is T, said amino acid at position 20 is T, said amino acid at position 23 is Q, said amino acid at position 99 is T, said amino acid at position 100 is Q, said amino acid at position 102 is T, said amino acid at position 110 is R, said amino acid at position 114 is Q, said amino acid at position 115 is Q, said amino acid at position 118 is S, and said amino acid at position 122 is Q, and wherein X represents any amino acid.

In one embodiment, the designed ankyrin repeat domain of the invention has an amino acid sequence which differs from SEQ ID NO: 105 by at least one, preferably at least two, more preferably at least three amino acids, and by up to 30, up to 25, up to 20, up to 15, up to 14, up to 13, up to 12, up to 11, up to ten, up to 9, up to 8, up to 7, up to 6, up to 5, preferably up to 4 amino acids, outside the positions comprising X, and wherein X represents any amino acid. In one embodiment, said designed ankyrin repeat domain has an amino acid sequence which differs from SEQ ID NO: 105 by the amino acids at positions 15 and 147, more preferably positions 8, 15, and 147, more preferably positions 8, 15, 143, and 147, and wherein X represents any amino acid. In one embodiment, said designed ankyrin repeat domain has an amino acid sequence which differs from SEQ ID NO: 105 by the amino acids at positions 15 and 147, more preferably positions 8, 14, and 147, more preferably positions 8, 15, 143, and 147, and wherein said amino acid at position 8 is Q, said amino acid at position 15 is L, said amino acid at position 143 is R, and said amino acid at position 147 is Q, and wherein X represents any amino acid. In one embodiment, said designed ankyrin repeat domain has an amino acid sequence which differs from SEQ ID NO: 105 by the amino acids at positions 4, 8, 15, 17, 20, 23, 132, 133, 135, 143, 147, 148, 151, and 155, and wherein X represents any amino acid. In one embodiment, said designed ankyrin repeat domain has an amino acid sequence which differs from SEQ ID NO: 105 by the amino acids at positions 4, 8, 15, 17, 20, 23, 132, 133, 135, 143, 147, 148, 151, and 155, and wherein said amino acid at position 4 is S, said amino acid at position 8 is Q, said amino acid at position 15 is L, said amino acid at position 17 is T, said amino acid at position 20 is T, said amino acid at position 23 is Q, said amino acid at position 132 is T, said amino acid at position 133 is Q, said amino acid at position 135 is T, said amino acid at position 143 is R, said amino acid at position 147 is Q, said amino acid at position 148 is Q, said amino acid at position 151 is S, and said amino acid at position 155 is Q, and wherein X represents any amino acid.

In one embodiment, the designed ankyrin repeat domain of the invention has an amino acid sequence which differs from SEQ ID NO: 103 by at least one, preferably at least two, more preferably at least three amino acids, and by up to 30, up to 25, up to 20, up to 15, up to 14, up to 13, up to 12, up to 11, up to ten, up to 9, up to 8, up to 7, up to 6, up to 5, preferably up to 4 amino acids, outside the positions comprising X, and wherein X represents any amino acid. In one embodiment, said designed ankyrin repeat domain has an amino acid sequence which differs from SEQ ID NO: 103 by the amino acids at positions 15 and 81, more preferably positions 8, 15, and 81, more preferably positions 8, 15, 77, and 81, and wherein X represents any amino acid. In one embodiment, said designed ankyrin repeat domain has an amino acid sequence which differs from SEQ ID NO: 103 by the amino acids at positions 15 and 81, more preferably positions 8, 15, and 81, more preferably positions 8, 15, 77, and 81, and wherein said amino acid at position 8 is Q, said amino acid at position 15 is L, said amino acid at position 77 is R, and said amino acid at position 81 is Q, and wherein X represents any amino acid. In one embodiment, said designed ankyrin repeat domain has an amino acid sequence which differs from SEQ ID NO: 103 by the amino acids at positions 4, 8, 15, 17, 20, 23, 66, 67, 69, 77, 81, 82, 85, and 89, and wherein X represents any amino acid. In one embodiment, said designed ankyrin repeat domain has an amino acid sequence which differs from SEQ ID NO: 103 by the amino acids at 4, 8, 15, 17, 20, 23, 66, 67, 69, 77, 81, 82, 85, and 89, and wherein said amino acid at position 4 is S, said amino acid at position 8 is Q, said amino acid at position 15 is L, said amino acid at position 17 is T, said amino acid at position 20 is T, said amino acid at position 23 is Q, said amino acid at position 66 is T, said amino acid at position 67 is Q, said amino acid at position 69 is T, said amino acid at position 77 is R, said amino acid at position 81 is Q, said amino acid at position 82 is Q, said amino acid at position 85 is S, and said amino acid at position 89 is Q, and wherein X represents any amino acid.

In one embodiment, the designed ankyrin repeat domain of the invention has an amino acid sequence which differs from SEQ ID NO: 106 by at least one, preferably at least two, more preferably at least three amino acids, and by up to 30, up to 25, up to 20, up to 15, up to 14, up to 13, up to 12, up to 11, up to ten, up to 9, up to 8, up to 7, up to 6, up to 5, preferably up to 4 amino acids, outside the positions comprising X, and wherein X represents any amino acid. In one embodiment, said designed ankyrin repeat domain has an amino acid sequence which differs from SEQ ID NO: 106 by the amino acids at positions 15 and 180, more preferably positions 8, 15, and 180, more preferably positions 8, 15, 176, and 180, and wherein X represents any amino acid. In one embodiment, said designed ankyrin repeat domain has an amino acid sequence which differs from SEQ ID NO: 106 by the amino acids at positions 15 and 180, more preferably positions 8, 15, and 180, more preferably positions 8, 15, 176, and 180, and wherein said amino acid at position 8 is Q, said amino acid at position 15 is L, said amino acid at position 176 is R, and said amino acid at position 180 is Q, and wherein X represents any amino acid. In one embodiment, said designed ankyrin repeat domain has an amino acid sequence which differs from SEQ ID NO: 106 by the amino acids at positions 4, 8, 15, 17, 20, 23, 66, 67, 69, 77, 81, 82, 85, and 89, and wherein X represents any amino acid. In one embodiment, said designed ankyrin repeat domain has an amino acid sequence which differs from SEQ ID NO: 106 by the amino acids at 4, 8, 15, 17, 20, 23, 165, 166, 168, 176, 180, 181, 184, and 188, and wherein said amino acid at position 4 is S, said amino acid at position 8 is Q, said amino acid at position 15 is L, said amino acid at position 17 is T, said amino acid at position 20 is T, said amino acid at position 23 is Q, said amino acid at position 165 is T, said amino acid at position 166 is Q, said amino acid at position 168 is T, said amino acid at position 176 is R, said amino acid at position 180 is Q, said amino acid at position 181 is Q, said amino acid at position 184 is S, and said amino acid at position 188 is Q, and wherein X represents any amino acid.

In a further embodiment, the designed ankyrin repeat domain of the invention has an amino acid sequence which is identical to SEQ ID NO: 104, with the exception of the amino acids at positions 15 and 114. In one embodiment, said designed ankyrin repeat domain has an amino acid sequence which is identical to SEQ ID NO: 104, with the exception of the amino acids at positions 8, 15, and 114. In one embodiment, said designed ankyrin repeat domain has an amino acid sequence which is identical to SEQ ID NO:

104, with the exception of the amino acids at positions 8, 15, 110 and 114. In one embodiment, said designed ankyrin repeat domain has an amino acid sequence which is identical to SEQ ID NO: 104, with the exception of the amino acids at positions 4, 8, 15, 17, 20, 23, 99, 100, 102, 110, 114, 115, 118, and 122. In one embodiment, said designed ankyrin repeat domain has an amino acid sequence which is identical to SEQ ID NO: 104, with the exception of the amino acids at positions 4, 8, 15, 17, 20, 23, 99, 100, 102, 110, 114, 115, 118, and 122, and wherein said amino acid at position 4 is S, said amino acid at position 8 is Q, said amino acid at position 15 is L, said amino acid at position 17 is T, said amino acid at position 20 is T, said amino acid at position 23 is Q, said amino acid at position 99 is T, said amino acid at position 100 is Q, said amino acid at position 102 is T, said amino acid at position 110 is R, said amino acid at position 114 is Q, said amino acid at position 115 is Q, said amino acid at position 118 is S, and said amino acid at position 122 is Q, and wherein X represents any amino acid. In one embodiment, said designed ankyrin repeat domain has an amino acid sequence which is identical to SEQ ID NO: 104, with the exception of the amino acids at positions 8, 15, 110 and 114, and wherein said amino acid at position 8 is Q, said amino acid at position 15 is L, said amino acid at position 110 is R, and said amino acid at position 114 is Q, and wherein X represents any amino acid. In one embodiment, said designed ankyrin repeat domain has an amino acid sequence which is identical to SEQ ID NO: 104, with the exception of the amino acids at positions 8, 15, and 114, and wherein said amino acid at position 8 is Q, said amino acid at position 15 is L, and said amino acid at position 114 is Q, and wherein X represents any amino acid. In one embodiment, said designed ankyrin repeat domain has an amino acid sequence which is identical to SEQ ID NO: 104, with the exception of the amino acids at positions 15 and 114, and wherein said amino acid at position 15 is L, and said amino acid at position 114 is Q, and wherein X represents any amino acid.

In one embodiment, the designed ankyrin repeat domain of the invention has an amino acid sequence which is identical to SEQ ID NO: 105, with the exception of the amino acids at positions 15 and 147. In one embodiment, said designed ankyrin repeat domain has an amino acid sequence which is identical to SEQ ID NO: 105, with the exception of the amino acids at positions 8, 15 and 147. In one embodiment, said designed ankyrin repeat domain has an amino acid sequence which is identical to SEQ ID NO: 105, with the exception of the amino acids at positions 8, 15, 143 and 147. In one embodiment, said designed ankyrin repeat domain has an amino acid sequence which is identical to SEQ ID NO: 105, with the exception of the amino acids at positions 4, 8, 15, 17, 20, 23, 132, 133, 135, 143, 147, 148, 151, and 155. In one embodiment, said designed ankyrin repeat domain has an amino acid sequence which is identical to SEQ ID NO: 105, with the exception of the amino acids at positions 4, 8, 15, 17, 20, 23, 132, 133, 135, 143, 147, 148, 151, and 155, and wherein said amino acid at position 4 is S, said amino acid at position 8 is Q, said amino acid at position 15 is L, said amino acid at position 17 is T, said amino acid at position 20 is T, said amino acid at position 23 is Q, said amino acid at position 132 is T, said amino acid at position 133 is Q, said amino acid at position 135 is T, said amino acid at position 143 is R, said amino acid at position 147 is Q, said amino acid at position 148 is Q, said amino acid at position 151 is S, and said amino acid at position 155 is Q, and wherein X represents any amino acid. In one embodiment, said designed ankyrin repeat domain has an amino acid sequence which is identical to SEQ ID NO: 105, with the exception of the amino acids at positions 8, 15, 143 and 147, and wherein said amino acid at position 8 is Q, said amino acid at position 15 is L, said amino acid at position 143 is R, and said amino acid at position 147 is Q, and wherein X represents any amino acid. In one embodiment, said designed ankyrin repeat domain is identical to SEQ ID NO: 105, with the exception of the amino acids at positions 8, 15 and 147 and wherein said amino acid at position 8 is Q, said amino acid at position 15 is L, and said amino acid at position 147 is Q, and wherein X represents any amino acid. In one embodiment, said designed ankyrin repeat domain is identical to SEQ ID NO: 105, with the exception of the amino acids at positions 15 and 147, and wherein said amino acid at position 15 is L, and said amino acid at position 147 is Q, and wherein X represents any amino acid.

In one embodiment, the designed ankyrin repeat domain of the invention has an amino acid sequence which is identical to SEQ ID NO: 103, with the exception of the amino acids at positions 15 and 81. In one embodiment, said designed ankyrin repeat domain has an amino acid sequence which is identical to SEQ ID NO: 103, with the exception of the amino acids at positions 8, 15 and 81. In one embodiment, said designed ankyrin repeat domain has an amino acid sequence which is identical to SEQ ID NO: 103, with the exception of the amino acids at positions 8, 15, 77 and 81. In one embodiment, said designed ankyrin repeat domain has an amino acid sequence which is identical to SEQ ID NO: 103, with the exception of the amino acids at positions 4, 8, 15, 17, 20, 23, 66, 67, 69, 77, 81, 82, 85, and 89. In one embodiment, said designed ankyrin repeat domain has an amino acid sequence which is identical to SEQ ID NO: 103, with the exception of the amino acids at positions 4, 8, 15, 17, 20, 23, 66, 67, 69, 77, 81, 82, 85, and 89, and wherein said amino acid at position 4 is S, said amino acid at position 8 is Q, said amino acid at position 15 is L, said amino acid at position 17 is T, said amino acid at position 20 is T, said amino acid at position 23 is Q, said amino acid at position 66 is T, said amino acid at position 67 is Q, said amino acid at position 69 is T, said amino acid at position 77 is R, said amino acid at position 81 is Q, said amino acid at position 82 is Q, said amino acid at position 85 is S, and said amino acid at position 89 is Q, and wherein X represents any amino acid. In one embodiment, said designed ankyrin repeat domain has an amino acid sequence which is identical to SEQ ID NO: 103, with the exception of the amino acids at positions 8, 15, 77 and 81, and wherein said amino acid at position 8 is Q, said amino acid at position 15 is L, said amino acid at position 77 is R, and said amino acid at position 81 is Q, and wherein X represents any amino acid. In one embodiment, said designed ankyrin repeat domain is identical to SEQ ID NO: 103, with the exception of the amino acids at positions 8, 15 and 81, and wherein said amino acid at position 8 is Q, said amino acid at position 15 is L, and said amino acid at position 81 is Q, and wherein X represents any amino acid. In one embodiment, said designed ankyrin repeat domain is identical to SEQ ID NO: 103, with the exception of the amino acids at positions 15 and 81, and wherein said amino acid at position 15 is L, and said amino acid at position 81 is Q, and wherein X represents any amino acid.

In one embodiment, the designed ankyrin repeat domain of the invention has an amino acid sequence which is identical to SEQ ID NO: 106, with the exception of the amino acids at positions 15 and 180. In one embodiment, said designed ankyrin repeat domain has an amino acid sequence which is identical to SEQ ID NO: 106, with the exception of the amino acids at positions 8, 15 and 180. In one embodiment, said designed ankyrin repeat domain has an amino acid sequence which is identical to SEQ ID NO: 106, with the exception of the amino acids at positions 8, 15, 176 and 180. In one embodiment, said designed ankyrin repeat domain has an amino acid sequence which is identical to SEQ ID NO: 106, with the exception of the amino acids at positions 4, 8, 15, 17, 20, 23, 165, 166, 168, 176, 180, 181, 184, and 188. In one embodiment, said designed ankyrin repeat domain has an amino acid sequence which is identical to SEQ ID NO: 106, with the exception of the amino acids at positions 4, 8, 15, 17, 20, 23, 165, 166, 168, 176, 180, 181, 184, and 188, and wherein said amino acid at position 4 is S, said amino acid at position 8 is Q, said amino acid at position 15 is L, said amino acid at position 17 is T, said amino acid at position 20 is T, said amino acid at position 23 is Q, said amino acid at position 165 is T, said amino acid at position 166 is Q, said amino acid at position 168 is T, said amino acid at position 176 is R, said amino acid at position 180 is Q, said amino acid at position 181 is Q, said amino acid at position 184 is S, and said amino acid at position 188 is Q, and wherein X represents any amino acid. In one embodiment, said designed ankyrin repeat domain has an amino acid sequence which is identical to SEQ ID NO: 106, with the exception of the amino acids at positions 8, 15, 176 and 180, and wherein said amino acid at position 8 is Q, said amino acid at position 15 is L, said amino acid at position 176 is R, and said amino acid at position 180 is Q, and wherein X represents any amino acid. In one embodiment, said designed ankyrin repeat domain is identical to SEQ ID NO: 106, with the exception of the amino acids at positions 8, 15 and 180, and wherein said amino acid at position 8 is Q, said amino acid at position 15 is L, and said amino acid at position 180 is Q, and wherein X represents any amino acid. In one embodiment, said designed ankyrin repeat domain is identical to SEQ ID NO: 106, with the exception of the amino acids at positions 15 and 180, and wherein said amino acid at position 15 is L, and said amino acid at position 180 is Q, and wherein X represents any amino acid.

In a further embodiment, the designed ankyrin repeat domain of the invention comprises an N-terminal capping module having the amino acid sequence $X_1X_2X_3X_4X_5X_6X_7QX_8X_9X_{10}X_{11}X_{12}X_{13}LX_{14}X_{15}X_{16}X_{17}X_{18}X_{19}X_{20}X_{21}X_{22}GADVNA$ (SEQ ID NO: 81), wherein $X_1$ represents any amino acid, preferably D;
$X_2$ represents any amino acid, preferably L;
$X_3$ represents any amino acid, preferably G;
$X_4$ represents any amino acid, preferably K or S;
$X_5$ represents any amino acid, preferably K;
$X_6$ represents any amino acid, preferably L;
$X_7$ represents any amino acid, preferably L;
$X_8$ represents any amino acid, preferably A;
$X_9$ represents any amino acid, preferably A;
$X_{10}$ represents any amino acid, preferably R;
$X_{11}$ represents any amino acid, preferably A;
$X_{12}$ represents any amino acid, preferably G;
$X_{13}$ represents any amino acid, preferably Q;
$X_{14}$ represents any amino acid, preferably D;
$X_{15}$ represents any amino acid, preferably E or T;
$X_{16}$ represents any amino acid, preferably V;
$X_{17}$ represents any amino acid, preferably R;
$X_{18}$ represents any amino acid, preferably E or T;
$X_{19}$ represents any amino acid, preferably L;
$X_{20}$ represents any amino acid, preferably L;
$X_{21}$ represents any amino acid, preferably K or Q; and
$X_{22}$ represents any amino acid, preferably A.

In one embodiment, $X_4$ is S. In one embodiment, $X_{15}$ is T. In one embodiment, $X_{18}$ is T. In one embodiment, $X_{21}$ is Q. In one embodiment, $X_4$ is S, $X_{15}$ is T, $X_{18}$ is T, and $X_{21}$ is Q. In a preferred embodiment, $X_6$ is L, $X_7$ is L, $X_8$ is A, $X_9$ is A, and $X_{12}$ is G (SEQ ID NO: 80). In a more preferred embodiment, $X_1$ is D, $X_2$ is L, $X_3$ is G, $X_6$ is L, $X_7$ is L, $X_8$ is A, $X_9$ is A, $X_{12}$ is G, $X_{13}$ is Q, $X_{14}$ is D, $X_1e$ is V, $X_{17}$ is R and $X_{19}$ is L (SEQ ID NO: 79). In an even more preferred embodiment $X_1$ is D, $X_2$ is L, $X_3$ is G, $X_5$ is K, $X_6$ is L, $X_7$ is L, $X_8$ is A, $X_9$ is A, $X_{12}$ is G, $X_{13}$ is Q, $X_{14}$ is D, $X_1e$ is V, $X_{17}$ is R, $X_{19}$ is L, $X_{20}$ is L and $X_{22}$ is A (SEQ ID NO: 78). In another even more preferred embodiment $X_1$ is D, $X_2$ is L, $X_3$ is G, $X_5$ is K, $X_6$ is L, $X_7$ is L, $X_8$ is A, $X_9$ is A, $X_{12}$ is G, $X_{13}$ is Q, $X_{14}$ is D, $X_{15}$ is E, $X_1e$ is V, $X_{17}$ is R, $X_{18}$ is E, $X_{19}$ is L, $X_{20}$ is L, $X_{21}$ is K and $X_{22}$ is A (SEQ ID NO: 77). In a most preferred embodiment, $X_1$ is D, $X_2$ is L, $X_3$ is G, $X_4$ is S, $X_5$ is K, $X_e$ is L, $X_7$ is L, $X_8$ is A, $X_9$ is A, $X_{10}$ is R, $X_{11}$ is A, $X_{12}$ is G, $X_{13}$ is Q, $X_{14}$ is D, $X_1$ is T, $X_1e$ is V, $X_{17}$ is R, $X_{18}$ is T, $X_{19}$ is L, $X_{20}$ is L, $X_{21}$ is Q, and $X_{22}$ is A (SEQ ID NO: 76). In an alternative most preferred embodiment, $X_1$ is D, $X_2$ is L, $X_3$ is G, $X_4$ is K, $X_5$ is K, $X_e$ is L, $X_7$ is L, $X_8$ is A, $X_9$ is A, $X_{10}$ is R, $X_{11}$ is A, $X_{12}$ is G, $X_{13}$ is Q, $X_{14}$ is D, $X_{15}$ is E, $X_1e$ is V, $X_{17}$ is R, $X_{18}$ is E, $X_{19}$ is L, $X_{20}$ is L, $X_{21}$ is K, and $X_{22}$ is A (SEQ ID NO: 75).

In a further embodiment, the designed ankyrin repeat domain of the invention comprises an N-terminal capping module comprising the amino acid sequence $DLGX_1X_2LLQAAX_3X_4GQLDX_5VRX_6LX_7X_8X_9$ (SEQ ID NO: 111), wherein $X_1$ represents any amino acid, preferably K or S;
$X_2$ represents any amino acid, preferably K;
$X_3$ represents any amino acid, preferably R;
$X_4$ represents any amino acid, preferably A;
$X_5$ represents any amino acid, preferably E or T;
$X_6$ represents any amino acid, preferably E or T;
$X_7$ represents any amino acid, preferably L;
$X_8$ represents any amino acid, preferably K or Q; and
$X_9$ represents any amino acid, preferably A.

In one embodiment, $X_1$ is S. In one embodiment, $X_5$ is T. In one embodiment, $X_6$ is T. In one embodiment, $X_8$ is Q. In one embodiment, $X_1$ is S, $X_5$ is T, $X_6$ is T, and $X_8$ is Q. In a preferred embodiment, $X_2$ is K, $X_7$ is L, and $X_9$ is A (SEQ ID NO: 110). In a more preferred embodiment, $X_2$ is K, $X_5$ is E, $X_6$ is E, $X_7$ is L, and $X_9$ is A (SEQ ID NO: 109). In a most preferred embodiment $X_1$ is S, $X_2$ is K, $X_3$ is R, $X_4$ is A, $X_5$ is T, $X_6$ is T, $X_7$ is L, $X_8$ is Q, and $X_9$ is A (SEQ ID NO: 108). In an alternative most preferred embodiment, $X_1$ is K, $X_2$ is K, $X_3$ is R, $X_4$ is A, $X_5$ is E, $X_6$ is E, $X_7$ is L, $X_8$ is K, and $X_9$ is A (SEQ ID NO: 107).

In a further embodiment, the designed ankyrin repeat domain of the invention comprises a C-terminal capping module having the amino acid sequence $X_1DX_2X_3GX_4TPX_5X_6X_7X_8X_9RX_{10}X_{11}X_{12}QX_{13}X_{14}X_{15}X_{16}X_{17}X_{18}X_{19}X_{20}X_{21}X_{22}$, wherein $X_1$ represents any amino acid, preferably Q;
$X_2$ represents any amino acid, preferably K or T;
$X_3$ represents any amino acid, preferably S or Q;
$X_4$ represents any amino acid, preferably K or T;
$X_5$ represents any amino acid, preferably A;
$X_6$ represents any amino acid, preferably D;
$X_7$ represents any amino acid, preferably L;
$X_8$ represents any amino acid, preferably A;
$X_9$ represents any amino acid, preferably A;
$X_{10}$ represents any amino acid, preferably A;
$X_{11}$ represents any amino acid, preferably G;
$X_{12}$ represents any amino acid, preferably H;
$X_{13}$ represents any amino acid, preferably D or Q;

$X_{14}$ represents any amino acid, preferably I;
$X_{15}$ represents any amino acid, preferably A;
$X_{16}$ represents any amino acid, preferably E or S;
$X_{17}$ represents any amino acid, preferably V;
$X_{18}$ represents any amino acid, preferably L;
$X_{19}$ represents any amino acid, preferably Q;
$X_{20}$ represents any amino acid, preferably K or Q;
$X_{21}$ represents any amino acid, preferably A; and
$X_{22}$ represents any amino acid, preferably A.

In one embodiment, $X_2$ is T. In one embodiment, $X_3$ is Q. In one embodiment, $X_4$ is T. In one embodiment, $X_{13}$ is Q. In one embodiment, $X_{16}$ is S. In one embodiment, $X_{20}$ is Q. In one embodiment, $X_2$ is T, $X_3$ is Q, $X_4$ is T, $X_{13}$ is Q, $X_{16}$ is S, and $X_{20}$ is Q. In a preferred embodiment, $X_{21}$ is A and $X_{22}$ is A (SEQ ID NO: 94). In another preferred embodiment, $X_9$ is A (SEQ ID NO: 93). In a more preferred embodiment, $X_8$ is A, $X_9$ is A, $X_{11}$ is G, $X_{21}$ is A and $X_{22}$ is A (SEQ ID NO: 92). In an even more preferred embodiment $X_5$ is A, $X_6$ is D, $X_8$ is A, $X_9$ is A, $X_{11}$ is G, $X_{12}$ is H, $X_{14}$ is I, $X_{15}$ is A, $X_{17}$ is V, $X_{18}$ is L, $X_{19}$ is Q, $X_{21}$ is A and $X_{22}$ is A (SEQ ID NO: 91). In another even more preferred embodiment $X_5$ is A, $X_6$ is D, $X_8$ is A, $X_9$ is A, X is G, $X_{12}$ is H, $X_{13}$ is D, $X_{14}$ is I, $X_{15}$ is A, $X_{16}$ is E, $X_{17}$ is V, $X_1$, is L, $X_{19}$ is Q, $X_{20}$ is K, $X_{21}$ is A and $X_{22}$ is A (SEQ ID NO: 90). In a most preferred embodiment, $X_1$ is Q, $X_2$ is T, $X_3$ is Q, $X_4$ is T, $X_5$ is A, $X_6$ is D, $X_7$ is L, $X_8$ is A, $X_9$ is A, $X_{10}$ is A, $X_{11}$ is G, $X_{12}$ is H, $X_{13}$ is Q, $X_{14}$ is I, $X_{15}$ is A, $X_{16}$ is S, $X_{17}$ is V, $X_{18}$ is L, $X_{19}$ is Q, $X_{20}$ is Q, $X_{21}$ is A and $X_{22}$ is A (SEQ ID NO: 89). In an alternative most preferred embodiment, $X_1$ is Q, $X_2$ is K, $X_3$ is S, $X_4$ is K, $X_5$ is A, $X_6$ is D, $X_7$ is L, $X_8$ is A, $X_9$ is A, $X_{10}$ is A, $X_{11}$ is G, $X_{12}$ is H, $X_{13}$ is D, $X_{14}$ is I, $X_{15}$ is A, $X_1e$ is E, $X_{17}$ is V, $X_{18}$ is L, $X_{19}$ is Q, $X_{20}$ is K, $X_{21}$ is A and $X_{22}$ is A (SEQ ID NO: 88).

The designed ankyrin repeat domains consisting of SEQ ID NOs: 10, 11, 13, 14, 15, 17, 18, 19, 21, 22, and 23 are examples of such designed ankyrin repeat domains of the invention.

In a second aspect, the invention provides a protein comprising one or more designed ankyrin repeat domains of the invention. In a preferred embodiment, said protein is a recombinant binding protein. In one embodiment, said protein comprises one, two, three, four or five designed ankyrin repeat domains of the invention. In the context of the present invention, when the protein of the invention comprises more than one designed ankyrin repeat domain of the invention, each of said designed ankyrin repeat domains may be independently selected among any one of the designed ankyrin repeat domains of the invention described herein. In one embodiment, said protein further comprises at least one moiety for half-life extension. In one preferred embodiment, said moiety for half-life extension is a designed ankyrin repeat domain with binding specificity for serum albumin.

In one embodiment, said protein further comprises one, two or three designed ankyrin repeat domains with binding specificity for serum albumin. In the context of the present invention, when the protein of the invention comprises more than one designed ankyrin repeat domains with binding specificity for serum albumin, each of said designed ankyrin repeat domains may be independently selected among any one of the designed ankyrin repeat domains with binding specificity for serum albumin described herein.

In one embodiment, said protein comprises (i) at least one designed ankyrin repeat domain of the invention, and (ii) at least one moiety for half-life extension. Such moieties for half-life extension are well-known in the art and comprise, amongst others, polyethylene-glycol (PEG), serum albumin-binding polypeptides, serum albumin-binding proteins, serum albumin, and immunoglobulin Fc fragments. In one preferred embodiment, a moiety for half-life extension is a designed ankyrin repeat domain with binding specificity for serum albumin.

In one embodiment, said protein comprises (i) at least one designed ankyrin repeat domain of the invention, and (ii) at least one designed ankyrin repeat domain with binding specificity for serum albumin.

In one embodiment, said protein comprises (i) at least one designed ankyrin repeat domain of the invention, and (ii) at least one designed ankyrin repeat domain with binding specificity for serum albumin, wherein said designed ankyrin repeat domain with binding specificity for serum albumin comprises an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, or 100% amino acid sequence identity with any one of SEQ ID NOs: 4 to 8, preferably SEQ ID NOs: 4 to 7, more preferably SEQ ID NOs: 4 to 6. In one embodiment, said designed ankyrin repeat domain with binding specificity for serum albumin comprises an amino acid sequence with at least 80% amino acid sequence identity with any one of SEQ ID NOs: 4 to 8, preferably SEQ ID NOs: 4 to 7, more preferably SEQ ID NOs: 4 to 6. In one embodiment, said designed ankyrin repeat domain with binding specificity for serum albumin comprises an amino acid sequence with at least 85% amino acid sequence identity with any one of SEQ ID NOs: 4 to 8, preferably SEQ ID NOs: 4 to 7, more preferably SEQ ID NOs: 4 to 6. In one embodiment, said designed ankyrin repeat domain with binding specificity for serum albumin comprises an amino acid sequence with at least 90% amino acid sequence identity with any one of SEQ ID NOs: 4 to 8, preferably SEQ ID NOs: 4 to 7, more preferably SEQ ID NOs: 4 to 6. In one embodiment, said designed ankyrin repeat domain with binding specificity for serum albumin comprises an amino acid sequence with at least 92% amino acid sequence identity with any one of SEQ ID NOs: 4 to 8, preferably SEQ ID NOs: 4 to 7, more preferably SEQ ID NOs: 4 to 6. In one embodiment, said designed ankyrin repeat domain with binding specificity for serum albumin comprises an amino acid sequence with at least 94% amino acid sequence identity with any one of SEQ ID NOs: 4 to 8, preferably SEQ ID NOs: 4 to 7, more preferably SEQ ID NOs: 4 to 6. In one embodiment, said designed ankyrin repeat domain with binding specificity for serum albumin comprises an amino acid sequence with at least 96% amino acid sequence identity with any one of SEQ ID NOs: 4 to 8, preferably SEQ ID NOs: 4 to 7, more preferably SEQ ID NOs: 4 to 6. In one embodiment, said designed ankyrin repeat domain with binding specificity for serum albumin comprises an amino acid sequence with at least 98% amino acid sequence identity with any one of SEQ ID NOs: 4 to 8, preferably SEQ ID NOs: 4 to 7, more preferably SEQ ID NOs: 4 to 6. In one embodiment, said designed ankyrin repeat domain with binding specificity for serum albumin comprises an amino acid sequence consisting of anyone of SEQ ID NOs: 4 to 8, preferably SEQ ID NOs: 4 to 7, more preferably SEQ ID NOs: 4 to 6. In one embodiment, said designed ankyrin repeat domain with binding specificity for serum albumin does not comprise an amino acid sequence selected from the group consisting of SEQ ID NOs: 75 to 81, and 88 to 94, wherein X represents any amino acid.

In one embodiment, said protein further comprises at least one peptide linker. In one particular embodiment, the protein of the invention comprises (i) at least one designed ankyrin repeat domain of the invention, (ii) at least one designed ankyrin repeat domain with binding specificity for serum albumin as described herein, and (iii) at least one peptide linker.

In one embodiment, said peptide linker is a proline-threonine rich peptide linker or a glycine-serine rich peptide linker. In one embodiment, said peptide linker is a proline-threonine rich peptide linker. In one embodiment, said peptide linker is a glycine-serine rich peptide linker. In one preferred embodiment, said peptide linker has the amino acid sequence of SEQ ID NO: 2 or 3. In one embodiment, said peptide linker has the amino acid sequence of SEQ ID NO: 2. In one embodiment, said peptide linker has the amino acid sequence of SEQ ID NO: 3.

The proteins consisting of SEQ ID NOs: 25, 26, 28, 29, 30, 32, 33, 34, 36, 37, 38, 40, 41, 43, 44, 45, 47, 48, 49, 51, 52, 53, 55, 56, 58, 59, 60, 62, 63, 64, 66, 67, and 68 are examples of such proteins of the invention.

In one embodiment, said protein comprises at least two designed ankyrin repeat domains of the invention. In one embodiment, said protein comprises (i) at least two designed ankyrin repeat domains of the invention, and (ii) at least one designed ankyrin repeat domain with binding specificity for serum albumin. In a preferred embodiment, said protein comprises (i) at least two designed ankyrin repeat domains of the invention, and (ii) at least one designed ankyrin repeat domain with binding specificity for serum albumin as described herein. In a preferred embodiment, said protein comprises (i) at least two designed ankyrin repeat domains of the invention, and (ii) at least one designed ankyrin repeat domain with binding specificity for serum albumin, wherein said designed ankyrin repeat domain with binding specificity for serum albumin has an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, or 100% amino acid sequence identity with any one of SEQ ID NOs: 4 to 8, more preferably 4 to 6. In one embodiment, said protein comprises (i) at least two designed ankyrin repeat domains of the invention, and (ii) at least two designed ankyrin repeat domains with binding specificity for serum albumin. In a preferred embodiment, said recombinant binding protein comprises (i) at least two designed ankyrin repeat domains of the invention, and (ii) at least two designed ankyrin repeat domains with binding specificity for serum albumin as described herein. In a preferred embodiment, said recombinant binding protein comprises (i) at least two designed ankyrin repeat domains of the invention, and (ii) at least two designed ankyrin repeat domains with binding specificity for serum albumin, wherein each of said designed ankyrin repeat domains with binding specificity for serum albumin independently has an amino acid sequence with at least 80%, 81%, 82%, 83%, 84%, 85%, 86%, 87%, 88%, 89%, 90%, 91%, 92%, 93%, 94%, 95%, 96%, 97%, 98%, 99%, or 100% amino acid sequence identity with any one of SEQ ID NOs: 4 to 8, more preferably 4 to 6. In one preferred embodiment, the protein of the invention is a recombinant binding protein.

The designed ankyrin repeat domain provided by the present invention and described herein comprises sequence modifications that lead to improved pharmacokinetic properties of said designed ankyrin repeat domain compared to the designed ankyrin repeat domain not comprising said sequence modifications. Moreover, said sequences modifications lead to improved pharmacokinetic properties of a protein comprising said designed ankyrin repeat domain, compared to a comparator protein which comprises the designed ankyrin repeat domain not comprising said sequence modifications and which is otherwise identical to said protein. The designed ankyrin repeat domains consisting of SEQ ID NOs: 10, 11, 13, 14, 15, 17, 18, 19, 21, 22, and 23 are examples of such designed ankyrin repeat domains with improved pharmacokinetic properties. The proteins consisting of SEQ ID NOs: 25, 26, 28, 29, 30, 32, 33, 34, 36, 37, 38, 40, 41, 43, 44, 45, 47, 48, 49, 51, 52, 53, 55, 56, 58, 59, 60, 62, 63, 64, 66, 67, and 68 are examples of proteins comprising such designed ankyrin repeat domains with improved pharmacokinetic properties.

The designed ankyrin repeat domains consisting of SEQ ID NOs: 10 and 11 are examples of designed ankyrin repeat domains comprising such sequence modifications (compared to the designed ankyrin repeat domain consisting of SEQ ID NO: 9, which does not comprise such sequence modifications), which exhibit improved pharmacokinetic properties, as shown by the pharmacokinetic profiles of Proteins #25 and #26 (comprising SEQ ID NOs: 10 and 11, respectively) in comparison to Protein #24 (comprising SEQ ID NO: 9). Likewise, the designed ankyrin repeat domains consisting of SEQ ID NOs: 13 to 15 are examples of designed ankyrin repeat domains comprising such sequence modifications (compared to the designed ankyrin repeat domain consisting of SEQ ID NO: 12, which does not comprise such sequence modifications), which exhibit improved pharmacokinetic properties, as shown by the pharmacokinetic profiles of Proteins #28, #29 and #30 (comprising SEQ ID NOs: 13, 14 and 15, respectively) in comparison to Protein #27 (comprising SEQ ID NO: 12). Likewise, the designed ankyrin repeat domains consisting of SEQ ID NOs: 17 to 19 are examples of designed ankyrin repeat domains comprising such sequence modifications (compared to the designed ankyrin repeat domain consisting of SEQ ID NO: 16, which does not comprise such sequence modifications), which exhibit improved pharmacokinetic properties, as shown by the pharmacokinetic profiles of Proteins #32, #33 and #34 (comprising SEQ ID NOs: 17, 18 and 19, respectively) in comparison to Protein #31 (comprising SEQ ID NO: 16). Likewise, the designed ankyrin repeat domains consisting of SEQ ID NOs: 21 to 23 are examples of designed ankyrin repeat domains comprising such sequence modifications (compared to the designed ankyrin repeat domain consisting of SEQ ID NO: 20, which does not comprise such sequence modifications), which exhibit improved pharmacokinetic properties, as shown by the pharmacokinetic profiles of Proteins #36, #37 and #38 (comprising SEQ ID NOs: 21, 22 and 23, respectively) in comparison to Protein #35 (comprising SEQ ID NO: 20). These examples are described in detail in the Examples.

In one embodiment, the term improved pharmacokinetic properties refers to an increased area under the curve, a reduced clearance, or an increased terminal half-life.

In one embodiment, the term improved pharmacokinetic properties refers to an increased area under the curve. In one embodiment, said increase in area under the curve is at least 5%, 10%, 15%, 20%, 25%, 30%, 35%, 40%, 45%, 50%, 55%, 60%, 65%, 70%, 75%, 80%, most preferably 85%.

In one embodiment, the term improved pharmacokinetic properties refers to a reduced clearance. In one embodiment, said reduction in clearance is at least 5%, 10%, 15%, 20%, 25%, 30%, 35%, 40%, most preferably 45%.

In one embodiment, the term improved pharmacokinetic properties refers to an increased terminal half-life. In one embodiment, said increase in terminal half-life is at least 5%, 10%, 15%, 20%, 25%, 30%, 35%, 40%, 45%, 50%, 55%, 60%, 65%, 70%, 75%, 80%, most preferably 85%.

In one embodiment the pharmacokinetic parameters are determined in mouse. Preferably, said pharmacokinetic parameters in mouse are determined by applying a protein at a dose of 1 mg/kg by intravenous injection into the tail vein of Balb/c mice. This procedure is described in Example 6.

In one embodiment the pharmacokinetic parameters are determined in cynomolgus monkey. Preferably, said pharmacokinetic parameters in cynomolgus monkey are determined by applying a protein at a dose of 1 mg/kg by 30 min intravenous injection. This procedure is described in Example 7.

In one embodiment, the pharmacokinetic properties of a designed ankyrin repeat domain of the invention are assessed by measuring the pharmacokinetic properties of a protein comprising (i) said designed ankyrin repeat domain of the invention, and (ii) a moiety for half-life extension, and by comparing the pharmacokinetic properties of said protein with a comparator protein as described herein. Preferably, said moiety for half-life extension is a designed ankyrin repeat domain with binding specificity for serum albumin. Proteins #25, #26, #28, #29, #30, #32, #33, #34, #36, #37, #38, #40, #41, #43, #44, #45, #47, #48, #49, #51, #52, #53, #55, #56, #58, #59, #60, #62, #63, #64, #66, #67, and #68 are examples of such proteins. Proteins #24, #27, #31, #35, #39, #42, #46, #46, #50, #54, #57, #61, and #65 are examples of such comparator proteins. Examples of designed ankyrin repeat domains with binding specificity for serum albumin are the designed ankyrin repeat domains consisting of SEQ ID NOs: 4 to 8. In one embodiment, the designed ankyrin repeat domain with binding specificity for serum albumin is N-terminal of the designed ankyrin repeat domain of the invention. In one embodiment, said improved pharmacokinetic properties are assessed by measuring the pharmacokinetic properties of a protein comprising (i) a designed ankyrin repeat domain of the invention, and (ii) a designed ankyrin repeat domain with binding specificity for serum albumin, wherein said designed ankyrin repeat domain with binding specificity for serum albumin consists of an amino acid sequence with at least 80% amino acid sequence identify with any of SEQ ID NOs: 4 to 8, preferably 4 to 6, more preferably 4, and by comparing the pharmacokinetic properties of said protein with a comparator protein as described herein.

In one embodiment, said pharmacokinetic properties are assessed by measuring the pharmacokinetic properties of a protein comprising (i) a designed ankyrin repeat domain of the invention, and (ii) a designed ankyrin repeat domain with binding specificity for serum albumin, wherein said designed ankyrin repeat domain with binding specificity for serum albumin consists of the amino acid sequence of SEQ ID NO: 4 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% amino acid sequence identify with SEQ ID NO: 4, and by comparing the pharmacokinetic properties of said protein with a comparator protein as described herein. In one embodiment, said pharmacokinetic properties are assessed by measuring the pharmacokinetic properties of a protein comprising (i) a designed ankyrin repeat domain of the invention, and (ii) a designed ankyrin repeat domain with binding specificity for serum albumin, wherein said designed ankyrin repeat domain with binding specificity for serum albumin consists of the amino acid sequence of SEQ ID NO: 4 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% amino acid sequence identify with SEQ ID NO: 4, and (iii) a polypeptide linker consisting of the amino acid sequence of SEQ ID NO: 3, and by comparing the pharmacokinetic properties of said protein with a comparator protein as described herein. In one embodiment, said pharmacokinetic properties are assessed by measuring the pharmacokinetic properties of a protein comprising from N-terminus to C-terminus (i) SEQ ID NO: 4, (ii) SEQ ID NO: 3, and (iii) a designed ankyrin repeat domain of the invention, and by comparing the pharmacokinetic properties of said protein with a comparator protein as described herein.

In one embodiment, said pharmacokinetic properties are assessed by measuring the pharmacokinetic properties of a protein comprising (i) a designed ankyrin repeat domain of the invention, and (ii) a designed ankyrin repeat domain with binding specificity for serum albumin, wherein said designed ankyrin repeat domain with binding specificity for serum albumin consists of the amino acid sequence of SEQ ID NO: 5 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% amino acid sequence identify with SEQ ID NO: 5, and by comparing the pharmacokinetic properties of said protein with a comparator protein as described herein. In one embodiment, said pharmacokinetic properties are assessed by measuring the pharmacokinetic properties of a protein comprising (i) a designed ankyrin repeat domain of the invention, and (ii) a designed ankyrin repeat domain with binding specificity for serum albumin, wherein said designed ankyrin repeat domain with binding specificity for serum albumin consists of the amino acid sequence of SEQ ID NO: 5 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% amino acid sequence identify with SEQ ID NO: 5, and (iii) a polypeptide linker consisting of the amino acid sequence of SEQ ID NO: 3, and by comparing the pharmacokinetic properties of said protein with a comparator protein as described herein. In one embodiment, said pharmacokinetic properties are assessed by measuring the pharmacokinetic properties of a protein comprising from N to C terminus (i) SEQ ID NO: 5, (ii) SEQ ID NO: 3, (iii) a designed ankyrin repeat domain of the invention.

In one embodiment, said pharmacokinetic properties are assessed by measuring the pharmacokinetic properties of a protein comprising (i) a designed ankyrin repeat domain of the invention, and (ii) a designed ankyrin repeat domain with binding specificity for serum albumin, wherein said designed ankyrin repeat domain with binding specificity for serum albumin consists of the amino acid sequence of SEQ ID NO: 6 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% amino acid sequence identify with SEQ ID NO: 6, and by comparing the pharmacokinetic properties of said protein with a comparator protein as described herein. In one embodiment, said pharmacokinetic properties are assessed by measuring the pharmacokinetic properties of a protein comprising (i) a designed ankyrin repeat domain of the invention, and (ii) a designed ankyrin repeat domain with binding specificity for serum albumin, wherein said designed ankyrin repeat domain with binding specificity for serum albumin consists of the amino acid sequence of SEQ ID NO: 6 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% amino acid sequence identify with SEQ ID NO: 6, and (iii) a polypeptide linker consisting of the amino acid sequence of SEQ ID NO: 3, and by comparing the pharmacokinetic properties of said protein with a comparator protein as described herein. In one embodiment, said pharmacokinetic properties are assessed by measuring the pharmacokinetic properties of a protein comprising from N to C terminus (i) SEQ ID NO: 6, (ii) SEQ ID NO: 3, (iii) a designed ankyrin repeat domain of the invention.

In a further embodiment, the designed ankyrin repeat domain of the invention, exhibits improved pharmacokinetic properties compared to a comparator designed ankyrin repeat domain,
  wherein said designed ankyrin repeat domain and said comparator designed ankyrin repeat domain have the identical amino acid sequence with the exception that said designed ankyrin repeat domain comprises (i) in the N-terminal capping module the amino acid Q at position 8 and the amino acid L at position 15, and (ii) in the C-terminal capping module the amino acid R at position 14 and the amino acid Q at position 18,
  and said comparator designed ankyrin repeat domain comprises (i) in the N-terminal capping module amino acids different from Q at position 8 and D at position 15, and (ii) in the C-terminal capping module amino acids different from R at position 14 and E at position 18,
  wherein said position numbers of positions of the N-terminal capping module are determined by alignment to SEQ ID NO: 69 using the position numbers of SEQ ID NO: 69, wherein said position numbers of positions of the C-terminal capping module are determined by alignment to SEQ ID NO: 82 using the position numbers of SEQ ID NO: 82, and wherein said alignment comprises no amino acid gaps, and
  wherein said pharmacokinetic properties are assessed by measuring the pharmacokinetic properties of a protein and a comparator protein,
    wherein said protein from N to C terminus consists of (i) a designed ankyrin repeat domain with binding specificity for serum albumin selected from the group consisting of SEQ ID NOs: 4 to 8, (ii) a polypeptide linker selected from the group consisting of SEQ ID NOs: 2 to 3, and (iii) said designed ankyrin repeat domain, and
    wherein said comparator protein from N to C terminus consists of (i) a designed ankyrin repeat domain with binding specificity for serum albumin selected from the group consisting of SEQ ID NOs: 4 to 8, (ii) a polypeptide linker selected from the group consisting of SEQ ID NOs: 2 to 3, and (iii) said comparator designed ankyrin repeat domain, and
    wherein the amino acid sequences of said designed ankyrin repeat domains with binding specificity for serum albumin of said protein and said comparator protein are identical, and wherein the amino acid sequences of said polypeptide linkers of said protein and said comparator protein are identical.

In one embodiment, the designed ankyrin repeat domain of the invention exhibits improved pharmacokinetic properties compared to a comparator designed ankyrin repeat domain,
  wherein said designed ankyrin repeat domain and said comparator designed ankyrin repeat domain have the identical amino acid sequence with the exception that said designed ankyrin repeat domain comprises (i) in the N-terminal capping module the amino acid Q at position 8 and the amino acid L at position 15, and (ii) in the C-terminal capping module the amino acid R at position 14 and the amino acid Q at position 18,
  and said comparator designed ankyrin repeat domain comprises (i) in the N-terminal capping module the amino acid E at position 8 and the amino acid D at position 15, and (ii) in the C-terminal capping module the amino acid D at position 14 and the amino acid E at position 18,
  wherein said position numbers of positions of the N-terminal capping module are determined by alignment to SEQ ID NO: 69 using the position numbers of SEQ ID NO: 69, wherein said position numbers of positions of the C-terminal capping module are determined by alignment to SEQ ID NO: 82 using the position numbers of SEQ ID NO: 82, and wherein said alignment comprises no amino acid gaps, and
  wherein said pharmacokinetic properties are assessed by measuring the pharmacokinetic properties of a protein and a comparator protein,
    wherein said protein from N to C terminus consists of (i) a designed ankyrin repeat domain with binding specificity for serum albumin selected from the group consisting of SEQ ID NOs: 4 to 8, (ii) a polypeptide linker selected from the group consisting of SEQ ID NOs: 2 to 3, and (iii) said designed ankyrin repeat domain, and
    wherein said comparator protein from N to C terminus consists of (i) a designed ankyrin repeat domain with binding specificity for serum albumin selected from the group consisting of SEQ ID NOs: 4 to 8, (ii) a polypeptide linker selected from the group consisting of SEQ ID NOs: 2 to 3, and (iii) said comparator designed ankyrin repeat domain, and
    wherein the amino acid sequences of said designed ankyrin repeat domains with binding specificity for serum albumin of said protein and said comparator protein are identical, and wherein the amino acid sequences of said polypeptide linkers of said protein and said comparator protein are identical.

In one embodiment, the protein of the invention comprises at least a first moiety and a second moiety,
  wherein said first moiety is a designed ankyrin repeat domain of the present invention, and
  wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and
  wherein said protein exhibits improved pharmacokinetic properties compared to a comparator protein,
  wherein said comparator protein consists of an identical amino acid sequence as said protein, with the exception that the designed ankyrin repeat domain of said comparator protein corresponding to said first moiety has (i) in the N-terminal capping module the amino acid E at position 8 and the amino acid D at position 15, and (ii) in the C-terminal capping module the amino acid D at position 14 and the amino acid E at position 18,
  wherein said position numbers of positions of the N-terminal capping module are determined by alignment to SEQ ID NO: 69 using the position numbers of SEQ ID NO: 69, wherein said position numbers of positions of the C-terminal capping module are determined by alignment to SEQ ID NO: 82 using the position numbers of SEQ ID NO: 82, and wherein said alignment comprises no amino acid gaps.

In one embodiment, the protein of the invention comprises at least a first moiety and a second moiety,
  wherein said first moiety is a designed ankyrin repeat domain of the present invention, and
  wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 5, and
  wherein said protein exhibits improved pharmacokinetic properties compared to a comparator protein,
  wherein said comparator protein consists of an identical amino acid sequence as said protein, with the exception that the designed ankyrin repeat domain of said comparator protein corresponding to said first moiety has (i) in the N-terminal capping module the amino acid E at position 8 and the amino acid D at position 15, and (ii) in the C-terminal capping module the amino acid D at position 14 and the amino acid E at position 18,
  wherein said position numbers of positions of the N-terminal capping module are determined by alignment to SEQ ID NO: 69 using the position numbers of SEQ ID NO: 69, wherein said position numbers of positions of the C-terminal capping module are determined by alignment to SEQ ID NO: 82 using the position numbers of SEQ ID NO: 82, and wherein said alignment comprises no amino acid gaps.

In one embodiment, the protein of the invention comprises at least a first moiety and a second moiety,
  wherein said first moiety is a designed ankyrin repeat domain of the present invention, and
  wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 6, and
  wherein said protein exhibits improved pharmacokinetic properties compared to a comparator protein,
  wherein said comparator protein consists of an identical amino acid sequence as said protein, with the exception that the designed ankyrin repeat domain of said comparator protein corresponding to said first moiety has (i) in the N-terminal capping module the amino acid E at position 8 and the amino acid D at position 15, and (ii) in the C-terminal capping module the amino acid D at position 14 and the amino acid E at position 18,
  wherein said position numbers of positions of the N-terminal capping module are determined by alignment to SEQ ID NO: 69 using the position numbers of SEQ ID NO: 69, wherein said position numbers of positions of the C-terminal capping module are determined by alignment to SEQ ID NO: 82 using the position numbers of SEQ ID NO: 82, and wherein said alignment comprises no amino acid gaps.

In one embodiment, the protein of the invention comprises at least a first moiety and a second moiety,
  wherein said first moiety is a designed ankyrin repeat domain of the present invention, and
  wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with any one of SEQ ID NOs: 4 to 8, and
  wherein said protein exhibits improved pharmacokinetic properties compared to a comparator protein,
  wherein said comparator protein consists of an identical amino acid sequence as said protein, with the exception that said designed ankyrin repeat domain of said first moiety comprises (i) any one of SEQ ID NOs: 75 to 81 and 107 to 111, preferably SEQ ID NOs: 75 to 80 and 107 to 111, more preferably SEQ ID NOs: 75 to 79 and 107 to 111, more preferably SEQ ID NOs: 75 to 78 and 107 to 110, more preferably SEQ ID NOs: 75 to 77 and 107 to 109, more preferably SEQ ID NOs: 75 to 76 and 107 to 108, more preferably SEQ ID NOs: 75 and 107, and (ii) any one of SEQ ID NOs: 88 or 94, preferably SEQ ID NOs: 88 to 93, more preferably SEQ ID NOs: 88 to 92, more preferably SEQ ID NOs: 88 to 91, more preferably SEQ ID NOs: 88 to 90, more preferably SEQ ID NOs: 88 to 89, more preferably SEQ ID NO: 88, whereas the designed ankyrin repeat domain of said comparator protein corresponding to said first moiety comprises SEQ ID NO: 69 instead of any one of SEQ ID NOs: 75 to 81 and 107 to 111 and SEQ ID NO: 82 instead of any one of SEQ ID NOs: 88 to 94.

In one embodiment, the protein of the invention comprises at least a first moiety and a second moiety,
  wherein said first moiety is a designed ankyrin repeat domain of the present invention, and
  wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and
  wherein said protein exhibits improved pharmacokinetic properties compared to a comparator protein,
  wherein said comparator protein consists of an identical amino acid sequence as said protein, with the exception that said designed ankyrin repeat domain of said first moiety comprises (i) any one of SEQ ID NOs: 75 to 81 and 107 to 111, preferably SEQ ID NOs: 75 to 80 and 107 to 111, more preferably SEQ ID NOs: 75 to 79 and 107 to 111, more preferably SEQ ID NOs: 75 to 78 and 107 to 110, more preferably SEQ ID NOs: 75 to 77 and 107 to 109, more preferably SEQ ID NOs: 75 to 76 and 107 to 108, more preferably SEQ ID NO: 75 and 107, and (ii) any one of SEQ ID NOs: 88 or 94, preferably SEQ ID NOs: 88 to 93, more preferably SEQ ID NOs: 88 to 92, more preferably SEQ ID NOs: 88 to 91, more preferably SEQ ID NOs: 88 to 90, more preferably SEQ ID NOs: 88 to 89, more preferably SEQ ID NO: 88, whereas the designed ankyrin repeat domain of said comparator protein corresponding to said first moiety comprises SEQ ID NO: 69 instead of any one of SEQ ID NOs: 75 to 81 and SEQ ID NO: 82 instead of any one of SEQ ID NOs: 88 to 94.

In one embodiment, the protein of the invention comprises at least a first moiety and a second moiety,
  wherein said first moiety is a designed ankyrin repeat domain of the present invention, and
  wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 5, and wherein said protein exhibits improved pharmacokinetic properties compared to a comparator protein, wherein said comparator protein consists of an identical amino acid sequence as said protein, with the exception that said designed ankyrin repeat domain of said first moiety comprises (i) any one of SEQ ID NOs: 75 to 81 and 107 to 111, preferably SEQ ID NOs: 75 to 80 and 107 to 111, more preferably SEQ ID NOs: 75 to 79 and 107 to 111, more preferably SEQ ID NOs: 75 to 78 and 107 to 110, more preferably SEQ ID NOs: 75 to 77 and 107 to 109, more preferably SEQ ID NOs: 75 to 76 and 107 to 108, more preferably SEQ ID NO: 75 and 107, and (ii) any one of SEQ ID NOs: 88 or 94, preferably SEQ ID NOs: 88 to 93, more preferably SEQ ID NOs: 88 to 92, more preferably SEQ ID NOs: 88 to 91, more preferably SEQ ID NOs: 88 to 90, more preferably SEQ ID NOs: 88 to 89, more preferably SEQ ID NO: 88, whereas the designed ankyrin repeat domain of said comparator protein corresponding to said first moiety comprises SEQ ID NO: 69 instead of any one of SEQ ID NOs: 75 to 81 and SEQ ID NO: 82 instead of any one of SEQ ID NOs: 88 to 94.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 6, and wherein said protein exhibits improved pharmacokinetic properties compared to a comparator protein, wherein said comparator protein consists of an identical amino acid sequence as said protein, with the exception that said designed ankyrin repeat domain of said first moiety comprises (i) any one of SEQ ID NOs: 75 to 81 and 107 to 111, preferably SEQ ID NOs: 75 to 80 and 107 to 111, more preferably SEQ ID NOs: 75 to 79 and 107 to 111, more preferably SEQ ID NOs: 75 to 78 and 107 to 110, more preferably SEQ ID NOs: 75 to 77 and 107 to 109, more preferably SEQ ID NOs: 75 to 76 and 107 to 108, more preferably SEQ ID NO: 75 and 107, and (ii) any one of SEQ ID NOs: 88 or 94, preferably SEQ ID NOs: 88 to 93, more preferably SEQ ID NOs: 88 to 92, more preferably SEQ ID NOs: 88 to 91, more preferably SEQ ID NOs: 88 to 90, more preferably SEQ ID NOs: 88 to 89, more preferably SEQ ID NO: 88, whereas the designed ankyrin repeat domain of said comparator protein corresponding to said first moiety comprises SEQ ID NO: 69 instead of any one of SEQ ID NOs: 75 to 81 and SEQ ID NO: 82 instead of any one of SEQ ID NOs: 88 to 94.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and wherein said protein exhibits improved pharmacokinetic properties compared to a comparator protein, wherein said comparator protein consists of an identical amino acid sequence as said protein, with the exception that said designed ankyrin repeat domain of said first moiety comprises SEQ ID NOs: 75 or 76, preferably SEQ ID NO: 75, and SEQ ID NOs: 88 or 89, preferably SEQ ID NO: 88, whereas the designed ankyrin repeat domain of said comparator protein corresponding to said first moiety comprises SEQ ID NO: 69 instead of SEQ ID NO: 75 or 76 and SEQ ID NO: 82 instead of SEQ ID NO: 88 or 89.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 5, and wherein said protein exhibits improved pharmacokinetic properties compared to a comparator protein, wherein said comparator protein consists of an identical amino acid sequence as said protein, with the exception that said designed ankyrin repeat domain of said first moiety comprises SEQ ID NOs: 75 or 76, preferably SEQ ID NO: 75, and SEQ ID NOs: 88 or 89, preferably SEQ ID NO: 88, whereas the designed ankyrin repeat domain of said comparator protein corresponding to said first moiety comprises SEQ ID NO: 69 instead of SEQ ID NO: 75 or 76 and SEQ ID NO: 82 instead of SEQ ID NO: 88 or 89.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 6, and wherein said protein exhibits improved pharmacokinetic properties compared to a comparator protein, wherein said comparator protein consists of an identical amino acid sequence as said protein, with the exception that said designed ankyrin repeat domain of said first moiety comprises SEQ ID NOs: 75 or 76, preferably SEQ ID NO: 75, and SEQ ID NOs: 88 or 89, preferably SEQ ID NO: 88, whereas the designed ankyrin repeat domain of said comparator protein corresponding to said first moiety comprises SEQ ID NO: 69 instead of SEQ ID NO: 75 or 76 and SEQ ID NO: 82 instead of SEQ ID NO: 88 or 89.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and wherein said protein exhibits improved pharmacokinetic properties compared to a comparator protein, wherein said comparator protein consists of an identical amino acid sequence as said protein, with the exception that said designed ankyrin repeat domain of said first moiety comprises any one of SEQ ID NOs: 75 to 81 and any one of SEQ ID NOs: 88 to 94, whereas the designed ankyrin repeat domain of said comparator protein corresponding to said first moiety comprises SEQ ID NO: 69 instead of any one of SEQ ID NOs: 75 to 81 and SEQ ID NO: 82 instead of any one of SEQ ID NOs: 88 to 94.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and wherein said protein exhibits improved pharmacokinetic properties compared to a comparator protein, wherein said comparator protein consists of an identical amino acid sequence as said protein, with the exception that said designed ankyrin repeat domain of said first moiety comprises any one of SEQ ID NOs: 75 to 80 and any one of SEQ ID NOs: 88 to 93, whereas the designed ankyrin repeat domain of said comparator protein corresponding to said first moiety comprises SEQ ID NO: 69 instead of any one of SEQ ID NOs: 75 to 80 and SEQ ID NO: 82 instead of any one of SEQ ID NOs: 88 to 93.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and wherein said protein exhibits improved pharmacokinetic properties compared to a comparator protein, wherein said comparator protein consists of an identical amino acid sequence as said protein, with the exception that said designed ankyrin repeat domain of said first moiety comprises any one of SEQ ID NOs: 75 to 79 and any one of SEQ ID NOs: 88 to 92, whereas the designed ankyrin repeat domain of said comparator protein corresponding to said first moiety comprises SEQ ID NO: 69 instead of any one of SEQ ID NOs: 75 to 79 and SEQ ID NO: 82 instead of any one of SEQ ID NOs: 88 to 92.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and wherein said protein exhibits improved pharmacokinetic properties compared to a comparator protein, wherein said comparator protein consists of an identical amino acid sequence as said protein, with the exception that said designed ankyrin repeat domain of said first moiety comprises any one of SEQ ID NOs: 75 to 78 and any one of SEQ ID NOs: 88 to 91, whereas the designed ankyrin repeat domain of said comparator protein corresponding to said first moiety comprises SEQ ID NO: 69 instead of any one of SEQ ID NOs: 75 to 78 and SEQ ID NO: 82 instead of any one of SEQ ID NOs: 88 to 91.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and wherein said protein exhibits improved pharmacokinetic properties compared to a comparator protein, wherein said comparator protein consists of an identical amino acid sequence as said protein, with the exception that said designed ankyrin repeat domain of said first moiety comprises any one of SEQ ID NOs: 75 to 77 and any one of SEQ ID NOs: 88 to 90, whereas the designed ankyrin repeat domain of said comparator protein corresponding to said first moiety comprises SEQ ID NO: 69 instead of any one of SEQ ID NOs: 75 to 77 and SEQ ID NO: 82 instead of any one of SEQ ID NOs: 88 to 90.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and wherein said protein exhibits improved pharmacokinetic properties compared to a comparator protein, wherein said comparator protein consists of an identical amino acid sequence as said protein, with the exception that said designed ankyrin repeat domain of said first moiety comprises any one of SEQ ID NOs: 75 to 76 and any one of SEQ ID NOs: 88 to 89, whereas the designed ankyrin repeat domain of said comparator protein corresponding to said first moiety comprises SEQ ID NO: 69 instead of any one of SEQ ID NOs: 75 to 76 and SEQ ID NO: 82 instead of any one of SEQ ID NOs: 88 to 89.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 5, and wherein said protein exhibits improved pharmacokinetic properties compared to a comparator protein, wherein said comparator protein consists of an identical amino acid sequence as said protein, with the exception that said designed ankyrin repeat domain of said first moiety comprises any one of SEQ ID NOs: 75 to 81 and any one of SEQ ID NOs: 88 to 94, whereas the designed ankyrin repeat domain of said comparator protein corresponding to said first moiety comprises SEQ ID NO: 69 instead of any one of SEQ ID NOs: 75 to 81 and SEQ ID NO: 82 instead of any one of SEQ ID NOs: 88 to 94.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 5, and wherein said protein exhibits improved pharmacokinetic properties compared to a comparator protein, wherein said comparator protein consists of an identical amino acid sequence as said protein, with the exception that said designed ankyrin repeat domain of said first moiety comprises any one of SEQ ID NOs: 75 to 80 and any one of SEQ ID NOs: 88 to 93, whereas the designed ankyrin repeat domain of said comparator protein corresponding to said first moiety comprises SEQ ID NO: 69 instead of any one of SEQ ID NOs: 75 to 80 and SEQ ID NO: 82 instead of any one of SEQ ID NOs: 88 to 93.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 5, and wherein said protein exhibits improved pharmacokinetic properties compared to a comparator protein, wherein said comparator protein consists of an identical amino acid sequence as said protein, with the exception that said designed ankyrin repeat domain of said first moiety comprises any one of SEQ ID NOs: 75 to 79 and any one of SEQ ID NOs: 88 to 92, whereas the designed ankyrin repeat domain of said comparator protein corresponding to said first moiety comprises SEQ ID NO: 69 instead of any one of SEQ ID NOs: 75 to 79 and SEQ ID NO: 82 instead of any one of SEQ ID NOs: 88 to 92.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 5, and wherein said protein exhibits improved pharmacokinetic properties compared to a comparator protein, wherein said comparator protein consists of an identical amino acid sequence as said protein, with the exception that said designed ankyrin repeat domain of said first moiety comprises any one of SEQ ID NOs: 75 to 78 and any one of SEQ ID NOs: 88 to 91, whereas the designed ankyrin repeat domain of said comparator protein corresponding to said first moiety comprises SEQ ID NO: 69 instead of any one of SEQ ID NOs: 75 to 78 and SEQ ID NO: 82 instead of any one of SEQ ID NOs: 88 to 91.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 5, and wherein said protein exhibits improved pharmacokinetic properties compared to a comparator protein, wherein said comparator protein consists of an identical amino acid sequence as said protein, with the exception that said designed ankyrin repeat domain of said first moiety comprises any one of SEQ ID NOs: 75 to 77 and any one of SEQ ID NOs: 88 to 90, whereas the designed ankyrin repeat domain of said comparator protein corresponding to said first moiety comprises SEQ ID NO: 69 instead of any one of SEQ ID NOs: 75 to 77 and SEQ ID NO: 82 instead of any one of SEQ ID NOs: 88 to 90.

In one embodiment, the protein of the invention comprises at least a first moiety and a second moiety, wherein said first moiety is a designed ankyrin repeat domain of the present invention, and wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 5, and wherein said protein exhibits improved pharmacokinetic properties compared to a comparator protein, wherein said comparator protein consists of an identical amino acid sequence as said protein, with the exception that said designed ankyrin repeat domain of said first moiety comprises any one of SEQ ID NOs: 75 to 76 and any one of SEQ ID NOs: 88 to 89, whereas the designed ankyrin repeat domain of said comparator protein corresponding to said first moiety comprises SEQ ID NO: 69 instead of any one of SEQ ID NOs: 75 to 76 and SEQ ID NO: 82 instead of any one of SEQ ID NOs: 88 to 89.

In one embodiment, the protein of the invention comprises at least a first moiety and a second moiety,
wherein said first moiety is a designed ankyrin repeat domain of the present invention, and
wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 5, and
wherein said protein exhibits improved pharmacokinetic properties compared to a comparator protein,
wherein said comparator protein consists of an identical amino acid sequence as said protein, with the exception that said designed ankyrin repeat domain of said first moiety comprises SEQ ID NO: 75 and SEQ ID NO: 88, whereas the designed ankyrin repeat domain of said comparator protein corresponding to said first moiety comprises SEQ ID NO: 69 instead of SEQ ID NO: 75 and SEQ ID NO: 82 instead of SEQ ID NO: 88.

In one embodiment, the protein of the invention comprises at least a first moiety and a second moiety,
wherein said first moiety is a designed ankyrin repeat domain of the present invention, and
wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 6, and
wherein said protein exhibits improved pharmacokinetic properties compared to a comparator protein,
wherein said comparator protein consists of an identical amino acid sequence as said protein, with the exception that said designed ankyrin repeat domain of said first moiety comprises any one of SEQ ID NOs: 75 to 81 and any one of SEQ ID NOs: 88 to 94, whereas the designed ankyrin repeat domain of said comparator protein corresponding to said first moiety comprises SEQ ID NO: 69 instead of any one of SEQ ID NOs: 75 to 81 and SEQ ID NO: 82 instead of any one of SEQ ID NOs: 88 to 94.

In one embodiment, the protein of the invention comprises at least a first moiety and a second moiety,
wherein said first moiety is a designed ankyrin repeat domain of the present invention, and
wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 6, and
wherein said protein exhibits improved pharmacokinetic properties compared to a comparator protein,
wherein said comparator protein consists of an identical amino acid sequence as said protein, with the exception that said designed ankyrin repeat domain of said first moiety comprises any one of SEQ ID NOs: 75 to 80 and any one of SEQ ID NOs: 88 to 93, whereas the designed ankyrin repeat domain of said comparator protein corresponding to said first moiety comprises SEQ ID NO: 69 instead of any one of SEQ ID NOs: 75 to 80 and SEQ ID NO: 82 instead of any one of SEQ ID NOs: 88 to 93.

In one embodiment, the protein of the invention comprises at least a first moiety and a second moiety,
wherein said first moiety is a designed ankyrin repeat domain of the present invention, and
wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 6, and
wherein said protein exhibits improved pharmacokinetic properties compared to a comparator protein,
wherein said comparator protein consists of an identical amino acid sequence as said protein, with the exception that said designed ankyrin repeat domain of said first moiety comprises any one of SEQ ID NOs: 75 to 79 and any one of SEQ ID NOs: 88 to 92, whereas the designed ankyrin repeat domain of said comparator protein corresponding to said first moiety comprises SEQ ID NO: 69 instead of any one of SEQ ID NOs: 75 to 79 and SEQ ID NO: 82 instead of any one of SEQ ID NOs: 88 to 92.

In one embodiment, the protein of the invention comprises at least a first moiety and a second moiety,
wherein said first moiety is a designed ankyrin repeat domain of the present invention, and
wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 6, and
wherein said protein exhibits improved pharmacokinetic properties compared to a comparator protein,
wherein said comparator protein consists of an identical amino acid sequence as said protein, with the exception that said designed ankyrin repeat domain of said first moiety comprises any one of SEQ ID NOs: 75 to 78 and any one of SEQ ID NOs: 88 to 91, whereas the designed ankyrin repeat domain of said comparator protein corresponding to said first moiety comprises SEQ ID NO: 69 instead of any one of SEQ ID NOs: 75 to 78 and SEQ ID NO: 82 instead of any one of SEQ ID NOs: 88 to 91.

In one embodiment, the protein of the invention comprises at least a first moiety and a second moiety,
wherein said first moiety is a designed ankyrin repeat domain of the present invention, and
wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 6, and
wherein said protein exhibits improved pharmacokinetic properties compared to a comparator protein,
wherein said comparator protein consists of an identical amino acid sequence as said protein, with the exception that said designed ankyrin repeat domain of said first moiety comprises any one of SEQ ID NOs: 75 to 77 and any one of SEQ ID NOs: 88 to 90, whereas the designed ankyrin repeat domain of said comparator protein corresponding to said first moiety comprises SEQ ID NO: 69 instead of any one of SEQ ID NOs: 75 to 77 and SEQ ID NO: 82 instead of any one of SEQ ID NOs: 88 to 90.

In one embodiment, the protein of the invention comprises at least a first moiety and a second moiety,
wherein said first moiety is a designed ankyrin repeat domain of the present invention, and
wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 6, and
wherein said protein exhibits improved pharmacokinetic properties compared to a comparator protein,
wherein said comparator protein consists of an identical amino acid sequence as said protein, with the exception that said designed ankyrin repeat domain of said first moiety comprises any one of SEQ ID NOs: 75 to 76 and any one of SEQ ID NOs: 88 to 89, whereas the designed ankyrin repeat domain of said comparator protein corresponding to said first moiety comprises SEQ ID NO: 69 instead of any one of SEQ ID NOs: 75 to 76 and SEQ ID NO: 82 instead of any one of SEQ ID NOs: 88 to 89.

In one embodiment, the protein of the invention comprises at least a first moiety and a second moiety,
wherein said first moiety is a designed ankyrin repeat domain of the present invention, and
wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 6, and
wherein said protein exhibits improved pharmacokinetic properties compared to a comparator protein,
wherein said comparator protein consists of an identical amino acid sequence as said protein, with the exception that said designed ankyrin repeat domain of said first moiety comprises SEQ ID NO: 75 and SEQ ID NO: 88, whereas the designed ankyrin repeat domain of said comparator protein corresponding to said first moiety comprises SEQ ID NO: 69 instead of SEQ ID NO: 75 and SEQ ID NO: 82 instead of SEQ ID NO: 88.

In one embodiment, the protein of the invention comprises at least a first moiety and a second moiety,
wherein said first moiety is a designed ankyrin repeat domain of the present invention, and
wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and
wherein said protein exhibits improved pharmacokinetic properties compared to a comparator protein,
wherein said comparator protein consists of an identical amino acid sequence as said protein, with the exception that said designed ankyrin repeat domain of said first moiety comprises SEQ ID NO: 75 and SEQ ID NO: 88, whereas the designed ankyrin repeat domain of said comparator protein corresponding to said first moiety comprises SEQ ID NO: 69 instead of SEQ ID NO: 75 and SEQ ID NO: 82 instead of SEQ ID NO: 88.

In one embodiment, the protein of the invention comprises at least a first moiety and a second moiety,
wherein said first moiety is a designed ankyrin repeat domain of the present invention, and
wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and
wherein said protein exhibits improved pharmacokinetic properties compared to a comparator protein,
wherein said comparator protein consists of an identical amino acid sequence as said protein, with the exception that said designed ankyrin repeat domain of said first moiety comprises SEQ ID NO: 76 and SEQ ID NO: 89, whereas the designed ankyrin repeat domain of said comparator protein corresponding to said first moiety comprises SEQ ID NO: 69 instead of SEQ ID NO: 76 and SEQ ID NO: 82 instead of SEQ ID NO: 89.

In one embodiment, the protein of the invention comprises at least a first moiety and a second moiety,
wherein said first moiety is a designed ankyrin repeat domain of the present invention, and
wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and
wherein said protein exhibits improved pharmacokinetic properties compared to a comparator protein,
wherein said comparator protein consists of an identical amino acid sequence as said protein, with the exception that said designed ankyrin repeat domain of said first moiety comprises SEQ ID NO: 77 and SEQ ID NO: 90, whereas the designed ankyrin repeat domain of said comparator protein corresponding to said first moiety comprises SEQ ID NO: 69 instead of SEQ ID NO: 77 and SEQ ID NO: 82 instead of SEQ ID NO: 90.

In one embodiment, the protein of the invention comprises at least a first moiety and a second moiety,
wherein said first moiety is a designed ankyrin repeat domain of the present invention, and
wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and
wherein said protein exhibits improved pharmacokinetic properties compared to a comparator protein,
wherein said comparator protein consists of an identical amino acid sequence as said protein, with the exception that said designed ankyrin repeat domain of said first moiety comprises SEQ ID NO: 78 and SEQ ID NO: 91, whereas the designed ankyrin repeat domain of said comparator protein corresponding to said first moiety comprises SEQ ID NO: 69 instead of SEQ ID NO: 78 and SEQ ID NO: 82 instead of SEQ ID NO: 91.

In one embodiment, the protein of the invention comprises at least a first moiety and a second moiety,
   wherein said first moiety is a designed ankyrin repeat domain of the present invention, and
   wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and
   wherein said protein exhibits improved pharmacokinetic properties compared to a comparator protein,
   wherein said comparator protein consists of an identical amino acid sequence as said protein, with the exception that said designed ankyrin repeat domain of said first moiety comprises SEQ ID NO: 79 and SEQ ID NO: 92, whereas the designed ankyrin repeat domain of said comparator protein corresponding to said first moiety comprises SEQ ID NO: 69 instead of SEQ ID NO: 79 and SEQ ID NO: 82 instead of SEQ ID NO: 92.

In one embodiment, the protein of the invention comprises at least a first moiety and a second moiety,
   wherein said first moiety is a designed ankyrin repeat domain of the present invention, and
   wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and
   wherein said protein exhibits improved pharmacokinetic properties compared to a comparator protein,
   wherein said comparator protein consists of an identical amino acid sequence as said protein, with the exception that said designed ankyrin repeat domain of said first moiety comprises SEQ ID NO: 79 and SEQ ID NO: 92, whereas the designed ankyrin repeat domain of said comparator protein corresponding to said first moiety comprises SEQ ID NO: 69 instead of SEQ ID NO: 79 and SEQ ID NO: 82 instead of SEQ ID NO: 92.

In one embodiment, the protein of the invention comprises at least a first moiety and a second moiety,
   wherein said first moiety is a designed ankyrin repeat domain of the present invention, and
   wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and
   wherein said protein exhibits improved pharmacokinetic properties compared to a comparator protein,
   wherein said comparator protein consists of an identical amino acid sequence as said protein, with the exception that said designed ankyrin repeat domain of said first moiety comprises SEQ ID NO: 80 and SEQ ID NO: 93, whereas the designed ankyrin repeat domain of said comparator protein corresponding to said first moiety comprises SEQ ID NO: 69 instead of SEQ ID NO: 80 and SEQ ID NO: 82 instead of SEQ ID NO: 93.

In one embodiment, the protein of the invention comprises at least a first moiety and a second moiety,
   wherein said first moiety is a designed ankyrin repeat domain of the present invention, and
   wherein said second moiety is a designed ankyrin repeat domain with binding specificity for serum albumin comprising an amino acid sequence with at least 80%, 81%, 82%, 83%, 84%, 85%, 86%, 87%, 88%, 89%, 90%, 91%, 92%, 93%, 94%, 95%, 96%, 97%, 98%, 99% or 100% amino acid sequence identity with SEQ ID NO: 4, and
   wherein said protein exhibits improved pharmacokinetic properties compared to a comparator protein,
   wherein said comparator protein consists of an identical amino acid sequence as said protein, with the exception that said designed ankyrin repeat domain of said first moiety comprises SEQ ID NO: 81 and SEQ ID NO: 94, whereas the designed ankyrin repeat domain of said comparator protein corresponding to said first moiety comprises SEQ ID NO: 69 instead of SEQ ID NO: 81 and SEQ ID NO: 82 instead of SEQ ID NO: 94.

In one embodiment, the designed ankyrin repeat domain of the invention, when fused C-terminally to SEQ ID NO: 4 via a polypeptide linker consisting of SEQ ID NO: 3, exhibits improved pharmacokinetic properties compared to a comparator designed ankyrin repeat domain fused C-terminally to SEQ ID NO:4 via a polypeptide linker consisting of SEQ ID NO: 3, and the amino acid sequences of said designed ankyrin repeat domain and said comparator designed ankyrin repeat domain only differ in residues, other than X, that differ between SEQ ID NO: 81 and SEQ ID NO: 74 and between SEQ ID NO: 94 and 87. In one embodiment, the amino acid sequences of said designed ankyrin repeat domain and said comparator designed ankyrin repeat domain only differ in residues, other than X, that differ between SEQ ID NO: 81 and SEQ ID NO: 74 and between SEQ ID NO: 93 and 86. In one embodiment, the amino acid sequences of said designed ankyrin repeat domain and said comparator designed ankyrin repeat domain only differ in residues, other than X, that differ between SEQ ID NO: 80 and SEQ ID NO: 73 and between SEQ ID NO: 92 and 85. In one embodiment, the amino acid sequences of said designed ankyrin repeat domain and said comparator designed ankyrin repeat domain only differ in residues, other than X, that differ between SEQ ID NO: 79 and SEQ ID NO: 72 and between SEQ ID NO: 91 and 84. In one embodiment, the amino acid sequences of said designed ankyrin repeat domain and said comparator designed ankyrin repeat domain only differ in residues, other than X, that differ between SEQ ID NO: 78 and SEQ ID NO: 71 and between SEQ ID NO: 90 and 83. In one embodiment, the amino acid sequences of said designed ankyrin repeat domain and said comparator designed ankyrin repeat domain only differ in residues, other than X, that differ between SEQ ID NO: 77 and SEQ ID NO: 70 and between SEQ ID NO: 90 and 83. In one embodiment, the amino acid sequences of said designed ankyrin repeat domain and said comparator designed ankyrin repeat domain only differ in residues that differ between SEQ ID NO: 76 and SEQ ID NO: 69 and between SEQ ID NO: 89 and 82. In one embodiment, the amino acid sequences of said designed ankyrin repeat domain and said comparator designed ankyrin repeat domain only differ in residues that differ between SEQ ID NO: 75 and SEQ ID NO: 69 and between SEQ ID NO: 88 and 82. In one embodiment, the amino acid sequences of said designed ankyrin repeat domain and said comparator designed ankyrin repeat domain only differ in position 8 and 15 of the N-terminal capping module and in position 14 and 18 of the C-terminal capping module, wherein the position numbers of the N-terminal capping module correspond to the positions in SEQ ID NO: 69 and the position numbers of the C-terminal capping module correspond to the positions in SEQ ID NO: 82.

In a third aspect, the invention provides nucleic acids encoding any designed ankyrin repeat domain and/or protein of the present invention. Furthermore, the invention provides vectors comprising any of said nucleic acids. In one preferred embodiment, said vector is an expression vector. Vectors and expression vectors are known to the person skilled in the art.

In a fourth aspect, the invention provides a pharmaceutical composition comprising a designed ankyrin repeat domain and/or a protein of the present invention, or a nucleic acid encoding a designed ankyrin repeat domain and/or a protein of the present invention, and optionally a pharmaceutically acceptable carrier and/or diluent. Pharmaceutically acceptable carriers and/or diluents are known to the person skilled in the art, and are explained in more detail below. Even further, a diagnostic composition is provided comprising one or more of the herein described designed ankyrin repeat domains and/or proteins of the invention.

In one embodiment, said pharmaceutical composition comprises proteins as described above and a pharmaceutically acceptable carrier, excipient or stabilizer, for example as described in Remington's Pharmaceutical Sciences $16^{th}$ edition, Osol, A. Ed. [1980]. Suitable carriers, excipients or stabilizers known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. A pharmaceutical composition may also be a combination formulation, comprising an additional active agent, such as an anti-cancer agent or an anti-angiogenic agent.

The formulations to be used for in vivo administration must be aseptic or sterile. This is readily accomplished by filtration through sterile filtration membranes.

The pharmaceutical composition of the invention may be administered by any suitable method within the knowledge of the skilled man. The preferred route of administration is parenterally. In parenteral administration, the pharmaceutical composition of the invention will be formulated in a unit dosage injectable form such as a solution, suspension or emulsion, in association with the pharmaceutically acceptable excipients as defined above. The dosage and mode of administration will depend on the individual to be treated and the particular disease.

In one embodiment, said pharmaceutical composition is for use in the treatment of a disorder. Also provided is the use of the designed ankyrin repeat domain of the invention or the protein of the invention for the manufacture of a medicament for the treatment of a disorder.

In a fifth aspect, the invention provides methods of treatment. In one particular aspect, the invention provides a method of treating a medical condition, the method comprising the step of administering, to a patient in need of such treatment, a therapeutically effective amount of a designed ankyrin repeat domain of the invention, a protein of the invention, a nucleic acid of the invention, or a pharmaceutical composition of the invention. In one embodiment, said protein is a recombinant binding protein. In one preferred embodiment, the patient is a mammal, including human. In one preferred embodiment, said medical condition is a cancer, an infectious disease, preferably a viral infectious disease, a metabolic disease, a neurological disease, an eye disease, an immunological disease, an inflammatory disease, or an autoimmune disease. In one embodiment, said medical condition is a cancer. In one embodiment, such cancer is selected from the group consisting of epithelial malignancies (primary and metastatic), including but not limited to lung, colorectal, gastric, bladder, ovarian and breast carcinomas, blood cell malignancies, including but not limited to leukemia, lymphoma, and myeloma, sarcomas, including but not limited to bone and soft tissue sarcomas, and melanoma. In one preferred embodiment, such cancer is selected from the group consisting of liposarcoma, neuroblastoma, synovial sarcoma, melanoma and ovarian cancer. In another preferred embodiment, such cancer is selected from the group consisting of melanoma, lung cancer, liver cancer, stomach cancer, skin cancer, neuroblastoma, soft tissue sarcoma, bladder cancer, testicular cancer and ovarian cancer.

In one embodiment, said medical condition is an infectious disease, preferably a viral infectious disease. In one preferred embodiment, such infectious disease is a viral infection caused by hepatitis B virus (HBV). In another preferred embodiment such infectious disease is a viral infection caused by Epstein-Barr virus (EBV). In one embodiment, said medical condition is an autoimmune disease. In one preferred embodiment, such autoimmune disease is selected from the group consisting of systemic lupus erythematosus, rheumatoid arthritis and type I diabetes.

In a sixth aspect, the invention provides a method for preparing a protein, the method comprising the steps of
(A) preparing a nucleic acid that encodes in one open reading frame
  (i) at least one designed ankyrin repeat domain of the invention, and
  (ii) at least one designed ankyrin repeat domain with binding specificity for serum albumin, and
(B) transferring said nucleic acid into an expression host.

The term "nucleic acid", "DNA", "open reading frame", and "expression host" are well-known to the practitioner in the art. Examples of expression hosts are, amongst others, *Escherichia coli* (*E. coli*; see examples), chinese hamster ovary cells (CHO cells), HEK293 cells, sf9 insect cells, or yeast (*Saccharomyces cerevisiae*). A preferred expression host is *E. coli*. The term "transferring" refers to procedures such as transformation of bacteria or transfection of eukaryotic cells, procedures well-known to the practitioner in the art. Preferably said nucleic acid further comprises the elements needed for protein expression in the respective expression host. Like this the expression host is able to express said protein encoded by said open reading frame. The method may additionally comprise the steps of expressing said protein and/or of purifying said protein. Preferably said step of purifying said protein may comprise multiple protein purification methods. Such purification methods like ion-exchange chromatography or hydrophobic-interaction chromatography or diafiltration and alike are well-known to the person skilled in the art. Preferably the protein purity at the end of said step of purifying said protein, is at least 95%, preferably 96%, 97%, 98%, most preferably 99% according to analysis by SDS-PAGE. SDS-PAGE is a method well-known to the person skilled in the art and is described in the examples.

The invention is not restricted to the particular embodiments described in the Examples.

This specification refers to a number of amino acid sequences and SEQ ID NOs that are disclosed in the appended Sequence Listing, which is herewith incorporated by reference in its entirety.

Definitions

Unless defined otherwise herein, all technical and scientific terms used herein shall have the meanings that are commonly understood by those of ordinary skill in the art to which the present invention belongs.

The term "polypeptide" relates to a molecule consisting of one or more chains of multiple, i.e. two or more, amino acids linked via peptide bonds. Preferably, a polypeptide consists of more than eight amino acids linked via peptide bonds. The term "polypeptide" also includes multiple chains of amino acids, linked together by S—S bridges of cysteines.

Polypeptides are well-known to the person skilled in the art.

The term "protein" refers to a molecule comprising a polypeptide, wherein at least part of the polypeptide has, or is able to acquire, a defined three-dimensional arrangement by forming secondary, tertiary, and/or quaternary structures within a single polypeptide chain and/or between multiple polypeptide chains. If a protein comprises two or more polypeptide chains, the individual polypeptide chains may be linked non-covalently or covalently, e.g. by a disulfide bond between two polypeptide chains. A part of a protein, which individually has, or is able to acquire, a defined three-dimensional arrangement by forming secondary and/or tertiary structures, is termed "protein domain". Such protein domains are well known to the practitioner skilled in the art.

Patent application WO2002/020565 and Forrer et al., 2003 (Forrer, P., Stumpp, M. T., Binz, H. K., Plückthun, A., 2003. FEBS Letters 539, 2-6), contain a general description of repeat protein, repeat domain and repeat module features, techniques and applications.

The term "repeat domain" refers to a protein domain comprising two or more consecutive repeat modules as structural units, wherein said repeat modules have structural and sequence homology. Preferably, a repeat domain also comprises an N-terminal and/or a C-terminal capping module. For clarity, a capping module can be a repeat module. Such repeat domains, repeat modules, and capping modules, sequence motives, as well as structural homology and sequence homology are well known to the practitioner in the art from examples of ankyrin repeat domains (Binz et al., J. Mol. Biol. 332, 489-503, 2003; Binz et al., 2004, loc. cit.; WO2002/020565; WO2012/069655), leucine-rich repeat domains (WO2002/020565), tetratricopeptide repeat domains (Main, E. R., Xiong, Y., Cocco, M. J., D'Andrea, L., Regan, L., Structure 11(5), 497-508, 2003), and armadillo repeat domains (WO2009/040338). It is further well known to the practitioner in the art, that such repeat domains are different from proteins comprising repeated amino acid sequences, where every repeated amino acid sequence is able to form an individual domain (for example FN3 domains of Fibronectin).

The term "ankyrin repeat domain" refers to a repeat domain comprising two or more consecutive ankyrin repeat modules as structural units, wherein said ankyrin repeat modules have structural and sequence homology.

The term "repeat modules" refers to the repeated amino acid sequence and structural units of the designed repeat domains, which are originally derived from the repeat units of naturally occurring repeat proteins. Each repeat module comprised in a repeat domain is derived from one or more repeat units of a family or subfamily of naturally occurring repeat proteins, preferably the family of ankyrin repeat proteins.

Accordingly, the term "ankyrin repeat module" refers to a repeat module, which is originally derived from the repeat units of naturally occurring ankyrin repeat proteins. Ankyrin repeat proteins are well known to the person skilled in the art.

For example, SEQ ID NOs: 4 to 8 and 12 to 23 each comprise one repeat domain comprising an N-terminal capping module (residues 1 to 30 of each of SEQ ID NOs: 4 to 8 and 12 to 23), two repeat modules (residues 31 to 63 and residues 64 to 96, respectively, of each of SEQ ID NOs: 4 to 8 and 12 to 23), and a C-terminal capping module (residues 97 to 124 of each of SEQ ID NOs: 4 to 8 and 12 to 23). As further examples, SEQ ID NOs: 9 to 11 each comprise one repeat domain comprising an N-terminal capping module (residues 1 to 30 of each of SEQ ID NOs: 9 to 11), three repeat modules (residues 31 to 63, residues 64 to 96, and residues 97 to 129, respectively, of each of SEQ ID NOs: 9 to 11), and a C-terminal capping module (residues 130 to 157 of each of SEQ ID NOs: 9 to 11). Furthermore, SEQ ID NOs: 69, 75, and 76 are examples of N-terminal capping modules, and SEQ ID NOs: 82, 88, and 89 are examples of C-terminal capping modules.

The term "designed" as used in designed repeat protein, designed repeat domain, designed ankyrin repeat domain, and the like refers to the property that such repeat proteins and repeat domains, respectively, are man-made and do not occur in nature.

The term "recombinant" as used in recombinant protein, recombinant binding protein, recombinant polypeptide, and the like, means that said protein or polypeptide is produced by the use of recombinant DNA technologies well known to the practitioner skilled in the art. For example, a recombinant DNA molecule (e.g. produced by gene synthesis) encoding a polypeptide can be cloned into a bacterial expression plasmid (e.g. pQE30, QIAgen), yeast expression plasmid, mammalian expression plasmid, or plant expression plasmid, or a DNA enabling in vitro expression. If, for example, such a recombinant bacterial expression plasmid is inserted into appropriate bacteria (e.g. *Escherichia coli*), these bacteria can produce the polypeptide(s) encoded by this recombinant DNA. The correspondingly produced polypeptide or protein is called a recombinant polypeptide or recombinant protein. In the context of the present invention, the term "binding protein" refers to a protein comprising a binding domain. A binding protein may also comprise two, three, four, five or more binding domains. Preferably, said binding protein is a recombinant binding protein.

The term "binding domain" means a protein domain exhibiting binding specificity for a target. Preferably, said binding domain is a recombinant binding domain.

The term "target" refers to an individual molecule such as a nucleic acid molecule, a peptide, polypeptide or protein, a carbohydrate, or any other naturally occurring molecule, including any part of such individual molecule, or to complexes of two or more of such molecules, or to a whole cell or a tissue sample, or to any non-natural compound. Preferably, a target is a naturally occurring or non-natural polypeptide or protein, or a polypeptide or protein containing chemical modifications, for example, naturally occurring or non-natural phosphorylation, acetylation, or methylation. For example, the target of each of the designed ankyrin repeat domains consisting of SEQ ID NOs: 4 to 8, is serum albumin.

The term "has binding specificity for a target", "specifically binding to a target", "binding to a target with high specificity", "specific for a target" or "target specificity" and the like means that a binding protein or binding domain binds in PBS to a target with a lower dissociation constant (i.e. it binds with higher affinity) than it binds to an unrelated protein such as the *E. coli* maltose binding protein (MBP). Preferably, the dissociation constant ("Kd") in PBS for the target is at least $10^2$; more preferably, at least 103; even more preferably, at least $10^4$; or most preferably, at least $10^1$ times lower than the corresponding dissociation constant for MBP. Methods to determine dissociation constants of protein-protein interactions, such as surface plasmon resonance (SPR) based technologies (e.g. SPR equilibrium analysis) or isothermal titration calorimetry (ITC) are well known to the person skilled in the art. The measured $K_D$ values of a particular protein-protein interaction can vary if measured under different conditions (e.g., salt concentration, pH). Thus, measurements of $K_D$ values are preferably made with standardized solutions of protein and a standardized buffer, such as PBS.

The term "polypeptide tag" refers to an amino acid sequence attached to a polypeptide/protein, wherein said amino acid sequence is useful for the purification, detection, or targeting of said polypeptide/protein, or wherein said amino acid sequence improves the physicochemical behavior of the polypeptide/protein, or wherein said amino acid sequence possesses an effector function. The individual polypeptide tags, moieties and/or domains of a binding protein may be connected to each other directly or via polypeptide linkers. These polypeptide tags are all well known in the art and are fully available to the person skilled in the art. Examples of polypeptide tags are small polypeptide sequences, for example, His (e.g. the His-tag consisting of SEQ ID NO: 1), myc, FLAG, or Strep-tags or moieties such as enzymes (for example enzymes like alkaline phosphatase), which allow the detection of said polypeptide/protein, or moieties which can be used for targeting (such as immunoglobulins or fragments thereof) and/or as effector molecules.

The term "polypeptide linker" refers to an amino acid sequence, which is able to link, for example, two protein domains, a polypeptide tag and a protein domain, a protein domain and a non-polypeptide moiety such as polyethylene glycol or two polypeptide tags tags. Such additional domains, tags, non-polypeptide moieties and linkers are known to the person skilled in the relevant art. Examples of such polypeptide linkers are the linkers consisting of SEQ ID NOs: 2 and 3.

The terms "nucleic acid" or "nucleic acid molecule" refer to a polynucleotide molecule, which may be a ribonucleic acid (RNA) or deoxyribonucleic acid (DNA) molecule, either single stranded or double stranded, and includes modified and artificial forms of DNA or RNA. A nucleic acid molecule may either be present in isolated form, or be comprised in recombinant nucleic acid molecules or vectors.

In the context of the invention, the terms "medical condition", "disease" and "disorder" are used interchangeably and include but are not limited to autoimmune disorders, inflammatory disorders, retinopathies (particularly proliferative retinopathies), neurodegenerative disorders, infectious diseases, metabolic diseases, and neoplastic diseases. A "medical condition" may be one that is characterized by inappropriate cell proliferation. A medical condition may be a hyperproliferative condition. A medical condition may be a neoplastic disease. The term "neoplastic disease", as used herein, refers to an abnormal state or condition of cells or tissue characterized by rapidly proliferating cell growth or neoplasm. A medical condition may be a malignant neoplastic disease. A medical condition may be a cancer. The terms "cancer" and "cancerous" are used herein to refer to or describe the physiological condition in mammals that is typically characterized by unregulated cell growth. Cancer encompasses solid tumors and liquid tumors, as well as primary tumors and metastases. A "tumor" comprises one or more cancerous cells. Solid tumors typically also comprise tumor stroma. Examples of cancer include, but are not limited to, primary and metastatic carcinoma, lymphoma, blastoma, sarcoma, myeloma, melanoma and leukemia, and any other epithelial and blood cell malignancies. More particular examples of such cancers include brain cancer, bladder cancer, breast cancer, ovarian cancer, kidney cancer, colorectal cancer, gastric cancer, head and neck cancer, lung cancer, pancreatic cancer, prostate cancer, malignant melanoma, osteosarcoma, soft tissue sarcoma, carcinoma, squameous cell carcinoma, clear cell kidney cancer, head/neck squamous cell carcinoma, lung adenocarcinoma, lung squamous cell carcinoma, non-small-cell lung cancer (NSCLC), renal cell carcinoma, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myelodysplastic syndrome (MDS), non-Hodgkin's lymphoma (NHL), Squamous Cell Carcinoma of the Head and Neck (SCCHN), chronic myelogenous leukemia (CML), small lymphocytic lymphoma (SLL), malignant mesothelioma, liposarcoma, neuroblastoma, or synovial sarcoma. The terms "autoimmune disease" and "autoimmune disorder" are used herein to refer to or describe disorders wherein the immune system of a mammal mounts a humoral or cellular immune response to the mammal's own tissue or to antigens that are not intrinsically harmful to the mammal, thereby producing tissue injury in such a mammal. Examples of autoimmune disorders are numerous and include, but are not limited to, systemic lupus erythematosus, rheumatoid arthritis and type I diabetes. Autoimmune diseases also include acute glomerulonephritis, Addison's disease, adult onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, Crohn's disease, dermatomyositis, dilated cardiomyopathy, eosinophilia-myalgia syndrome, epidernolisis bullosa acquisita (EBA), giant cell arteritis, Goodpasture's syndrome, Graves' disease, Guillain-Barre syndrome, hemochromatosis, Henoch-Schonlein purpura, idiopathic IgA nephropathy, insulin-dependent diabetes mellitus (IDDM), juvenile rheumatoid arthritis, Lambert-Eaton syndrome, linear IgA dermatosis, lupus erythematosus, multiple sclerosis, myasthenia gravis, myocarditis, narcolepsy, necrotizing vasculitis, neonatal lupus syndrome (NLE), nephrotic syndrome, pemphigoid, phemphigus, polymyositis, primary sclerosing cholangitis, psoriasis, rapidly progressive glomerulonephritis (RPGN), Reiter's syndrome, rheumatoid arthritis, scleroderma, Sjogren's syndrome, stiff-man syndrome, thyroiditis, and ulcerative colitis. The terms "infectious disease" and "infection" are used herein to refer to or describe the invasion and multiplication of microorganisms in body tissues, especially causing pathological symptoms. Examples of infectious diseases include without limitation, viral diseases and bacterial diseases, such as, e.g., HIV infection, West Nile virus infection, hepatitis A, B, and C, small pox, tuberculosis, Vesicular Stomatitis Virus (VSV) infection, Respiratory Syncytial Virus (RSV) infection, human papilloma virus (HPV) infection, SARS, influenza, Ebola, viral meningitis, herpes, anthrax, lyme disease, and E. Coli infections, among others.

The term "treatment" or "treating" refers to both therapeutic treatment and prophylactic or preventative measures. Those in need of treatment include those who have already the disorder as well as those in which the disorder is to be prevented.

The term "therapeutically effective amount" refers to the amount sufficient to induce a desired biological, pharmacological, or therapeutic outcome in a subject. A therapeutically effective amount in the context of the invention means a sufficient amount of the binding protein to treat or prevent a disease or disorder at a reasonable benefit/risk ratio applicable to any medical treatment.

The term "mammal" for purposes of treatment refers to any animal classified as a mammal, including human, domestic and farm animals, nonhuman primates, and zoo, sports, or pet animals, such as dogs, horses, cats, cows, etc.

The term "incubation" refers to incubation at pH 7.4. In one embodiment, said incubation at pH 7.4 refers to an incubation in PBS.

The term "PBS" means a phosphate buffered water solution containing 137 mM NaCl, 10 mM phosphate and 2.7 mM KCl and having a pH of 7.4.

The term improved pharmacokinetic properties refers to an increased area under the curve, a reduced clearance, or an increased terminal half-life. These parameters of pharmacokinetic properties and ways to determine them are well known in the art (see, e.g., Mahmood, I., Methods to determine pharmacokinetic profiles of therapeutic proteins, *Drug Discov Today: Technol., Volume* 5, Issues 2-3. Autumn 2008, Pages e65-e59, doi:10.1016/j.ddtec.2008.12.001).

In the context of the present invention, the term "any amino acids" preferably means any of the 20 most often naturally occurring amino acids, namely alanine (ala; A), arginine (arg; R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), valine (val, V).

EXAMPLES

Proteins used in the examples:

Protein #4 (SEQ ID NO: 4 with a His-tag (SEQ ID NO: 1) fused to its N-terminus);
Protein #5 (SEQ ID NO: 5 with a His-tag (SEQ ID NO: 1) fused to its N-terminus);
Protein #6 (SEQ ID NO: 6 with a His-tag (SEQ ID NO: 1) fused to its N-terminus);
Protein #7 (SEQ ID NO: 7 with a His-tag (SEQ ID NO: 1) fused to its N-terminus);
Protein #8 (SEQ ID NO: 8 with a His-tag (SEQ ID NO: 1) fused to its N-terminus);
Protein #9 (SEQ ID NO: 9 with a His-tag (SEQ ID NO: 1) fused to its N-terminus);
Protein #10 (SEQ ID NO: 10 with a His-tag (SEQ ID NO: 1) fused to its N-terminus);
Protein #11 (SEQ ID NO: 11 with a His-tag (SEQ ID NO: 1) fused to its N-terminus);
Protein #12 (SEQ ID NO: 12 with a His-tag (SEQ ID NO: 1) fused to its N-terminus);
Protein #13 (SEQ ID NO: 13 with a His-tag (SEQ ID NO: 1) fused to its N-terminus);
Protein #14 (SEQ ID NO: 14 with a His-tag (SEQ ID NO: 1) fused to its N-terminus);
Protein #15 (SEQ ID NO: 15 with a His-tag (SEQ ID NO: 1) fused to its N-terminus);
Protein #16 (SEQ ID NO: 16 with a His-tag (SEQ ID NO: 1) fused to its N-terminus);
Protein #17 (SEQ ID NO: 17 with a His-tag (SEQ ID NO: 1) fused to its N-terminus);
Protein #18 (SEQ ID NO: 18 with a His-tag (SEQ ID NO: 1) fused to its N-terminus);
Protein #19 (SEQ ID NO: 19 with a His-tag (SEQ ID NO: 1) fused to its N-terminus);
Protein #20 (SEQ ID NO: 20 with a His-tag (SEQ ID NO: 1) fused to its N-terminus);
Protein #21 (SEQ ID NO: 21 with a His-tag (SEQ ID NO: 1) fused to its N-terminus);
Protein #22 (SEQ ID NO: 22 with a His-tag (SEQ ID NO: 1) fused to its N-terminus);
Protein #23 (SEQ ID NO: 23 with a His-tag (SEQ ID NO: 1) fused to its N-terminus);
Protein #24 (SEQ ID NO: 24 with a His-tag (SEQ ID NO: 1) fused to its N-terminus);
Protein #25 (SEQ ID NO: 25 with a His-tag (SEQ ID NO: 1) fused to its N-terminus);
Protein #26 (SEQ ID NO: 26 with a His-tag (SEQ ID NO: 1) fused to its N-terminus);
Protein #27 (SEQ ID NO: 27 with a His-tag (SEQ ID NO: 1) fused to its N-terminus);
Protein #28 (SEQ ID NO: 28 with a His-tag (SEQ ID NO: 1) fused to its N-terminus);
Protein #29 (SEQ ID NO: 29 with a His-tag (SEQ ID NO: 1) fused to its N-terminus);
Protein #30 (SEQ ID NO: 30 with a His-tag (SEQ ID NO: 1) fused to its N-terminus);
Protein #31 (SEQ ID NO: 31 with a His-tag (SEQ ID NO: 1) fused to its N-terminus);
Protein #32 (SEQ ID NO: 32 with a His-tag (SEQ ID NO: 1) fused to its N-terminus);
Protein #33 (SEQ ID NO: 33 with a His-tag (SEQ ID NO: 1) fused to its N-terminus);
Protein #34 (SEQ ID NO: 34 with a His-tag (SEQ ID NO: 1) fused to its N-terminus);
Protein #35 (SEQ ID NO: 35 with a His-tag (SEQ ID NO: 1) fused to its N-terminus);
Protein #36 (SEQ ID NO: 36 with a His-tag (SEQ ID NO: 1) fused to its N-terminus);
Protein #37 (SEQ ID NO: 37 with a His-tag (SEQ ID NO: 1) fused to its N-terminus);
Protein #38 (SEQ ID NO: 38 with a His-tag (SEQ ID NO: 1) fused to its N-terminus);
Protein #39 (SEQ ID NO: 39 with a His-tag (SEQ ID NO: 1) fused to its N-terminus);
Protein #40 (SEQ ID NO: 40 with a His-tag (SEQ ID NO: 1) fused to its N-terminus);
Protein #41 (SEQ ID NO: 41 with a His-tag (SEQ ID NO: 1) fused to its N-terminus);
Protein #42 (SEQ ID NO: 42 with a His-tag (SEQ ID NO: 1) fused to its N-terminus);
Protein #43 (SEQ ID NO: 43 with a His-tag (SEQ ID NO: 1) fused to its N-terminus);
Protein #44 (SEQ ID NO: 44 with a His-tag (SEQ ID NO: 1) fused to its N-terminus);
Protein #45 (SEQ ID NO: 45 with a His-tag (SEQ ID NO: 1) fused to its N-terminus);

Protein #46 (SEQ ID NO: 46 with a His-tag (SEQ ID NO: 1) fused to its N-terminus);
Protein #47 (SEQ ID NO: 47 with a His-tag (SEQ ID NO: 1) fused to its N-terminus);
Protein #48 (SEQ ID NO: 48 with a His-tag (SEQ ID NO: 1) fused to its N-terminus);
Protein #49 (SEQ ID NO: 49 with a His-tag (SEQ ID NO: 1) fused to its N-terminus);
Protein #50 (SEQ ID NO: 50 with a His-tag (SEQ ID NO: 1) fused to its N-terminus);
Protein #51 (SEQ ID NO: 51 with a His-tag (SEQ ID NO: 1) fused to its N-terminus);
Protein #52 (SEQ ID NO: 52 with a His-tag (SEQ ID NO: 1) fused to its N-terminus);
Protein #53 (SEQ ID NO: 53 with a His-tag (SEQ ID NO: 1) fused to its N-terminus);
Protein #54 (SEQ ID NO: 54 with a His-tag (SEQ ID NO: 1) fused to its N-terminus);
Protein #55 (SEQ ID NO: 55 with a His-tag (SEQ ID NO: 1) fused to its N-terminus);
Protein #56 (SEQ ID NO: 56 with a His-tag (SEQ ID NO: 1) fused to its N-terminus);
Protein #57 (SEQ ID NO: 57 with a His-tag (SEQ ID NO: 1) fused to its N-terminus);
Protein #58 (SEQ ID NO: 58 with a His-tag (SEQ ID NO: 1) fused to its N-terminus);
Protein #59 (SEQ ID NO: 59 with a His-tag (SEQ ID NO: 1) fused to its N-terminus);
Protein #60 (SEQ ID NO: 60 with a His-tag (SEQ ID NO: 1) fused to its N-terminus);
Protein #61 (SEQ ID NO: 61 with a His-tag (SEQ ID NO: 1) fused to its N-terminus);
Protein #62 (SEQ ID NO: 62 with a His-tag (SEQ ID NO: 1) fused to its N-terminus);
Protein #63 (SEQ ID NO: 63 with a His-tag (SEQ ID NO: 1) fused to its N-terminus);
Protein #64 (SEQ ID NO: 64 with a His-tag (SEQ ID NO: 1) fused to its N-terminus);
Protein #65 (SEQ ID NO: 65 with a His-tag (SEQ ID NO: 1) fused to its N-terminus);
Protein #66 (SEQ ID NO: 66 with a His-tag (SEQ ID NO: 1) fused to its N-terminus);
Protein #67 (SEQ ID NO: 67 with a His-tag (SEQ ID NO: 1) fused to its N-terminus); and
Protein #68 (SEQ ID NO: 68 with a His-tag (SEQ ID NO: 1) fused to its N-terminus).

If not described otherwise, experiments were performed according to methods well-known to the person skilled in the art. The experimental conditions for some examples are also further described in WO2012069654 and WO2016156596.

Example 1: Construction of Designed Ankyrin Repeat Domains with Improved Pharmacokinetic Properties Proteins #9, #12, #16, and #20 are different examples of designed ankyrin repeat domains that, when fused to designed ankyrin repeat domains with binding specificity for serum albumin (resulting e.g. in Proteins #24, #27, #31, and #35, respectively) exhibit fast clearance and short terminal half-life. The pharmacokinetic properties are clearly inferior to the ones observed for designed ankyrin repeat domains with binding specificity for serum albumin (Steiner et al., 2017, loc.cit.). For Proteins #24, #27, #31, and #35, there are no known clearance mechanisms involved such as e.g. target mediated clearance.

The present invention provides amino acid sequences for designed ankyrin repeat domains that lead to improved pharmacokinetic profiles (See FIG. 1). We surprisingly found that we can modulate the pharmacokinetic properties by applying certain amino acid mutations in the designed ankyrin repeat domains. We mutated the proteins at different positions. Substituting every position of a protein of 124 amino acid lengths by the 19 alternative amino acids and generating the combinations thereof would result in a theoretical diversity of >$10^{158}$ variants. As this is not experimentally feasible, we used rational approaches to refine the process. In the first two rounds we selected mostly surface exposed residues and exchanged them for charged/polar/neutral/hydrophobic amino acids and evaluated the impact on pharmacokinetic properties (as fusion proteins to designed ankyrin repeat domains with binding specificity for serum albumin). We combined multiple amino acid changes per construct and could like this identify variants with favorable amino acid compositions. In further three rounds, we analyzed the multiple amino acid changes in detail to identify the critical amino acid changes that lead to favorable pharmacokinetic properties. In the next two rounds we combined the critical amino acid changes again leading to constructs with minimal changes and improved pharmacokinetic properties. These amino acid changes are described in detail in this application. In summary, through a rationally designed process involving several rounds of amino acid changes at a multitude of positions and characterizing the resulting protein variants in vitro and in vivo, novel sequence patterns and motifs were identified which surprisingly led to improved pharmacokinetic properties when introduced in a designed ankyrin repeat domain. These amino acid sequence motifs are comprised in SEQ ID NOs: 75 to 81, 88 to 94, and 107 to 111. Proteins #10, #11, #13, #14, #15, #17, #18, #19, #21, #22, and #23 are examples of designed ankyrin repeat domains comprising such novel amino acid sequence motifs. Similarly, Proteins #25, #26, #28, #29, #30, #32, #33, #34, #36, #37, #38, #40, #41, #43, #44, #45, #47, #48, #49, #51, #52, #53, #55, #56, #58, #59, #60, #62, #63, #64, #66, #67, and #68 are examples of proteins comprising designed ankyrin repeat domains comprising such novel amino acid sequence motifs. The production and characterization as well as the use of these particularly selected sequence motifs is described in the following examples.

Example 2: Expression and Purification of Proteins

The DNA encoding each of the designed ankyrin repeat domain consisting of SEQ ID NOs: 4 to 23 and the DNA encoding each of the proteins consisting of SEQ ID NOs: 24 to 68 was cloned into a pQE (QIAgen, Germany) based expression vector providing an N-terminal His-tag to facilitate simple protein purification as described below. Proteins consisting of SEQ ID NOs: 4 to 68, additionally having a His-tag SEQ ID NO: 1 fused to their N termini, were produced in E. coli, purified to homogeneity, and stored in PBS buffer. Methods for the production and purification of proteins are well known to the practitioner in the art. For clarity, proteins #4 to #23 are individual designed ankyrin repeat domains, proteins #24 to #68 are proteins consisting two designed ankyrin repeat domains, of which one is a designed ankyrin repeat domain with binding specificity for serum albumin. Proteins expressed and purified as described in this paragraph were used for the experiments of Examples 3 to 11.

Alternatively, proteins consisting of SEQ ID NOs: 4 to 68, additionally having the amino acids GS at the N terminus, are produced in E. coli, purified to homogeneity, and stored in PBS buffer. In case the amino acids GS are at the N terminus, the Met residue additionally encoded by the expression vector is efficiently cleaved off in the cytoplasm of E. coli from the expressed polypeptide since the start Met is followed by a small Gly residue. The proteins consisting of SEQ ID NOs: 4 to 68, additionally having the amino acids GS at the N terminus, exhibit equivalent results in Examples 3 to 11 as the proteins consisting of SEQ ID NOs: 4 to 68, additionally having a His-tag (SEQ ID NO: 1) fused to the N terminus.

Example 3: Storage Stability Assessment

Proteins of Example 2 were tested for storage stability by incubating them at 100 micromolar protein concentration at 60° C. at pH 7.4 for 1 week (7 days). Buffer used was PBS (pH 7.4; 137 mM NaCl, 10 mM phosphate and 2.7 mM KCl). Upon mixing the protein with the PBS, the resulting pH value was pH 7.4. In parallel to the incubations at 60° C., aliquots of the proteins were incubated at −80° C. for 1 week (7 days) as controls.

Example 4: SDS-PAGE of Storage Stability Analysis Samples

Figure 4A:
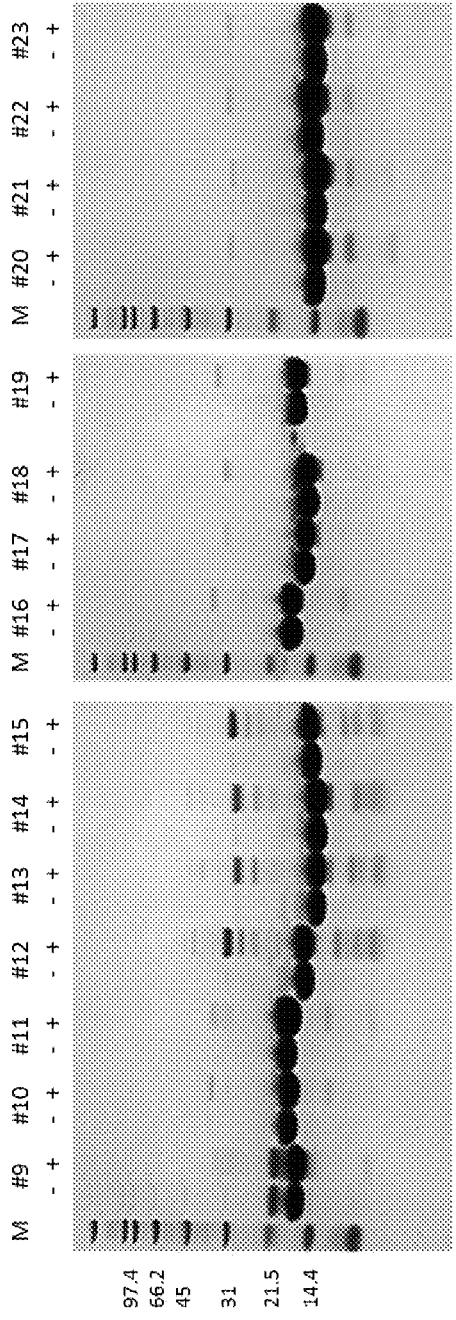
FIGS. 4A and 4B.
Figure 4B:
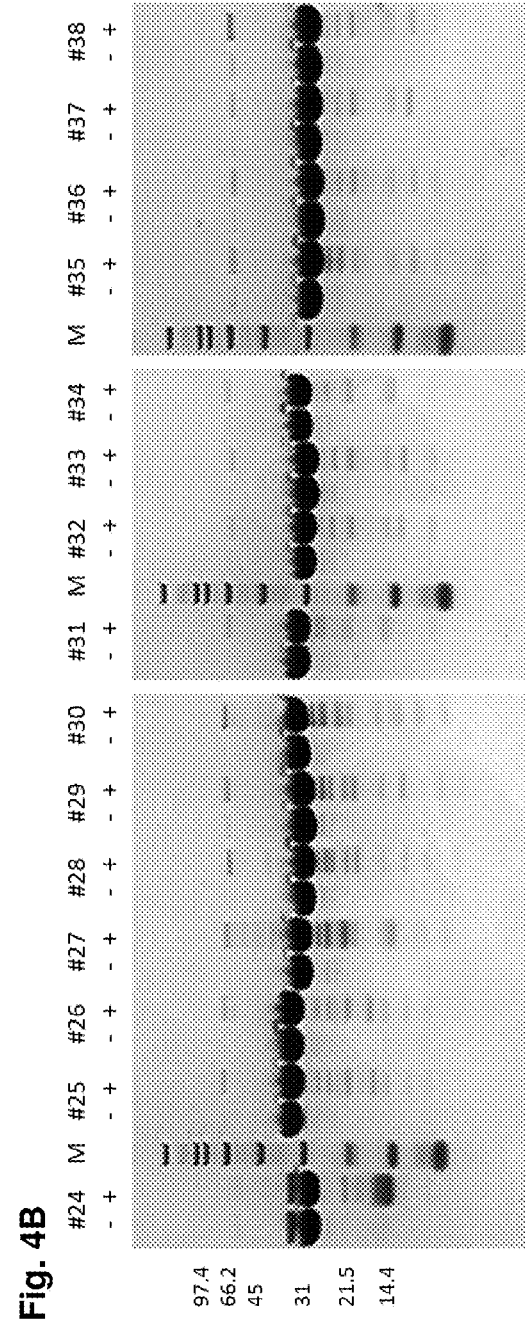

Samples of proteins of Example 3 (10 microgram protein each lane) were analyzed on NuPAGE 4-12% Bis-Tris sodium dodecyl polyacrylamide gel electrophoresis (SDS-PAGE) gels (Thermo Fisher), stained with instant blue staining (Sigma Aldrich). Results are shown in FIG. 4. The SDS-PAGE analysis indicates high purity of all purified proteins. Similar results are obtained when analyzing proteins #39 to #68.

Example 5: Size-Exclusion Chromatography Analysis

Samples of Example 3 were analyzed on a GE Superdex 200 150/5 column on an Agilent 1200 HPLC system in PBS at 0.5 ml/min flow rate. Of each protein, 0.1 ml at 100 micromolar concentration were analyzed. Proteins #9 to #38 all elute as monomeric peaks with at least 95% of the area under the curve corresponding to monomer fraction. Results are shown in Table 1. These results indicate that the proteins are monomeric. Importantly, proteins #24 to #38, which were used for the pharmacokinetic analyses (Example 6), eluted at monomeric peak both after incubation at −80° C. and at 60° C. as described in Example 3.

This indicates that these proteins are stable upon incubation at elevated temperature.

Similar results are obtained when analyzing Proteins #39 to #68.

TABLE 1

Size exclusion chromatography of Proteins #9 to #38

| Protein* | Relative area % | Retention time [min] |
|---|---|---|
| #9 | 100.00 | 4.31 |
| #10 | 100.00 | 4.46 |
| #11 | 100.00 | 4.19 |
| #12 | 100.00 | 4.05 |
| #13 | 100.00 | 4.28 |

TABLE 1-continued

Size exclusion chromatography of Proteins #9 to #38

| Protein* | Relative area % | Retention time [min] |
|---|---|---|
| #14 | 98.86 | 4.84 |
| #15 | 100.00 | 4.02 |
| #16 | 100.00 | 4.31 |
| #17 | 100.00 | 4.44 |
| #18 | 100.00 | 4.45 |
| #19 | 100.00 | 4.37 |
| #20 | 100.00 | 4.41 |
| #21 | 100.00 | 4.59 |
| #22 | 100.00 | 4.46 |
| #23 | 100.00 | 4.55 |
| #24 | 100.00 | 4.00 |
| #25 | 100.00 | 3.98 |
| #26 | 100.00 | 3.91 |
| #27 | 100.00 | 3.94 |
| #28 | 100.00 | 3.99 |
| #29 | 100.00 | 4.07 |
| #30 | 100.00 | 3.95 |
| #31 | 100.00 | 3.92 |
| #32 | 100.00 | 3.97 |
| #33 | 100.00 | 3.96 |
| #34 | 100.00 | 3.94 |
| #35 | 100.00 | 3.85 |
| #36 | 100.00 | 3.98 |
| #37 | 100.00 | 3.97 |
| #38 | 100.00 | 3.80 |

*Proteins #9 to #38 in this table represent proteins consisting of the corresponding amino acid sequence of SEQ ID NO: 9 to 38, and additionally an N-terminal His-tag (SEQ ID NO: 1).

Example 6: Mouse Pharmacokinetic Profiles of Protein Variants

Pharmacokinetic analyses were performed in female Balb/c mice using Proteins #24 to #38, produced as described in Example 2. Proteins were applied at 1 mg/kg by intravenous injection into the tail vein. Six mice, divided in two groups of 3 mice each, were used for each protein. For every protein, blood was collected from the mice of one group 5 min, 24 h, 72 h, and 168 h post injection, and from the mice of the other group 6 h, 48 h, 96 h, and 168 h post injection. The blood samples were allowed to stand at room temperature and were centrifuged to generate serum using procedures well-known to the person skilled in the art, followed by storage at −80° C. pending analyses. Serum concentrations of Proteins #24 to #38 were determined by sandwich ELISA using a rabbit monoclonal anti-DARPin antibody as capture reagent and an anti-RGS-His antibody-HRP conjugate as detection reagent, and using a standard curve. The monoclonal anti-DARPin antibody was generated using conventional rabbit immunization and hybridoma generation techniques well known to the person skilled in the art, and the binding of the monoclonal antibody to Proteins #24 to #38 was verified prior to concentration determination experiments. Briefly, 100 µl of goat-anti-rabbit antibody (10 nM) (Thermo Scientific) in PBS per well were immobilized in a Maxisorp plate (Nunc, Denmark) overnight at 4° C. After washing 5 times with 300 µl PBST (PBS supplemented with 0.1% Tween 20), the wells were blocked with 300 µl PBST-C (PBST supplemented with 0.25% casein) for 1 h at room temperature with shaking at 450 rpm on a Titramax 1000 shaker (Heidolph, Germany). After washing 5 times as described above, 100 µl/well rabbit-anti-DARPin antibody (5 nM) in PBST-C were added for 1 h at room temperature with shaking at 450 rpm. After washing 5 times as described above, different dilutions of serum samples or standard references, diluted in PBST-C, were added for 2 hours at room temperature with shaking at 450 rpm. After washing 5 times as described above, 50 μl mouse anti-RGS-His antibody-HRP conjugate (QIAgen) (100 ng/ml) in PBST-C was added for 30 min at room temperature with shaking at 450 rpm. After washing 5 times as described above, the ELISA was developed using 50 μl TMB substrate. The reaction was stopped after 5 min using 100 μl 1 M $H_2SO_4$. The OD (OD 450 nm-OD 620 nm) was then recorded. Pharmacokinetic parameters were determined using standard software such as Phoenix WinNonLin (Certara, Princeton, USA) or GraphPadPrism (GraphPad Software, La Jolla, USA) and standard analyses such as non-compartmental analyses, all well-known to the person skilled in the art. The resulting pharmacokinetic profiles are shown in FIG. 5. The pharmacokinetic parameters area under the curve, clearance, volume of distribution, and half-life, derived from the measurements, are listed in Table 2, Table 3, Table 4, and Table 5.

TABLE 2

Mouse pharmacokinetic parameters of Proteins #24 to #26

| Parameter Protein | AUCINF_D_pred h*(nmol/L) | Cl_pred L/(h*kg) | Vss_pred L/kg | HL_Lambda_z h |
|---|---|---|---|---|
| #24* | 4398 | 0.0071 | 0.031 | 5.1 |
| #25* | 12221 | 0.0025 | 0.06 | 18.8 |
| #26* | 27102 | 0.0011 | 0.057 | 37.3 |

*Proteins #24 to #26 in this table represent proteins consisting of the corresponding amino acid sequence of SEQ ID NO: 24 to 26, and additionally an N-terminal His-tag (SEQ ID NO: 1).

TABLE 3

Mouse pharmacokinetic parameters of Proteins #27 to #30

| Parameter Protein | AUCINF_D_pred h*(nmol/L) | Cl_pred L/(h*kg) | Vss_pred L/kg | HL_Lambda_z h |
|---|---|---|---|---|
| #27* | 11332 | 0.003 | 0.046 | 13.1 |
| #28* | 21910 | 0.0016 | 0.075 | 36.7 |
| #29* | 30314 | 0.0011 | 0.051 | 33.1 |
| #30* | 22127 | 0.0016 | 0.052 | 25.4 |

*Proteins #27 to #30 in this table represent proteins consisting of the corresponding amino acid sequence of SEQ ID NO: 27 to 30, and additionally an N-terminal His-tag (SEQ ID NO: 1).

TABLE 4

Mouse pharmacokinetic parameters of Proteins #31 to #34

| Parameter Protein | AUCINF_D_pred h*(nmol/L) | Cl_pred L/(h*kg) | Vss_pred L/kg | HL_Lambda_z h |
|---|---|---|---|---|
| #31* | 11619 | 0.003 | 0.046 | 13.9 |
| #32* | 21758 | 0.0016 | 0.057 | 27.9 |
| #33* | 42071 | 0.0008 | 0.036 | 34.5 |
| #34* | 23398 | 0.0015 | 0.043 | 25.8 |

*Proteins #31 to #34 in this table represent proteins consisting of the corresponding amino acid sequence of SEQ ID NO: 31 to 34, and additionally an N-terminal His-tag (SEQ ID NO: 1).

TABLE 5

Mouse pharmacokinetic parameters of Proteins #35 to #38

| Parameter Protein | AUCINF_D_pred h*(nmol/L) | Cl_pred L/(h*kg) | Vss_pred L/kg | HL_Lambda_z h |
|---|---|---|---|---|
| #35* | 4222 | 0.0082 | 0.036 | 4.4 |
| #36* | 28590 | 0.0012 | 0.057 | 36.6 |
| #37* | 23517 | 0.0015 | 0.083 | 42.7 |
| #38* | 30107 | 0.0011 | 0.04 | 27.4 |

*Proteins #35 to #38 in this table represent proteins consisting of the corresponding amino acid sequence of SEQ ID NO: 35 to 38, and additionally an N-terminal His-tag (SEQ ID NO: 1).

These findings indicate that the sequence modifications described here lead to improved pharmacokinetic properties. In particular, Proteins #25 and #26 exhibit slower clearance, larger area under the curve, and longer terminal half-life than Proteins #24. Also, Proteins #28, #29 and #30 exhibit slower clearance, larger area under the curve, and longer terminal half-life than Protein #27. Similarly, Proteins #32, #33 and #34 exhibit slower clearance, larger area under the curve, and longer terminal half-life than Protein #31. And Proteins #36, #37 and #38 exhibit slower clearance, larger area under the curve, and longer terminal half-life than Protein #35.

Similar results are obtained when comparing the mouse pharmacokinetic parameters of Proteins #39 to #53. In particular, Proteins #40 and #41 exhibit slower clearance, larger area under the curve, and longer terminal half-life than Protein #39. Also, Proteins #43, #44 and #45 exhibit slower clearance, larger area under the curve, and longer terminal half-life than Protein #42. Similarly, Proteins #47, #48 and #49 exhibit slower clearance, larger area under the curve, and longer terminal half-life than Protein #46. And Proteins #51, #52 and #53 exhibit slower clearance, larger area under the curve, and longer terminal half-life than Protein #50. Likewise, similar results are obtained when comparing the mouse pharmacokinetic parameters of Proteins #54 to #68. In particular, Proteins #55 and #56 exhibit slower clearance, larger area under the curve, and longer terminal half-life than Protein #54. Also, Proteins #58, #59 and #60 exhibit slower clearance, larger area under the curve, and longer terminal half-life than Protein #57. Similarly, Proteins #62, #63 and #64 exhibit slower clearance, larger area under the curve, and longer terminal half-life than Protein #61. And Proteins #66, #67 and #68 exhibit slower clearance, larger area under the curve, and longer terminal half-life than Protein #65. The effect of the sequence modifications on pharmacokinetic properties of the proteins in mouse is thus observed when using different designed ankyrin repeat domains with binding specificity for serum albumin as means for half-life extension. The effect of the sequence modifications on pharmacokinetic properties of the proteins in mouse is thus also observed when using different linker sequences (e.g. Pro-Thr-rich linker instead of Gly-Ser-rich linker).

Example 7: Cynomolqus Monkey Pharmacokinetic Parameters Protein Variants

Pharmacokinetic analyses are performed in two male *Macaca fascicularis* for each protein using Proteins #24 to #38, produced as described in Example 2. Proteins are dosed at 1 mg/kg via 30 min intravenous infusion administration. For every protein, blood is collected from every animal 5 min, 6 h, 24 h, 72 h, 120 h, 168 h, 336 h, 408 h, 504 h, and 672 h post injection. The blood samples are allowed to stand at room temperature and are centrifuged to generate serum using procedures well-known to the person skilled in the art, followed by storage at −80° C. pending analyses. Serum concentrations of Proteins #24 to #68 are determined by sandwich ELISA as described in Example 6. Pharmacokinetic parameters are determined using standard software such as Phoenix WinNonLin (Certara, Princeton, USA) or GraphPadPrism (GraphPad Software, La Jolla, USA) and standard analyses such as non-compartmental analyses, all well-known to the person skilled in the art. The pharmacokinetic parameters area under the curve, clearance, volume of distribution, and half-life, are derived from the measurements.

The measurements indicate that the sequence modifications described herein lead to improved pharmacokinetic properties. In particular, Proteins #25 and #26 exhibit slower clearance, larger area under the curve, and longer terminal half-life than Protein #24. Also, Proteins #28, #29 and #30 exhibit slower clearance, larger area under the curve, and longer terminal half-life than Protein #27. Similarly, Proteins #32, #33 and #34 exhibit slower clearance, larger area under the curve, and longer terminal half-life than Protein #31. And Proteins #36, #37 and #38 exhibit slower clearance, larger area under the curve, and longer terminal half-life than Protein #35.

Similar results are obtained when comparing the cynomolgus monkey pharmacokinetic parameters of Proteins #39 to #53. In particular, Protein #40 and #41 exhibit slower clearance, larger area under the curve, and longer terminal half-life than Protein #39. Also, Proteins #43, #44 and #45 exhibit slower clearance, larger area under the curve, and longer terminal half-life than Protein #42. Similarly, Proteins #47, #48 and #49 exhibit slower clearance, larger area under the curve, and longer terminal half-life than Protein #46. And Proteins #51, #52 and #53 exhibit slower clearance, larger area under the curve, and longer terminal half-life than Protein #50. Likewise, similar results are obtained when comparing the cynomolgus monkey pharmacokinetic parameters of Proteins #54 to #68. In particular, Proteins #55 and #56 exhibit slower clearance, larger area under the curve, and longer terminal half-life than Protein #54. Also, Proteins #58, #59 and #60 exhibit slower clearance, larger area under the curve, and longer terminal half-life than Protein #57. Similarly, Proteins #62, #63 and #64 exhibit slower clearance, larger area under the curve, and longer terminal half-life than Protein #61. And Proteins #66, #67 and #68 exhibit slower clearance, larger area under the curve, and longer terminal half-life than Protein #65. The effect of the sequence modifications on pharmacokinetic properties of the proteins in cynomolgus monkey is thus observed when using different designed ankyrin repeat domains with binding specificity for serum albumin as means for half-life extension. The effect of the sequence modifications on pharmacokinetic properties of the proteins in cynomolgus monkey is thus also observed when using different linker sequences (e.g. Pro-Thr-rich linker instead of Gly-Ser-rich linker).

Example 8: Generation of Proteins

Proteins of the invention, comprising designed ankyrin repeat domain(s) with sequence modifications described herein, and comparator proteins described herein are generated by recombinant DNA technology or DNA synthesis well-known to the practitioner in the art.

One example of such a protein of the invention is a protein comprising from N terminus to C terminus, (i) a designed ankyrin repeat domain consisting of SEQ ID NO: 4, (ii) a ProThr-rich linker consisting of SEQ ID NO: 3, (iii) a designed ankyrin repeat domain consisting of SEQ ID NO: 11, (iv) a ProThr-rich linker consisting of SEQ ID NO: 3, (v) a designed ankyrin repeat domain consisting of SEQ ID NO: 11, (vi) a ProThr-rich linker consisting of SEQ ID NO: 3, and (vii) a designed ankyrin repeat domain consisting of SEQ ID NO: 4 (i.e. SEQ ID NOs: 4-3-11-3-11-3-4). Similarly, one example of such a protein of the invention is a protein comprising from N terminus to C terminus, (i) a designed ankyrin repeat domain consisting of SEQ ID NO: 4, (ii) a ProThr-rich linker consisting of SEQ ID NO: 3, (iii) a designed ankyrin repeat domain consisting of SEQ ID NO:

10, (iv) a ProThr-rich linker consisting of SEQ ID NO: 3, (v) a designed ankyrin repeat domain consisting of SEQ ID NO: 10, (vi) a ProThr-rich linker consisting of SEQ ID NO: 3, and (vii) a designed ankyrin repeat domain consisting of SEQ ID NO: 4 (i.e. SEQ ID NOs: 4-3-10-3-10-3-4). Similarly, one example of such a comparator protein is a protein comprising from N terminus to C terminus, (i) a designed ankyrin repeat domain consisting of SEQ ID NO: 4, (ii) a ProThr-rich linker consisting of SEQ ID NO: 3, (iii) a designed ankyrin repeat domain consisting of SEQ ID NO: 9, (iv) a ProThr-rich linker consisting of SEQ ID NO: 3, (v) a designed ankyrin repeat domain consisting of SEQ ID NO: 9, (vi) a ProThr-rich linker consisting of SEQ ID NO: 3, and (vii) a designed ankyrin repeat domain consisting of SEQ ID NO: 4 (i.e. SEQ ID NOs: 4-3-9-3-9-3-4). Analogously, proteins of the invention are prepared using designed ankyrin repeat domains with binding specificity for serum albumin consisting of SEQ ID NOs: 4 to 6, polypeptide linkers consisting of SEQ ID NOs: 2 or 3, and designed ankyrin repeat domains consisting of SEQ ID NOs: 10, 11, 13 to 15, 17 to 19 and 21 to 23. Analogously, comparator proteins as described herein are prepared using designed ankyrin repeat domains with binding specificity for serum albumin consisting of SEQ ID NOs: 4 to 6, polypeptide linkers consisting of SEQ ID NOs: 2 or 3, and designed ankyrin repeat domains consisting of SEQ ID NOs: 9, 12, 16, and 20. Examples of such proteins of the inventions are recombinant binding proteins (See FIG. 1). An example of a recombinant binding protein of the invention is a variant of the recombinant binding protein consisting of SEQ ID NO: 134 of WO2016156596, wherein position 158 is Q, position 165 is L, position 293 is R, position 297 is Q, position 339 is Q, position 346 is L, position 441 is R, and position 445 is Q.

Methods to generate such proteins, for example recombinant binding proteins, are well-known to the practitioner in the art from e.g. WO2016156596 or WO2018054971.

Example 9: Production of Proteins

Proteins as described in Example 8, additionally having a His-tag (SEQ ID NO: 1) fused to the N terminus are produced as described in Example 2. Similarly, proteins as described in Example 8, additionally carrying the amino acids MGS at the N terminus (wherein the N-terminal methionine is efficiently cleaved off from the expressed polypeptide in the cytoplasm of E. coli since the start Met is followed by a small Gly residue), can be produced in E. coli and be purified using conventional methods. Similarly, a recombinant binding protein as described in Example 8, additionally carrying the amino acids MGS at the N terminus (wherein the N-terminal methionine is efficiently cleaved off from the expressed polypeptide in the cytoplasm of E. coli since the start Met is followed by a small Gly residue), can be produced in E. coli and be purified using conventional methods.

Example 10: Mouse Pharmacokinetic Profiles of Proteins

Proteins or recombinant binding proteins produced as described in Example 9 are tested in mouse to determine pharmacokinetic parameters as described in Example 6. It is observed that a protein consisting of SEQ ID NOs: 4-3-11-3-11-3-4 and a protein consisting of SEQ ID NOs: 4-3-10-3-10-3-4, exhibit slower clearance, larger area under the curve, and longer terminal half-life than a protein consisting of SEQ ID NOs: 4-3-9-3-9-3-4. Similarly, it is observed that a protein consisting of SEQ ID NOs: 5-3-14-3-14-3-5, a protein consisting of SEQ ID NOs: 5-3-13-3-13-3-5, or a protein consisting of SEQ ID NOs: 5-3-15-3-15-3-5, exhibit slower clearance, larger area under the curve, and longer terminal half-life than a protein consisting of SEQ ID NOs: 5-3-12-3-12-3-5. Similarly, it is observed that a protein consisting of SEQ ID NOs: 6-2-19-2-19-2-6, a protein consisting of SEQ ID NOs: 6-2-18-2-18-2-6, or a protein consisting of SEQ ID NOs: 6-2-17-2-17-2-6, exhibit slower clearance, larger area under the curve, and longer terminal half-life than a protein consisting of SEQ ID NOs: 6-2-16-2-16-2-6. Similarly, it is observed that a protein consisting of SEQ ID NOs: 4-3-23-3-23-3-4, a protein consisting of SEQ ID NOs: 4-3-22-3-22-3-4, or a protein consisting of SEQ ID NOs: 4-3-21-3-21-3-4, exhibit slower clearance, larger area under the curve, and longer terminal half-life than a protein consisting of SEQ ID NOs: 4-3-20-3-20-3-4.

Example 11: Cynomolgus Monkey Pharmacokinetic Profiles of Proteins

Proteins or recombinant binding proteins produced as described in Example 9 are tested in cynomolgus monkey to determine pharmacokinetic parameters as described in Example 7.

It is observed that a protein consisting of SEQ ID NOs: 4-3-11-3-11-3-4 and a protein consisting of SEQ ID NOs: 4-3-10-3-10-3-4, exhibit slower clearance, larger area under the curve, and longer terminal half-life than a protein consisting of SEQ ID NOs: 4-3-9-3-9-3-4. Similarly, it is observed that a protein consisting of SEQ ID NOs: 5-3-14-3-14-3-5, a protein consisting of SEQ ID NOs: 5-3-13-3-13-3-5, or a protein consisting of SEQ ID NOs: 5-3-15-3-15-3-5, exhibit slower clearance, larger area under the curve, and longer terminal half-life than a protein consisting of SEQ ID NOs: 5-3-12-3-12-3-5. Similarly, it is observed that a protein consisting of SEQ ID NOs: 6-2-19-2-19-2-6, a protein consisting of SEQ ID NOs: 6-2-18-2-18-2-6, or a protein consisting of SEQ ID NOs: 6-2-17-2-17-2-6, exhibit slower clearance, larger area under the curve, and longer terminal half-life than a protein consisting of SEQ ID NOs: 6-2-16-2-16-2-6. Similarly, it is observed that a protein consisting of SEQ ID NOs: 4-3-23-3-23-3-4, a protein consisting of SEQ ID NOs: 4-3-22-3-22-3-4, or a protein consisting of SEQ ID NOs: 4-3-21-3-21-3-4, exhibit slower clearance, larger area under the curve, and longer terminal half-life than a protein consisting of SEQ ID NOs: 4-3-20-3-20-3-4.

Additional examples of N-terminal capping modules and designed ankyrin repeat domains comprising the surface design of the invention are provided in SEQ ID NOs: 112 to 142. These sequences additionally have the amino acids GS at the N terminus.

The invention claimed is:

1. A designed ankyrin repeat domain comprising an N-terminal capping module having a leucine (L), valine (V), isoleucine (I), methionine (M), or alanine (A) at a position corresponding to position 15 of SEQ ID NO: 69.

2. The ankyrin repeat domain of claim 1, wherein said N-terminal capping module has a glutamine (Q) at a position corresponding to position 8 of SEQ ID NO: 69.

3. The ankyrin repeat domain of claim 1, wherein said ankyrin repeat domain comprises an N-terminal capping module having a leucine (L) at a position corresponding to position 15 of SEQ ID NO: 69.

4. The ankyrin repeat domain of claim 1, wherein said ankyrin repeat domain comprises an N-terminal capping module having an amino acid sequence selected from SEQ ID NOs: 75 to 81 and 107 to 114, wherein X represents any amino acid.

5. The ankyrin repeat domain of claim 1, wherein said ankyrin repeat domain comprises an N-terminal capping module having the amino acid sequence of SEQ ID NO: 75, 76, 112, 113, or 114.

6. The ankyrin repeat domain of claim 1, wherein said ankyrin repeat domain comprises an N-terminal capping module having the amino acid sequence of SEQ ID NO: 81, wherein X represents any amino acid.

7. The ankyrin repeat domain of claim 1, wherein said ankyrin repeat domain comprises an N-terminal capping module having the amino acid sequence of SEQ ID NO: 111, wherein X represents any amino acid.

8. The ankyrin repeat domain of claim 1, wherein said N-terminal capping module comprises an amino acid sequence of 30 amino acids.

9. The ankyrin repeat domain of claim 1, wherein said ankyrin repeat domain has a prolonged terminal half-life compared to an ankyrin repeat domain comprising an N-terminal capping module having an aspartic acid (D) at a position corresponding to position 15 of SEQ ID NO: 69.

10. A protein comprising the ankyrin repeat domain of claim 1.

11. A designed ankyrin repeat domain comprising an N-terminal capping module having an amino acid sequence DLGKKLLQAARAGQLDEVRELLKAGADVNA (SEQ ID NO: 75), wherein up to 10 amino acids of SEQ ID NO: 75 in positions other than position 15 are optionally exchanged by other amino acids.

12. The ankyrin repeat domain of claim 11, wherein said ankyrin repeat domain comprises an N-terminal capping module having an amino acid sequence DLGKKLLQAARAGQLDEVRELLKAGADVNA (SEQ ID NO: 75), wherein up to 7 amino acids of SEQ ID NO: 75 in positions other than position 15 are optionally exchanged by other amino acids.

13. The ankyrin repeat domain of claim 11, wherein said ankyrin repeat domain comprises an N-terminal capping module having an amino acid sequence DLGKKLLQAARAGQLDEVRELLKAGADVNA (SEQ ID NO: 75), wherein up to 4 amino acids of SEQ ID NO: 75 in positions other than position 15 are optionally exchanged by other amino acids.

14. The ankyrin repeat domain of claim 1, wherein said ankyrin repeat domain has an amino acid sequence selected from SEQ ID NOs: 10, 11, 13 to 15, 17 to 19, 21 to 23, 118 to 140 and 142.

15. The protein of claim 10, wherein said protein has an amino acid sequence selected from SEQ ID NOs: 25, 26, 28 to 30, 32 to 34, 36 to 38, 40, 41, 43 to 45, 47 to 49, 51 to 53, 55, 56, 58 to 60, 62 to 64, 66 to 68, and 115 to 117.

16. A protein comprising a designed ankyrin repeat domain, wherein said ankyrin repeat domain comprises an N-terminal capping module having a leucine (L), valine (V), isoleucine (I), methionine (M), or alanine (A) at a position corresponding to position 15 of SEQ ID NO: 69, wherein said protein has a prolonged terminal half-life compared to a protein comprising an ankyrin repeat domain comprising an N-terminal capping module having an aspartic acid (D) at a position corresponding to position 15 of SEQ ID NO: 69.

17. The protein of claim 16, wherein said N-terminal capping module has a leucine (L) at a position corresponding to position 15 of SEQ ID NO: 69.

18. A method of prolonging the terminal half-life of a protein comprising a designed ankyrin repeat domain, the method comprising the step of introducing in an N-terminal capping module of said ankyrin repeat domain a leucine (L), valine (V), isoleucine (I), methionine (M), or alanine (A) at a position corresponding to position 15 of SEQ ID NO: 69.

19. The method of claim 18, the method comprising the step of introducing in an N-terminal capping module of said ankyrin repeat domain a leucine (L) at a position corresponding to position 15 of SEQ ID NO: 69.

20. A nucleic acid encoding the ankyrin repeat domain of claim 1.

21. A pharmaceutical composition comprising the ankyrin repeat domain of claim 1, and optionally a pharmaceutical acceptable carrier and/or diluent.

* * * * *